(12) United States Patent
Conn et al.

(10) Patent No.: US 8,592,422 B2
(45) Date of Patent: Nov. 26, 2013

(54) BICYCLIC TRIAZOLE AND PYRAZOLE LACTAMS AS ALLOSTERIC MODULATORS OF MGLUR5 RECEPTORS

(75) Inventors: P. Jeffrey Conn, Brentwood, TN (US); Craig W. Lindsley, Brentwood, TN (US); Shaun R. Stauffer, Brentwood, TN (US); José Manuel Bartolomé-Nebreda, Toledo (ES); Susana Conde-Ceide, Toledo (ES); Gregor James MacDonald, Beerse (BE); Han Min Tong, Toledo (ES); Carrie K. Jones, Nashville, TN (US); Manuel Jesús Alcázar-Vaca, Toledo (ES); José Ignacio Andrés-Gil, Toledo (ES); Chrysa Malosh, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/329,025

(22) Filed: Dec. 16, 2011

(65) Prior Publication Data

US 2012/0225844 A1    Sep. 6, 2012

Related U.S. Application Data

(60) Provisional application No. 61/424,557, filed on Dec. 17, 2010.

(51) Int. Cl.
*A61K 31/4985*    (2006.01)
*A61P 25/00*    (2006.01)
*C07D 487/04*    (2006.01)

(52) U.S. Cl.
USPC ...... 514/249; 514/383; 514/406; 514/255.02; 544/350; 548/262.4; 548/360.5

(58) Field of Classification Search
USPC ............ 514/249, 383, 406, 255.02; 544/350; 548/262.4, 360.5
See application file for complete search history.

(56) References Cited

U.S. PATENT DOCUMENTS

2009/0270362 A1* 10/2009 Conn et al. ............... 514/210.21

* cited by examiner

*Primary Examiner* — Sreeni Padmanabhan
*Assistant Examiner* — Irina Neagu
(74) *Attorney, Agent, or Firm* — Ballard Spahr LLP

(57) ABSTRACT

In one aspect, the invention relates to bicyclic triazole and pyrazole lactams, derivatives thereof, and related compounds, which are useful as positive allosteric modulators of the metabotropic glutamate receptor subtype 5 (mGluR5); synthetic methods for making the compounds; pharmaceutical compositions comprising the compounds; and methods of treating neurological and psychiatric disorders associated with glutamate dysfunction using the compounds and compositions. This abstract is intended as a scanning tool for purposes of searching in the particular art and is not intended to be limiting of the present invention.

12 Claims, 3 Drawing Sheets

BICYCLIC TRIAZOLE AND PYRAZOLE LACTAMS AS ALLOSTERIC MODULATORS OF MGLUR5 RECEPTORS

CROSS-REFERENCE TO RELATED APPLICATIONS

This application claims the benefit of U.S. Application No. 61/424,557, filed Dec. 17, 2010, which is hereby incorporated by reference in their entirety.

STATEMENT REGARDING FEDERALLY SPONSORED RESEARCH

This invention was made with U.S. Government support under grant numbers MH062646, MH073676, MH082867 and NS031373, awarded by the National Institutes of Health (NIH). The U.S. government has certain rights in the invention.

BACKGROUND

Glutamate (L-glutamic acid) is the major excitatory transmitter in the mammalian central nervous system, exerting its effects through both ionotropic and metabotropic glutamate receptors. The metabotropic glutamater receptors (mGluRs) belong to family C (also known as family 3) of the G-protein-coupled receptors (GPCRs). They are characterized by a seven transmembrane (7TM) α-helical domain connected via a cysteine rich-region to a large bi-lobed extracellular amino-terminal domain (FIG. 1). While the orthosteric binding site is contained in the amino-terminal domain, currently known allosteric binding sites reside in the 7TM domain. The mGluR family comprises eight known mGluRs receptor types (designated as mGluR1 through mGluR8). Several of the receptor types are expressed as specific splice variants, e.g. mGluR5a and mGluR5b or mGluR8a, mGluR8b and mGluR8c. The family has been classified into three groups based on their structure, preferred signal transduction mechanisms, and pharmacology.

Group I receptors (mGluR1 and mGluR5) are coupled to Gαq, a process that results in stimulation of phospholipase C and an increase in intracellular calcium and inositol phosphate levels. Group II receptors (mGluR2 and mGluR3) and group III receptors (mGluR4, mGluR6, mGluR7, and mGluR8) are coupled to Gαi, which leads to decreases in cyclic adenosine monophosphate (cAMP) levels. While the Group I receptors are predominately located postsynaptically and typically enhance postsynaptic signaling, the group II and III receptors are located presynaptically and typically have inhibitory effects on neurotransmitter release. Without wishing to be bound by a particular theory, metabotropic glutamate receptors, including mGluR5, have been implicated in a wide range of biological functions, indicating a potential role for the mGluR5 receptor in a variety of disease processes in mammals. Ligands of metabotropic glutamate receptors can be used for the treatment or prevention of acute and/or chronic neurological and/or psychiatric disorders associated with glutamate dysfunction, such as psychosis, schizophrenia, age-related cognitive decline, and the like. Further, without wishing to be bound by theory, increasing evidence indicates mGluRs play an important role in lasting changes in synaptic transmission, and studies of synaptic plasticity in the FmrI knockout mouse have identified a connection between the fragile X phenotype and mGluR signaling.

The identification of small molecule mGluR agonists that bind at the orthosteric site has greatly increased the understanding of the roles played by these receptors and their corresponding relation to disease. Because the majority of these agonists were designed as analogs of glutamate, they typically lack the desired characteristics for drugs targeting mGluR such as oral bioavailability and/or distribution to the central nervous system (CNS). Moreover, because of the highly conserved nature of the glutamate binding site, most orthosteric agonists lack selectivity among the various mGluRs.

Selective positive allosteric modulators ("PAMs") are compounds that do not directly activate receptors by themselves, but binding of these compounds potentiates the response of the receptor to glutamate or other orthosteric agonists by increasing the affinity of an orthosteric agonist at the orthosteric binding site. PAMs are thus an attractive mechanism for enhancing appropriate physiological receptor activation.

Unfortunately, there is a scarcity of selective positive allosteric modulators for the mGluR5 receptor. Further, conventional mGluR5 receptor modulators typically lack satisfactory aqueous solubility and exhibit poor oral bioavailability. Therefore, there remains a need for methods and compositions that overcome these deficiencies and that effectively provide selective positive allosteric modulators for the mGluR5 receptor.

SUMMARY

In accordance with the purpose(s) of the invention, as embodied and broadly described herein, the invention, in one aspect, relates to compounds useful as positive allosteric modulators (i.e., potentiators) of the metabotropic glutamate receptor subtype 5 (mGluR5), methods of making same, pharmaceutical compositions comprising same, and methods of treating neurological and psychiatric disorders associated with glutamate dysfunction using same.

Disclosed are compounds having a structure represented by a formula:

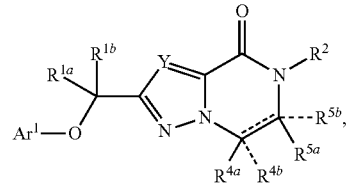

wherein each _____ is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—R$^3$, wherein R$^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein R$^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein R$^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or R$^{4a}$ and R$^{4b}$ are covalently bonded and, together with the intermediate carbon, comprise an optionally substituted 3- to 7-membered spirocycloalkyl; wherein R$^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein R$^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or R$^{5a}$ and R$^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

Also disclosed are compounds having a structure represented by a formula:

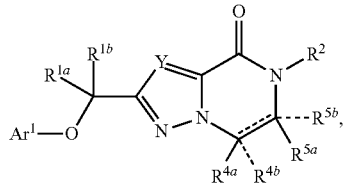

wherein each ____ is independently an optional covalent bond, wherein valence is satisfied; wherein Ar$^1$ is phenyl with 0-3 substituents selected from halogen, cyano, C1-C4 alkyl, C1-C4 alkyloxy, monohalo C1-C4 alkyl, and polyhalo C1-C4 alkyl, or Ar$^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of R$^{1a}$ and R$^{1b}$ is independently selected from hydrogen and C1-C4 alkyl; wherein R$^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—R$^3$, wherein R$^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein R$^{4a}$ is selected from hydrogen and C1-C4 alkyl; wherein R$^{4b}$, when present, is selected from hydrogen and C1-C4 alkyl, or R$^{4a}$ and R$^{4b}$ are covalently bonded and, together with the intermediate carbon, comprise an optionally substituted 3- to 7-membered spirocycloalkyl; wherein R$^{5a}$ is selected from hydrogen and C1-C4 alkyl; and wherein R$^{5b}$, when present, is selected from hydrogen and C1-C4 alkyl, or R$^{5a}$ and R$^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

The present invention also relates to a pharmaceutical composition comprising a therapeutically effective amount of a compound as defined herein and a pharmaceutically acceptable carrier or excipient. Also disclosed are pharmaceutical compositions comprising a therapeutically effective amount of a disclosed compound and a pharmaceutically acceptable carrier.

Furthermore, the invention relates to a process for preparing a pharmaceutical composition according to the invention, characterized in that a pharmaceutically acceptable carrier is intimately mixed with a therapeutically effective amount of a compound as described herein.

Also disclosed are synthetic method comprising the steps of: (a) providing a compound having a structure represented by a formula:

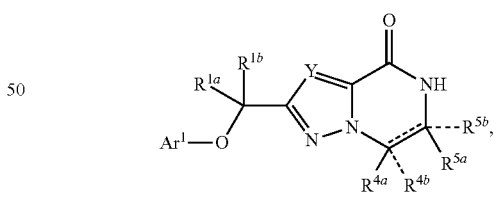

wherein each ____ is independently an optional covalent bond, wherein valence is satisfied; wherein Ar$^1$ is phenyl with 0-3 substituents selected from halogen, cyano, C1-C4 alkyl, C1-C4 alkyloxy, monohalo C1-C4 alkyl, and polyhalo C1-C4 alkyl, or Ar$^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of R$^{1a}$ and R$^{1b}$ is independently selected from hydrogen and C1-C4 alkyl; wherein Y is N or C—R$^3$, wherein R$^3$, when present, is selected from hydrogen, halogen, cyano, and C1-C4 alkyl; wherein R$^{4a}$ is selected from hydrogen and C1-C4 alkyl; wherein R$^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl, and (b) reacting the compound with $R^2X$, wherein X is a leaving group, and wherein $R^2$ is selected from C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; and C2-C5 heterocyclyl; thereby alkylating the amide.

Also disclosed are synthetic methods comprising the steps of: (a) providing a compound having a structure represented by a formula:

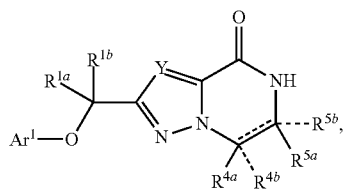

wherein each ____ is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl, and (b) coupling the compound with $R^2X$, in the presence of a coupling reagent, wherein X is bromo or iodo, and wherein $R^2$ is selected from C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; thereby substituting at the amide.

Also disclosed are synthetic methods comprising the steps of: (a) providing a compound having a structure represented by a formula:

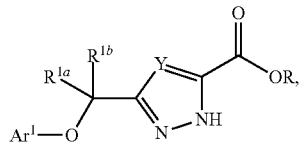

wherein R is hydrogen or alkyl; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein Y is N or C—$R^3$, wherein $R^3$, when present, is selected from hydrogen, halogen, cyano, and C1-C4 alkyl; and (b) reacting the compound with:

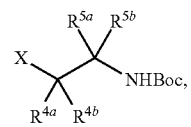

wherein X is a leaving group; wherein each of $R^{4a}$ and $R^{4b}$ is independently selected from hydrogen and C1-C4 alkyl, or are covalently bonded and, together with the intermediate carbon, comprise an optionally substituted 3- to 7-membered spirocycloalkyl; and wherein each of $R^{5a}$ and $R^{5b}$ is independently selected from hydrogen and C1-C4 alkyl, or are covalently bonded and, together with the intermediate carbon, comprise an optionally substituted 3- to 7-membered spirocycloalkyl, thereby forming:

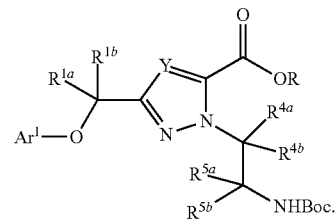

Also disclosed are synthetic methods comprising the steps of: (a) providing a compound having a structure represented by a formula:

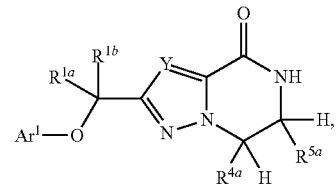

wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl;

wherein each of $R^{1a}$ and $R^{1b}$ is independently selected from hydrogen and C1-C4 alkyl; wherein Y is N or C—$R^3$, wherein $R^3$, when present, is selected from hydrogen, halogen, cyano, and C1-C4 alkyl; and wherein $R^{4a}$ is selected from hydrogen and C1-C4 alkyl; wherein $R^{5a}$ is selected from hydrogen and C1-C4 alkyl, and (b) oxidizing the compound with an oxidating reagent, thereby yielding a compound having a structure represented by a formula:

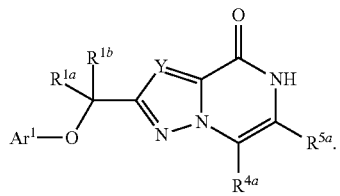

Also disclosed are synthetic methods comprising the steps of: (a) providing a compound having a structure represented by a formula:

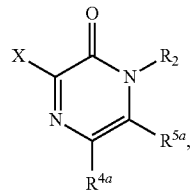

wherein X is halogen or pseudohalogen; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein $R^{4a}$ is selected from hydrogen and C1-C4 alkyl; and wherein $R^{5a}$ is selected from hydrogen and C1-C4 alkyl, and (b) coupling, in the presence of a coupling reagent, the compound with an aryloxyacetamide having a structure represented by a formula:

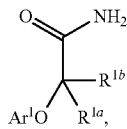

wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; and wherein each of $R^{1a}$ and $R^{1b}$ is independently selected from hydrogen and C1-C4 alkyl; thereby yielding a compound having a structure represented by a formula:

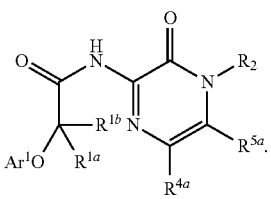

Also disclosed are methods for the treatment of a neurological and/or psychiatric disorder associated with glutamate dysfunction in a mammal comprising the step of administering to the mammal a therapeutically effective amount of at least one compound having a structure represented by a formula:

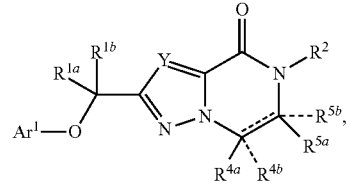

wherein each _____ is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various further aspects, disclosed are methods for the treatment of a neurological and/or psychiatric disorder associated with glutamate dysfunction in a mammal comprising the step of administering to the mammal a therapeutically effective amount of at least one compound having a structure represented by a formula:

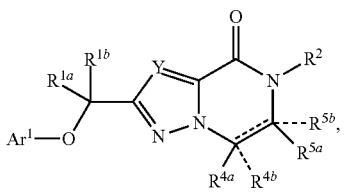

wherein each _____ is independently an optional covalent bond, wherein valence is satisfied; wherein Ar¹ is phenyl with 0-3 substituents selected from halogen, cyano, hydroxyl, —NH₂, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or Ar¹ is pyridinyl, pyridazinyl, pyrimidinyl, or pyrazinyl and has 0-3 substituents selected from halogen, cyano, hydroxyl, —NH₂, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In one aspect, the invention relates to a method for the treatment of a disorder of uncontrolled cellular proliferation in a mammal comprising the step of administering to the mammal a therapeutically effective amount of at least one compound having a structure represented by a formula:

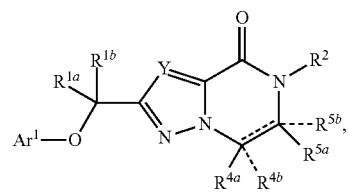

wherein each _____ is independently an optional covalent bond, wherein valence is satisfied; wherein Ar¹ is phenyl with 0-3 substituents selected from halogen, cyano, C1-C4 alkyl, C1-C4 alkyloxy, monohalo C1-C4 alkyl, and polyhalo C1-C4 alkyl, or Ar¹ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various further aspects, the invention relates to a method for the treatment of a disorder of uncontrolled cellular proliferation in a mammal comprising the step of administering to the mammal a therapeutically effective amount of at least one compound having a structure represented by a formula:

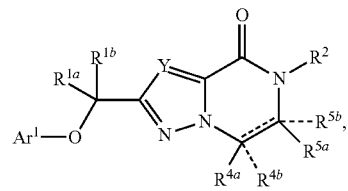

wherein each ____ is independently an optional covalent bond, wherein valence is satisfied; wherein Ar$^1$ is phenyl with 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or Ar$^1$ is pyridinyl, pyridazinyl, pyrimidinyl, or pyrazinyl and has 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

Additionally, the invention relates to a compound as defined herein for use in the treatment or in the prevention of disorders of uncontrolled cellular proliferation.

Also disclosed are methods for potentiation of metabotropic glutamate receptor activity in a mammal comprising the step of administering to the mammal a therapeutically effective amount of at least one compound having a structure represented by a formula:

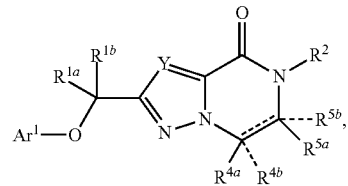

wherein each ____ is independently an optional covalent bond, wherein valence is satisfied; wherein Ar$^1$ is phenyl with 0-3 substituents selected from halogen, cyano, C1-C4 alkyl, C1-C4 alkyloxy, monohalo C1-C4 alkyl, and polyhalo C1-C4 alkyl, or Ar$^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various further aspects, disclosed are methods for potentiation of metabotropic glutamate receptor activity in a mammal comprising the step of administering to the mammal a therapeutically effective amount of at least one compound having a structure represented by a formula:

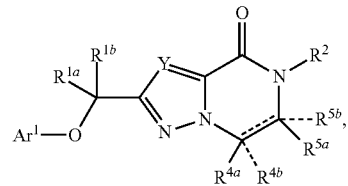

wherein each ____ is independently an optional covalent bond, wherein valence is satisfied; wherein Ar$^1$ is phenyl with 0-3 substituents selected from halogen, cyano, hydroxyl, —NH₂, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or Ar¹ is pyridinyl, pyridazinyl, pyrimidinyl, or pyrazinyl and has 0-3 substituents selected from halogen, cyano, hydroxyl, —NH₂, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

Also disclosed are methods for partial agonism of metabotropic glutamate receptor activity in a mammal comprising the step of administering to the mammal a therapeutically effective amount of at least one compound having a structure represented by a formula:

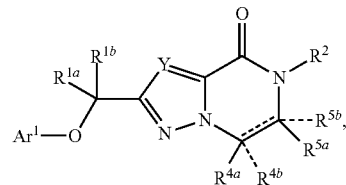

wherein each ____ is independently an optional covalent bond, wherein valence is satisfied; wherein Ar¹ is phenyl with 0-3 substituents selected from halogen, cyano, C1-C4 alkyl, C1-C4 alkyloxy, monohalo C1-C4 alkyl, and polyhalo C1-C4 alkyl, or Ar¹ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various aspects, disclosed are methods for partial agonism of metabotropic glutamate receptor activity in a mammal comprising the step of administering to the mammal a therapeutically effective amount of at least one compound having a structure represented by a formula:

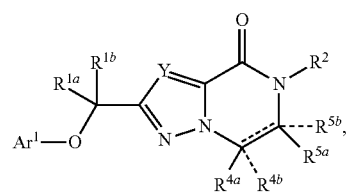

wherein each ____ is independently an optional covalent bond, wherein valence is satisfied; wherein Ar¹ is phenyl with 0-3 substituents selected from halogen, cyano, hydroxyl, —NH₂, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or Ar¹ is pyridinyl, pyridazinyl, pyrimidinyl, or pyrazinyl and has 0-3 substituents selected from halogen, cyano, hydroxyl, —NH₂, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of R$^{1a}$ and R$^{1b}$ is independently selected from hydrogen and C1-C4 alkyl; wherein R$^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—R$^3$, wherein R$^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein R$^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein R$^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or R$^{4a}$ and R$^{4b}$ are covalently bonded and, together with the intermediate carbon, comprise an optionally substituted 3- to 7-membered spirocycloalkyl; wherein R$^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein R$^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or R$^{5a}$ and R$^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

Also disclosed are methods for enhancing cognition in a mammal comprising the step of administering to the mammal an effective amount of at least one compound having a structure represented by a formula:

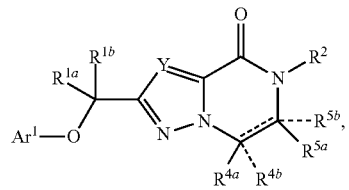

wherein each ____ is independently an optional covalent bond, wherein valence is satisfied; wherein Ar$^1$ is phenyl with 0-3 substituents selected from halogen, cyano, C1-C4 alkyl, C1-C4 alkyloxy, monohalo C1-C4 alkyl, and polyhalo C1-C4 alkyl, or Ar$^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of R$^{1a}$ and R$^{1b}$ is independently selected from hydrogen and C1-C4 alkyl; wherein R$^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—R$^3$, wherein R$^3$, when present, is selected from hydrogen, halogen, cyano, and C1-C4 alkyl; wherein R$^{4a}$ is selected from hydrogen and C1-C4 alkyl; wherein R$^{4b}$, when present, is selected from hydrogen and C1-C4 alkyl, or R$^{4a}$ and R$^{4b}$ are covalently bonded and, together with the intermediate carbon, comprise an optionally substituted 3- to 7-membered spirocycloalkyl; wherein R$^{5a}$ is selected from hydrogen and C1-C4 alkyl; and wherein R$^{5b}$, when present, is selected from hydrogen and C1-C4 alkyl, or R$^{5a}$ and R$^{5b}$ are covalently bonded and, together with the intermediate carbon, comprise an optionally substituted 3- to 7-membered spirocycloalkyl; or a pharmaceutically acceptable salt thereof.

In various further aspects, disclosed are methods for enhancing cognition in a mammal comprising the step of administering to the mammal an effective amount of at least one compound having a structure represented by a formula:

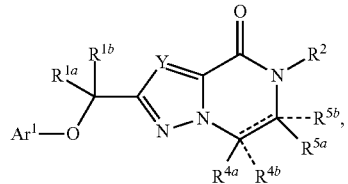

wherein each ____ is independently an optional covalent bond, wherein valence is satisfied; wherein Ar$^1$ is phenyl with 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or Ar$^1$ is pyridinyl, pyridazinyl, pyrimidinyl, or pyrazinyl and has 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of R$^{1a}$ and R$^{1b}$ is independently selected from hydrogen and C1-C4 alkyl; wherein R$^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-

C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—R$^3$, wherein R$^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein R$^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein R$^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or R$^{4a}$ and R$^{4b}$ are covalently bonded and, together with the intermediate carbon, comprise an optionally substituted 3- to 7-membered spirocycloalkyl; wherein R$^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein R$^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or R$^{5a}$ and R$^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

Also disclosed are methods for modulating mGluR5 activity in a mammal comprising the step of administering to the mammal an effective amount of at least one compound having a structure represented by a formula:

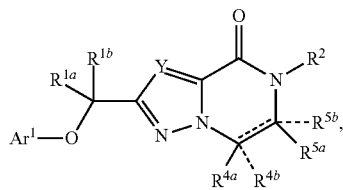

wherein each _____ is independently an optional covalent bond, wherein valence is satisfied; wherein Ar$^1$ is phenyl with 0-3 substituents selected from halogen, cyano, C1-C4 alkyl, C1-C4 alkyloxy, monohalo C1-C4 alkyl, and polyhalo C1-C4 alkyl, or Ar$^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of R$^{1a}$ and R$^{1b}$ is independently selected from hydrogen and C1-C4 alkyl; wherein R$^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—R$^3$, wherein R$^3$, when present, is selected from hydrogen, halogen, cyano, and C1-C4 alkyl; wherein R$^{4a}$ is selected from hydrogen and C1-C4 alkyl; wherein R$^{4b}$, when present, is selected from hydrogen and C1-C4 alkyl, or R$^{4a}$ and R$^{4b}$ are covalently bonded and, together with the intermediate carbon, comprise an optionally substituted 3- to 7-membered spirocycloalkyl; wherein R$^{5a}$ is selected from hydrogen and C1-C4 alkyl; and wherein R$^{5b}$, when present, is selected from hydrogen and C1-C4 alkyl, or R$^{5a}$ and R$^{5b}$ are covalently bonded and, together with the intermediate carbon, comprise an optionally substituted 3- to 7-membered spirocycloalkyl; or a pharmaceutically acceptable salt thereof.

In various further aspects, disclosed are methods for modulating mGluR5 activity in a mammal comprising the step of administering to the mammal an effective amount of at least one compound having a structure represented by a formula:

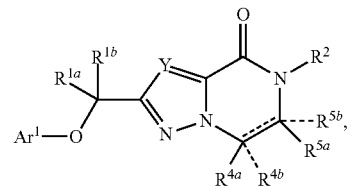

wherein each _____ is independently an optional covalent bond, wherein valence is satisfied; wherein Ar$^1$ is phenyl with 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or Ar$^1$ is pyridinyl, pyridazinyl, pyrimidinyl, or pyrazinyl and has 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of R$^{1a}$ and R$^{1b}$ is independently selected from hydrogen and C1-C4 alkyl; wherein R$^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—R$^3$, wherein R$^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

Also disclosed are methods for modulating mGluR5 activity in at least one cell, comprising the step of contacting the at least one cell with an effective amount of at least one compound having a structure represented by a formula:

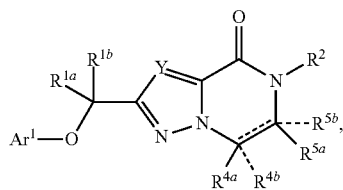

wherein each ----- is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various further aspects, disclosed are methods for modulating mGluR5 activity in at least one cell, comprising the step of contacting the at least one cell with an effective amount of at least one compound having a structure represented by a formula:

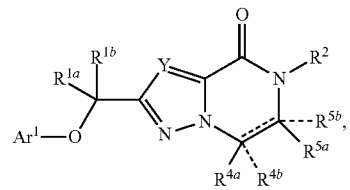

wherein each ----- is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

Also disclosed are kits comprising at least one disclosed compound or at least one disclosed product and one or more of at least one agent known to increase mGluR5 activity; at least one agent known to decrease mGluR5 activity; at least one agent known to treat a neurological and/or psychiatric disorder; at least one agent known to treat a disease of uncontrolled cellular proliferation; or instructions for treating a disorder associated with glutamate dysfunction.

Additionally, the invention also relates to a product comprising a compound as described herein and an additional pharmaceutical agent, as a combined preparation for simultaneous, separate or sequential use in the treatment or prevention of neurological and psychiatric disorders and diseases.

Also disclosed are methods for manufacturing a medicament comprising combining at least one disclosed compound or at least one disclosed product with a pharmaceutically acceptable carrier or diluent. Additionally, the invention relates to a compound as defined herein for use as a medicament, and to a compound as defined herein for use in the treatment or in the prevention of neurological and psychiatric disorders and diseases.

Also disclosed are uses of a disclosed compound or a disclosed product in the manufacture of a medicament for the treatment of a disorder associated with glutamate dysfunction in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
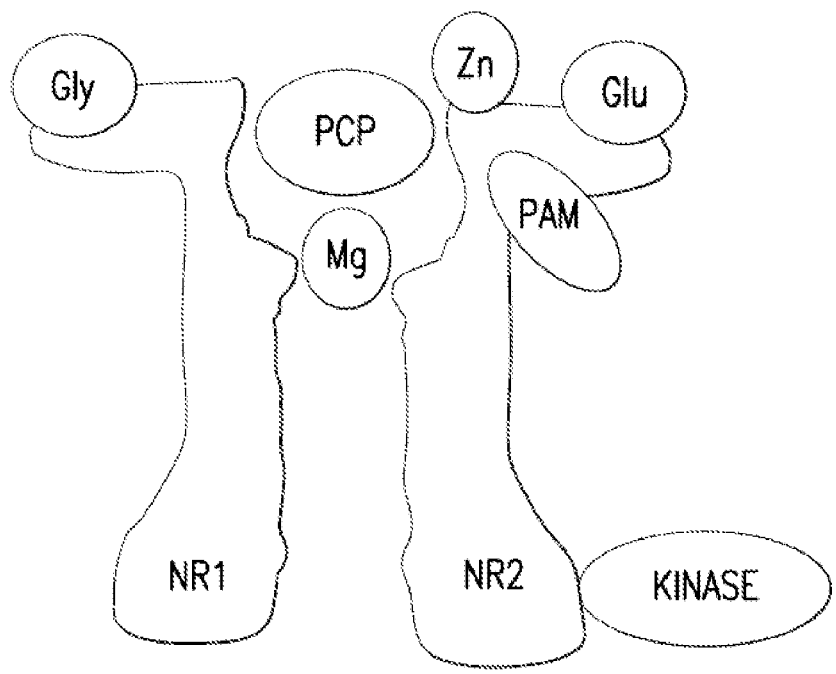
FIG. 1 shows a schematic of the NMDA receptor.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "allosteric site" refers to a ligand binding site that is topographically distinct from the orthosteric binding site.

As used herein, the term "modulator" refers to a molecular entity (e.g., but not limited to, a ligand and a disclosed compound) that modulates the activity of the target receptor protein.

As used herein, the term "ligand" refers to a a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous ligand" are used interchangeably, and refer to a naturally occurring ligand, found in nature, which binds to a receptor.

As used herein, the term "orthosteric site" refers to the primary binding site on a receptor that is recognized by the endogenous ligand or agonist for that receptor. For example, the orthosteric site in the mGluR5 receptor is the site that glutamate binds.

As used herein, the term "mGluR5 receptor positive allosteric modulator" refers to any exogenously administered compound or agent that directly or indirectly augments the activity of the mGluR5 receptor in the presence or in the absence of glutamate in an animal, in particular a mammal, for example a human. In one aspect, a mGluR5 receptor positive allosteric modulator increases the activity of the mGluR5 receptor in a cell in the presence of extracellular glutamate. The cell can be human embryonic kidney cells transfected with human mGluR5. The cell can be human embryonic kidney cells transfected with rat mGluR5. The cell can be human embryonic kidney cells transfected with a mammalian mGluR5 The term "mGluR5 receptor positive allosteric modulator" includes a compound that is a "mGluR5 receptor allosteric potentiator" or a "mGluR5 receptor allosteric agonist," as well as a compound that has mixed activity comprising pharmacology of both an "mGluR5 receptor allosteric potentiator" and an "mGluR5 receptor allosteric agonist". The term "mGluR5 receptor positive allosteric modulator" also includes a compound that is a "mGluR5 receptor allosteric enhancer."

As used herein, the term "mGluR5 receptor allosteric potentiator" refers to any exogenously administered compound or agent that directly or indirectly augments the response produced by the endogenous ligand (such as glutamate) when the endogenous ligand binds to the orthosteric site of the mGluR5 receptor in an animal, in particular a mammal, for example a human. The mGluR5 receptor allosteric potentiator binds to a site other than the orthosteric site, that is, an allosteric site, and positively augments the response of the receptor to an agonist or the endogenous ligand. In one aspect, an allosteric potentiator does not induce desensitization of the receptor, activity of a compound as an mGluR5 receptor allosteric potentiator provides advantages over the use of a pure mGluR5 receptor allosteric agonist. Such advantages can include, for example, increased safety margin, higher tolerability, diminished potential for abuse, and reduced toxicity.

As used herein, the term "mGluR5 receptor allosteric enhancer" refers to any exogenously administered compound or agent that directly or indirectly augments the response produced by the endogenous ligand in an animal, in particular a mammal, for example a human. In one aspect, the allosteric enhancer increases the affinity of the natural ligand or agonist for the orthosteric site. In another aspect, an allosteric enhancer increases the agonist efficacy. The mGluR5 receptor allosteric enhancer binds to a site other than the orthosteric site, that is, an allosteric site, and positively augments the response of the receptor to an agonist or the endogenous ligand. An allosteric enhancer has no effect on the receptor by itself and requires the presence of an agonist or the natural ligand to realize a receptor effect.

As used herein, the term "mGluR5 receptor allosteric agonist" refers to any exogenously administered compound or agent that directly activates the activity of the mGluR5 receptor in the absence of the endogenous ligand (such as glutamate) in an animal, in particular a mammal, for example a human. The mGluR5 receptor allosteric agonist binds to a site that is distinct from the orthosteric glutamate site of the mGluR5. Because it does not require the presence of the endogenous ligand, activity of a compound as an mGluR5 receptor allosteric agonist provides advantages over the use of a pure mGluR5 receptor allosteric potentiator, such as more rapid onset of action.

As used herein, the term "mGluR5 receptor neutral allosteric ligand" refers to any exogenously administered compound or agent that binds to an allosteric site without affecting the binding or function of agonists or the natural ligand at the orthosteric site in an animal, in particular a mammal, for example a human. However, a neutral allosteric ligand can block the action of other allosteric modulators that act via the same site.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with glutamate dysfunction prior to the administering step. In some aspects of the disclosed method, the subject has been diagnosed with a need for positive allosteric modulation of metabotropic glutamate receptor activity prior to the administering step. In some aspects of the disclosed method, the subject has been diagnosed with a need for partial agonism of metabotropic glutamate receptor activity prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by modulation of mGluR5" means having been subjected to a physical examination by a person of skill, for example, a physician, and found to have a condition that can be diagnosed or treated by a compound or composition that can modulate mGluR5. As a further example, "diagnosed with a need for modulation of mGluR5" refers to having been subjected to a physical examination by a person of skill, for example, a physician, and found to have a condition characterized by mGluR5 activity. Such a diagnosis can be in reference to a disorder, such as a neurodegenerative disease, and the like, as discussed herein. For example, the term "diagnosed with a need for positive allosteric modulation of metabotropic glutamate receptor activity" refers to having been subjected to a physical examination by a person of skill, for example, a physician, and found to have a condition that can be diagnosed or treated by positive allosteric modulation of metabotropic glutamate receptor activity. For example, "diagnosed with a need for partial agonism of metabotropic glutamate receptor activity" means having been subjected to a physical examination by a person of skill, for example, a physician, and found to have a condition that can be diagnosed or treated by partial agonism of metabotropic glutamate receptor activity. For example, "diagnosed with a need for treatment of one or more neurological and/or psychiatric disorder associated with glutamate dysfunction" means having been subjected to a physical examination by a person of skill, for example, a physician, and found to have one or more neurological and/or psychiatric disorder associated with glutamate dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mGluR5 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target metabotropic glutamate receptor, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14 th edition), the Physicians' Desk Reference (64 th edition), and The Pharmacological Basis of Therapeutics (12 th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$EC_{50}$," is intended to refer to the concentration of a substance (e.g., a compound or a drug) that is required for 50% activation or enhancement of a biological process, or component of a process, including a protein, subunit, organelle, ribonucleoprotein, etc. For example, $EC_{50}$ can refer to the concentration of agonist that provokes a response halfway between the baseline and maximum response in an in vitro assay. For example, an $IC_{50}$ for mGluR5 receptor can be determined in an in vitro or cell-based assay system. Such in vitro assay systems frequently utilize a cell line that either expresses endogenously a target of interest, or has been transfected with a suitable expression vector that directs expression of a recombinant form of the target such as mGluR5. For example, the $EC_{50}$ for mGluR5 can be determined using human embryonic kidney (HEK) cells transfected with human mGluR5. Alternatively, the $EC_{50}$ for mGluR5 can be determined using human embryonic kidney (HEK) cells transfected with rat mGluR5. In another example, the $EC_{50}$ for mGluR5 can be determined using human embryonic kidney (HEK) cells transfected with a mammalian mGluR5.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, $IC_{50}$ refers to the half maximal (50%) inhibitory concentration (IC) of a substance as determined in a suitable assay. For example, an $IC_{50}$ for mGluR5 receptor can be determined in an in vitro or cell-based assay system. Frequently, receptor assays, including suitable assays for mGluR5, make use of a suitable cell-line, e.g. a cell line that either expresses endogenously a target of interest, or has been transfected with a suitable expression vector that directs expression of a recombinant form of the target such as mGluR5. For example, the $IC_{50}$ for mGluR5 can be determined using human embryonic kidney (HEK) cells transfected with human mGluR5. Alternatively, the $IC_{50}$ for mGluR5 can be determined using human embryonic kidney (HEK) cells transfected with rat mGluR5. In another example, the $IC_{50}$ for mGluR5 can be determined using human embryonic kidney (HEK) cells transfected with a mammalian mGluR5.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group is acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $-NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —$N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an interger from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $—N_3$.

The term "nitro" as used herein is represented by the formula $—NO_2$.

The term "nitrile" or "cyano" as used herein is represented by the formula —CN.

The term "silyl" as used herein is represented by the formula $—SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}—CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; —CH=CHPh, which may be substituted with $R^\circ$; $—(CH_2)_{0-4}O(CH_2)_{0-1}$-pyridyl which may be substituted with $R^\circ$; $—NO_2$; —CN; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ C(O)NR^\circ_2$; $—N(R^\circ)C(S)NR^\circ_2$; $—(CH_2)_{0-4}N(R^\circ C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched) alkylene)$O—N(R^\circ)_2$; or $—(C_{1-4}$ straight or branched)alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, $-(CH_2)_{0-2} R^\bullet$, $-(haloR^\bullet)$, $-(CH_2)_{0-2}OH$, $-(CH_2)_{0-2}$, $-(CH_2)_{0-2} CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2} SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^o$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

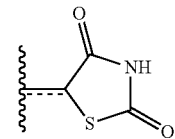

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, monosubstituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

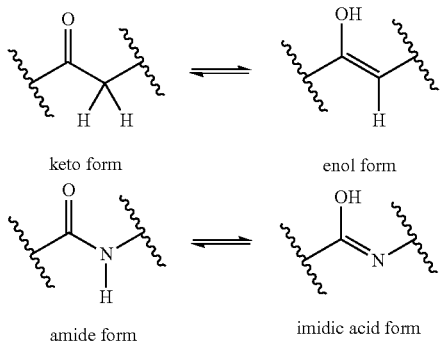

Likewise, amides with an N-hydrogen can exist in an equilibrium of the amide form and the imidic acid form. As another example, pyridinones can exist in two tautomeric forms, as shown below.

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

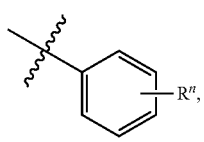

which is understood to be equivalent to a formula:

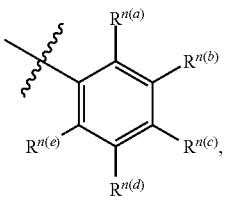

wherein n is typically an integer. That is, $R''$ is understood to represent five independent substituents, $R''^{(a)}$, $R''^{(b)}$, $R''^{(c)}$, $R''^{(d)}$, $R''^{(e)}$. By "independent substituents," it is meant that each R substituent can be independently defined. For example, if in one instance $R''^{(a)}$ is halogen, then $R''^{(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

The following abbreviations are used herein. ACN: acetonitrile. AcOEt: ethyl acetate. BuOH: 1-Butanol. CAN: ammonium cerium (IV) nitrate. DAST: (diethylamino)sulfur trifluoride. DIPEA or DIEA: N,N-diisopropylethylamine. DMAP: 4-Dimethylaminopyridine. DCM: Dichloromethane. DCE: 1,2-dichloroethane. DIPE: diisopropylether. DMF: dimethyl formamide. DMSO: dimethylsulfoxide. DTBAD: di-tert-butyl azodicarboxylate. EDC: 1-ethyl-3-[3-dimethylaminopropyl]carbodiimide hydrochloride. EtOH: ethanol. h: Hours. HATU: 2-(7-aza-1H-benzotriazole-1-yl)-1,1,3,3-tetramethyluronium hexafluorophosphate. RP-HPLC: reverse phase high-performance liquid chromatography. HOBt: 1-hydroxybenzotriazole. iPrOH: 2-Propanol. LCMS: liquid chromatography/mass spectrometry. [M+H]+: protonated mass of the free base of the compound. M.p.: melting point. MeOH: methanol. Min: Minutes. NMR: nuclear magnetic resonance. Rt: retention time (in minutes). RT: Room temperature. TBAF: tetrabutylammonium fluoride. TEA: triethylamine. TFA: trifluoroacetic acid. THF: tetrahydrofuran.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful as positive allosteric modulators of the metabotropic glutamate receptor subtype 5 (mGluR5). More specifically, in one aspect, the present invention relates to compounds that allosterically modulate mGluR5 receptor activity, affecting the sensitivity of mGluR5 receptors to agonists without acting as orthosteric agonists themselves. The compounds can, in one aspect, exhibit subtype selectivity.

In one aspect, the disclosed compounds exhibit positive allosteric modulation of mGluR5 response to glutamate as an increase in response to non-maximal concentrations of glutamate in human embryonic kidney cells transfected with rat mGluR5 in the presence of the compound, compared to the response to glutamate in the absence of the compound. In further aspect, the human embryonic kidney cells are transfected with human mGluR5. In yet a further aspect, human embryonic kidney cells are transfected with mGluR5 of a mammal.

In one aspect, the compounds of the invention are useful in the treatment neurological and psychiatric disorders associated with glutamate dysfunction and other diseases in which metabotropic glutamate receptors are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

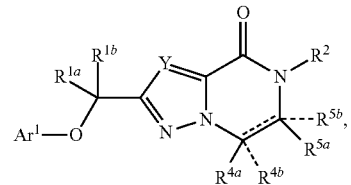

wherein each ____ is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In various further aspects, the invention relates to a compound having a structure represented by a formula:

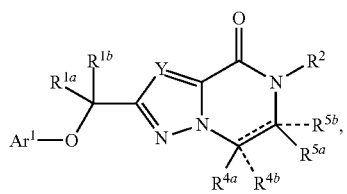

wherein each ____ is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In various further aspects, the invention relates to a compound having a structure represented by a formula:

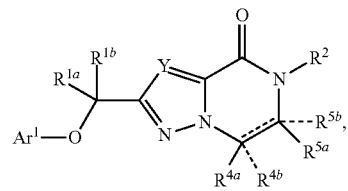

wherein each ____ is independently an optional covalent bond, wherein valence is satisfied; wherein $Ar^1$ is phenyl optionally substituted with fluoro; or $Ar^1$ is pyridinyl optionally substituted with fluoro; wherein each of $R^{1a}$, $R^{1b}$, $R^{4a}$, $R^{4b}$, $R^{5a}$, and $R^{5b}$ is hydrogen; wherein $R^2$ is phenyl substituted with 1-2 substituents selected from fluoro, methyl, and methoxy, or $R^2$ is pyridinyl substituted with 1-2 substituents selected from fluoro, methyl, and methoxy; wherein Y is CH; or a pharmaceutically acceptable salt thereof. In a further aspect, the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In various further aspects, the invention relates to a compound having a structure represented by a formula:

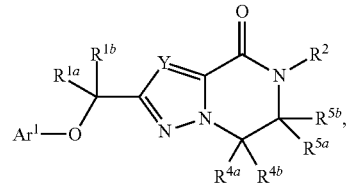

wherein $Ar^1$ is phenyl optionally substituted with fluoro; or $Ar^1$ is pyridinyl optionally substituted with fluoro; wherein each of $R^{1a}$, $R^{1b}$, $R^{4a}$, $R^{4b}$, $R^{5a}$, and $R^{5b}$ is hydrogen; wherein $R^2$ is phenyl substituted with 1-2 substituents selected from fluoro, methyl, and methoxy, or $R^2$ is pyridinyl substituted with 1-2 substituents selected from fluoro, methyl, and methoxy; wherein Y is CH; or a pharmaceutically acceptable salt thereof. In a further aspect, the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In a further aspect, the compound has a structure represented by a formula:

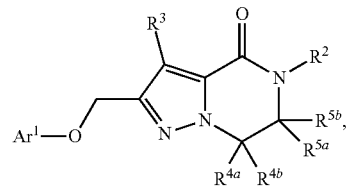

47

-continued

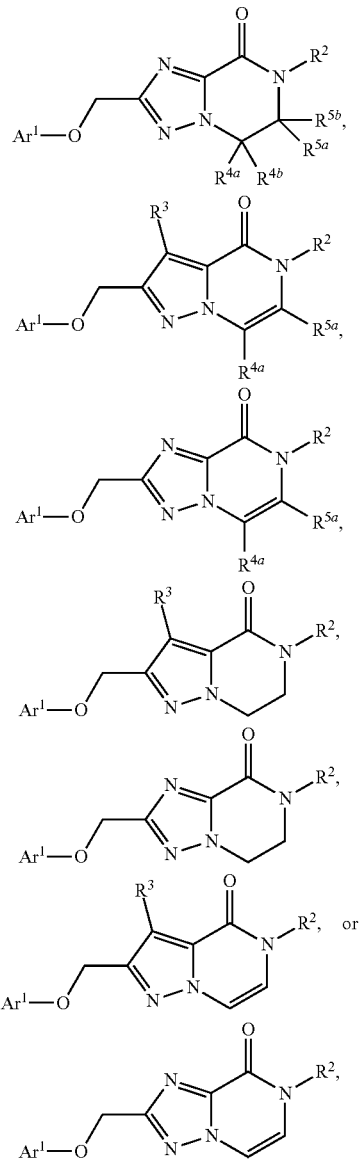

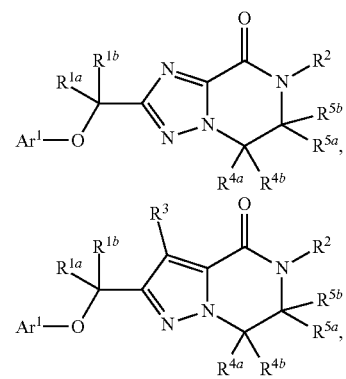

and wherein all variables are as defined herein.

In a further aspect, the compound has a structure represented by a formula:

48

-continued

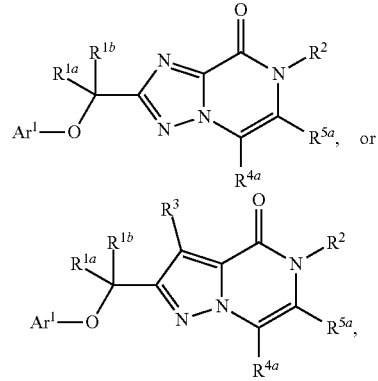

and wherein all variables are as defined herein.

In a further aspect, the compound has a structure represented by a formula:

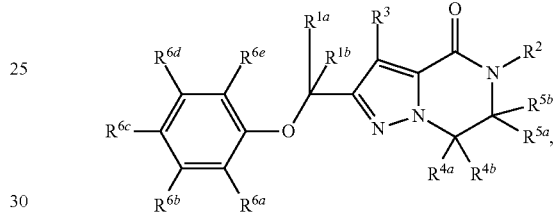

wherein each of $R^{6a}$, $R^{6b}$, $R^{6c}$, $R^{6d}$, and $R^{6e}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that at least two of $R^{6a}$, $R^{6b}$, $R^{6c}$, $R^{6d}$, and $R^{6e}$ are hydrogen, and wherein all other variables are as defined herein. In an even further aspect, each of $R^{6a}$, $R^{6b}$, $R^{6c}$, $R^{6d}$, and $R^{6e}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that three of $R^{6a}$, $R^{6b}$, $R^{6c}$, $R^{6d}$, and $R^{6e}$ are hydrogen. In a still further aspect, each of $R^{6a}$, $R^{6b}$, $R^{6c}$, $R^{6d}$, and $R^{6e}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that four of $R^{6a}$, $R^{6b}$, $R^{6c}$, $R^{6d}$, and $R^{6e}$ are hydrogen, and wherein all other variables are as defined herein. In a yet further aspect, each of $R^{6a}$, $R^{6b}$, $R^{6c}$, $R^{6d}$, and $R^{6e}$ is hydrogen. In a still further aspect, the compound has a structure represented by a formula:

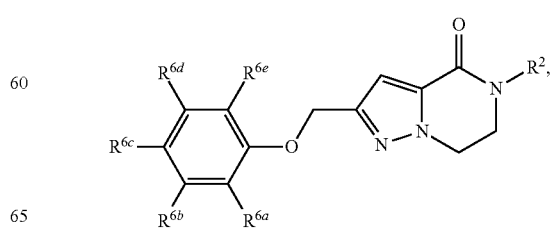

wherein each of $R^{6a}$, $R^{6b}$, $R^{6c}$, $R^{6d}$, and $R^{6e}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that at least two of $R^{6a}$, $R^{6b}$, $R^{6c}$, $R^{6d}$, and $R^{6e}$ are hydrogen, and wherein all other variables are as defined herein.

In a further aspect, the compound has a structure represented by a formula:

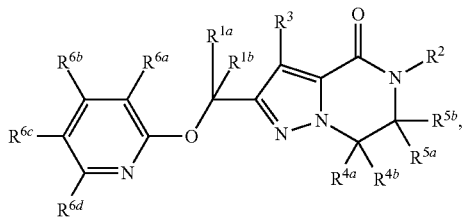

wherein each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that at least one of $R^{6a}$, $R^{6b}$, $R^{6c}$, $R^{6d}$ is hydrogen, and wherein all other variables are as defined herein. In an even further aspect, each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that two of $R^{6a}$, $R^{6b}$, $R^{6c}$, $R^{6d}$ are hydrogen. In a yet further aspect, each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that three of $R^{6a}$, $R^{6b}$, $R^{6c}$, $R^{6d}$ are hydrogen. In an even further aspect, each of $R^{6a}$, $R^{6b}$, $R^{6c}$, and $R^{6d}$ is hydrogen. In a still further aspect, the compound has a structure represented by a formula:

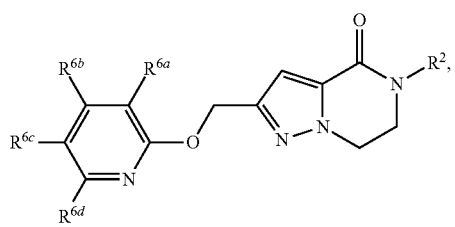

wherein each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that at least one of $R^{6a}$, $R^{6b}$, $R^{6c}$, and $R^{6d}$ is hydrogen, and wherein all other variables are as defined herein.

In a further aspect, the compound has a structure represented by a formula:

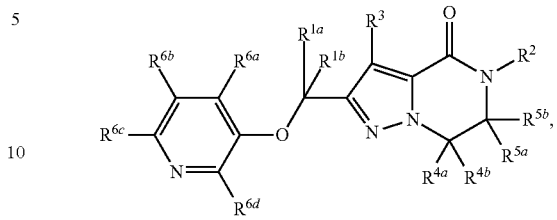

wherein each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that at least one of $R^{6a}$, $R^{6b}$, $R^{6c}$, $R^{6d}$ is hydrogen, and wherein all other variables are as defined herein. In a still further aspect, each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that two of $R^{6a}$, $R^{6b}$, $R^{6c}$, $R^{6d}$ are hydrogen. In an even further aspect, each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that three of $R^{6a}$, $R^{6b}$, $R^{6c}$, $R^{6d}$ are hydrogen. In a yet further aspect, each of $R^{6a}$, $R^{6b}$, $R^{6c}$, and $R^{6d}$ is hydrogen. In a still further aspect, the compound has a structure represented by a formula:

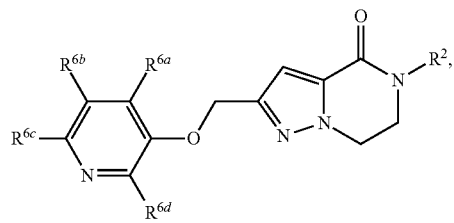

wherein each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that at least one of $R^{6a}$, $R^{6b}$, $R^{6c}$, and $R^{6d}$ is hydrogen, and all other variables are as defined herein.

In a further aspect, the compound has a structure represented by a formula:

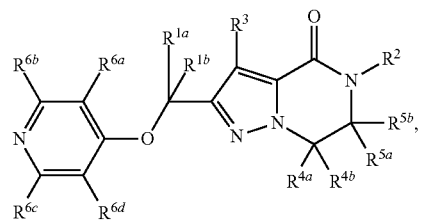

wherein each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that at least one of $R^{6a}$, $R^{6b}$, $R^{6c}$, $R^{6d}$ is hydrogen, and wherein all other variables are as defined herein. In a yet further aspect, each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that two of $R^{6a}$, $R^{6b}$, $R^{6c}$, $R^{6d}$ are hydrogen. In an even further aspect, each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that three of $R^{6a}$, $R^{6b}$, $R^{6c}$, $R^{6d}$ are hydrogen. In a yet further aspect, each of $R^{6a}$, $R^{6b}$, $R^{6c}$, and $R^{6d}$ is hydrogen. In a still further aspect, the compound has a structure represented by a formula:

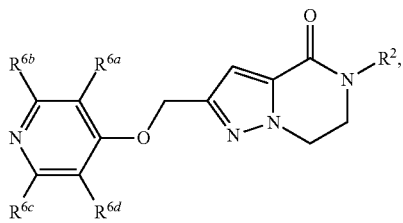

wherein each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that at least one of $R^{6a}$, $R^{6b}$, $R^{6c}$, and $R^{6d}$ is hydrogen, and wherein all other variables are as defined herein.

In a further aspect, the compound has a structure represented by a formula:

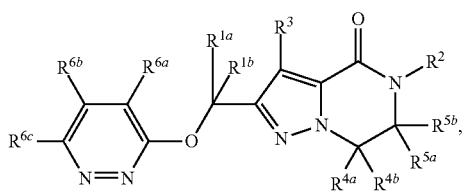

wherein each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, and wherein all other variables are as defined herein. In a yet further aspect, each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that one of $R^{6a}$, $R^{6b}$, and $R^{6c}$ is hydrogen. In an even further aspect, each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that two of $R^{6a}$, $R^{6b}$, and $R^{6c}$ are hydrogen. In a yet further aspect, each of $R^{6a}$, $R^{6b}$, and $R^{6c}$ is hydrogen. In a still further aspect, the compound has a structure represented by a formula:

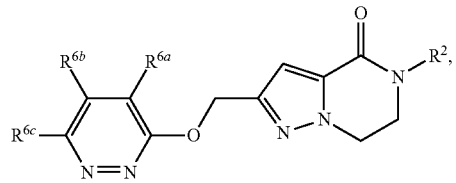

wherein each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, and wherein all other variables are as defined herein.

In a further aspect, the compound has a structure represented by a formula:

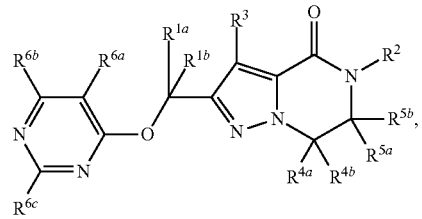

wherein each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, and wherein all other variables are as defined herein. In a yet further aspect, each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that one of $R^{6a}$, $R^{6b}$, and $R^{6c}$ is hydrogen. In an even further aspect, each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that two of $R^{6a}$, $R^{6b}$, and $R^{6c}$ are hydrogen. In a yet further aspect, each of $R^{6a}$, $R^{6b}$, and $R^{6c}$ is hydrogen. In a still further aspect, the compound has a structure represented by a formula:

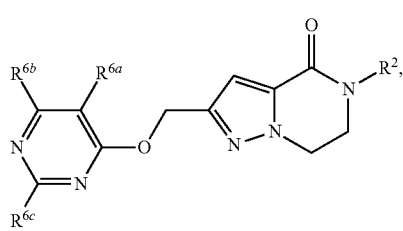

wherein each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, and wherein all other variables are as defined herein.

In a further aspect, the compound has a structure represented by a formula:

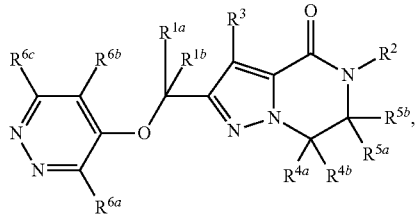

wherein each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, and wherein all other variables are as defined herein. In a yet further aspect, each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that one of $R^{6a}$, $R^{6b}$, and $R^{6c}$ is hydrogen. In an even further aspect, each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that two of $R^{6a}$, $R^{6b}$, and $R^{6c}$ are hydrogen. In a yet further aspect, each of $R^{6a}$, $R^{6b}$, and $R^{6c}$ is hydrogen. In a still further aspect, the compound has a structure represented by a formula:

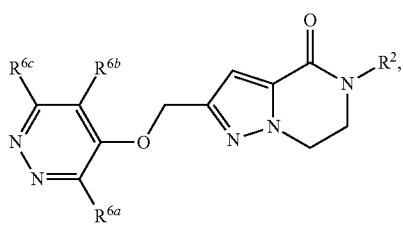

wherein each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, and wherein all other variables are as defined herein.

In a further aspect, the compound has a structure represented by a formula:

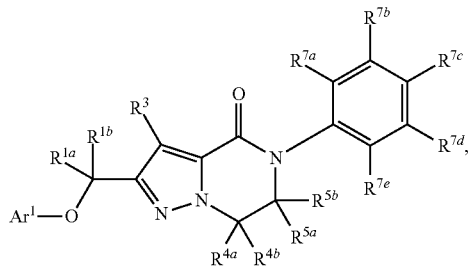

wherein each of $R^{7a}$, $R^{7b}$, $R^{7c}$, $R^{7d}$, and $R^{7e}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least two of $R^{7a}$, $R^{7b}$, $R^{7c}$, $R^{7d}$, and $R^{7e}$ are hydrogen, and wherein all other variables are as defined herein. In a yet further aspect, each of $R^{7a}$, $R^{7b}$, $R^{7c}$, $R^{7d}$, and $R^{7e}$ is hydrogen. In a still further aspect, the compound has a structure represented by a formula:

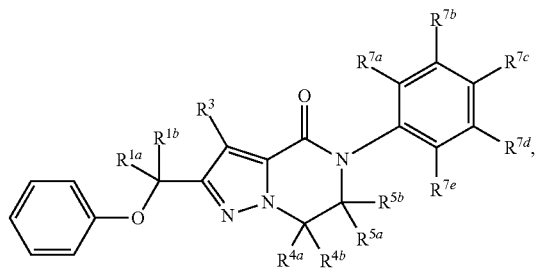

wherein each of $R^{7a}$, $R^{7b}$, $R^{7c}$, $R^{7d}$, and $R^{7e}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least two of $R^{7a}$, $R^{7b}$, $R^{7c}$, $R^{7d}$, and $R^{7e}$ are hydrogen, and wherein all other variables are as defined herein.

In a further aspect, the compound has a structure represented by a formula:

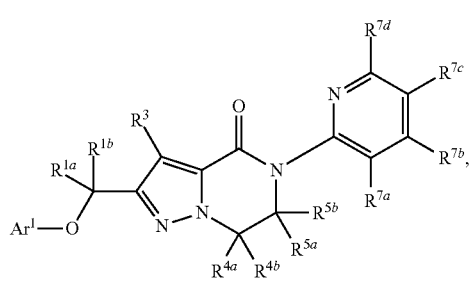

wherein each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least one of $R^{7a}$, $R^{7b}$, $R^{7c}$, and $R^{7d}$ is hydrogen, and wherein all other variables are as defined herein. In a yet further aspect, each of $R^{7a}$, $R^{7b}$, $R^{7c}$, and $R^{7d}$ is hydrogen. In a still further aspect, the compound has a structure represented by a formula:

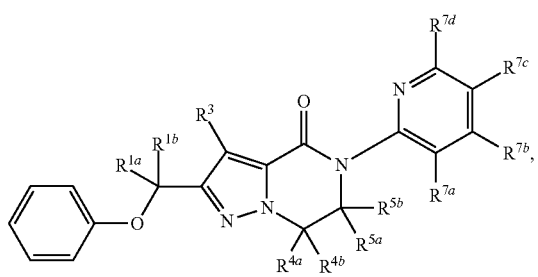

wherein each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least one of $R^{7a}$, $R^{7b}$, $R^{7c}$, and $R^{7d}$ is hydrogen, and wherein all other variables are as defined herein.

In a further aspect, the compound has a structure represented by a formula:

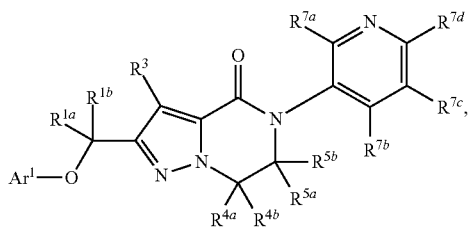

wherein each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least one of $R^{7a}$, $R^{7b}$, $R^{7c}$, and $R^{7d}$ is hydrogen, and wherein all other variables are as defined herein. In a yet further aspect, each of $R^{7a}$, $R^{7b}$, $R^{7c}$, and $R^{7d}$ is hydrogen. In a still further aspect, the compound has a structure represented by a formula:

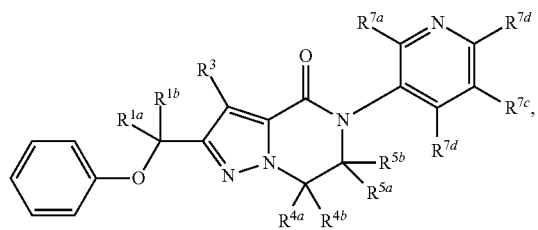

wherein each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least one of $R^{7a}$, $R^{7b}$, $R^{7c}$, and $R^{7d}$ is hydrogen, and wherein all other variables are as defined herein.

In a further aspect, the compound has a structure represented by a formula:

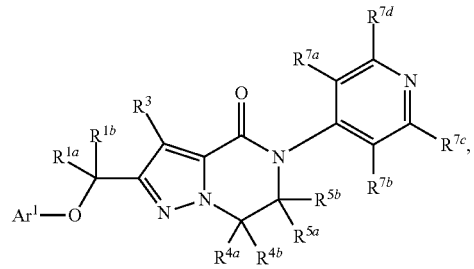

wherein each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least one of $R^{7a}$, $R^{7b}$, $R^{7c}$, and $R^{7d}$ is hydrogen, and wherein all other variables are as defined herein. In a yet further aspect, each of $R^{7a}$, $R^{7b}$, $R^{7c}$, and $R^{7d}$ is hydrogen. In a still further aspect, the compound has a structure represented by a formula:

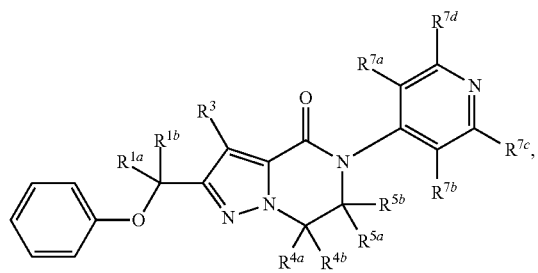

wherein each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least one of $R^{7a}$, $R^{7b}$, $R^{7c}$, and $R^{7d}$ is hydrogen, and wherein all other variables are as defined herein.

In a further aspect, the compound has a structure represented by a formula:

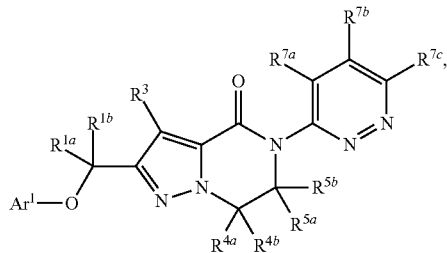

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein. In a yet further aspect, each of $R^{7a}$, $R^{7b}$, and $R^{7c}$ is hydrogen. In a still further aspect, the compound has a structure represented by a formula:

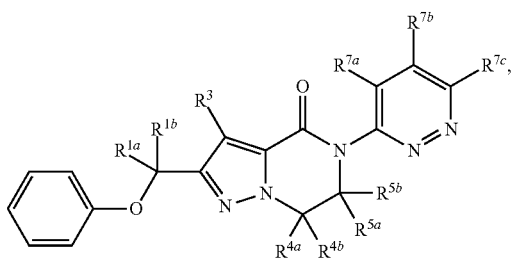

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein.

In a further aspect, the compound has a structure represented by a formula:

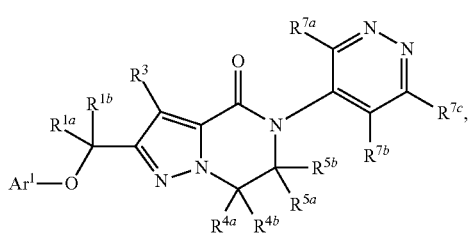

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein. In a yet further aspect, each of $R^{7a}$, $R^{7b}$, and $R^{7c}$ is hydrogen. In a still further aspect, the compound has a structure represented by a formula:

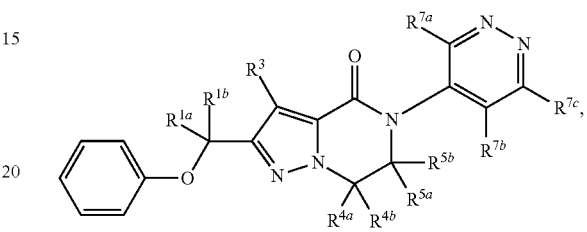

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein.

In a further aspect, the compound has a structure represented by a formula:

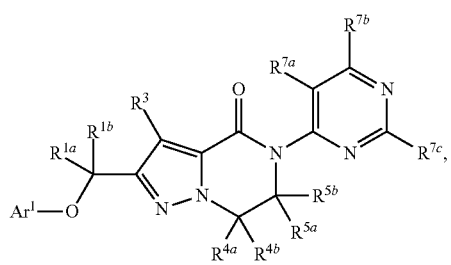

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein. In a yet further aspect, each of $R^{7a}$, $R^{7b}$, and $R^{7c}$ is hydrogen. In a still further aspect, the compound has a structure represented by a formula:

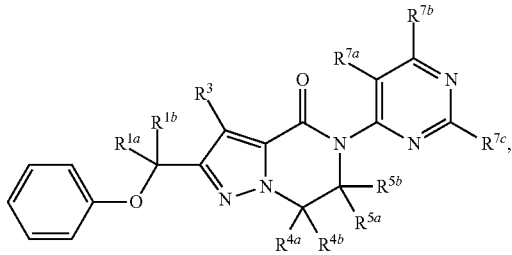

wherein each of $R^{7a}$, $R^{7b}$, and $R^{7e}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein.

In a further aspect, the compound has a structure represented by a formula:

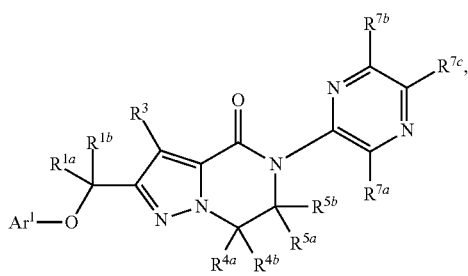

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein. In a yet further aspect, each of $R^{7a}$, $R^{7b}$, and $R^{7c}$ is hydrogen. In a still further aspect, the compound has a structure represented by a formula:

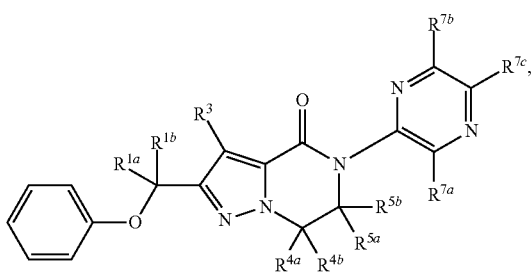

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein.

In a further aspect, the compound has a structure represented by a formula:

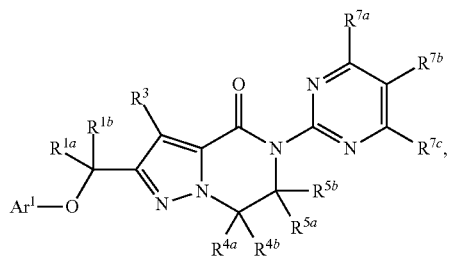

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein. In a yet further aspect, each of $R^{7a}$, $R^{7b}$, and $R^{7c}$ is hydrogen. In a still further aspect, the compound has a structure represented by a formula:

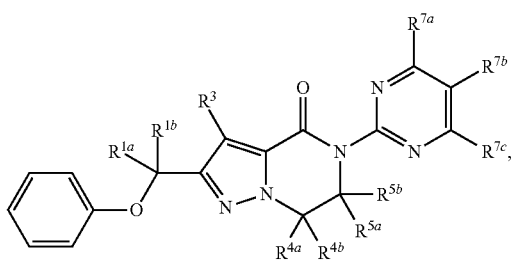

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein.

In a further aspect, the compound has a structure represented by a formula:

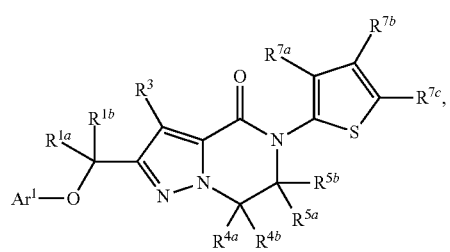

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein. In a yet further aspect, each of $R^{7a}$, $R^{7b}$, and $R^{7c}$ is hydrogen. In a still further aspect, the compound has a structure represented by a formula:

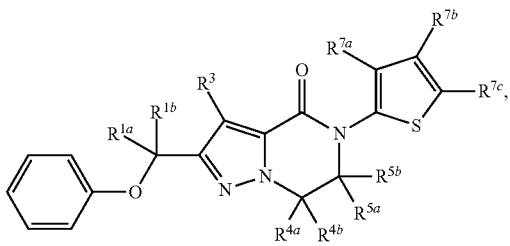

wherein each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein.

In a further aspect, the compound has a structure represented by a formula:

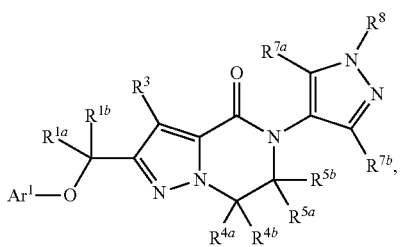

wherein each of $R^{7a}$ and $R^{7b}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein $R^8$ is selected from hydrogen and C1-C6 alkyl; and wherein all other variables are as defined herein. In a yet further aspect, each of $R^{7a}$, $R^{7b}$, and $R^8$ is hydrogen. In a still further aspect, the compound has a structure represented by a formula:

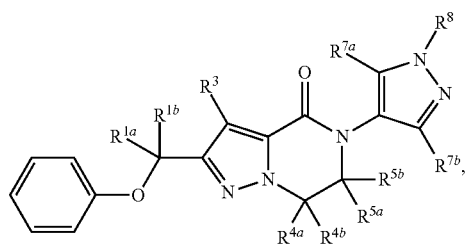

wherein each of $R^{7a}$ and $R^{7b}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein $R^8$ is selected from hydrogen and C1-C6 alkyl; and wherein all other variables are as defined herein.

In a further aspect, the compound has a structure represented by a formula:

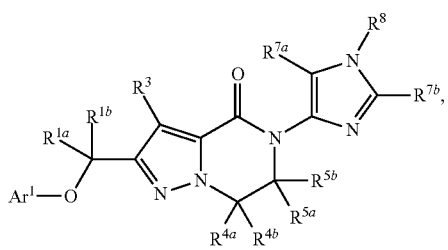

wherein each of $R^{7a}$ and $R^{7b}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein $R^8$ is selected from hydrogen and C1-C6 alkyl; and wherein all other variables are as defined herein. In a yet further aspect, each of $R^{7a}$, $R^{7b}$, and $R^8$ is hydrogen. In a still further aspect, the compound has a structure represented by a formula:

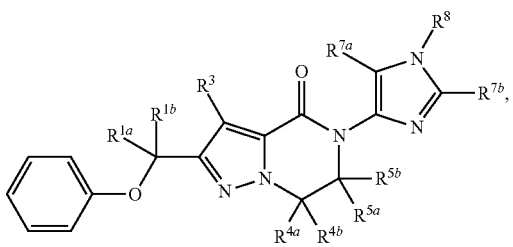

wherein each of $R^{7a}$ and $R^{7b}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein R⁸ is selected from hydrogen and C1-C6 alkyl; and wherein all other variables are as defined herein.

In a further aspect, the compound has a structure represented by a formula:

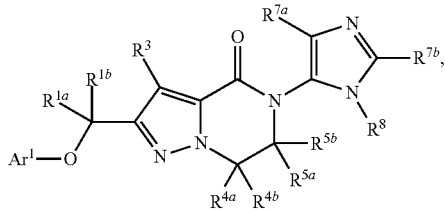

wherein each of $R^{7a}$ and $R^{7b}$ is independently selected from hydrogen, halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein R⁸ is selected from hydrogen and C1-C6 alkyl; and wherein all other variables are as defined herein. In a yet further aspect, each of $R^{7a}$, $R^{7b}$, and R⁸ is hydrogen. In a still further aspect, the compound has a structure represented by a formula:

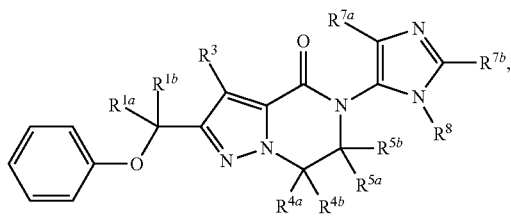

wherein each of $R^{7a}$ and $R^{7b}$ is independently selected from hydrogen, halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein R⁸ is selected from hydrogen and C1-C6 alkyl; and wherein all other variables are as defined herein.

In a further aspect, the compound has a structure represented by a formula:

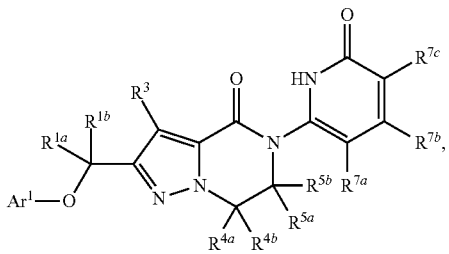

wherein each of $R^{7a}$, $R^{7b}$, and $R^{7c}$ is independently selected from hydrogen, halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein. In a yet further aspect, each of $R^{7a}$, $R^{7b}$, and $R^{7c}$ is hydrogen. In a still further aspect, the compound has a structure represented by a formula:

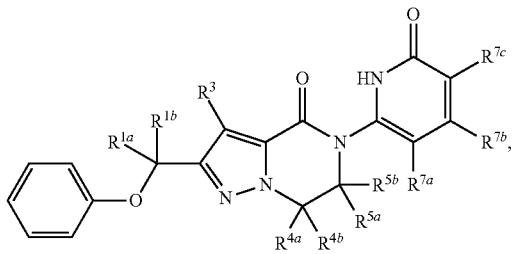

wherein each of $R^{7a}$, $R^{7b}$, and $R^{7c}$ is independently selected from hydrogen, halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, and wherein all other variables are as defined herein.

In a further aspect, the compound has a structure represented by a formula:

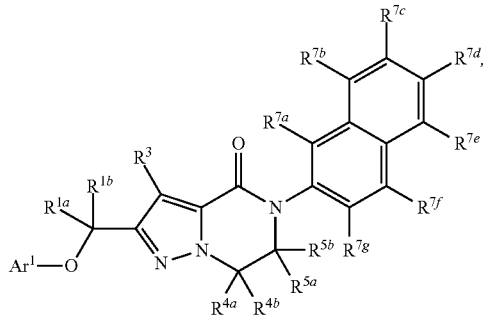

wherein each of $R^{7a}$, $R^{7b}$, $R^{7c}$, $R^{7d}$, $R^{7e}$, $R^{7f}$, and $R^{7g}$ is independently selected from hydrogen, halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least four of $R^{7a}$, $R^{7b}$, $R^{7c}$, $R^{7d}$, $R^{7e}$, $R^{7f}$, and $R^{7g}$ are hydrogen, and wherein all other variables are as defined herein. In a yet further aspect, each of $R^{7a}$, $R^{7b}$, $R^{7c}$, $R^{7d}$, $R^{7e}$, $R^{7f}$, and $R^{7g}$ is hydrogen. In a still further aspect, the compound has a structure represented by a formula:

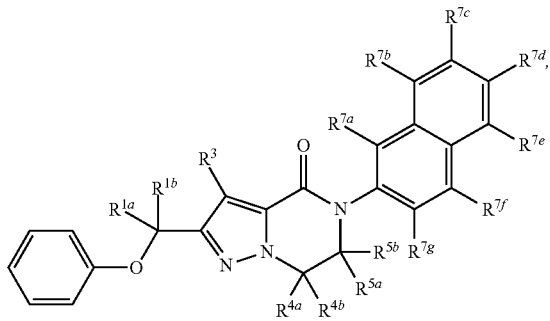

wherein each of $R^{7a}$, $R^{7b}$, $R^{7c}$, $R^{7d}$, $R^{7e}$, $R^{7f}$, and $R^{7g}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least four of $R^{7a}$, $R^{7b}$, $R^{7c}$, $R^{7d}$, $R^{7e}$, $R^{7f}$, and $R^{7g}$ are hydrogen, and wherein all other variables are as defined herein.

In a further aspect, the compound has a structure represented by a formula:

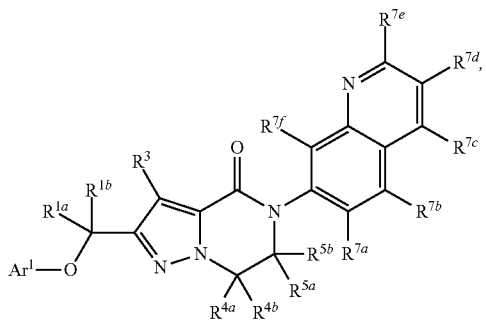

wherein each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, $R^{7d}$, $R^{7e}$, and $R^{7f}$ are hydrogen, and wherein all other variables are as defined herein. In a yet further aspect, each of $R^{7a}$, $R^{7b}$, $R^{7c}$, $R^{7d}$, $R^{7e}$, and $R^{7f}$ is hydrogen. In a still further aspect, the compound has a structure represented by a formula:

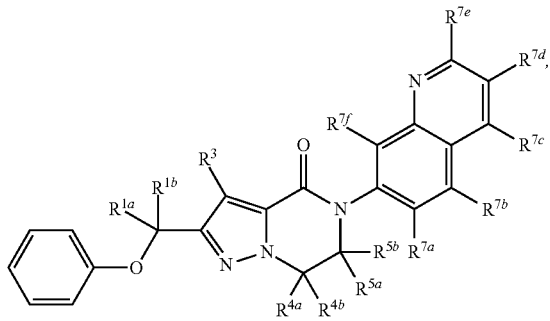

wherein each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, $R^{7d}$, $R^{7e}$, and $R^{7f}$ are hydrogen, and wherein all other variables are as defined herein.

In a further aspect, the compound has a structure represented by a formula:

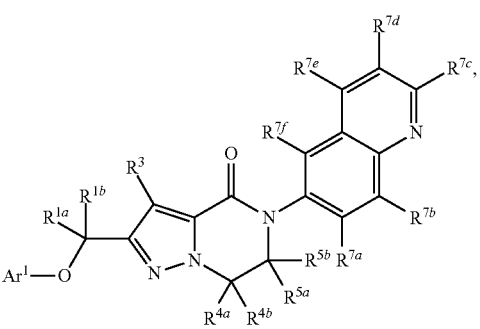

wherein each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, $R^{7d}$, $R^{7e}$, and $R^{7f}$ are hydrogen, and wherein all other variables are as defined herein. In a yet further aspect, each of $R^{7a}$, $R^{7b}$, $R^{7c}$, $R^{7d}$, $R^{7e}$, and $R^{7f}$ is hydrogen. In a still further aspect, the compound has a structure represented by a formula:

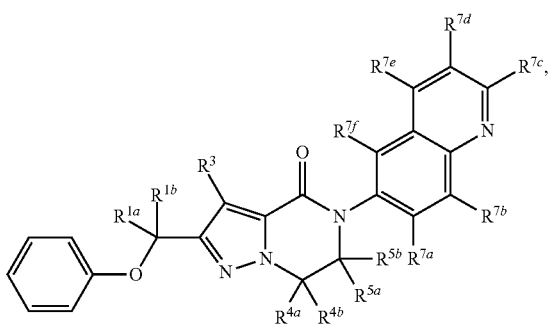

wherein each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, $R^{7d}$, $R^{7e}$, and $R^{7f}$ are hydrogen, and wherein all other variables are as defined herein.

In a further aspect, the compound has a structure represented by a formula:

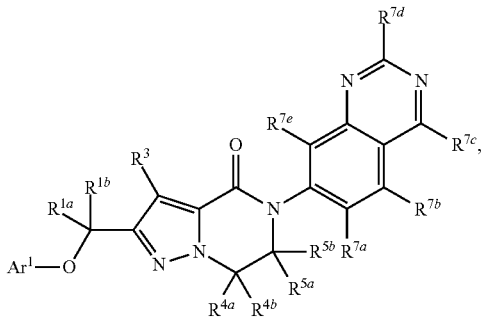

wherein each of $R^{7a}$, $R^{7b}$, $R^{7c}$, $R^{7d}$, and $R^{7e}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least two of $R^{7a}$, $R^{7b}$, $R^{7c}$, $R^{7d}$, and $R^{7e}$ are hydrogen, and wherein all other variables are as defined herein. In a yet further aspect, each of $R^{7a}$, $R^{7b}$, $R^{7c}$, $R^{7d}$, and $R^{7e}$ is hydrogen. In a still further aspect, the compound has a structure represented by a formula:

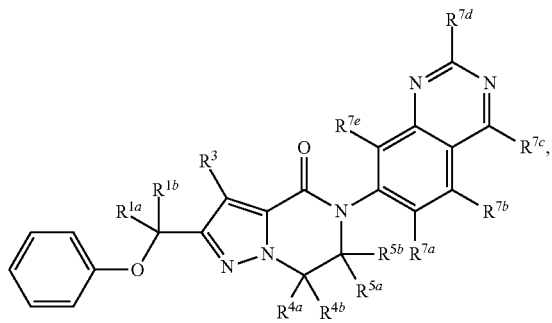

wherein each of $R^{7a}$, $R^{7b}$, $R^{7c}$, $R^{7d}$, and $R^{7e}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least two of $R^{7a}$, $R^{7b}$, $R^{7c}$, $R^{7d}$, and $R^{7e}$ are hydrogen, and wherein all other variables are as defined herein.

In a further aspect, the compound has a structure represented by a formula:

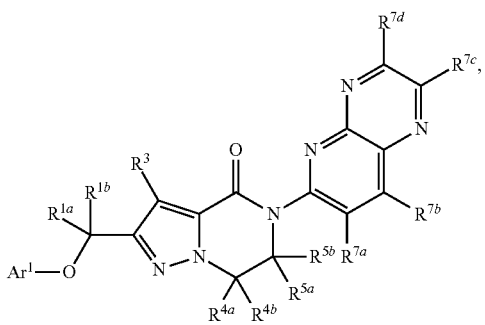

wherein each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least one of $R^{7a}$, $R^{7b}$, $R^{7c}$, and $R^{7d}$ is hydrogen, and wherein all other variables are as defined herein. In a yet further aspect, each of $R^{7a}$, $R^{7b}$, $R^{7c}$, and $R^{7d}$ is hydrogen. In a still further aspect, the compound has a structure represented by a formula:

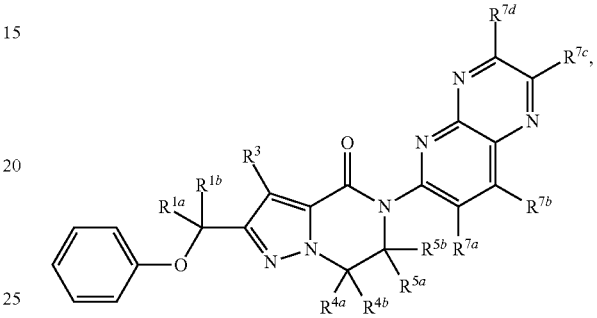

wherein each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least one of $R^{7a}$, $R^{7b}$, $R^{7c}$, and $R^{7d}$ is hydrogen, and wherein all other variables are as defined herein.

In a further aspect, the compound has a structure represented by a formula:

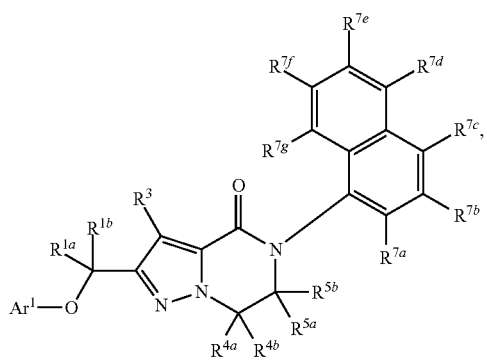

wherein each of $R^{7a}$, $R^{7b}$, $R^{7c}$, $R^{7d}$, $R^{7e}$, $R^{7f}$, and $R^{7g}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least four of $R^{7a}$, $R^{7b}$, $R^{7c}$, $R^{7d}$, $R^{7e}$, $R^{7f}$, and $R^{7g}$ are hydrogen, and wherein all other variables are as defined herein. In a yet further aspect, each of $R^{7a}$, $R^{7b}$, $R^{7c}$, $R^{7d}$, $R^{7e}$, $R^{7f}$, and $R^{7g}$ is hydrogen. In a still further aspect, the compound has a structure represented by a formula:

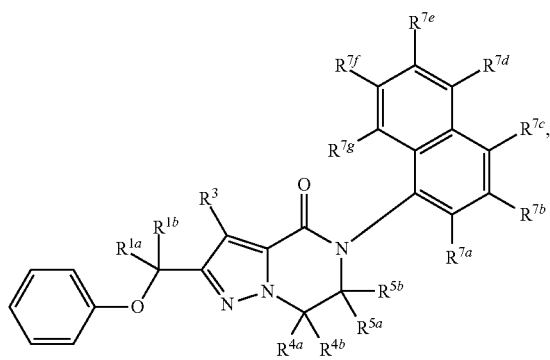

wherein each of $R^{7a}$, $R^{7b}$, $R^{7c}$, $R^{7d}$, $R^{7e}$, $R^{7f}$, and $R^{7g}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least four of $R^{7a}$, $R^{7b}$, $R^{7c}$, $R^{7d}$, $R^{7e}$, $R^{7f}$, and $R^{7g}$ are hydrogen, and wherein all other variables are as defined herein.

In a further aspect, the compound has a structure represented by a formula:

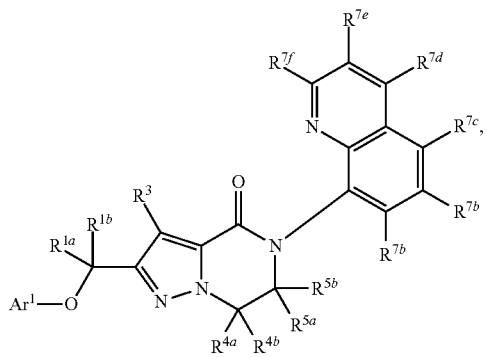

wherein each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, $R^{7d}$, $R^{7e}$, and $R^{7f}$ are hydrogen, and wherein all other variables are as defined herein. In a yet further aspect, each of $R^{7a}$, $R^{7b}$, $R^{7c}$, $R^{7d}$, $R^{7e}$, and $R^{7f}$ is hydrogen. In a still further aspect, the compound has a structure represented by a formula:

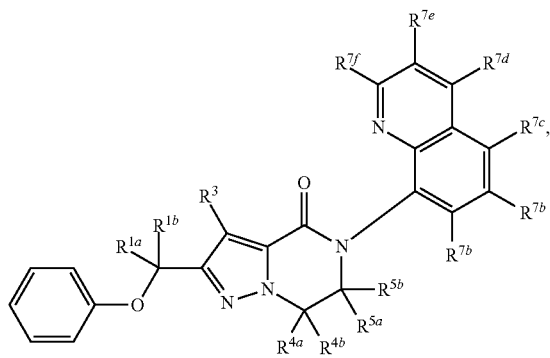

wherein each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, $R^{7d}$, $R^{7e}$, and $R^{7f}$ are hydrogen, and wherein all other variables are as defined herein.

In a further aspect, the compound has a structure represented by a formula:

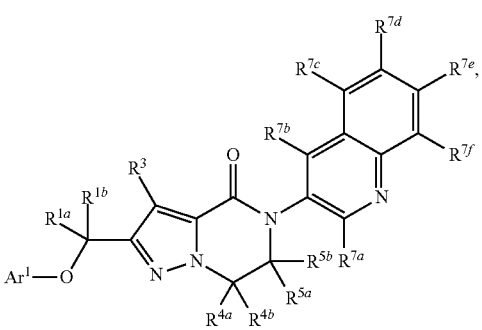

wherein each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, $R^{7d}$, $R^{7e}$, and $R^{7f}$ are hydrogen, and wherein all other variables are as defined herein. In a yet further aspect, each of $R^{7a}$, $R^{7b}$, $R^{7c}$, $R^{7d}$, $R^{7e}$, and $R^{7f}$ is hydrogen. In a still further aspect, the compound has a structure represented by a formula:

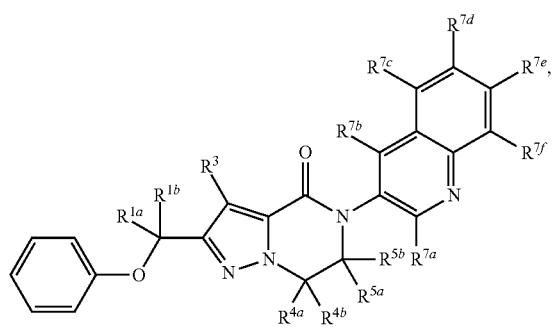

wherein each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, $R^{7d}$, $R^{7e}$, and $R^{7f}$ are hydrogen, and wherein all other variables are as defined herein.

In various aspects, as described above, the disclosed compounds bear substituents, as shown in the formula below:

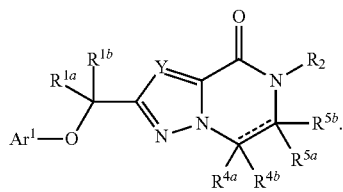

Suitable substituents are described below.

a. Halogen

In one aspect, halogen is fluoro, chloro, bromo or iodo. In a further aspect, halogen is fluoro, chloro, or bromo. In a still further aspect, halogen is fluoro. In a yet further aspect, halogen is fluoro or chloro. In a yet further aspect, halogen is bromo.

b. $Ar^1$ Groups

In one aspect, $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl. In a further aspect, $Ar^1$ is unsubstituted. In a still further aspect, $Ar^1$ has 1, 2, or 3 substituents.

In various aspects, $Ar^1$ is substituted with 1-3 groups selected from halogen, cyano, C1-C4 alkyl, C1-C4 alkyloxy, monohalo C1-C4 alkyl, and polyhalo C1-C4 alkyl. In a further aspect, $Ar^1$ is substituted with 1-3 halogens. In a still further aspect, $Ar^1$ is substituted with 1-3 groups selected from halogen, cyano, C1-C4 alkyl, and C1-C4 alkyloxy. In a yet further aspect, $Ar^1$ is substituted with 1-3 groups selected from halogen, methyl, trifluoromethyl, ethyl, propyl, and butyl. In an even further aspect, $Ar^1$ is substituted with 1-3 groups selected from methoxy, trifluoromethoxy, ethoxy, propyloxy, or butyloxy. In a yet further aspect, $Ar^1$ is substituted with 1-3 groups selected from fluoro, chloro, cyano, hydroxyl, —$NHCH_3$, —$N(CH_3)_2$, methyl, trifluoromethyl, ethyl, propyl, and butyl, methoxy, trifluoromethoxy, ethoxy, propyloxy, or butyloxy. In a still further aspect, $Ar^1$ is substituted with 1-3 groups selected from fluoro, chloro, cyano, hydroxyl, —$NHCH_3$, —$N(CH_3)_2$, methyl, and methoxy.

In one aspect, $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl. In a yet further aspect, $Ar^1$ is phenyl optionally substituted with fluoro; or $Ar^1$ is pyridinyl optionally substituted with fluoro.

In one aspect, $Ar^1$ is phenyl. In a further aspect, $Ar^1$ is phenyl with 1-3 substituents selected from halogen, cyano, C1-C4 alkyl, C1-C4 alkyloxy, monohalo C1-C4 alkyl, and polyhalo C1-C4 alkyl. In an even further aspect, $Ar^1$ is phenyl with 1-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl. In a still further aspect, $Ar^1$ is phenyl with 1-2 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl. In a yet further aspect, $Ar^1$ is phenyl with 2 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl. In an even further aspect, $Ar^1$ is phenyl with monosubstituted with a group selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl. In a yet further aspect, $Ar^1$ is phenyl optionally substituted with fluoro.

In a further aspect, $Ar^1$ is phenyl substituted with 1-3 groups selected from fluoro, chloro, cyano, hydroxyl, —$NHCH_3$, —$N(CH_3)_2$, methyl, trifluoromethyl, ethyl, propyl, and butyl, methoxy, trifluoromethoxy, ethoxy, propyloxy, or butyloxy. In a still further aspect, $Ar^1$ is phenyl substituted with 1-3 groups selected from fluoro, chloro, cyano, hydroxyl, —$NHCH_3$, —$N(CH_3)_2$, methyl, and methoxy.

In a further aspect, $Ar^1$ is phenyl substituted with 1-2 groups selected from fluoro, chloro, cyano, hydroxyl, —$NHCH_3$, —$N(CH_3)_2$, methyl, trifluoromethyl, ethyl, propyl, and butyl, methoxy, trifluoromethoxy, ethoxy, propyloxy, or butyloxy. In a still further aspect, $Ar^1$ is phenyl substituted with 1-2 groups selected from fluoro, chloro, cyano, hydroxyl, —$NHCH_3$, —$N(CH_3)_2$, methyl, and methoxy.

In a further aspect, $Ar^1$ is phenyl substituted with 2 groups selected from fluoro, chloro, cyano, hydroxyl, —$NHCH_3$, —$N(CH_3)_2$, methyl, trifluoromethyl, ethyl, propyl, and butyl, methoxy, trifluoromethoxy, ethoxy, propyloxy, or butyloxy. In a still further aspect, $Ar^1$ is phenyl substituted with 2 groups selected from fluoro, chloro, cyano, hydroxyl, —$NHCH_3$, —$N(CH_3)_2$, methyl, and methoxy.

In a further aspect, $Ar^1$ is phenyl monosubstituted with a group selected from fluoro, chloro, cyano, hydroxyl, —$NHCH_3$, —$N(CH_3)_2$, methyl, trifluoromethyl, ethyl, propyl, and butyl, methoxy, trifluoromethoxy, ethoxy, propyloxy, or butyloxy. In a still further aspect, $Ar^1$ is phenyl monosubstituted with a group selected from fluoro, chloro, cyano, hydroxyl, —$NHCH_3$, —$N(CH_3)_2$, methyl, and methoxy.

In one aspect, $Ar^1$ is pyridinyl, pyridazinyl, pyrimidinyl, or pyrazinyl. In a further aspect, $Ar^1$ is pyridinyl, pyridazinyl, pyrimidinyl, or pyrazinyl and has 1-3 substituents selected from halogen, cyano, C1-C4 alkyl, C1-C4 alkyloxy, monohalo C1-C4 alkyl, and polyhalo C1-C4 alkyl. In a yet further aspect, $Ar^1$ is pyridinyl, pyridazinyl, pyrimidinyl, or pyrazinyl and has 1-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl. In a still further aspect, $Ar^1$ is pyridinyl, pyridazinyl, pyrimidinyl, or pyrazinyl and has 1-2 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl. In an even further aspect, $Ar^1$ is pyridinyl, pyridazinyl, pyrimidinyl, or pyrazinyl and has 2 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl. In a yet further aspect, $Ar^1$ is pyridinyl, pyridazinyl, pyrimidinyl, or pyrazinyl and is monosubstituted with a group selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl.

In a further aspect, $Ar^1$ is pyridinyl, pyridazinyl, pyrimidinyl, or pyrazinyl and has 1-3 substituents selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In a still further aspect, $Ar^1$ is pyridinyl, pyridazinyl, pyrimidinyl, or pyrazinyl and has 1-3 substituents selected from fluoro, chloro, cyano, hydroxyl, —NHCH$_3$, —N(CH$_3$)$_2$, methyl, and methoxy.

In a further aspect, $Ar^1$ is pyridinyl, pyridazinyl, pyrimidinyl, or pyrazinyl and has 1-2 substituents selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In a still further aspect, $Ar^1$ is pyridinyl, pyridazinyl, pyrimidinyl, or pyrazinyl and has 1-2 substituents selected from fluoro, chloro, cyano, hydroxyl, —NHCH$_3$, —N(CH$_3$)$_2$, methyl, and methoxy.

In a further aspect, $Ar^1$ is pyridinyl, pyridazinyl, pyrimidinyl, or pyrazinyl and has 2 substituents selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In a still further aspect, $Ar^1$ is pyridinyl, pyridazinyl, pyrimidinyl, or pyrazinyl and has 2 substituents selected from fluoro, chloro, cyano, hydroxyl, —NHCH$_3$, —N(CH$_3$)$_2$, methyl, and methoxy.

In a further aspect, $Ar^1$ is pyridinyl, pyridazinyl, pyrimidinyl, or pyrazinyl and is monosubstituted with a group selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In a still further aspect, $Ar^1$ is pyridinyl, pyridazinyl, pyrimidinyl, or pyrazinyl and is monosubstituted with a group selected from fluoro, chloro, cyano, hydroxyl, —NHCH$_3$, —N(CH$_3$)$_2$, methyl, and methoxy.

In a further aspect, $Ar^1$ is pyridinyl and has 1-2 substituents selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In a still further aspect, $Ar^1$ is pyridinyl and has 1-2 substituents selected from fluoro, chloro, cyano, hydroxyl, —NHCH$_3$, —N(CH$_3$)$_2$, methyl, and methoxy. In a yet further aspect, $Ar^1$ is pyridinyl and is monosubstituted with a group selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In an even further aspect, $Ar^1$ is pyridinyl and is monosubstituted with a group selected from fluoro, chloro, cyano, hydroxyl, —NHCH$_3$, —N(CH$_3$)$_2$, methyl, and methoxy. In a still further aspect, $Ar^1$ is pyridinyl optionally substituted with fluoro. In various aspects, pyridinyl is pyridin-2-yl, pyridin-3-yl, or pyridin-4-yl. In a yet further aspect, pyridinyl is pyridin-2-yl. In a still further aspect, pyridinyl is pyridin-3-yl. In an even further aspect, pyridinyl is pyridin-4-yl.

In a further aspect, $Ar^1$ is pyridazinyl and has 1-2 substituents selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In a still further aspect, $Ar^1$ is pyridazinyl and has 1-2 substituents selected from fluoro, chloro, cyano, hydroxyl, —NHCH$_3$, —N(CH$_3$)$_2$, methyl, and methoxy. In a yet further aspect, $Ar^1$ is pyridazinyl and is monosubstituted with a group selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In an even further aspect, $Ar^1$ is pyridazinyl and is monosubstituted with a group selected from fluoro, chloro, cyano, hydroxyl, —NHCH$_3$, —N(CH$_3$)$_2$, methyl, and methoxy. In a still further aspect, $Ar^1$ is pyridazinyl optionally substituted with fluoro. In various aspects, pyridazinyl is pyridazin-3-yl or pyridazin-4-yl.

In a further aspect, $Ar^1$ is pyrimidinyl and has 1-2 substituents selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In a still further aspect, $Ar^1$ is pyrimidinyl and has 1-2 substituents selected from fluoro, chloro, cyano, hydroxyl, —NHCH$_3$, —N(CH$_3$)$_2$, methyl, and methoxy. In a yet further aspect, $Ar^1$ is pyrimidinyl and is monosubstituted with a group selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In an even further aspect, $Ar^1$ is pyrimidinyl and is monosubstituted with a group selected from fluoro, chloro, cyano, hydroxyl, —NHCH$_3$, —N(CH$_3$)$_2$, methyl, and methoxy. In a still further aspect, $Ar^1$ is pyrimidinyl optionally substituted with fluoro. In various aspects, pyrimidinyl is pyrimidin-2-yl, pyrimidin-4-yl or pyrimidin-5-yl. In a yet further aspect, In various aspects, pyrimidinyl is pyrimidin-4-yl.

In a further aspect, $Ar^1$ is pyrazinyl and has 1-2 substituents selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In a still further aspect, $Ar^1$ is pyrazinyl and has 1-2 substituents selected from fluoro, chloro, cyano, hydroxyl, —NHCH$_3$, —N(CH$_3$)$_2$, methyl, and methoxy. In a yet further aspect, $Ar^1$ is pyrazinyl and is monosubstituted with a group selected from fluoro, chloro, cyano, hydroxyl, —NHCH$_3$, —N(CH$_3$)$_2$, methyl, trifluoromethyl, ethyl, propyl, butyl, methoxy, trifluoromethoxy, ethoxy, propyloxy, and butyloxy. In an even further aspect, $Ar^1$ is pyrazinyl and is monosubstituted with a group selected from fluoro, chloro, cyano, hydroxyl, —NHCH$_3$, —N(CH$_3$)$_2$, methyl, and methoxy. In a still further aspect, $Ar^1$ is pyrazinyl optionally substituted with fluoro.

c. Y Groups

In one aspect, Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl.

In one aspect, Y is N. In a further aspect, Y is N and $R^{1a}$ and $R^{1b}$ are each hydrogen. In a still further aspect, Y is N and $R^{1a}$, $R^{1b}$, and $R^3$ are each hydrogen. In a yet further aspect, wherein Y is N and $R^{1a}$, $R^{1b}$, $R^{4a}$, $R^{4b}$, $R^{5a}$ and $R^{5b}$ are each hydrogen. In an even further aspect, Y is N and $R^{1a}$, $R^{1b}$, $R^3$, $R^{4a}$, $R^{4b}$, $R^{5a}$ and $R^{5b}$ are each hydrogen.

In a further aspect, Y is C—$R^3$. In a further aspect, Y is C—$R^3$ and $R^{1a}$ and $R^{1b}$ are each hydrogen. In a still further aspect, Y is C—$R^3$ and $R^{1a}$, $R^{1b}$, and $R^3$ are each hydrogen. In a yet further aspect, wherein Y is C—$R^3$ and $R^{1a}$, $R^{1b}$, $R^{4a}$, $R^{4b}$, $R^{5a}$ and $R^{5b}$ are each hydrogen. In an even further aspect, Y is C—$R^3$ and $R^{1a}$, $R^{1b}$, $R^3$, $R^{4a}$, $R^{4b}$, $R^{5a}$ and $R^{5b}$ are each hydrogen.

In a further aspect, Y is CH. In a further aspect, Y is CH and $R^{1a}$ and $R^{1b}$ are each hydrogen. In a still further aspect, Y is CH and $R^{1a}$, $R^{1b}$, and $R^3$ are each hydrogen. In a yet further aspect, wherein Y is CH and $R^{1a}$, $R^{1b}$, $R^{4a}$, $R^{4b}$, $R^{5a}$ and $R^{5b}$ are each hydrogen. In an even further aspect, Y is CH and $R^{1a}$, $R^{1b}$, $R^3$, $R^{4a}$, $R^{4b}$, $R^{5a}$ and $R^{5b}$ are each hydrogen.

In a further aspect, Y is C—CH$_3$. In a further aspect, Y is C—CH$_3$ and R$^{1a}$ and R$^{1b}$ are each hydrogen. In a still further aspect, Y is C—CH$_3$ and R$^{1a}$, R$^{1b}$, and R$^3$ are each hydrogen. In a yet further aspect, wherein Y is C—CH$_3$ and R$^{1a}$, R$^{1b}$, R$^{4a}$, R$^{4b}$, R$^{5a}$, and R$^{5b}$ are each hydrogen. In an even further aspect, Y is C—CH$_3$ and R$^{1a}$, R$^{1b}$, R$^3$, R$^{4a}$, R$^{4b}$, R$^{5a}$ and R$^{5b}$ are each hydrogen.

In a further aspect, Y is C—Cl. In a further aspect, Y is C—Cl and R$^{1a}$ and R$^{1b}$ are each hydrogen. In a still further aspect, Y is C—Cl and R$^{1a}$, R$^{1b}$, and R$^3$ are each hydrogen. In a yet further aspect, wherein Y is C—Cl and R$^{1a}$, R$^{1b}$, R$^{4a}$, R$^{4b}$, R$^{5a}$ and R$^{5b}$ are each hydrogen. In an even further aspect, Y is C—Cl and R$^{1a}$, R$^{1b}$, R$^3$, R$^{4a}$, R$^{4b}$, R$^{5a}$ and R$^{5b}$ are each hydrogen.

d. R$^{1a}$ Groups

In one aspect, each of R$^{1a}$ and R$^{1b}$ is independently selected from hydrogen and C1-C4 alkyl. In various aspects, R$^{1a}$ is selected from hydrogen, C1-C4 alkyl, monohalo C1-C4 alkyl, and polyhalo C1-C4 alkyl. In a further aspect, R$^{1a}$ is selected from hydrogen and C1-C4 alkyl. In a still further aspect, R$^{1a}$ is selected from hydrogen, methyl and ethyl. In a still further aspect, R$^{1a}$ is selected from hydrogen and methyl.

In a further aspect, R$^{1a}$ is hydrogen. In a further aspect, R$^{1a}$, R$^{1b}$, and R$^2$ are each hydrogen. In a still further aspect, R$^{1a}$, R$^{1b}$, R$^2$, and R$^3$, when present, are each hydrogen. In a yet further aspect, R$^{1a}$, R$^{1b}$, and R$^3$, when present, are each hydrogen. In an even further aspect, R$^{1a}$, R$^{1b}$, R$^2$, R$^3$, when present, R$^{4a}$, R$^{4b}$, R$^{5a}$, and R$^{5b}$ are each hydrogen. In a still further aspect, R$^{1a}$, R$^{1b}$, R$^3$, when present, R$^{4a}$, R$^{4b}$, R$^{5a}$, and R$^{5b}$ are each hydrogen. In a yet further aspect, R$^{1a}$, R$^{1b}$, R$^{4a}$, R$^{4b}$, R$^{5a}$, and R$^{5b}$ are each hydrogen. In an even further aspect, each of R$^{1a}$, R$^{1b}$, R$^{4a}$, R$^{4b}$, R$^{5a}$, and R$^{5b}$ is hydrogen.

e. R$^{1b}$ Groups

In one aspect, R$^{1b}$ is selected from hydrogen, C1-C4 alkyl, monohalo C1-C4 alkyl, and polyhalo C1-C4 alkyl. In a further aspect, R$^{1b}$ is selected from hydrogen and C1-C4 alkyl. In a yet further aspect, R$^{1b}$ is selected from hydrogen, methyl, and ethyl. In an even further aspect, R$^{1b}$ is selected from hydrogen and methyl. In a still further aspect, R$^{1b}$ is hydrogen.

f. R$^2$ Groups

In one aspect, R$^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl. In a further aspect, R$^2$ is hydrogen.

In one aspect, R$^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl.

In one aspect, R$^2$ is selected from phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl. In a further aspect, R$^2$ is selected from C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; and C2-C5 heterocyclyl. In a still further aspect, R$^2$ is selected from hydrogen and C1-C6 alkyl.

In one aspect, R$^2$ is phenyl. In a further aspect, R$^2$ is phenyl with 1-3 substituents selected from halogen, cyano, C1-C4 alkyl, C1-C4 alkyloxy, monohalo C1-C4 alkyl, and polyhalo C1-C4 alkyl.

In one aspect, R$^2$ is pyridinyl, pyridazinyl, pyrimidinyl, or pyrazinyl. In a further aspect, R$^2$ is pyridinyl, pyridazinyl, pyrimidinyl, or pyrazinyl; and R$^2$ has 1-3 substituents selected from halogen, cyano, C1-C4 alkyl, C1-C4 alkyloxy, monohalo C1-C4 alkyl, and polyhalo C1-C4 alkyl.

In a one aspect, R$^2$ is selected from methyl, trifluoromethyl, ethyl, propyl, butyl, pentyl, and hexyl.

In various aspects, R$^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In an even further aspect, R$^2$ is phenyl substituted with 1-2 substituents selected from fluoro, methyl, and methoxy, or R$^2$ is pyridinyl substituted with 1-2 substituents selected from fluoro, methyl, and methoxy.

In a further aspect, R$^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, and (C2-C5 heterocyclyl) C1-C6 alkyl. In a still further aspect, R$^2$ is selected from a group having a structure represented by a formula: —H, —CH$_3$, —CH$_2$CH$_3$, —(CH$_2$)$_2$CH$_3$, —C(CH$_3$)$_3$, —CH(CH$_3$)C(CH$_3$)$_3$, —CF$_3$, —CH$_2$CF$_3$, —(CH$_2$)$_2$CF$_3$, —CH(CF$_3$)$_2$, —CH$_2$CH(CH$_3$)(CF$_3$), —(CH$_2$)$_2$OH, —(CH$_2$)$_3$OH, —CH$_2$CH(CH$_3$)OH, —CH(CH$_3$)CH$_2$OH, —CH(CH$_3$)CH$_2$CH$_2$OH, —OCH$_3$, —OCH$_2$CH$_3$, —O(CH$_2$)$_2$CH$_3$, —OCH(CH$_3$)C(CH$_3$)$_3$, —CH$_2$OCH$_3$, —(CH$_2$)$_2$OCH$_3$, —(CH$_2$)$_2$OCH$_3$, —CH(CH$_3$)OCH$_3$,

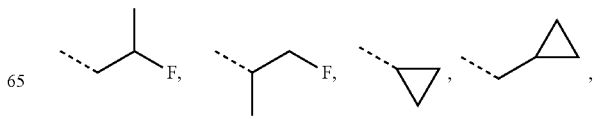

In a further aspect, R² is aryl with 0-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a still further aspect, R² is phenyl with 0-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a yet further aspect, R² is naphthalenyl with 0-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In an even further aspect, R² is naphthalen-1-yl with 0-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a yet further aspect, R² is naphthalen-2-yl with 0-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl.

In a further aspect, R² is aryl with 1-2 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a still further aspect, R² is aryl with 1-2 substituents selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —OCH(CH₂CH₃)₂(CH₃), —OCH₂OCH₃, —O(CH₂)₂OCH₃, —O(CH₂)₃OCH₃, —OCH₂OCH₂CH₃, —O—(CH₂)₂OCH₂CH₃, —CH₂OCH₃, —(CH₂)₂OCH₃, —(CH₂)₃OCH₃, —CH₂OCH₂CH₃, —(CH₂)₂OCH₂CH₃, —CH₂—O—(CH₂)₂CH₃, —CH₂OCH(CH₃)₂, —CH₂OCH(CH₂CH₃)₂(CH₃), —OCH₂F, —OCH₂CH₂F, —O—(CH₂)₂CH₂F, —OCH(CH₃)(CH₂F), —OCH(CH₂CH₃)₂(CH₂F), —OCH₂Cl, —OCH₂CH₂Cl, —O—(CH₂)₂CH₂Cl, —OCH(CH₃)(CH₂Cl), —OCH(CH₂CH₃)₂(CH₂Cl), —NHCH₃, —NHCH₂CH₃, —NH(CH₂)₂CH₃, —N(CH₃)₂, —N(CH₃)CH₂CH₃, —N(CH₃)(CH₂)₂CH₃, tetrahydro-2H-pyranyl, piperidinyl, tetrahydrofuranyl, and pyrrolidinyl. In a yet further aspect, R² is aryl with 1-2 substituents selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH₂F, —CH₂Cl, —CH₂CH₂F, —CH₂CH₂Cl, —CF₃, —OCH₃, —OCH₂CH₃, —O(CH₂)₂OCH₃, —CH₂OCH₃, —(CH₂)₂OCH₃, —OCH₂CH₂F, —O(CH₂)₂CH₂F, —NHCH₃, —N(CH₃)₂, tetrahydro-2H-pyranyl, piperidinyl, tetrahydrofuranyl, and pyrrolidinyl. In an even further aspect, R² is aryl monosubstituted with a group selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH₂F, —CH₂Cl, —CH₂CH₂F, —CH₂CH₂Cl, —CF₃, —OCH₃, —OCH₂CH₃, —O(CH₂)₂OCH₃, —CH₂OCH₃, —(CH₂)₂OCH₃, —OCH₂CH₂F, —O(CH₂)₂CH₂F, —NHCH₃, —N(CH₃)₂, tetrahydro-2H-pyranyl, piperidinyl, tetrahydrofuranyl, and pyrrolidinyl. In a still further aspect, R² is an unsubstituted aryl.

In a further aspect, R² is phenyl with 1-2 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a still further aspect, R² is phenyl with 1-2 substituents selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —OCH(CH₂CH₃)₂(CH₃), —OCH₂OCH₃, —O(CH₂)₂OCH₃, —O(CH₂)₃OCH₃, —OCH₂OCH₂CH₃, —O(CH₂)₂OCH₂CH₃, —CH₂OCH₃, —(CH₂)₂OCH₃, —(CH₂)₃OCH₃, —CH₂OCH₂CH₃, —(CH₂)₂OCH₂CH₃, —CH₂—O—(CH₂)₂CH₃, —CH₂OCH(CH₃)₂, —CH₂OCH(CH₂CH₃)₂(CH₃), —OCH₂F, —OCH₂CH₂F, —O(CH₂)₂CH₂F, —OCH(CH₃)(CH₂F), —OCH(CH₂CH₃)₂(CH₂F), —OCH₂Cl, —OCH₂CH₂Cl, —O(CH₂)₂CH₂Cl, —OCH(CH₃)(CH₂Cl), —OCH(CH₂CH₃)₂(CH₂Cl), —NHCH₃, —NHCH₂CH₃, —NH(CH₂)₂CH₃, —N(CH₃)₂, —N(CH₃)CH₂CH₃, —N(CH₃)(CH₂)₂CH₃, tetrahydro-2H-pyranyl, piperidinyl, tetrahydrofuranyl, and pyrrolidinyl. In a yet further aspect, R² is phenyl with 1-2 substituents selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O(CH$_2$)$_2$OCH$_3$, —CH$_2$OCH$_3$, —(CH$_2$)$_2$OCH$_3$, —OCH$_2$CH$_2$F, —O(CH$_2$)$_2$CH$_2$F, —NHCH$_3$, —N(CH$_3$)$_2$, tetrahydro-2H-pyranyl, piperidinyl, tetrahydrofuranyl, and pyrrolidinyl. In an even further aspect, R$^2$ is phenyl monosubstituted with a group selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O(CH$_2$)$_2$OCH$_3$, —CH$_2$OCH$_3$, —(CH$_2$)$_2$OCH$_3$, —OCH$_2$CH$_2$F, —O(CH$_2$)$_2$CH$_2$F, —NHCH$_3$, —N(CH$_3$)$_2$, tetrahydro-2H-pyranyl, piperidinyl, tetrahydrofuranyl, and pyrrolidinyl. In a still further aspect, R$^2$ is an unsubstituted phenyl. In an even further aspect, R$^2$ is phenyl substituted with 1-2 substituents selected from fluoro, methyl, and methoxy.

In a further aspect, R$^2$ is naphthalenyl with 1-2 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a still further aspect, R$^2$ is naphthalenyl with 1-2 substituents selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —OCH$_2$OCH$_3$, —O(CH$_2$)$_2$OCH$_3$, —O(CH$_2$)$_3$OCH$_3$, —OCH$_2$OCH$_2$CH$_3$, —O(CH$_2$)$_2$OCH$_2$CH$_3$, —CH$_2$OCH$_3$, —(CH$_2$)$_2$OCH$_3$, —(CH$_2$)$_3$OCH$_3$, —CH$_2$OCH$_2$CH$_3$, —(CH$_2$)$_2$OCH$_2$CH$_3$, —CH$_2$—O—(CH$_2$)$_2$CH$_3$, —CH$_2$OCH(CH$_3$)$_2$, —CH$_2$OCH(CH$_2$CH$_3$)(CH$_3$), —OCH$_2$F, —OCH$_2$CH$_2$F, —O(CH$_2$)$_2$CH$_2$F, —OCH(CH$_3$)(CH$_2$F), —OCH(CH$_2$CH$_3$)$_2$(CH$_2$F), —OCH$_2$Cl, —OCH$_2$CH$_2$Cl, —O(CH$_2$)$_2$CH$_2$Cl, —OCH(CH$_3$)(CH$_2$Cl), —OCH(CH$_2$CH$_3$)$_2$(CH$_2$Cl), —NHCH$_3$, —NHCH$_2$CH$_3$, —NH(CH$_2$)$_2$CH$_3$, —N(CH$_3$)$_2$, —N(CH$_3$)CH$_2$CH$_3$, —N(CH$_3$)(CH$_2$)$_2$CH$_3$, tetrahydro-2H-pyranyl, piperidinyl, tetrahydrofuranyl, and pyrrolidinyl. In a yet further aspect, R$^2$ is naphthalenyl with 1-2 substituents selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O(CH$_2$)$_2$OCH$_3$, —CH$_2$OCH$_3$, —(CH$_2$)$_2$OCH$_3$, —OCH$_2$CH$_2$F, —O—(CH$_2$)$_2$CH$_2$F, —NHCH$_3$, —N(CH$_3$)$_2$, tetrahydro-2H-pyranyl, piperidinyl, tetrahydrofuranyl, and pyrrolidinyl. In an even further aspect, R$^2$ is naphthalenyl monosubstituted with a group selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O—(CH$_2$)$_2$OCH$_3$, —CH$_2$OCH$_3$, —(CH$_2$)$_2$OCH$_3$, —OCH$_2$CH$_2$F, —O(CH$_2$)$_2$CH$_2$F, —NHCH$_3$, —N(CH$_3$)$_2$, tetrahydro-2H-pyranyl, piperidinyl, tetrahydrofuranyl, and pyrrolidinyl. In a still further aspect, R$^2$ is an unsubstituted naphthalenyl.

In a further aspect, R$^2$ is naphthalen-1-yl with 1-2 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a still further aspect, R$^2$ is naphthalene-1-yl with 1-2 substituents selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —OCH$_2$OCH$_3$, —O(CH$_2$)$_2$OCH$_3$, —O(CH$_2$)$_3$OCH$_3$, —OCH$_2$OCH$_2$CH$_3$, —O—(CH$_2$)$_2$OCH$_2$CH$_3$, —CH$_2$OCH$_3$, —(CH$_2$)$_2$OCH$_3$, —(CH$_2$)$_3$ OCH$_3$, —CH$_2$OCH$_2$CH$_3$, —(CH$_2$)$_2$OCH$_2$CH$_3$, —CH$_2$—O—(CH$_2$)$_2$ CH$_3$, —CH$_2$OCH(CH$_3$)$_2$, —CH$_2$OCH(CH$_2$CH$_3$)$_2$(CH$_3$), —OCH$_2$F, —OCH$_2$CH$_2$F, —O—(CH$_2$)$_2$CH$_2$F, —OCH(CH$_3$)(CH$_2$F), —OCH(CH$_2$CH$_3$)$_2$(CH$_2$F), —OCH$_2$Cl, —OCH$_2$CH$_2$Cl, —O(CH$_2$)$_2$CH$_2$Cl, —OCH(CH$_3$)(CH$_2$Cl), —OCH(CH$_2$CH$_3$)$_2$(CH$_2$Cl), —NHCH$_3$, —NHCH$_2$CH$_3$, —NH(CH$_2$)$_2$CH$_3$, —N(CH$_3$)$_2$, —N(CH$_3$)CH$_2$CH$_3$, —N(CH$_3$)(CH$_2$)$_2$CH$_3$, tetrahydro-2H-pyranyl, piperidinyl, tetrahydrofuranyl, and pyrrolidinyl. In a yet further aspect, R$^2$ is naphthalene-1-yl with 1-2 substituents selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O—(CH$_2$)$_2$OCH$_3$, —CH$_2$OCH$_3$, —(CH$_2$)$_2$OCH$_3$, —OCH$_2$CH$_2$F, —O(CH$_2$)$_2$CH$_2$F, —NHCH$_3$, —N(CH$_3$)$_2$, tetrahydro-2H-pyranyl, piperidinyl, tetrahydrofuranyl, and pyrrolidinyl. In an even further aspect, R$^2$ is naphthalene-1-yl monosubstituted with a group selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O—(CH$_2$)$_2$OCH$_3$, —CH$_2$OCH$_3$, —(CH$_2$)$_2$OCH$_3$, —OCH$_2$CH$_2$F, —O(CH$_2$)$_2$CH$_2$F, —NHCH$_3$, —N(CH$_3$)$_2$, tetrahydro-2H-pyranyl, piperidinyl, tetrahydrofuranyl, and pyrrolidinyl. In a still further aspect, R$^2$ is an unsubstituted naphthalene-1-yl.

In a further aspect, R$^2$ is naphthalen-2-yl with 1-2 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a still further aspect, R$^2$ is naphthalene-2-yl with 1-2 substituents selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —OCH(CH₂CH₃)₂(CH₃), —OCH₂OCH₃, —O(CH₂)₂OCH₃, —O(CH₂)₃OCH₃, —OCH₂OCH₂CH₃, —O—(CH₂)₂OCH₂CH₃, —CH₂OCH₃, —(CH₂)₂OCH₃, —(CH₂)₃OCH₃, —CH₂OCH₂CH₃, —(CH₂)₂OCH₂CH₃, —CH₂—O—(CH₂)₂CH₃, —CH₂OCH(CH₃)₂, —CH₂OCH(CH₂CH₃)₂(CH₃), —OCH₂F, —OCH₂CH₂F, —O—(CH₂)₂CH₂F, —OCH(CH₃)(CH₂F), —OCH(CH₂CH₃)₂(CH₂F), —OCH₂Cl, —OCH₂CH₂Cl, —O(CH₂)₂CH₂Cl, —OCH(CH₃)(CH₂Cl), —OCH(CH₂CH₃)₂(CH₂Cl), —NHCH₃, —NHCH₂CH₃, —NH(CH₂)₂CH₃, —N(CH₃)₂, —N(CH₃)CH₂CH₃, —N(CH₃)(CH₂)₂CH₃, tetrahydro-2H-pyranyl, piperidinyl, tetrahydrofuranyl, and pyrrolidinyl. In a yet further aspect, R² is naphthalene-2-yl with 1-2 substituents selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH₂F, —CH₂Cl, —CH₂CH₂F, —CH₂CH₂Cl, —CF₃, —OCH₃, —OCH₂CH₃, —O—(CH₂)₂OCH₃, —CH₂OCH₃, —(CH₂)₂OCH₃, —OCH₂CH₂F, —O(CH₂)₂CH₂F, —NHCH₃, —N(CH₃)₂, tetrahydro-2H-pyranyl, piperidinyl, tetrahydrofuranyl, and pyrrolidinyl. In an even further aspect, R² is naphthalene-2-yl monosubstituted with a group selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH₂F, —CH₂Cl, —CH₂CH₂F, —CH₂CH₂Cl, —CF₃, —OCH₃, —OCH₂CH₃, —O—(CH₂)₂OCH₃, —CH₂OCH₃, —(CH₂)₂OCH₃, —OCH₂CH₂F, —O(CH₂)₂CH₂F, —NHCH₃, —N(CH₃)₂, tetrahydro-2H-pyranyl, piperidinyl, tetrahydrofuranyl, and pyrrolidinyl. In a still further aspect, R² is an unsubstituted naphthalene-2-yl.

In a further aspect, R² is heteroaryl with 0-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a still further aspect, R² is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is substituted with 0-3 groups selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a yet further aspect, R² is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is substituted with 0-3 groups selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —OCH(CH₂CH₃)₂(CH₃), —OCH₂OCH₃, —O—(CH₂)₂OCH₃, —O(CH₂)₃OCH₃, —OCH₂OCH₂CH₃, —O—(CH₂)₂OCH₂CH₃, —CH₂OCH₃, —(CH₂)₂OCH₃, —(CH₂)₃OCH₃, —CH₂OCH₂CH₃, —(CH₂)₂OCH₂CH₃, —CH₂—O—(CH₂)₂CH₃, —CH₂OCH(CH₃)₂, —CH₂OCH(CH₂CH₃)₂(CH₃), —OCH₂F, —OCH₂CH₂F, —O—(CH₂)₂CH₂F, —OCH(CH₃)(CH₂F), —OCH(CH₂CH₃)₂(CH₂F), —OCH₂Cl, —OCH₂CH₂Cl, —O—(CH₂)₂CH₂Cl, —OCH(CH₃)(CH₂Cl), —OCH(CH₂CH₃)₂(CH₂Cl), —NHCH₃, —NHCH₂CH₃, —NH(CH₂)₂CH₃, —N(CH₃)₂, —N(CH₃)CH₂CH₃, and —N(CH₃)(CH₂)₂CH₃. In an even further aspect, R² is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is substituted with 0-3 groups selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH₂F, —CH₂Cl, —CH₂CH₂F, —CH₂CH₂Cl, —CF₃, —OCH₃, —OCH₂CH₃, —O(CH₂)₂OCH₃, —CH₂OCH₃, —(CH₂)₂OCH₃, —OCH₂CH₂F, —O(CH₂)₂CH₂F, —NHCH₃, and —N(CH₃)₂.

In a further aspect, R² is heteroaryl with 1-3 substituents selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a still further aspect, R² is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is substituted with 1-3 groups selected from halogen, cyano, hydroxyl, —NH₂, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a yet further aspect, R² is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is substituted with 1-3 groups selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH₂F, —CH₂Cl, —CH₂CH₂F, —CH₂CH₂Cl, —(CH₂)₂CH₂F, —(CH₂)₂CH₂Cl, —CHF₂, —CF₃, —CHCl₂, —CCl₃, —CH₂CHF₂, —CH₂CF₃, —CH₂CHCl₂, —CH₂CCl₃, —(CH₂)₂CHF₂, —(CH₂)₂CF₃, —(CH₂)₂CHCl₂, —(CH₂)₂CCl₃, —OCH₃, —OCH₂CH₃, —O(CH₂)₂CH₃, —OCH(CH₃)₂, —OCH(CH₂CH₃)₂(CH₃), —OCH₂OCH₃, —O—(CH₂)₂OCH₃, —O(CH₂)₃OCH₃, —OCH$_2$OCH$_2$CH$_3$, —O—(CH$_2$)$_2$OCH$_2$CH$_3$, —CH$_2$OCH$_3$, —(CH$_2$)$_2$OCH$_3$, —(CH$_2$)$_3$OCH$_3$, —CH$_2$OCH$_2$CH$_3$, —(CH$_2$)$_2$OCH$_2$CH$_3$, —CH$_2$—O—(CH$_2$)$_2$CH$_3$, —CH$_2$OCH(CH$_3$)$_2$, —CH$_2$OCH(CH$_2$CH$_3$)$_2$(CH$_3$), —OCH$_2$F, —OCH$_2$CH$_2$F, —O—(CH$_2$)$_2$CH$_2$F, —OCH(CH$_3$)(CH$_2$F), —OCH(CH$_2$CH$_3$)$_2$(CH$_2$F), —OCH$_2$Cl, —OCH$_2$CH$_2$Cl, —O—(CH$_2$)$_2$CH$_2$Cl, —OCH(CH$_3$)(CH$_2$Cl), —OCH(CH$_2$CH$_3$)$_2$(CH$_2$Cl), —NHCH$_3$, —NHCH$_2$CH$_3$, —NH(CH$_2$)$_2$CH$_3$, —N(CH$_3$)$_2$, —N(CH$_3$)CH$_2$CH$_3$, and —N(CH$_3$)(CH$_2$)$_2$CH$_3$. In an even further aspect, R$^2$ is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is substituted with 1-3 groups selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O—(CH$_2$)$_2$OCH$_3$, —CH$_2$OCH$_3$, —(CH$_2$)$_2$OCH$_3$, —OCH$_2$CH$_2$F, —O(CH$_2$)$_2$CH$_2$F, —NHCH$_3$, and —N(CH$_3$)$_2$.

In a further aspect, R$^2$ is heteroaryl with 1-2 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a still further aspect, R$^2$ is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is substituted with 1-2 groups selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a yet further aspect, R$^2$ is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is substituted with 1-2 groups selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —OCH$_2$OCH$_3$, —O—(CH$_2$)$_2$OCH$_3$, —O(CH$_2$)$_3$OCH$_3$, —OCH$_2$OCH$_2$CH$_3$, —O—(CH$_2$)$_2$OCH$_2$CH$_3$, —CH$_2$OCH$_3$, —(CH$_2$)$_2$OCH$_3$, —(CH$_2$)$_3$OCH$_3$, —CH$_2$OCH$_2$CH$_3$, —(CH$_2$)$_2$OCH$_2$CH$_3$, —CH$_2$—O—(CH$_2$)$_2$CH$_3$, —CH$_2$OCH(CH$_3$)$_2$, —CH$_2$OCH(CH$_2$CH$_3$)$_2$(CH$_3$), —OCH$_2$F, —OCH$_2$CH$_2$F, —O—(CH$_2$)$_2$CH$_2$F, —OCH(CH$_3$)(CH$_2$F), —OCH(CH$_2$CH$_3$)$_2$(CH$_2$F), —OCH$_2$Cl, —OCH$_2$CH$_2$Cl, —O—(CH$_2$)$_2$CH$_2$Cl, —OCH(CH$_3$)(CH$_2$Cl), —OCH(CH$_2$CH$_3$)$_2$(CH$_2$Cl), —NHCH$_3$, —NHCH$_2$CH$_3$, —NH(CH$_2$)$_2$CH$_3$, —N(CH$_3$)$_2$, —N(CH$_3$)CH$_2$CH$_3$, and —N(CH$_3$)(CH$_2$)$_2$CH$_3$. In an even further aspect, R$^2$ is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is substituted with 1-2 groups selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O—(CH$_2$)$_2$OCH$_3$, —CH$_2$OCH$_3$, —(CH$_2$)$_2$OCH$_3$, —OCH$_2$CH$_2$F, —O(CH$_2$)$_2$CH$_2$F, —NHCH$_3$, and —N(CH$_3$)$_2$.

In a further aspect, R$^2$ is a heteroaryl monosubstituted with a group selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a still further aspect, R$^2$ is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is monosubstituted with a group selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a yet further aspect, R$^2$ is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is monosubstituted with a group selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —OCH$_2$OCH$_3$, —O—(CH$_2$)$_2$OCH$_3$, —O(CH$_2$)$_3$OCH$_3$, —OCH$_2$OCH$_2$CH$_3$, —O—(CH$_2$)$_2$OCH$_2$CH$_3$, —CH$_2$OCH$_3$, —(CH$_2$)$_2$OCH$_3$, —(CH$_2$)$_3$OCH$_3$, —CH$_2$OCH$_2$CH$_3$, —(CH$_2$)$_2$OCH$_2$CH$_3$, —CH$_2$—O—(CH$_2$)$_2$CH$_3$, —CH$_2$OCH(CH$_3$)$_2$, —CH$_2$OCH(CH$_2$CH$_3$)$_2$(CH$_3$), —OCH$_2$F, —OCH$_2$CH$_2$F, —O—(CH$_2$)$_2$CH$_2$F, —OCH(CH$_3$)(CH$_2$F), —OCH(CH$_2$CH$_3$)$_2$(CH$_2$F), —OCH$_2$Cl, —OCH$_2$CH$_2$Cl, —O—(CH$_2$)$_2$CH$_2$Cl, —OCH(CH$_3$)(CH$_2$Cl), —OCH(CH$_2$CH$_3$)$_2$(CH$_2$Cl), —NHCH$_3$, —NHCH$_2$CH$_3$, —NH(CH$_2$)$_2$CH$_3$, —N(CH$_3$)$_2$, —N(CH$_3$)CH$_2$CH$_3$, and —N(CH$_3$)(CH$_2$)$_2$CH$_3$. In an even further aspect, R$^2$ is a heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl; and the heteroaryl is monosubstituted with a group selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O(CH$_2$)$_2$OCH$_3$, —CH$_2$OCH$_3$, —(CH$_2$)$_2$OCH$_3$, —OCH$_2$CH$_2$F, —O(CH$_2$)$_2$CH$_2$F, —NHCH$_3$, and —N(CH$_3$)$_2$.

In a further aspect, R$^2$ is pyridinyl substituted with 1-2 groups selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a yet further aspect, R$^2$ is pyridinyl substituted with 1-2 groups selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —OCH$_2$OCH$_3$, —O(CH$_2$)$_2$OCH$_3$, —O(CH$_2$)$_3$OCH$_3$, —OCH$_2$OCH$_2$CH$_3$, —O—(CH$_2$)$_2$OCH$_2$CH$_3$, —CH$_2$OCH$_3$, —(CH$_2$)$_2$OCH$_3$, —(CH$_2$)$_3$ OCH$_3$, —CH$_2$OCH$_2$CH$_3$, —(CH$_2$)$_2$OCH$_2$CH$_3$, —CH$_2$—O—(CH$_2$)$_2$ CH$_3$, —CH$_2$OCH(CH$_3$)$_2$, —CH$_2$OCH(CH$_2$CH$_3$)$_2$(CH$_3$), —OCH$_2$F, —OCH$_2$CH$_2$F, —O—(CH$_2$)$_2$CH$_2$F, —OCH(CH$_3$)(CH$_2$F), —OCH(CH$_2$CH$_3$)$_2$(CH$_2$F), —OCH$_2$Cl, —OCH$_2$CH$_2$Cl, —O(CH$_2$)$_2$CH$_2$Cl, —OCH(CH$_3$)(CH$_2$Cl), —OCH(CH$_2$CH$_3$)$_2$(CH$_2$Cl), —NHCH$_3$, —NHCH$_2$CH$_3$, —NH(CH$_2$)$_2$CH$_3$, —N(CH$_3$)$_2$, —N(CH$_3$)CH$_2$CH$_3$, and —N(CH$_3$)(CH$_2$)$_2$CH$_3$. In an even further aspect, R$^2$ is pyridinyl substituted with 1-2 groups selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O(CH$_2$)$_2$OCH$_3$, —CH$_2$OCH$_3$, —(CH$_2$)$_2$OCH$_3$, —OCH$_2$CH$_2$F, —O(CH$_2$)$_2$CH$_2$F, —NHCH$_3$, and —N(CH$_3$)$_2$. In a still further aspect, R$^2$ is pyridinyl substituted with 1-2 groups selected from fluoro, methyl, and methoxy. In a yet further aspect, R$^2$ is pyridinyl and is unsubstituted. In various aspects, pyridinyl is pyridin-2-yl, pyridin-3-yl, or pyridin-4-yl. In a yet further aspect, pyridinyl is pyridin-2-yl. In a still further aspect, pyridinyl is pyridin-3-yl. In an even further aspect, pyridinyl is pyridin-4-yl.

In a further aspect, R$^2$ is pyrimidinyl substituted with 1-2 groups selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a yet further aspect, R$^2$ is pyrimidinyl substituted with 1-2 groups selected from —F, —Cl, cyano, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, cyclopropyl, cyclobutyl, cyclohexyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —OCH$_2$OCH$_3$, —O(CH$_2$)$_2$OCH$_3$, —O(CH$_2$)$_3$OCH$_3$, —OCH$_2$OCH$_2$CH$_3$, —O—(CH$_2$)$_2$OCH$_2$CH$_3$, —CH$_2$OCH$_3$, —(CH$_2$)$_2$OCH$_3$, —(CH$_2$)$_3$ OCH$_3$, —CH$_2$OCH$_2$CH$_3$, —(CH$_2$)$_2$OCH$_2$CH$_3$, —CH$_2$—O—(CH$_2$)$_2$ CH$_3$, —CH$_2$OCH(CH$_3$)$_2$, —CH$_2$OCH(CH$_2$CH$_3$)$_2$(CH$_3$), —OCH$_2$F, —OCH$_2$CH$_2$F, —O—(CH$_2$)$_2$CH$_2$F, —OCH(CH$_3$)(CH$_2$F), —OCH(CH$_2$CH$_3$)$_2$(CH$_2$F), —OCH$_2$Cl, —OCH$_2$CH$_2$Cl, —O(CH$_2$)$_2$CH$_2$Cl, —OCH(CH$_3$)(CH$_2$Cl), —OCH(CH$_2$CH$_3$)$_2$(CH$_2$Cl), —NHCH$_3$, —NHCH$_2$CH$_3$, —NH(CH$_2$)$_2$CH$_3$, —N(CH$_3$)$_2$, —N(CH$_3$)CH$_2$CH$_3$, and —N(CH$_3$)(CH$_2$)$_2$CH$_3$. In an even further aspect, R$^2$ is pyrimidinyl substituted with 1-2 groups selected from —F, —Cl, cyano, methyl, ethyl, propyl, isopropyl, tert-butyl, sec-butyl, isobutyl, tert-butyl, neopentyl, isopentyl, sec-pentyl, tert-pentylcyclopropyl, —CH$_2$F, —CH$_2$Cl, —CH$_2$CH$_2$F, —CH$_2$CH$_2$Cl, —CF$_3$, —OCH$_3$, —OCH$_2$CH$_3$, —O(CH$_2$)$_2$ OCH$_3$, —CH$_2$OCH$_3$, —(CH$_2$)$_2$OCH$_3$, —OCH$_2$CH$_2$F, —O(CH$_2$)$_2$CH$_2$F, —NHCH$_3$, and —N(CH$_3$)$_2$. In a still further aspect, R$^2$ is pyrimidinyl substituted with 1-2 groups selected from fluoro, methyl, and methoxy. In a yet further aspect, R$^2$ is pyrimidinyl and is unsubstituted. In various aspects, pyrimidinyl is pyrimidin-2-yl, pyrimidin-4-yl or pyrimidin-5-yl. In a yet further aspect, In various aspects, pyrimidinyl is pyrimidin-2-yl. In a still further aspect, In various aspects, pyrimidinyl is pyrimidin-4-yl. In an even further aspect, In various aspects, pyrimidinyl is pyrimidin-5-yl.

In a further aspect, R$^2$ is an unsubstituted heteroaryl. In a still further aspect, R$^2$ is a unsubstituted heteroaryl selected from pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

g. R$^3$ Groups

In one aspect, R$^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl.

In one aspect, R$^3$, when present, is hydrogen. In a further aspect, R$^3$, when present, is selected from halogen, cyano, and C1-C4 alkyl. In a still further aspect, R$^3$, when present, is selected from hydrogen and C1-C4 alkyl. In a yet further aspect, rein R$^3$, when present, is selected from hydrogen, halogen, cyano, and C1-C4 alkyl.

In a further aspect, R$^3$, when present, is selected from hydrogen, halogen, and C1-C4 alkyl. In a still further aspect, R$^3$, when present, is selected from hydrogen, fluoro chloro, methyl, ethyl and propyl. In a yet further aspect, R$^3$, when present, is selected from hydrogen, chloro, and methyl. In an even further aspect, R$^3$, when present, is hydrogen. In a still further aspect, R$^3$, when present, is methyl. In a yet further aspect, R$^3$, when present, is chloro.

h. R$^{4a}$ Groups

In one aspect, R$^{4a}$ is selected from hydrogen and C1-C4 alkyl. In a further aspect, R$^{4a}$ is hydrogen. In a yet further aspect, R$^{4a}$ is C1-C4 alkyl. In a still further aspect, R$^{4a}$ is methyl. In an even further aspect, $R^{4a}$ and $R^{5a}$ are each methyl. In a yet further aspect, $R^{4a}$ is selected from methyl, trifluoromethyl, ethyl, propyl, and butyl.

In one aspect, each of $R^{4a}$ and $R^{4b}$, when present, is independently selected from hydrogen and C1-C4 alkyl. In a further aspect, $R^{4a}$ and $R^{4b}$, when present, are both hydrogen.

In one aspect, $R^{4a}$ and $R^{5a}$ are not directly covalently bonded. In a further aspect, $R^{4a}$ and $R^{5a}$ are directly covalently bonded to comprise, together with the intermediate atoms, a 3-, 4-, 5-, 6-, or 7-membered fused cycloalkyl. In a yet further aspect, $R^{4a}$ and $R^{5a}$ are directly covalently bonded to comprise, together with the intermediate atoms, a substituted 3-, 4-, 5-, 6-, or 7-membered fused cycloalkyl. In a still further aspect, the fused cycloalkyl is substituted with 1 or 2 groups selected from methyl, ethyl, and propyl.

In various aspects, $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl. In a further aspect, $R^{4a}$ is selected from hydrogen, —F, —Cl, hydroxyl, —CH$_3$, —CF$_3$, —CH$_2$F, —CH$_2$OH, —OCH$_3$, —CH$_2$OCH$_3$, —CCl$_3$, —CH$_2$Cl, —OCH$_2$CH$_3$, —(CH$_2$)$_2$OCH$_3$, and —CH$_2$OCH$_2$CH$_3$. In a further aspect, $R^{4a}$ is selected from hydrogen, —F, hydroxyl, —CH$_3$, —CF$_3$, —CH$_2$F, —CH$_2$OH, —OCH$_3$, and —CH$_2$OCH$_3$.

In a further aspect, $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl, and $R^{4b}$, when present, is hydrogen. In a further aspect, $R^{4a}$ is selected from hydrogen, —F, —Cl, hydroxyl, —CH$_3$, —CF$_3$, —CH$_2$F, —CH$_2$OH, —OCH$_3$, —CH$_2$OCH$_3$, —CCl$_3$, —CH$_2$Cl, —OCH$_2$CH$_3$, —(CH$_2$)$_2$OCH$_3$, and —CH$_2$OCH$_2$CH$_3$, and $R^{4b}$, when present, is hydrogen. In a further aspect, $R^{4a}$ is selected from hydrogen, —F, hydroxyl, —CH$_3$, —CF$_3$, —CH$_2$F, —CH$_2$OH, —OCH$_3$, and —CH$_2$OCH$_3$, and $R^{4b}$, when present, is hydrogen.

In a further aspect, $R^{4a}$ and $R^{4b}$, when present, are each —CH$_3$. In a still further aspect, each of, $R^{4a}$ and $R^{4b}$ are each —CH$_2$OH. In a yet further aspect, $R^{4a}$ and $R^{4b}$, when present, are each —F. In an even further aspect, $R^{4a}$ and $R^{4b}$, when present, are each —OH. In a still further aspect, $R^{4a}$ and $R^{4b}$, when present, are each —OCH$_3$.

i. $R^{4b}$ Groups

In one aspect, $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl. In a further aspect, $R^{4b}$, when present, is hydrogen. In a yet further aspect, $R^{4b}$, when present, is C1-C4 alkyl. In a still further aspect, $R^{4b}$, when present, is selected from methyl, trifluoromethyl, ethyl, propyl, and butyl.

In one aspect, $R^{4b}$ is present, and $R^{4a}$ and $R^{4b}$ are covalently bonded and, together with the intermediate carbon, comprise a 3- to 7-membered spirocycloalkyl. In a further aspect, $R^{4b}$ is present, and $R^{4a}$ and $R^{4b}$ are covalently bonded and, together with the intermediate carbon, comprise a substituted 3- to 7-membered spirocycloalkyl. In a yet further aspect, the spirocycloalkyl is substituted with 1 or 2 groups selected from methyl, ethyl, and propyl.

In various aspects, $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl. In a further aspect, $R^{4b}$, when present, is selected from hydrogen, —F, —Cl, hydroxyl, —CH$_3$, —CF$_3$, —CH$_2$F, —CH$_2$OH, —OCH$_3$, —CH$_2$OCH$_3$, —CCl$_3$, —CH$_2$Cl, —OCH$_2$CH$_3$, —(CH$_2$)$_2$ OCH$_3$, and —CH$_2$OCH$_2$CH$_3$. In a further aspect, $R^{4b}$, when present, is selected from hydrogen, —F, hydroxyl, —CH$_3$, —CF$_3$, —CH$_2$F, —CH$_2$OH, —OCH$_3$, and —CH$_2$OCH$_3$.

j. $R^{5a}$ Groups

In one aspect, $R^{5a}$ is selected from hydrogen and C1-C4 alkyl. In a further aspect, $R^{5a}$ is methyl. In a yet further aspect, $R^{5a}$ is hydrogen. In a still further aspect, $R^{5a}$ is C1-C4 alkyl.

In one aspect, each of $R^{5a}$ and $R^{5b}$, when present, is independently selected from hydrogen and C1-C4 alkyl. In a further aspect, $R^{5a}$ and $R^{5b}$, when present, are both hydrogen.

In one aspect, $R^{5a}$ is selected from methyl, trifluoromethyl, ethyl, propyl, and butyl.

In various aspects, $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl. In a further aspect, $R^{5a}$ is selected from hydrogen, —F, —Cl, hydroxyl, —CH$_3$, —CF$_3$, —CH$_2$F, —CH$_2$OH, —OCH$_3$, —CH$_2$OCH$_3$, —CCl$_3$, —CH$_2$Cl, —OCH$_2$CH$_3$, —(CH$_2$)$_2$OCH$_3$, and —CH$_2$OCH$_2$CH$_3$. In a further aspect, $R^{5a}$ is selected from hydrogen, —F, hydroxyl, —CH$_3$, —CF$_3$, —CH$_2$F, —CH$_2$OH, —OCH$_3$, and —CH$_2$OCH$_3$.

In a further aspect, $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl, and $R^{5b}$, when present, is hydrogen. In a further aspect, $R^{5a}$ is selected from hydrogen, —F, —Cl, hydroxyl, —CH$_3$, —CF$_3$, —CH$_2$F, —CH$_2$OH, —OCH$_3$, —CH$_2$OCH$_3$, —CCl$_3$, —CH$_2$Cl, —OCH$_2$CH$_3$, —(CH$_2$)$_2$ OCH$_3$, and —CH$_2$OCH$_2$CH$_3$, and $R^{5b}$, when present, is hydrogen. In a further aspect, $R^{5a}$ is selected from hydrogen, —F, hydroxyl, —CH$_3$, —CF$_3$, —CH$_2$F, —CH$_2$OH, —OCH$_3$, and —CH$_2$OCH$_3$, and $R^{5b}$, when present, is hydrogen.

In a further aspect, $R^{5a}$ and $R^{5b}$, when present, are each —CH$_3$. In a still further aspect, $R^{5a}$ and $R^{5b}$, when present, are each —CH$_2$OH. In a yet further aspect, $R^{5a}$ and $R^{5b}$, when present, are each —F. In an even further aspect, $R^{5a}$ and $R^{5b}$, when present, are each —OH. In a still further aspect, $R^{4a}$ and $R^{4b}$, when present, are each —OCH$_3$.

k. $R^{5b}$ Groups

In one aspect, $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl. In a further aspect, $R^{5b}$, when present, is hydrogen. In a still further aspect, $R^{5b}$, when present, is C1-C4 alkyl.

In one aspect, $R^{5b}$, when present, is selected from methyl, trifluoromethyl, ethyl, propyl, and butyl.

In one aspect, $R^{5b}$ is present, and $R^{5a}$ and $R^{5b}$ are covalently bonded and, together with the intermediate carbon, comprise a 3- to 7-membered spirocycloalkyl. In a further aspect, $R^{5b}$ is present, and $R^{5a}$ and $R^{5b}$ are covalently bonded and, together with the intermediate carbon, comprise a substituted 3- to 7-membered spirocycloalkyl. In a yet further aspect, the spirocycloalkyl is substituted with 1 or 2 groups selected from methyl, ethyl, and propyl.

In various aspects, $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl. In a further aspect, $R^{5b}$, when present, is selected from hydrogen, —F, —Cl, hydroxyl, —CH$_3$, —CF$_3$, —CH$_2$F, —CH$_2$OH, —OCH$_3$, —CH$_2$OCH$_3$, —CCl$_3$, —CH$_2$Cl, —OCH$_2$CH$_3$, —(CH$_2$)$_2$ OCH$_3$, and —CH$_2$OCH$_2$CH$_3$. In a further aspect, $R^{5b}$, when present, is selected from hydrogen, —F, hydroxyl, —CH$_3$, —CF$_3$, —CH$_2$F, —CH$_2$OH, —OCH$_3$, and —CH$_2$OCH$_3$.

l. $R^{6a}$, $R^{6b}$, $R^{6c}$, $R^{6d}$, and $R^{6e}$ Groups

In one aspect, $R^{6a}$, $R^{6b}$, $R^{6c}$, $R^{6d}$, and $R^{6e}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that at least two of $R^{6a}$, $R^{6b}$, $R^{6c}$, $R^{6d}$, and $R^{6e}$ are hydrogen. In an even further aspect, each of $R^{6a}$, $R^{6b}$, $R^{6c}$, $R^{6d}$, and $R^{6e}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that three of $R^{6a}$, $R^{6b}$, $R^{6c}$, $R^{6d}$, and $R^{6e}$ are hydrogen. In a still further aspect, each of $R^{6a}$, $R^{6b}$, $R^{6c}$, $R^{6d}$, and $R^{6e}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that four of $R^{6a}$, $R^{6b}$, $R^{6c}$, $R^{6d}$, and $R^{6e}$ are hydrogen. In a yet further aspect, each of $R^{6a}$, $R^{6b}$, $R^{6c}$, $R^{6d}$, and $R^{6e}$ is independently selected from hydrogen, —OH, —F, —Cl, —CN, methyl, ethyl, propyl, isopropyl, tert-butyl, sec-butyl, isobutyl, tert-butyl, neopentyl, isopentyl, sec-pentyl, tert-pentyl, CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —CH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$, provided that at least two of $R^{6a}$, $R^{6b}$, $R^{6c}$, $R^{6d}$, and $R^{6e}$ are hydrogen. In an even further aspect, each of $R^{6a}$, $R^{6b}$, $R^{6c}$, $R^{6d}$, and $R^{6e}$ is independently selected from hydrogen, —OH, —F, —Cl, —CN, —CH$_3$, —CH$_2$CH$_3$, —OCH$_3$, —OCH$_2$CH$_3$, —NHCH$_3$, and —N(CH$_3$)$_2$, provided that at least two of $R^{6a}$, $R^{6b}$, $R^{6c}$, $R^{6d}$, and $R^{6e}$ are hydrogen. In a still further aspect, each of $R^{6a}$, $R^{6b}$, $R^{6c}$, $R^{6d}$, and $R^{6e}$ is hydrogen.

In one aspect, each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that at least one of $R^{6a}$, $R^{6b}$, $R^{6c}$, $R^{6d}$ is hydrogen. In an even further aspect, each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that two of $R^{6a}$, $R^{6b}$, $R^{6c}$, $R^{6d}$ are hydrogen. In a yet further aspect, each of $R^{6a}$, $R^{6b}$, $R^{6c}$, and $R^{6d}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that three of $R^{6a}$, $R^{6b}$, $R^{6c}$, $R^{6d}$ are hydrogen. In an even further aspect, each of $R^{6a}$, $R^{6b}$, $R^{6c}$, and $R^{6d}$ is hydrogen. In a yet further aspect, each of $R^{6a}$, $R^{6b}$, $R^{6c}$, and $R^{6d}$ is independently selected from hydrogen, —OH, —F, —Cl, —CN, methyl, ethyl, propyl, isopropyl, tert-butyl, sec-butyl, isobutyl, tert-butyl, neopentyl, isopentyl, sec-pentyl, tert-pentyl, CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH (CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$, provided that at least one of $R^{6a}$, $R^{6b}$, $R^{6c}$, $R^{6d}$ is hydrogen. In an even further aspect, each of $R^{6a}$, $R^{6b}$, $R^{6c}$, and $R^{6d}$ is independently selected from hydrogen, —OH, —F, —Cl, —CN, —CH$_3$, —CH$_2$CH$_3$, —OCH$_3$, —OCH$_2$CH$_3$, —NHCH$_3$, and —N(CH$_3$)$_2$, provided that at least one of $R^{6a}$, $R^{6b}$, $R^{6c}$, $R^{6d}$ is hydrogen. In a still further aspect, each of $R^{6a}$, $R^{6b}$, $R^{6c}$, $R^{6d}$, and $R^{6e}$ is hydrogen.

In one aspect, each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl. In a yet further aspect, each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that one of $R^{6a}$, $R^{6b}$, and $R^{6c}$ is hydrogen. In an even further aspect, each of $R^{6a}$, $R^{6b}$, and $R^{6c}$ is independently selected from hydrogen, halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl, provided that two of $R^{6a}$, $R^{6b}$, and $R^{6c}$ are hydrogen. In a yet further aspect, each of $R^{6a}$, $R^{6b}$, and $R^{6c}$ is hydrogen. In a yet further aspect, each of $R^{6a}$, $R^{6b}$, and $R^{6c}$ is independently selected from hydrogen, —OH, —F, —Cl, —CN, methyl, ethyl, propyl, isopropyl, tert-butyl, sec-butyl, isobutyl, tert-butyl, neopentyl, isopentyl, sec-pentyl, tert-pentyl, CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —OCH$_3$, —OCH$_2$CH$_3$, —O(CH$_2$)$_2$CH$_3$, —OCH(CH$_3$)$_2$, —OCH(CH$_2$CH$_3$)$_2$(CH$_3$), —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In an even further aspect, each of $R^{6a}$, $R^{6b}$, and $R^{6c}$ is independently selected from hydrogen, —OH, —F, —Cl, —CN, —CH$_3$, —CH$_2$CH$_3$, —OCH$_3$, —OCH$_2$CH$_3$, —NHCH$_3$, and —N(CH$_3$)$_2$. In a still further aspect, each of $R^{6a}$, $R^{6b}$, $R^{6c}$, $R^{6d}$, and $R^{6e}$ is hydrogen.

m. $R^{7a}$, $R^{7b}$, $R^{7c}$, $R^{7d}$, $R^{7e}$, $R^{7f}$, and $R^{7g}$ Groups In one aspect, each of $R^{7a}$, $R^{7b}$, $R^{7c}$, $R^{7d}$, $R^{7e}$, $R^{7f}$, and $R^{7g}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least four of $R^{7a}$, $R^{7b}$, $R^{7c}$, $R^{7d}$, $R^{7e}$, $R^{7f}$, and $R^{7g}$ are hydrogen. In a further aspect, each of $R^{7a}$, $R^{7b}$, $R^{7c}$, $R^{7d}$, $R^{7e}$, $R^{7f}$, and $R^{7g}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least five of $R^{7a}$, $R^{7b}$, $R^{7c}$, $R^{7d}$, $R^{7e}$, $R^{7f}$, and $R^{7g}$ are hydrogen. In a still further aspect, each of $R^{7a}$, $R^{7b}$, $R^{7c}$, $R^{7d}$, $R^{7e}$, $R^{7f}$, and $R^{7g}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least six of $R^{7a}$, $R^{7b}$, $R^{7c}$, $R^{7d}$, $R^{7e}$, $R^{7f}$, and $R^{7g}$ are hydrogen. In a yet further aspect, each of $R^{7a}$, $R^{7b}$, $R^{7c}$, $R^{7d}$, $R^{7e}$, $R^{7f}$, and $R^{7g}$ is hydrogen.

In one aspect, each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, $R^{7d}$, $R^{7e}$, and $R^{7f}$ are hydrogen. In a further aspect, each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least four of $R^{7a}$, $R^{7b}$, $R^{7c}$, $R^{7d}$, $R^{7e}$, and $R^{7f}$ are hydrogen. In a still further aspect, each of $R^{7a}$, $R^{7b}$, $R^{7c}$, $R^{7d}$, $R^{7e}$, and $R^{7f}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least five of $R^{7a}$, $R^{7b}$, $R^{7c}$, $R^{7d}$, $R^{7e}$, and $R^{7f}$ are hydrogen. In a yet further aspect, each of $R^{7a}$, $R^{7b}$, $R^{7c}$, $R^{7d}$, $R^{7e}$, and $R^{7f}$ is hydrogen.

In one aspect, each of $R^{7a}$, $R^{7b}$, $R^{7c}$, $R^{7d}$, and $R^{7e}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least two of $R^{7a}$, $R^{7b}$, $R^{7c}$, $R^{7d}$, and $R^{7e}$ are hydrogen. In a further aspect, each of $R^{7a}$, $R^{7b}$, $R^{7c}$, $R^{7d}$, and $R^{7e}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, $R^{7d}$, and $R^{7e}$ are hydrogen. In a still further aspect, each of $R^{7a}$, $R^{7b}$, $R^{7c}$, $R^{7d}$, and $R^{7e}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least four of $R^{7a}$, $R^{7b}$, $R^{7c}$, $R^{7d}$, and $R^{7e}$ are hydrogen. In a yet further aspect, each of $R^{7a}$, $R^{7b}$, $R^{7c}$, $R^{7d}$, and $R^{7e}$ is hydrogen.

In one aspect, each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least one of $R^{7a}$, $R^{7b}$, $R^{7c}$, and $R^{7d}$ is hydrogen. In a further aspect, each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least two of $R^{7a}$, $R^{7b}$, $R^{7c}$, and $R^{7d}$ are hydrogen. In a still further aspect, each of $R^{7a}$, $R^{7b}$, $R^{7c}$, and $R^{7d}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least three of $R^{7a}$, $R^{7b}$, $R^{7c}$, and $R^{7d}$ are hydrogen. In a yet further aspect, each of $R^{7a}$, $R^{7b}$, $R^{7c}$, and $R^{7d}$ is hydrogen.

In one aspect, each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a further aspect, each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least one of $R^{7a}$, $R^{7b}$, and $R^{7c}$ is hydrogen. In a still further aspect, each of $R^{7a}$, $R^{7b}$, and $R^{7c}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl, provided that at least two of $R^{7a}$, $R^{7b}$, and $R^{7c}$ is hydrogen. In a yet further aspect, each of $R^{7a}$, $R^{7b}$, and $R^{7c}$ is hydrogen.

In one aspect, each of $R^{7a}$ and $R^{7b}$ is independently selected from hydrogen, halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a yet further aspect, each of $R^{7a}$ and $R^{7b}$ is hydrogen. In a still further aspect, each of $R^{7a}$, $R^{7b}$, and $R^8$ is hydrogen. In an even further aspect, each of $R^{7a}$ and $R^{7b}$ is hydrogen, and $R^8$ is selected from hydrogen and methyl.

n. $R^8$ Groups

In one aspect, $R^8$ is selected from hydrogen and C1-C6 alkyl. In a further aspect, $R^8$ is selected from hydrogen, methyl and ethyl. In a still further aspect, $R^8$ is selected from hydrogen and methyl. In an even further aspect, $R^8$ is hydrogen. In a yet further aspect, $R^8$ is methyl. In a yet further aspect, $R^8$ is ethyl.
2. Example Compounds
In one aspect, a compound can be present as:
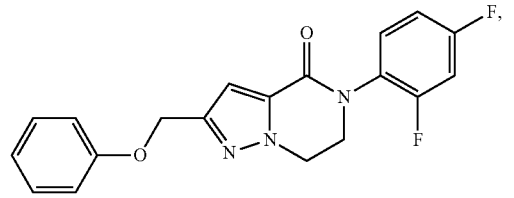
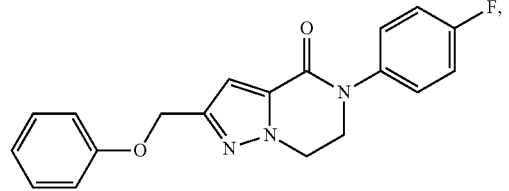
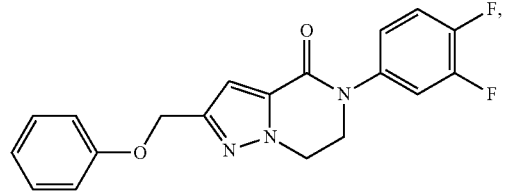
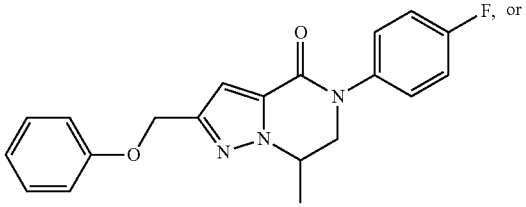
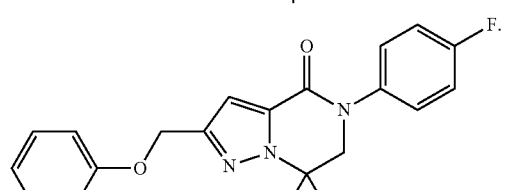
In one aspect, a compound can be present as:
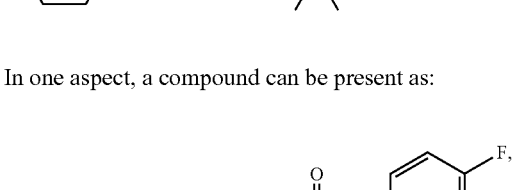
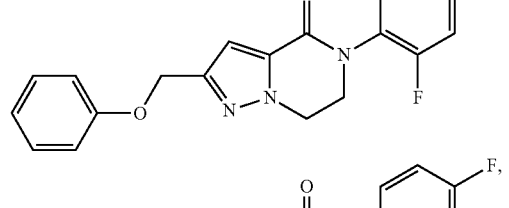
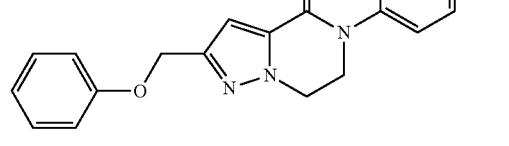
-continued
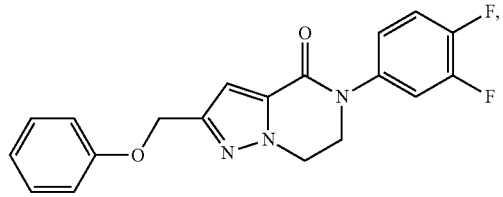
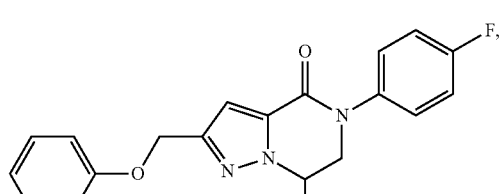
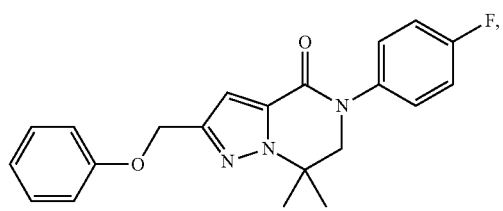
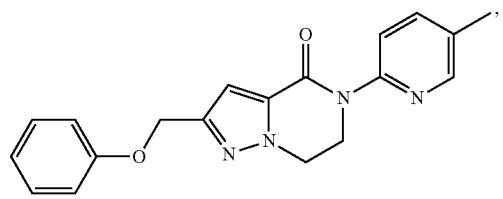
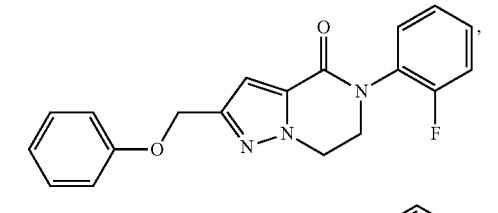
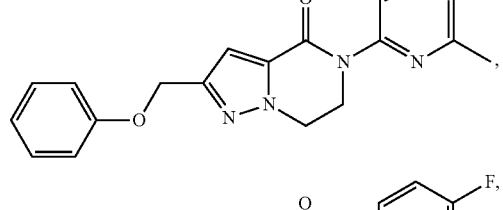
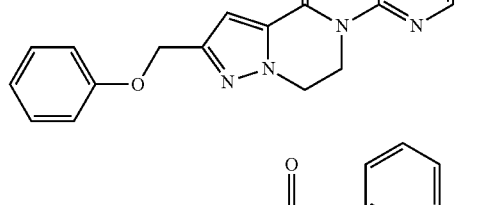
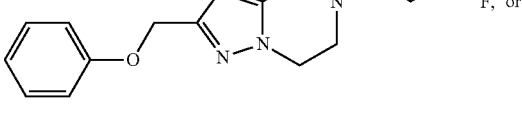

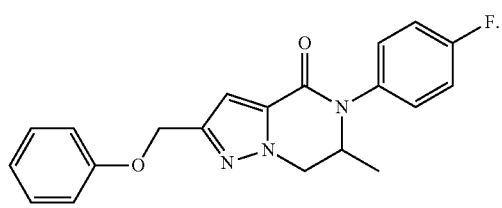
In one aspect, a compound can be present as:
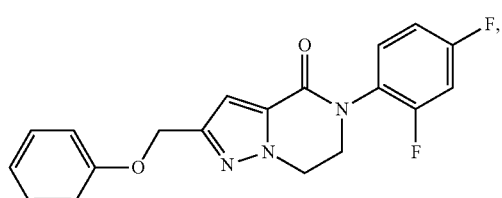
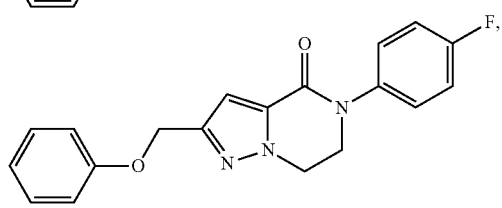
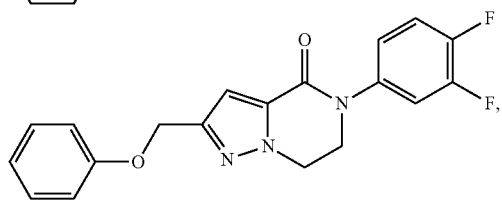
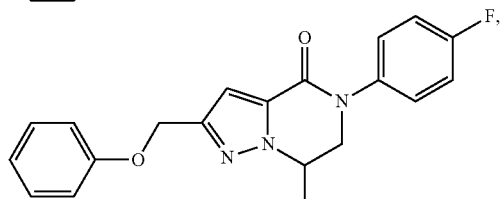
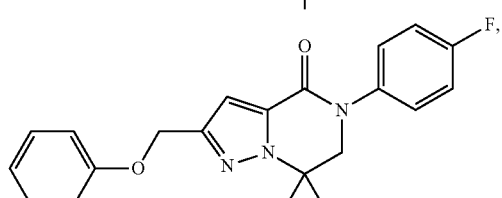
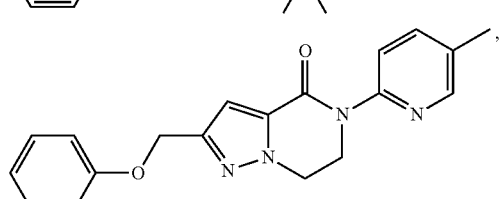
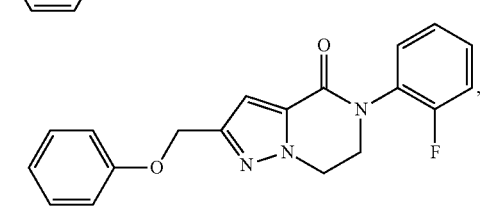
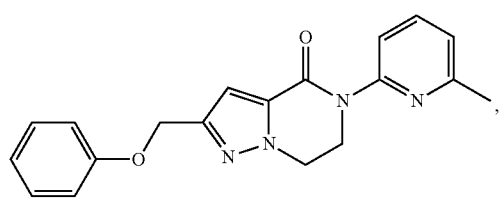
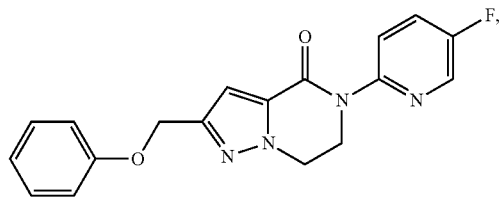
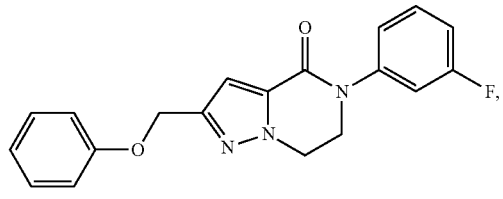
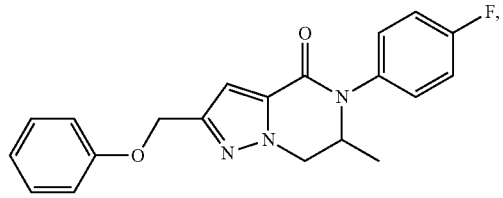
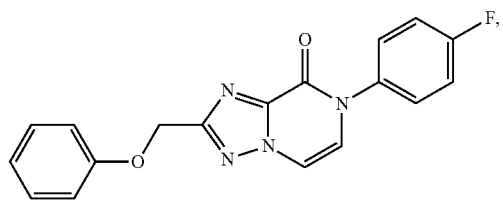
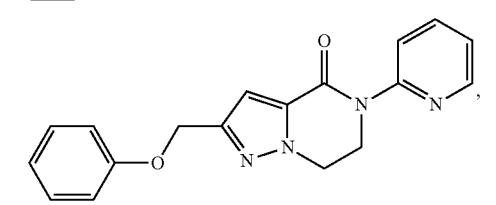
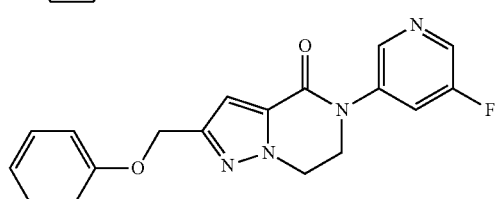
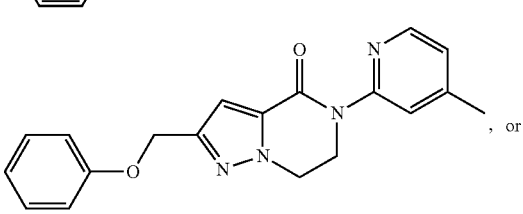, or

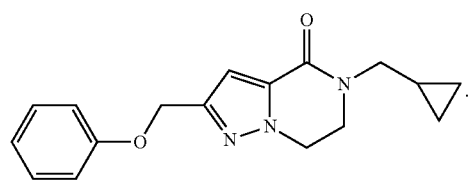
In one aspect, a compound can be present as:
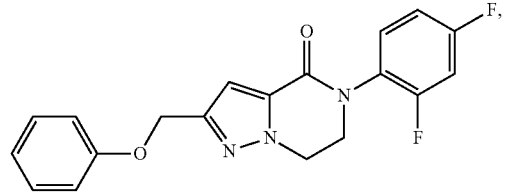
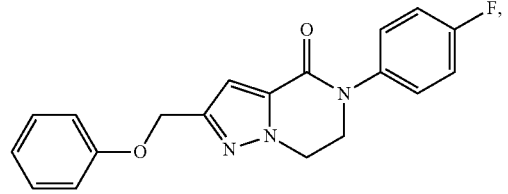
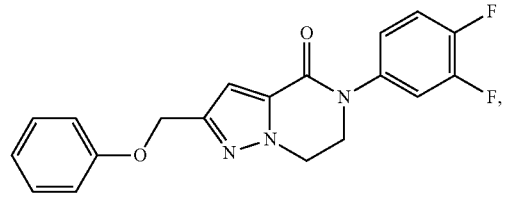
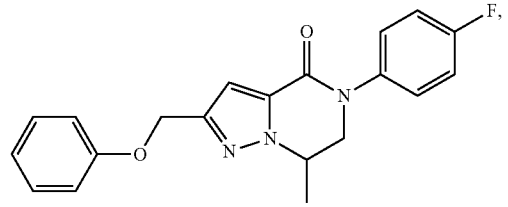
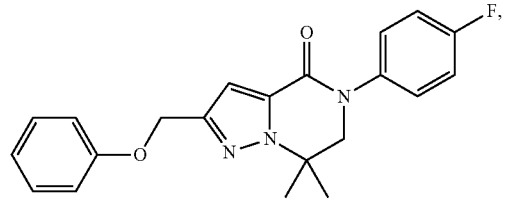
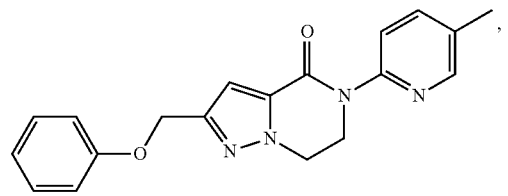
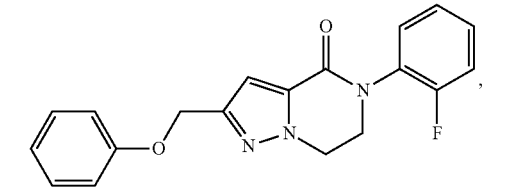
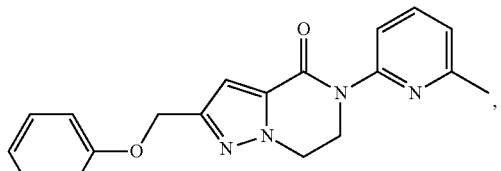
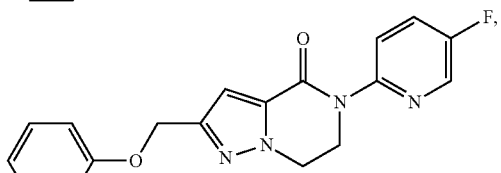
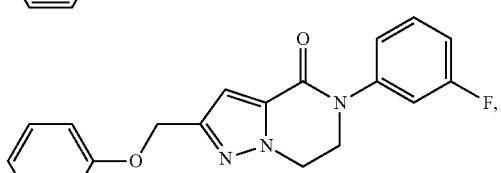
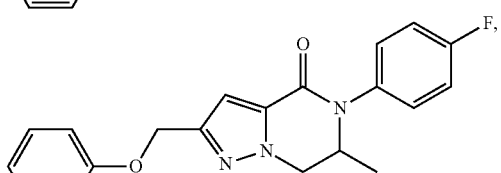
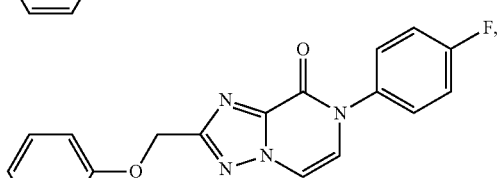
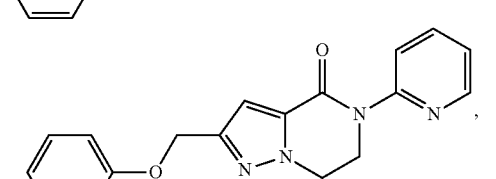
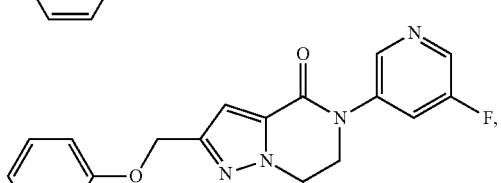
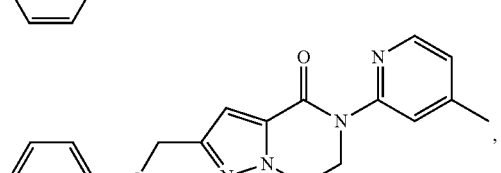
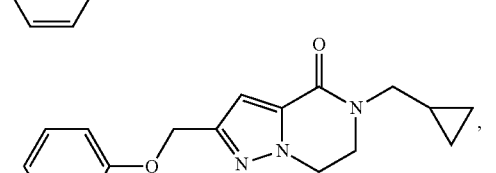

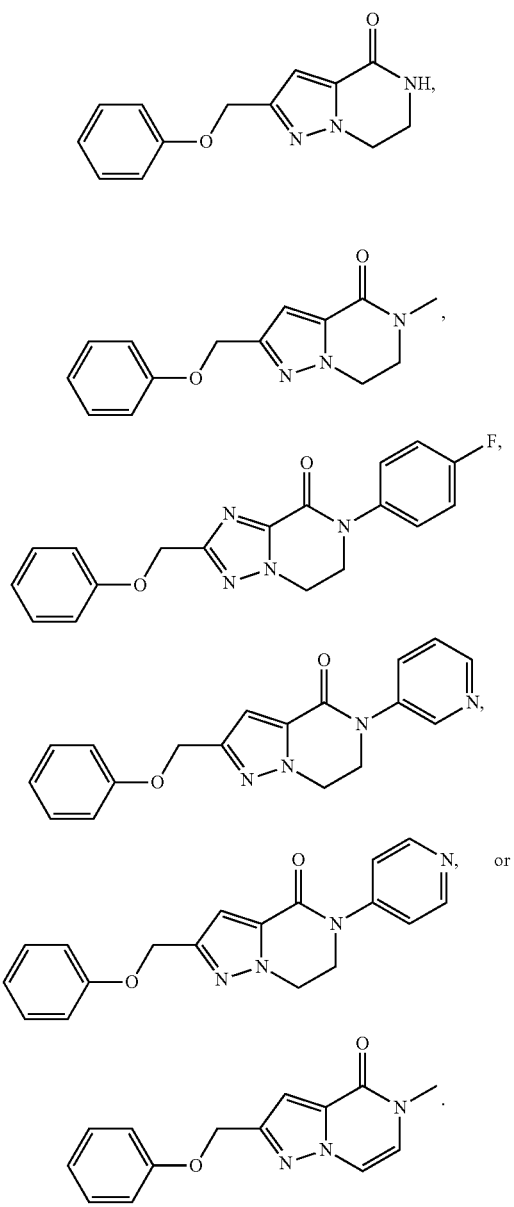
In one aspect, a compound can be present as:
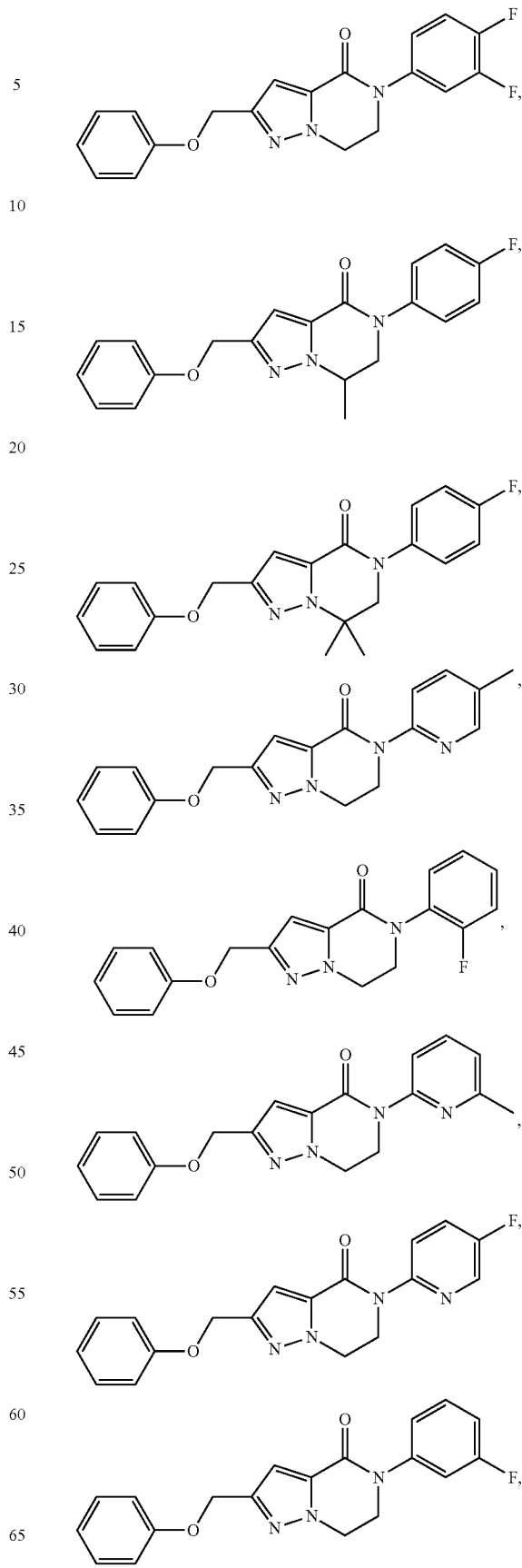

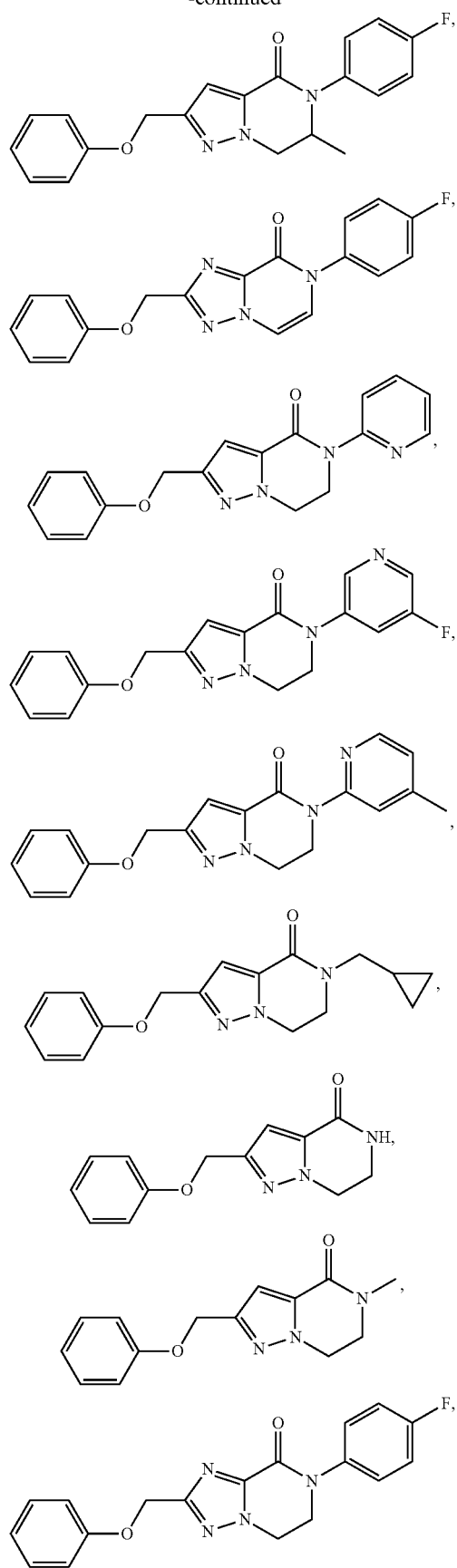
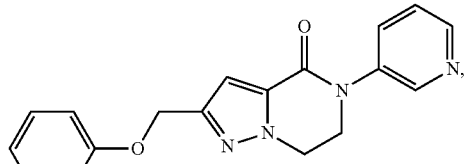
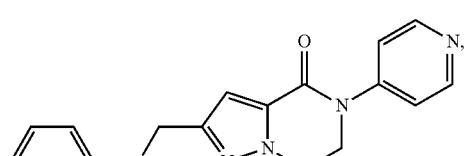
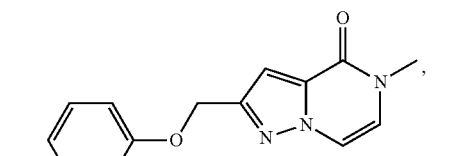
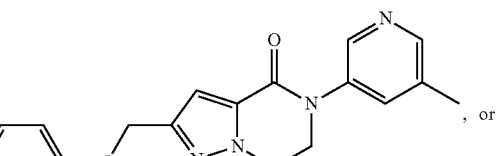
In one aspect, a compound can be present as:
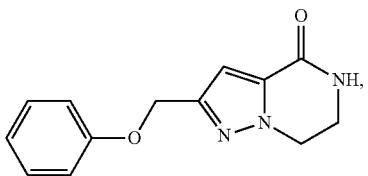
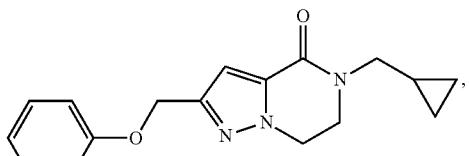
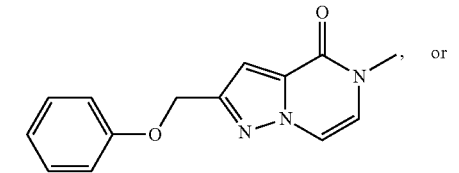

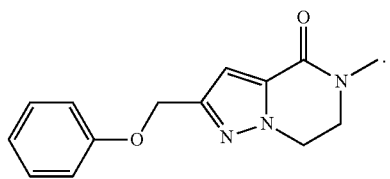
In one aspect, a compound can be present as:
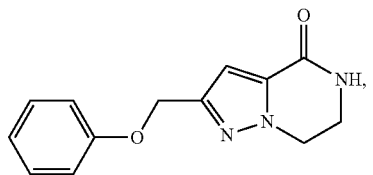
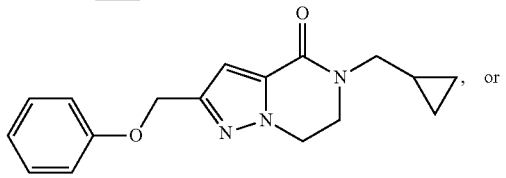, or
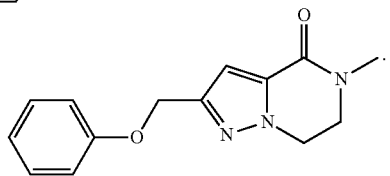
In one aspect, a compound can be present as:
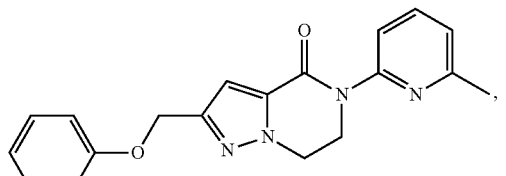
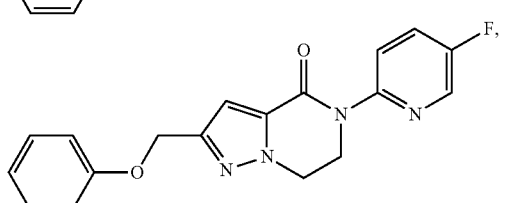
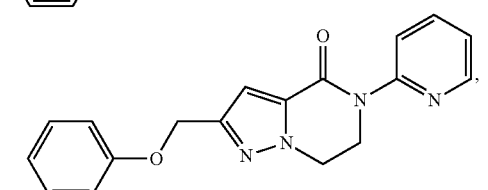
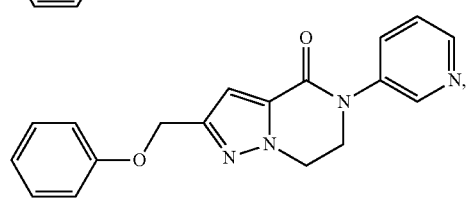
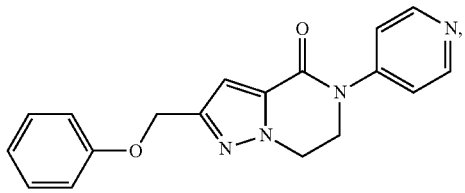
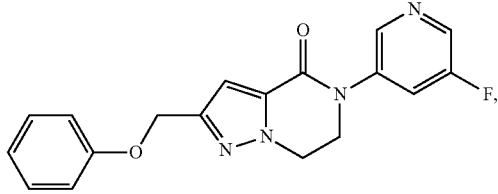
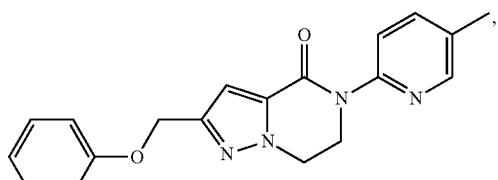
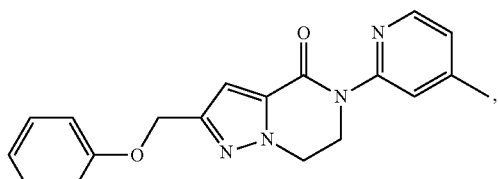
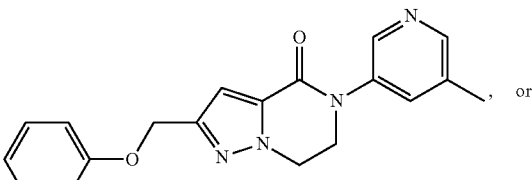, or
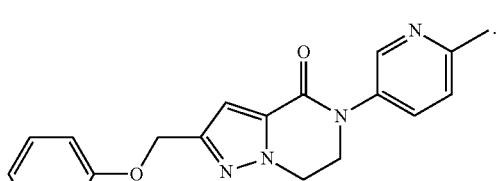
In one aspect, a compound can be present as:
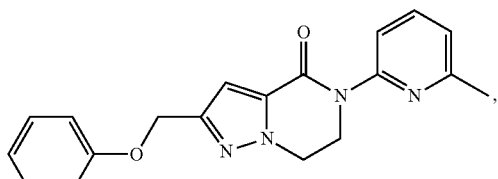
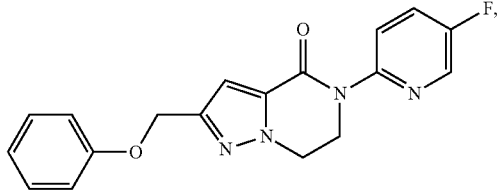 [SMILES: Cc1ccc(N2CCn3nc(COc4ccccc4)cc3C2=O)cn1]

105
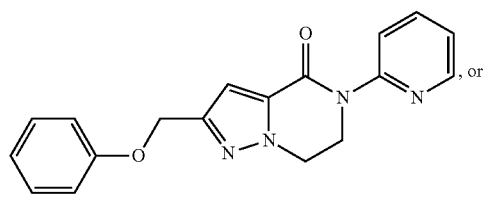, or
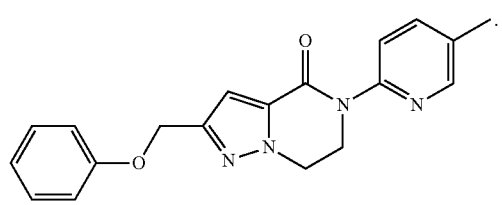.
In one aspect, a compound can be present as:
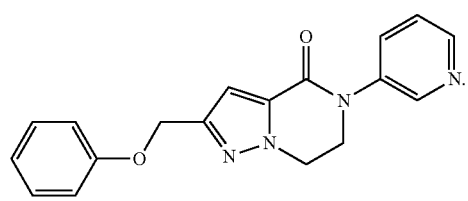 [SMILES: O=C1c2cc(COc3ccccc3)nn2CCN1c1cccnc1].
In one aspect, a compound can be present as:
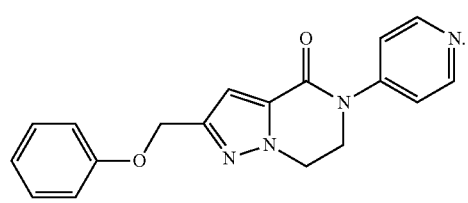 [SMILES: O=C1c2cc(COc3ccccc3)nn2CCN1c1ccncc1]
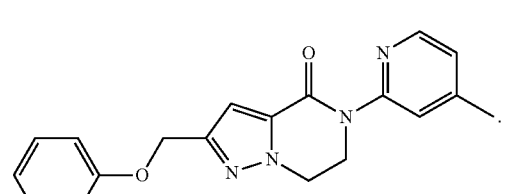, or
106
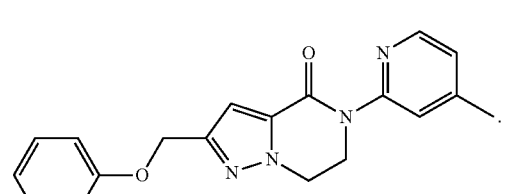.
In one aspect, a compound can be present as:
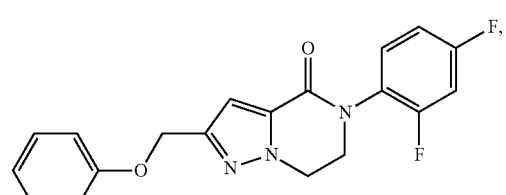.
In one aspect, a compound can be present as:
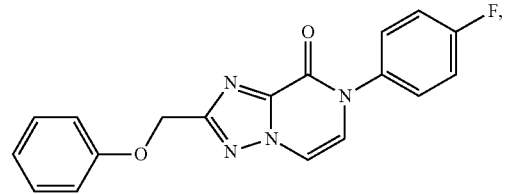
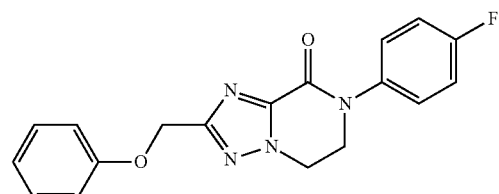
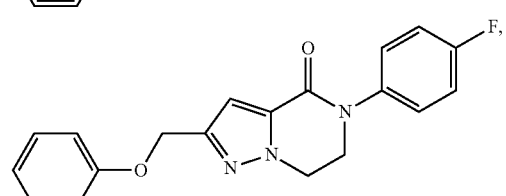
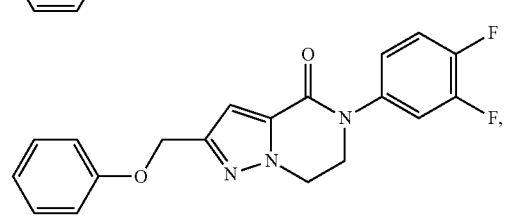

-continued
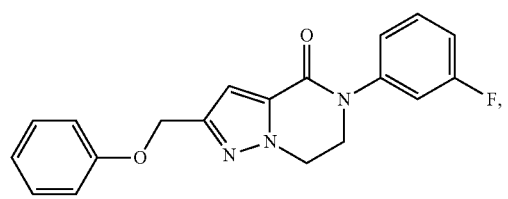
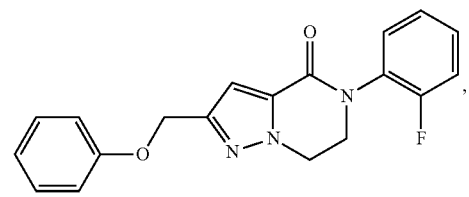
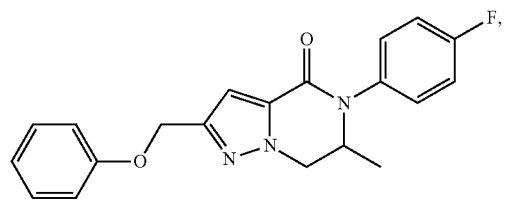
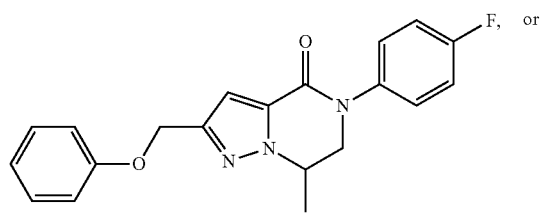, or
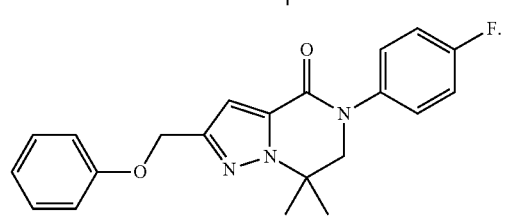
In one aspect, a compound can be present as:
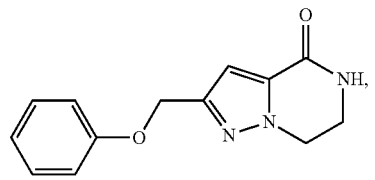
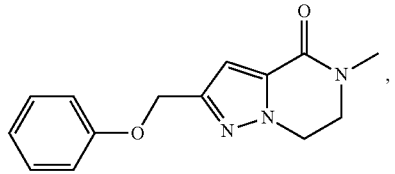
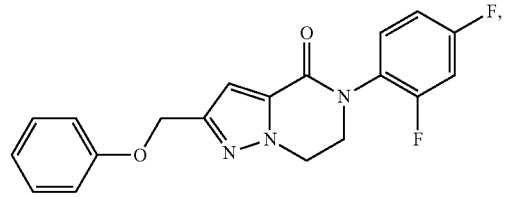
-continued
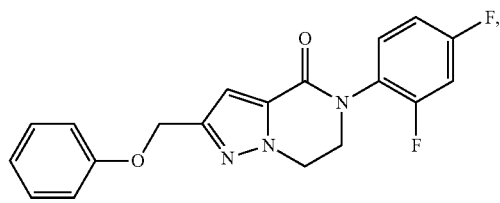
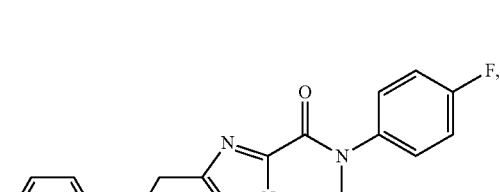
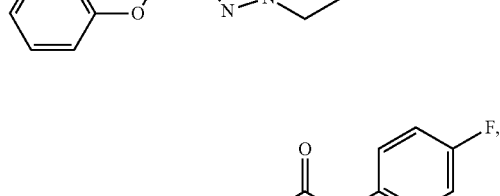
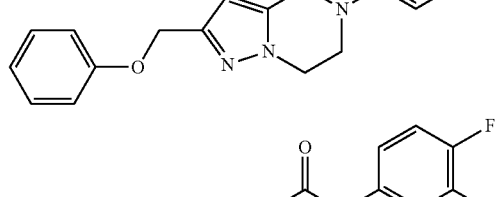
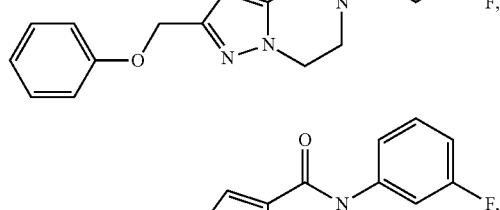
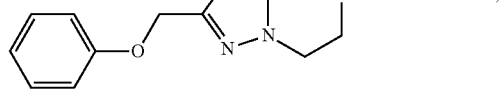
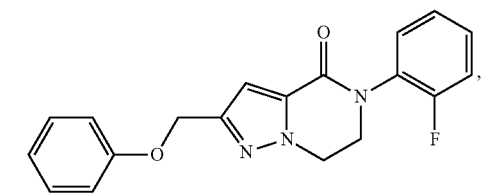
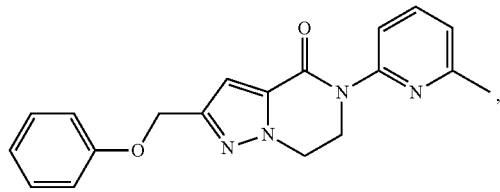
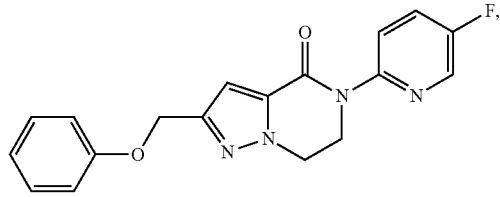

-continued

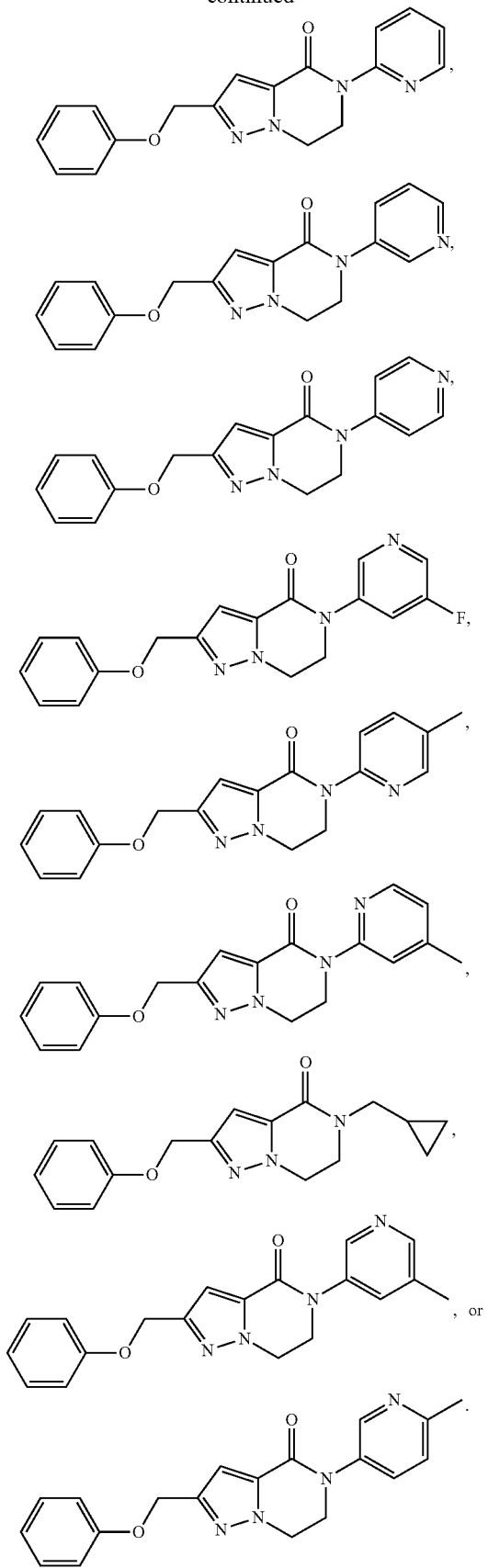

In one aspect, a compound can be present as:

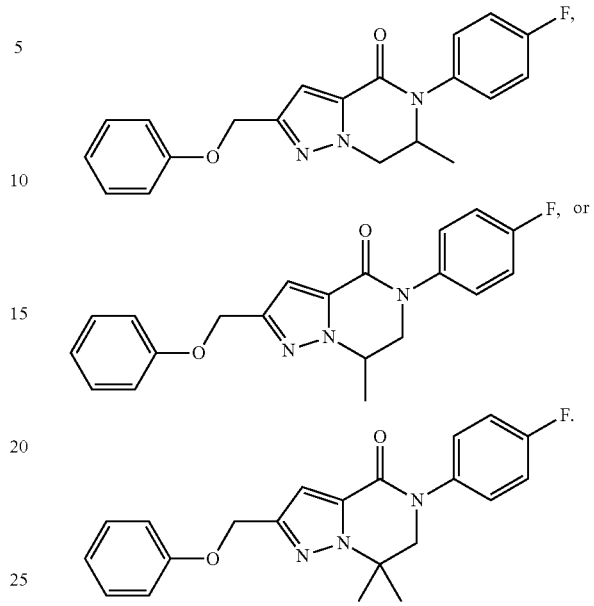

In one aspect, a compound can be present as:

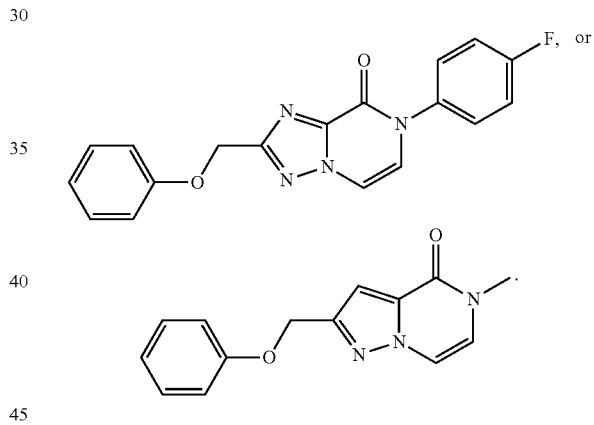

Compounds are shown above are depicted having a basic group or acidic group and named as the free base acid. Depending on the reaction and purification conditions, various compounds having a basic group were isolated in either the free base form, or as a salt (e.g. HCl salt), or in both free base and salt forms.

In one aspect, a compound can be present as: 2-(phenoxymethyl)-6,7-dihydropyrazolo[1,5-a]pyrazin-4(5H)-one, 5-methyl-2-(phenoxymethyl)-6,7-dihydropyrazolo[1,5-a]pyrazin-4(5H)-one, 5-(2,4-difluorophenyl)-2-(phenoxymethyl)-6,7-dihydropyrazolo[1,5-a]pyrazin-4(5H)-one, 7-(4-fluorophenyl)-2-(phenoxymethyl)[1,2,4]triazolo[1,5-a]pyrazin-8(7H)-one, 7-(4-fluorophenyl)-2-(phenoxymethyl)-6,7-dihydro[1,2,4]triazolo[1,5-a]pyrazin-8(5H)-one, 5-(4-fluorophenyl)-2-(phenoxymethyl)-6,7-dihydropyrazolo[1,5-a]pyrazin-4(5H)-one, 5-(3,4-difluorophenyl)-2-(phenoxymethyl)-6,7-dihydropyrazolo[1,5-a]pyrazin-4(5H)-one, 5-(3-fluorophenyl)-2-(phenoxymethyl)-6,7-dihydropyrazolo[1,5-a]pyrazin-4(5H)-one, 5-(2-fluorophenyl)-2-(phenoxymethyl)-6,7-dihydropyrazolo[1,5-a]pyrazin-4(5H)-one, 5-(6- methylpyridin-2-yl)-2-(phenoxymethyl)-6,7-dihydropyrazolo[1,5-a]pyrazin-4(5H)-one, 5-(5-fluoropyridin-2-yl)-2-(phenoxymethyl)-6,7-dihydropyrazolo[1,5-a]pyrazin-4(5H)-one, 2-(phenoxymethyl)-5-pyridin-2-yl-6,7-dihydropyrazolo[1,5-a]pyrazin-4(5H)-one, 2-(phenoxymethyl)-5-pyridin-3-yl-6,7-dihydropyrazolo[1,5-a]pyrazin-4(5H)-one, 2-(phenoxymethyl)-5-pyridin-4-yl-6,7-dihydropyrazolo[1,5-a]pyrazin-4(5H)-one, 5-(5-fluoropyridin-3-yl)-2-(phenoxymethyl)-6,7-dihydropyrazolo[1,5-a]pyrazin-4(5H)-one, 5-(5-methylpyridin-2-yl)-2-(phenoxymethyl)-6,7-dihydropyrazolo[1,5-a]pyrazin-4(5H)-one, 5-(4-methylpyridin-2-yl)-2-(phenoxymethyl)-6,7-dihydropyrazolo[1,5-a]pyrazin-4(5H)-one, 5-(4-fluorophenyl)-6-methyl-2-(phenoxymethyl)-6,7-dihydropyrazolo[1,5-a]pyrazin-4(5H)-one, 5-(4-fluorophenyl)-7-methyl-2-(phenoxymethyl)-6,7-dihydropyrazolo[1,5-a]pyrazin-4(5H)-one, 5-(4-fluorophenyl)-7,7-dimethyl-2-(phenoxymethyl)-6,7-dihydropyrazolo[1,5-a]pyrazin-4(5H)-one, 5-(cyclopropylmethyl)-2-(phenoxymethyl)-6,7-dihydropyrazolo[1,5-a]pyrazin-4(5H)-one, 5-(5-methylpyridin-3-yl)-2-(phenoxymethyl)-6,7-dihydropyrazolo[1,5-a]pyrazin-4(5H)-one, 5-(6-methylpyridin-3-yl)-2-(phenoxymethyl)-6,7-dihydropyrazolo[1,5-a]pyrazin-4(5H)-one, 2-(phenoxymethyl)-5-(2,2,2-trifluoroethyl)-6,7-dihydropyrazolo[1,5-a]pyrazin-4(5H)-one, 5-(1-methylethyl)-2-(phenoxymethyl)-6,7-dihydropyrazolo[1,5-a]pyrazin-4(5H)-one, 5-(2-methylpropyl)-2-(phenoxymethyl)-6,7-dihydropyrazolo[1,5-a]pyrazin-4(5H)-one, 5-(cyclobutylmethyl)-2-(phenoxymethyl)-6,7-dihydropyrazolo[1,5-a]pyrazin-4(5H)-one, 5-[(2,2-difluorocyclopropyl)methyl]-2-(phenoxymethyl)-6,7-dihydropyrazolo[1,5-a]pyrazin-4(5H)-one, 5-(3-fluoropyridin-4-yl)-2-(phenoxymethyl)-6,7-dihydropyrazolo[1,5-a]pyrazin-4(5H)-one, 5-(3-methylpyridin-2-yl)-2-(phenoxymethyl)-6,7-dihydropyrazolo[1,5-a]pyrazin-4(5H)-one, 2-(phenoxymethyl)-5-pyrimidin-5-yl-6,7-dihydropyrazolo[1,5-a]pyrazin-4(5H)-one, 5-(4-methylpyridin-3-yl)-2-(phenoxymethyl)-6,7-dihydropyrazolo[1,5-a]pyrazin-4(5H)-one, 5-(2-methylpyrimidin-5-yl)-2-(phenoxymethyl)-6,7-dihydropyrazolo[1,5-a]pyrazin-4(5H)-one, 5-(5-fluoro-6-methylpyridin-2-yl)-2-(phenoxymethyl)-6,7-dihydropyrazolo[1,5-a]pyrazin-4(5H)-one, 5-cyclopropyl-2-(phenoxymethyl)-6,7-dihydropyrazolo[1,5-a]pyrazin-4(5H)-one, 5-(6-ethylpyridin-2-yl)-2-(phenoxymethyl)-6,7-dihydropyrazolo[1,5-a]pyrazin-4(5H)-one, 5-methyl-2-(phenoxymethyl)pyrazolo[1,5-a]pyrazin-4(5H)-one, 5-[(1R)-1-cyclopropylethyl]-2-(phenoxymethyl)-6,7-dihydropyrazolo[1,5-a]pyrazin-4(5H)-one, 2-(phenoxymethyl)-5-[(1R)-1,2,2-trimethylpropyl]-6,7-dihydropyrazolo[1,5-a]pyrazin-4(5H)-one, 5-(2-methoxy-1-methylethyl)-2-(phenoxymethyl)-6,7-dihydropyrazolo[1,5-a]pyrazin-4(5H)-one, 5-[(1S)-1-cyclopropylethyl]-2-(phenoxymethyl)-6,7-dihydropyrazolo[1,5-a]pyrazin-4(5H)-one, 2-(phenoxymethyl)-5-[(1S)-1,2,2-trimethylpropyl]-6,7-dihydropyrazolo[1,5-a]pyrazin-4(5H)-one, 5-(2-methoxypropyl)-2-(phenoxymethyl)-6,7-dihydropyrazolo[1,5-a]pyrazin-4(5H)-one, 5-(2-fluoropropyl)-2-(phenoxymethyl)-6,7-dihydropyrazolo[1,5-a]pyrazin-4(5H)-one, 5-(2-fluoro-1-methylethyl)-2-(phenoxymethyl)-6,7-dihydropyrazolo[1,5-a]pyrazin-4(5H)-one, 5-tert-Butyl-2-(phenoxymethyl)-6,7-dihydropyrazolo[1,5-a]pyrazin-4(5H)-one, 5-(2-methoxyphenyl)-2-(phenoxymethyl)-6,7-dihydropyrazolo[1,5-a]pyrazin-4(5H)-one, 5-(3-methylphenyl)-2-(phenoxymethyl)-6,7-dihydropyrazolo[1,5-a]pyrazin-4(5H)-one, 5-(4-methylphenyl)-2-(phenoxymethyl)-6,7-dihydropyrazolo[1,5-a]pyrazin-4(5H)-one, 5-(4-methoxyphenyl)-2-(phenoxymethyl)-6,7-dihydropyrazolo[1,5-a]pyrazin-4(5H)-one, 5-(4-fluoro-3-methoxyphenyl)-2-(phenoxymethyl)-6,7-dihydropyrazolo[1,5-a]pyrazin-4(5H)-one, 5-(4-fluoro-3-methylphenyl)-2-(phenoxymethyl)-6,7-dihydropyrazolo[1,5-a]pyrazin-4(5H)-one, 5-(3-methoxyphenyl)-2-(phenoxymethyl)-6,7-dihydropyrazolo[1,5-a]pyrazin-4(5H)-one, 5-(4-fluoro-2-methoxyphenyl)-2-(phenoxymethyl)-6,7-dihydropyrazolo[1,5-a]pyrazin-4(5H)-one, 5-(2-methylphenyl)-2-(phenoxymethyl)-6,7-dihydropyrazolo[1,5-a]pyrazin-4(5H)-one, 5-(2,3-dimethylphenyl)-2-(phenoxymethyl)-6,7-dihydropyrazolo[1,5-a]pyrazin-4(5H)-one, 5-(2-ethoxyphenyl)-2-(phenoxymethyl)-6,7-dihydropyrazolo[1,5-a]pyrazin-4(5H)-one, 5-(3-fluoro-4-methoxyphenyl)-2-(phenoxymethyl)-6,7-dihydropyrazolo[1,5-a]pyrazin-4(5H)-one, 5-(3-ethoxyphenyl)-2-(phenoxymethyl)-6,7-dihydropyrazolo[1,5-a]pyrazin-4(5H)-one, 5-(4-fluoro-2-methylphenyl)-2-(phenoxymethyl)-6,7-dihydropyrazolo[1,5-a]pyrazin-4(5H)-one, 5-(5-fluoro-2-methylphenyl)-2-(phenoxymethyl)-6,7-dihydropyrazolo[1,5-a]pyrazin-4(5H)-one, 5-(3-fluoro-4-methylphenyl)-2-(phenoxymethyl)-6,7-dihydropyrazolo[1,5-a]pyrazin-4(5H)-one, 5-[2-(methoxymethyl)phenyl]-2-(phenoxymethyl)-6,7-dihydropyrazolo[1,5-a]pyrazin-4(5H)-one, 5-(2-methylpyridin-3-yl)-2-(phenoxymethyl)-6,7-dihydropyrazolo[1,5-a]pyrazin-4(5H)-one, 5-[6-(3-methylbutyl)pyridin-2-yl]-2-(phenoxymethyl)-6,7-dihydropyrazolo[1,5-a]pyrazin-4(5H)-one, 5-(6-cyclopropylpyridin-2-yl)-2-(phenoxymethyl)-6,7-dihydropyrazolo[1,5-a]pyrazin-4(5H)-one, 5-[6-(2-methylpropyl)pyridin-2-yl]-2-(phenoxymethyl)-6,7-dihydropyrazolo[1,5-a]pyrazin-4(5H)-one, 5-(3-chloropyridin-2-yl)-2-(phenoxymethyl)-6,7-dihydropyrazolo[1,5-a]pyrazin-4(5H)-one, 5-[6-(2-methoxyethyl)pyridin-2-yl]-2-(phenoxymethyl)-6,7-dihydropyrazolo[1,5-a]pyrazin-4(5H)-one, 5-(6-methoxypyridin-2-yl)-2-(phenoxymethyl)-6,7-dihydropyrazolo[1,5-a]pyrazin-4(5H)-one, 5-(5-methoxypyridin-2-yl)-2-(phenoxymethyl)-6,7-dihydropyrazolo[1,5-a]pyrazin-4(5H)-one, 5-(5-fluoro-4-methylpyridin-2-yl)-2-(phenoxymethyl)-6,7-dihydropyrazolo[1,5-a]pyrazin-4(5H)-one, 5-(5-fluoro-6-methoxypyridin-2-yl)-2-(phenoxymethyl)-6,7-dihydropyrazolo[1,5-a]pyrazin-4(5H)-one, 5-[6-(2-fluoroethoxy)pyridin-2-yl]-2-(phenoxymethyl)-6,7-dihydropyrazolo[1,5-a]pyrazin-4(5H)-one, 5-[6-(2-fluoroethyl)pyridin-2-yl]-2-(phenoxymethyl)-6,7-dihydropyrazolo[1,5-a]pyrazin-4(5H)-one, 5-[6-(fluoromethyl)pyridin-2-yl]-2-(phenoxymethyl)-6,7-dihydropyrazolo[1,5-a]pyrazin-4(5H)-one, 2-(phenoxymethyl)-5-pyrimidin-2-yl-6,7-dihydropyrazolo[1,5-a]pyrazin-4(5H)-one, 5-(4-methoxypyrimidin-2-yl)-2-(phenoxymethyl)-6,7-dihydropyrazolo[1,5-a]pyrazin-4(5H)-one, 5-(3-methoxypyridin-2-yl)-2-(phenoxymethyl)-6,7-dihydropyrazolo[1,5-a]pyrazin-4(5H)-one, 2-(phenoxymethyl)-5-pyrimidin-4-yl-6,7-dihydropyrazolo[1,5-a]pyrazin-4(5H)-one, 5-(3-fluoropyridin-2-yl)-2-(phenoxymethyl)-6,7-dihydropyrazolo[1,5-a]pyrazin-4(5H)-one, 5-(4-methylpyrimidin-2-yl)-2-(phenoxymethyl)-6,7-dihydropyrazolo[1,5-a]pyrazin-4(5H)-one, 5-(6-methylpyrimidin-4-yl)-2-(phenoxymethyl)-6,7-dihydropyrazolo[1,5-a]pyrazin-4(5H)-one, 5-(6-methylpyridazin-3-yl)-2-(phenoxymethyl)-6,7-dihydropyrazolo[1,5-a]pyrazin-4(5H)-one, 5-[6-(2-methoxyethoxy)pyridin-2-yl]-2-(phenoxymethyl)-6,7-dihydropyrazolo[1,5-a]pyrazin-4(5H)-one, 5-(5-fluoro-3- methylpyridin-2-yl)-2-(phenoxymethyl)-6,7-dihydropyrazolo[1,5-a]pyrazin-4(5H)-one, 2-(phenoxymethyl)-5-pyrazin-2-yl-6,7-dihydropyrazolo[1,5-a]pyrazin-4(5H)-one, 5-(3-fluoro-6-methylpyridin-2-yl)-2-(phenoxymethyl)-6,7-dihydropyrazolo[1,5-a]pyrazin-4(5H)-one, 5-(6-methoxypyridazin-3-yl)-2-(phenoxymethyl)-6,7-dihydropyrazolo[1,5-a]pyrazin-4(5H)-one, 5-(5-fluoro-4-methylpyrimidin-2-yl)-2-(phenoxymethyl)-6,7-dihydropyrazolo[1,5-a]pyrazin-4(5H)-one, 5-(5-fluoro-4-methoxypyrimidin-2-yl)-2-(phenoxymethyl)-6,7-dihydropyrazolo[1,5-a]pyrazin-4(5H)-one, 5-(6-methylpyrazin-2-yl)-2-(phenoxymethyl)-6,7-dihydropyrazolo[1,5-a]pyrazin-4(5H)-one, 5-(5-methylpyridazin-3-yl)-2-(phenoxymethyl)-6,7-dihydropyrazolo[1,5-a]pyrazin-4(5H)-one, 5-(2-methylpyrimidin-4-yl)-2-(phenoxymethyl)-6,7-dihydropyrazolo[1,5-a]pyrazin-4(5H)-one, 6-[4-oxo-2-(phenoxymethyl)-6,7-dihydropyrazolo[1,5-a]pyrazin-5(4H)-yl]pyridine-2-carbonitrile, 5-(2-methoxypyridin-3-yl)-2-(phenoxymethyl)-6,7-dihydropyrazolo[1,5-a]pyrazin-4(5H)-one, 5-(4-methoxy-5-methylpyrimidin-2-yl)-2-(phenoxymethyl)-6,7-dihydropyrazolo[1,5-a]pyrazin-4(5H)-one, 5-(2-methoxy-6-methylpyrimidin-4-yl)-2-(phenoxymethyl)-6,7-dihydropyrazolo[1,5-a]pyrazin-4(5H)-one, 5-(4-methoxy-6-methylpyrimidin-2-yl)-2-(phenoxymethyl)-6,7-dihydropyrazolo[1,5-a]pyrazin-4(5H)-one, 5-(5-methylpyrazin-2-yl)-2-(phenoxymethyl)-6,7-dihydropyrazolo[1,5-a]pyrazin-4(5H)-one, 5-(5-methoxypyrazin-2-yl)-2-(phenoxymethyl)-6,7-dihydropyrazolo[1,5-a]pyrazin-4(5H)-one, 5-(5-methoxy-6-methylpyrazin-2-yl)-2-(phenoxymethyl)-6,7-dihydropyrazolo[1,5-a]pyrazin-4(5H)-one, 5-(3-methoxypyrazin-2-yl)-2-(phenoxymethyl)-6,7-dihydropyrazolo[1,5-a]pyrazin-4(5H)-one, 5-(6-methoxy-4-methylpyridin-2-yl)-2-(phenoxymethyl)-6,7-dihydropyrazolo[1,5-a]pyrazin-4(5H)-one, 5-(6-methoxy-2-methylpyrimidin-4-yl)-2-(phenoxymethyl)-6,7-dihydropyrazolo[1,5-a]pyrazin-4(5H)-one, 5-(2-methoxy-5-methylpyrimidin-4-yl)-2-(phenoxymethyl)-6,7-dihydropyrazolo[1,5-a]pyrazin-4(5H)-one, 5-(4,5-dimethoxypyrimidin-2-yl)-2-(phenoxymethyl)-6,7-dihydropyrazolo[1,5-a]pyrazin-4(5H)-one, 5-(6-methoxy-5-methylpyridin-2-yl)-2-(phenoxymethyl)-6,7-dihydropyrazolo[1,5-a]pyrazin-4(5H)-one, 5-(6-methoxy-3-methylpyridin-2-yl)-2-(phenoxymethyl)-6,7-dihydropyrazolo[1,5-a]pyrazin-4(5H)-one, 5-(2-methoxypyrimidin-4-yl)-2-(phenoxymethyl)-6,7-dihydropyrazolo[1,5-a]pyrazin-4(5H)-one, 5-[6-(1-methylethyl)pyridin-2-yl]-2-(phenoxymethyl)-6,7-dihydropyrazolo[1,5-a]pyrazin-4(5H)-one, 5-(6-methoxypyrazin-2-yl)-2-(phenoxymethyl)-6,7-dihydropyrazolo[1,5-a]pyrazin-4(5H)-one, 5-(4-methoxypyrimidin-5-yl)-2-(phenoxymethyl)-6,7-dihydropyrazolo[1,5-a]pyrazin-4(5H)-one, 5-(6-methoxy-2-methylpyridin-3-yl)-2-(phenoxymethyl)-6,7-dihydropyrazolo[1,5-a]pyrazin-4(5H)-one, 5-(4-methoxypyridin-2-yl)-2-(phenoxymethyl)-6,7-dihydropyrazolo[1,5-a]pyrazin-4(5H)-one, 5-(2,6-dimethylpyridin-3-yl)-2-(phenoxymethyl)-6,7-dihydropyrazolo[1,5-a]pyrazin-4(5H)-one, 5-(3-methylpyrazin-2-yl)-2-(phenoxymethyl)-6,7-dihydropyrazolo[1,5-a]pyrazin-4(5H)-one, 5-(5-methoxypyrimidin-4-yl)-2-(phenoxymethyl)-6,7-dihydropyrazolo[1,5-a]pyrazin-4(5H)-one, 5-(5-methoxy-2-methylpyrimidin-4-yl)-2-(phenoxymethyl)-6,7-dihydropyrazolo[1,5-a]pyrazin-4(5H)-one, 5-(3,6-dimethylpyrazin-2-yl)-2-(phenoxymethyl)-6,7-dihydropyrazolo[1,5-a]pyrazin-4(5H)-one, 5-[6-(methoxymethyl)pyridin-2-yl]-2-(phenoxymethyl)-6,7-dihydropyrazolo[1,5-a]pyrazin-4(5H)-one, 5-(2,6-dimethoxypyrimidin-4-yl)-2-(phenoxymethyl)-6,7-dihydropyrazolo[1,5-a]pyrazin-4(5H)-one, 5-(5-chloropyrimidin-2-yl)-2-(phenoxymethyl)-6,7-dihydropyrazolo[1,5-a]pyrazin-4(5H)-one, 5-(6-chloro-4-methoxypyridazin-3-yl)-2-(phenoxymethyl)-6,7-dihydropyrazolo[1,5-a]pyrazin-4(5H)-one, 5-(5-methoxypyridazin-3-yl)-2-(phenoxymethyl)-6,7-dihydropyrazolo[1,5-a]pyrazin-4(5H)-one, 5-(5-fluoropyrimidin-2-yl)-2-(phenoxymethyl)-6,7-dihydropyrazolo[1,5-a]pyrazin-4(5H)-one, 5-(4,6-dimethoxypyrimidin-2-yl)-2-(phenoxymethyl)-6,7-dihydropyrazolo[1,5-a]pyrazin-4(5H)-one, (7*S)-5-(cyclopropylmethyl)-7-methyl-2-(phenoxymethyl)-6,7-dihydropyrazolo[1,5-a]pyrazin-4(5H)-one, (7*R)-5-(cyclopropylmethyl)-7-methyl-2-(phenoxymethyl)-6,7-dihydropyrazolo[1,5-a]pyrazin-4(5H)-one, (7*S)-5-(4-fluorophenyl)-7-methyl-2-(phenoxymethyl)-6,7-dihydropyrazolo[1,5-a]pyrazin-4(5H)-one, (7*R)-5-(4-fluorophenyl)-7-methyl-2-(phenoxymethyl)-6,7-dihydropyrazolo[1,5-a]pyrazin-4(5H)-one, (7*S)-5-(5-fluoropyridin-2-yl)-7-methyl-2-(phenoxymethyl)-6,7-dihydropyrazolo[1,5-a]pyrazin-4(5H)-one, (7*R)-5-(5-fluoropyridin-2-yl)-7-methyl-2-(phenoxymethyl)-6,7-dihydropyrazolo[1,5-a]pyrazin-4(5H)-one, (7*S)-5-(5-fluoro-6-methylpyridin-2-yl)-7-methyl-2-(phenoxymethyl)-6,7-dihydropyrazolo[1,5-a]pyrazin-4(5H)-one, (7*R)-5-(5-fluoro-6-methylpyridin-2-yl)-7-methyl-2-(phenoxymethyl)-6,7-dihydropyrazolo[1,5-a]pyrazin-4(5H)-one, (6S)-5-(cyclopropylmethyl)-6-methyl-2-(phenoxymethyl)-6,7-dihydropyrazolo[1,5-a]pyrazin-4(5H)-one, (6R)-5-(cyclopropylmethyl)-6-methyl-2-(phenoxymethyl)-6,7-dihydropyrazolo[1,5-a]pyrazin-4(5H)-one, (6S)-5-(5-fluoro-6-methylpyridin-2-yl)-6-methyl-2-(phenoxymethyl)-6,7-dihydropyrazolo[1,5-a]pyrazin-4(5H)-one, (6S)-5-(5-fluoropyridin-2-yl)-6-methyl-2-(phenoxymethyl)-6,7-dihydropyrazolo[1,5-a]pyrazin-4(5H)-one, (6R)-5-(5-fluoro-6-methylpyridin-2-yl)-6-methyl-2-(phenoxymethyl)-6,7-dihydropyrazolo[1,5-a]pyrazin-4(5H)-one, (6R)-5-(5-fluoropyridin-2-yl)-6-methyl-2-(phenoxymethyl)-6,7-dihydropyrazolo[1,5-a]pyrazin-4(5H)-one, (6R)-5-(4-fluorophenyl)-6-methyl-2-(phenoxymethyl)-6,7-dihydropyrazolo[1,5-a]pyrazin-4(5H)-one, (6R)-5-(4-fluoro-3-methoxyphenyl)-6-methyl-2-(phenoxymethyl)-6,7-dihydropyrazolo[1,5-a]pyrazin-4(5H)-one, (6R)-5-(4-fluoro-3-methylphenyl)-6-methyl-2-(phenoxymethyl)-6,7-dihydropyrazolo[1,5-a]pyrazin-4(5H)-one, (6R)-5-(2-methoxypyrimidin-4-yl)-6-methyl-2-(phenoxymethyl)-6,7-dihydropyrazolo[1,5-a]pyrazin-4(5H)-one, (6R)-5-(6-methoxypyrazin-2-yl)-6-methyl-2-(phenoxymethyl)-6,7-dihydropyrazolo[1,5-a]pyrazin-4(5H)-one, (6R)-5-(5-fluoro-4-methoxypyrimidin-2-yl)-6-methyl-2-(phenoxymethyl)-6,7-dihydropyrazolo[1,5-a]pyrazin-4(5H)-one, (6R)-5-(2-methoxypyridin-3-yl)-6-methyl-2-(phenoxymethyl)-6,7-dihydropyrazolo[1,5-a]pyrazin-4(5H)-one, (6R)-5-(3-methoxypyrazin-2-yl)-6-methyl-2-(phenoxymethyl)-6,7-dihydropyrazolo[1,5-a]pyrazin-4(5H)-one, (6R)-5-(2-methoxyphenyl)-6-methyl-2-(phenoxymethyl)-6,7-dihydropyrazolo[1,5-a]pyrazin-4(5H)-one, (6R)-6-methyl-5-(4-methylphenyl)-2-(phenoxymethyl)-6,7-dihydropyrazolo[1,5-a]pyrazin-4(5H)-one, (6R)-5-(3-methoxyphenyl)-6-methyl-2-(phenoxymethyl)-6,7-dihydropyrazolo[1,5-a]pyrazin-4(5H)-one, (6R)-6-methyl-5-(3-methylphenyl)-2-(phenoxymethyl)-6,7-dihydropyrazolo[1,5-a]pyrazin-4

(5H)-one, (6R)-6-methyl-5-(2-methylphenyl)-2-(phenoxymethyl)-6,7-dihydropyrazolo[1,5-a]pyrazin-4(5H)-one, (6R)-5-(5-fluoro-4-methylpyridin-2-yl)-6-methyl-2-(phenoxymethyl)-6,7-dihydropyrazolo[1,5-a]pyrazin-4(5H)-one, (6R)-5-(4-methoxy-5-methylpyrimidin-2-yl)-6-methyl-2-(phenoxymethyl)-6,7-dihydropyrazolo[1,5-a]pyrazin-4(5H)-one, (6S)-5-(4-fluorophenyl)-6-methyl-2-(phenoxymethyl)-6,7-dihydropyrazolo[1,5-a]pyrazin-4(5H)-one, 5-(4-fluorophenyl)-2-[(pyridin-3-yloxy)methyl]-6,7-dihydropyrazolo[1,5-a]pyrazin-4(5H)-one, 5-(4-fluorophenyl)-2-[(pyridin-2-yloxy)methyl]-6,7-dihydropyrazolo[1,5-a]pyrazin-4(5H)-one, 5-(4-fluorophenyl)-2-[(pyridin-4-yloxy)methyl]-6,7-dihydropyrazolo[1,5-a]pyrazin-4(5H)-one, 5-(4-fluorophenyl)-2-{[(5-fluoropyridin-3-yl)oxy]methyl}-6,7-dihydropyrazolo[1,5-a]pyrazin-4(5H)-one, 5-(cyclopropylmethyl)-2-[(pyridin-2-yloxy)methyl]-6,7-dihydropyrazolo[1,5-a]pyrazin-4(5H)-one, 5-(cyclopropylmethyl)-2-[(pyridin-4-yloxy)methyl]-6,7-dihydropyrazolo[1,5-a]pyrazin-4(5H)-one, 3-{[5-(cyclopropylmethyl)-4-oxo-4,5,6,7-tetrahydropyrazolo[1,5-a]pyrazin-2-yl]methoxy}benzonitrile, 2-[(4-fluorophenoxy)methyl]-5-(4-fluorophenyl)-6,7-dihydropyrazolo[1,5-a]pyrazin-4(5H)-one, 5-(4-fluorophenyl)-2-[(3-methylphenoxy)methyl]-6,7-dihydropyrazolo[1,5-a]pyrazin-4(5H)-one, 5-(cyclopropylmethyl)-2-[(4-fluorophenoxy)methyl]-6,7-dihydropyrazolo[1,5-a]pyrazin-4(5H)-one, 5-(cyclopropylmethyl)-2-[(3-methylphenoxy)methyl]-6,7-dihydropyrazolo[1,5-a]pyrazin-4(5H)-one, 3-{[5-(4-fluorophenyl)-4-oxo-4,5,6,7-tetrahydropyrazolo[1,5-a]pyrazin-2-yl]methoxy}benzonitrile, 5-(cyclopropylmethyl)-2-[(pyridin-3-yloxy)methyl]-6,7-dihydropyrazolo[1,5-a]pyrazin-4(5H)-one, 5-(cyclopropylmethyl)-2-{[(5-fluoropyridin-3-yl)oxy]methyl}-6,7-dihydropyrazolo[1,5-a]pyrazin-4(5H)-one, 5-(5-fluoropyridin-2-yl)-2-[(pyridin-2-yloxy)methyl]-6,7-dihydropyrazolo[1,5-a]pyrazin-4(5H)-one, 5-(4-fluorophenyl)-2-{[(6-methylpyridin-2-yl)oxy]methyl}-6,7-dihydropyrazolo[1,5-a]pyrazin-4(5H)-one, 5-(4-fluorophenyl)-2-{[(2-methylpyridin-4-yl)oxy]methyl}-6,7-dihydropyrazolo[1,5-a]pyrazin-4(5H)-one, 2-{[(2,6-dimethylpyridin-4-yl)oxy]methyl}-5-(4-fluorophenyl)-6,7-dihydropyrazolo[1,5-a]pyrazin-4(5H)-one, 5-(5-fluoropyridin-2-yl)-2-[(pyridin-4-yloxy)methyl]-6,7-dihydropyrazolo[1,5-a]pyrazin-4(5H)-one, 5-(5-fluoropyridin-2-yl)-2-[(3-methylphenoxy)methyl]-6,7-dihydropyrazolo[1,5-a]pyrazin-4(5H)-one, 2-[(3-fluorophenoxy)methyl]-5-(5-fluoropyridin-2-yl)-6,7-dihydropyrazolo[1,5-a]pyrazin-4(5H)-one, 2-[(4-fluorophenoxy)methyl]-5-(5-fluoropyridin-2-yl)-6,7-dihydropyrazolo[1,5-a]pyrazin-4(5H)-one, 2-{[(5-fluoro-4-methylpyridin-2-yl)oxy]methyl}-5-(4-fluorophenyl)-6,7-dihydropyrazolo[1,5-a]pyrazin-4(5H)-one, 5-(4-fluorophenyl)-2-{[(5-fluoropyridin-2-yl)oxy]methyl}-6,7-dihydropyrazolo[1,5-a]pyrazin-4(5H)-one, 5-(4-fluorophenyl)-2-{[(2-methylpyrimidin-4-yl)oxy]methyl}-6,7-dihydropyrazolo[1,5-a]pyrazin-4(5H)-one, 5-(4-fluorophenyl)-2-{[(5-methylpyridin-2-yl)oxy]methyl}-6,7-dihydropyrazolo[1,5-a]pyrazin-4(5H)-one, 5-(4-fluorophenyl)-2-{[(4-methylpyridin-2-yl)oxy]methyl}-6,7-dihydropyrazolo[1,5-a]pyrazin-4(5H)-one, 5-(4-fluorophenyl)-2-{[(3-methylpyridin-2-yl)oxy]methyl}-6,7-dihydropyrazolo[1,5-a]pyrazin-4(5H)-one, 5-(4-fluorophenyl)-2-{[(4-methylpyrimidin-2-yl)oxy]methyl}-6,7-dihydropyrazolo[1,5-a]pyrazin-4(5H)-one, 5-(4-fluorophenyl)-2-{[(3-fluoropyridin-2-yl)oxy]methyl}-6,7-dihydropyrazolo[1,5-a]pyrazin-4(5H)-one, 2-[(3-fluorophenoxy)methyl]-5-(4-fluorophenyl)-6,7-dihydropyrazolo[1,5-a]pyrazin-4(5H)-one, 5-(4-fluorophenyl)-2-{[(3-methylpyridin-4-yl)oxy]methyl}-6,7-dihydropyrazolo[1,5-a]pyrazin-4(5H)-one, 2-[(2-fluorophenoxy)methyl]-5-(4-fluorophenyl)-6,7-dihydropyrazolo[1,5-a]pyrazin-4(5H)-one, 5-(4-fluorophenyl)-2-[(2-methylphenoxy)methyl]-6,7-dihydropyrazolo[1,5-a]pyrazin-4(5H)-one, 5-(4-fluorophenyl)-2-[(4-methylphenoxy)methyl]-6,7-dihydropyrazolo[1,5-a]pyrazin-4(5H)-one, 2-{[5-(4-fluorophenyl)-4-oxo-4,5,6,7-tetrahydropyrazolo[1,5-a]pyrazin-2-yl]methoxy}pyridine-4-carbonitrile, 5-(4-fluorophenyl)-2-[(pyrimidin-2-yloxy)methyl]-6,7-dihydropyrazolo[1,5-a]pyrazin-4(5H)-one, 5-(4-fluorophenyl)-2-{[(4-methoxypyridin-2-yl)oxy]methyl}-6,7-dihydropyrazolo[1,5-a]pyrazin-4(5H)-one, 5-(4-fluorophenyl)-2-{[(6-methylpyrimidin-4-yl)oxy]methyl}-6,7-dihydropyrazolo[1,5-a]pyrazin-4(5H)-one, 5-(4-fluorophenyl)-2-[(pyrazin-2-yloxy)methyl]-6,7-dihydropyrazolo[1,5-a]pyrazin-4(5H)-one, 2-{[(3-fluoro-4-methylpyridin-2-yl)oxy]methyl}-5-(4-fluorophenyl)-6,7-dihydropyrazolo[1,5-a]pyrazin-4(5H)-one, 5-(4-fluorophenyl)-2-[(pyrimidin-4-yloxy)methyl]-6,7-dihydropyrazolo[1,5-a]pyrazin-4(5H)-one, 5-(4-fluorophenyl)-2-{[(6-methylpyrazin-2-yl)oxy]methyl}-6,7-dihydropyrazolo[1,5-a]pyrazin-4(5H)-one, 5-(4-fluorophenyl)-2-[(pyridazin-4-yloxy)methyl]-6,7-dihydropyrazolo[1,5-a]pyrazin-4(5H)-one, 5-(4-fluorophenyl)-2-[(pyridazin-3-yloxy)methyl]-6,7-dihydropyrazolo[1,5-a]pyrazin-4(5H)-one, 5-(4-fluoro-3-methylphenyl)-2-[(pyridin-2-yloxy)methyl]-6,7-dihydropyrazolo[1,5-a]pyrazin-4(5H)-one, 5-(4-fluoro-3-methoxyphenyl)-2-[(pyridin-2-yloxy)methyl]-6,7-dihydropyrazolo[1,5-a]pyrazin-4(5H)-one, 5-(5-fluoro-6-methylpyridin-2-yl)-2-[(pyridin-2-yloxy)methyl]-6,7-dihydropyrazolo[1,5-a]pyrazin-4(5H)-one, 5-(6-methylpyridin-2-yl)-2-[(pyridin-2-yloxy)methyl]-6,7-dihydropyrazolo[1,5-a]pyrazin-4(5H)-one, 5-[6-(1-methylethyl)pyridin-2-yl]-2-[(pyridin-2-yloxy)methyl]-6,7-dihydropyrazolo[1,5-a]pyrazin-4(5H)-one, 5-(3-fluoro-6-methoxypyridin-2-yl)-2-[(pyridin-2-yloxy)methyl]-6,7-dihydropyrazolo[1,5-a]pyrazin-4(5H)-one, 5-(5-fluoro-4-methoxypyrimidin-2-yl)-2-[(pyridin-2-yloxy)methyl]-6,7-dihydropyrazolo[1,5-a]pyrazin-4(5H)-one, 5-(2-methoxypyrimidin-4-yl)-2-[(pyridin-2-yloxy)methyl]-6,7-dihydropyrazolo[1,5-a]pyrazin-4(5H)-one, 5-(2-methoxypyridin-3-yl)-2-[(pyridin-2-yloxy)methyl]-6,7-dihydropyrazolo[1,5-a]pyrazin-4(5H)-one, 5-(3-methoxypyrazin-2-yl)-2-[(pyridin-2-yloxy)methyl]-6,7-dihydropyrazolo[1,5-a]pyrazin-4(5H)-one, 5-(6-methoxypyrazin-2-yl)-2-[(pyridin-2-yloxy)methyl]-6,7-dihydropyrazolo[1,5-a]pyrazin-4(5H)-one, 5-(2-methoxyphenyl)-2-[(pyridin-2-yloxy)methyl]-6,7-dihydropyrazolo[1,5-a]pyrazin-4(5H)-one, 5-(5-fluoro-4-methylpyridin-2-yl)-2-[(pyridin-2-yloxy)methyl]-6,7-dihydropyrazolo[1,5-a]pyrazin-4(5H)-one, 5-(3-methylphenyl)-2-[(pyridin-2-yloxy)methyl]-6,7-dihydropyrazolo[1,5-a]pyrazin-4(5H)-one, 5-(4-methoxy-5-methylpyrimidin-2-yl)-2-[(pyridin-2-yloxy)methyl]-6,7-dihydropyrazolo[1,5-a]pyrazin-4(5H)-one, 5-(4-methylphenyl)-2-[(pyridin-2-yloxy)methyl]-6,7-dihydropyrazolo[1,5-a]pyrazin-4(5H)-one, 5-(2-methylphenyl)-2-[(pyridin-2-yloxy)methyl]-6,7-dihydropyrazolo[1,5-a]pyrazin-4(5H)-one, 2-[(4-fluorophenoxy)methyl]-5-(3-methoxyphenyl)-6,7-dihydropyrazolo[1,5-a]pyrazin-4(5H)-one, 2-[(4-fluorophenoxy)methyl]-5-(2-methoxyphenyl)-6,7-dihydropyrazolo[1,5-a]pyrazin-4(5H)-one, 2-[(4-fluorophenoxy)methyl]-5-(4-methylphenyl)-6,7-dihydropyrazolo[1,5-a]pyrazin-4(5H)-one, 2-[(4-fluorophenoxy)methyl]-5-(2-methylphenyl)-6,7- dihydropyrazolo[1,5-a]pyrazin-4(5H)-one, 2-[(4-fluorophenoxy)methyl]-5-(3-methylphenyl)-6,7-dihydropyrazolo[1,5-a]pyrazin-4(5H)-one, 5-(4-fluoro-3-methylphenyl)-2-[(4-fluorophenoxy)methyl]-6,7-dihydropyrazolo[1,5-a]pyrazin-4(5H)-one, 2-[(4-fluorophenoxy)methyl]-5-(3-methoxypyrazin-2-yl)-6,7-dihydropyrazolo[1,5-a]pyrazin-4(5H)-one, 2-[(4-fluorophenoxy)methyl]-5-(2-methoxypyrimidin-4-yl)-6,7-dihydropyrazolo[1,5-a]pyrazin-4(5H)-one, 5-(4-fluoro-3-methoxyphenyl)-2-[(4-fluorophenoxy)methyl]-6,7-dihydropyrazolo[1,5-a]pyrazin-4(5H)-one, 2-[(4-fluorophenoxy)methyl]-5-(2-methoxypyridin-3-yl)-6,7-dihydropyrazolo[1,5-a]pyrazin-4(5H)-one, 2-[(4-fluorophenoxy)methyl]-5-(4-methoxy-5-methylpyrimidin-2-yl)-6,7-dihydropyrazolo[1,5-a]pyrazin-4(5H)-one, 2-[(4-fluorophenoxy)methyl]-5-(6-methoxypyrazin-2-yl)-6,7-dihydropyrazolo[1,5-a]pyrazin-4(5H)-one, 5-(5-fluoro-4-methylpyridin-2-yl)-2-[(4-fluorophenoxy)methyl]-6,7-dihydropyrazolo[1,5-a]pyrazin-4(5H)-one, 3-{[5-(5-fluoropyridin-2-yl)-4-oxo-4,5,6,7-tetrahydropyrazolo[1,5-a]pyrazin-2-yl]methoxy}benzonitrile, 2-[(4-fluorophenoxy)methyl]-5-(4-fluorophenyl)-7-methyl-6,7-dihydropyrazolo[1,5-a]pyrazin-4(5H)-one, 2-[(4-fluorophenoxy)methyl]-5-(3-fluorophenyl)-7-methyl-6,7-dihydropyrazolo[1,5-a]pyrazin-4(5H)-one, 5-(5-fluoro-6-methylpyridin-2-yl)-2-[(4-fluorophenoxy)methyl]-7-methyl-6,7-dihydropyrazolo[1,5-a]pyrazin-4(5H)-one, 2-[(4-fluorophenoxy)methyl]-5-(5-fluoropyridin-2-yl)-7-methyl-6,7-dihydropyrazolo[1,5-a]pyrazin-4(5H)-one, (7*S)-2-[(4-fluorophenoxy)methyl]-5-(4-fluorophenyl)-7-methyl-6,7-dihydropyrazolo[1,5-a]pyrazin-4(5H)-one, (7*S)-2-[(3-fluorophenoxy)methyl]-5-(4-fluorophenyl)-7-methyl-6,7-dihydropyrazolo[1,5-a]pyrazin-4(5H)-one, (7*R)-5-(4-fluorophenyl)-7-methyl-2-[(pyridin-2-yloxy)methyl]-6,7-dihydropyrazolo[1,5-a]pyrazin-4(5H)-one, 3-{[(7*R)-5-(4-fluorophenyl)-7-methyl-4-oxo-4,5,6,7-tetrahydropyrazolo[1,5-a]pyrazin-2-yl]methoxy}benzonitrile, (7*R)-5-(4-fluorophenyl)-7-methyl-2-[(3-methylphenoxy)methyl]-6,7-dihydropyrazolo[1,5-a]pyrazin-4(5H)-one, (6R)-5-(4-fluorophenyl)-6-methyl-2-[(3-methylphenoxy)methyl]-6,7-dihydropyrazolo[1,5-a]pyrazin-4(5H)-one, (6R)-2-[(3-fluorophenoxy)methyl]-5-(4-fluorophenyl)-6-methyl-6,7-dihydropyrazolo[1,5-a]pyrazin-4(5H)-one, (6R)-2-[(4-fluorophenoxy)methyl]-5-(4-fluorophenyl)-6-methyl-6,7-dihydropyrazolo[1,5-a]pyrazin-4(5H)-one, 3-{[(6R)-5-(4-fluorophenyl)-6-methyl-4-oxo-4,5,6,7-tetrahydropyrazolo[1,5-a]pyrazin-2-yl]methoxy}benzonitrile, (6R)-5-(4-fluorophenyl)-6-methyl-2-[(pyridin-2-yloxy)methyl]-6,7-dihydropyrazolo[1,5-a]pyrazin-4(5H)-one, 2-[(3-fluorophenoxy)methyl]-6,7-dihydropyrazolo[1,5-a]pyrazin-4(5H)-one, 2-[(4-fluorophenoxy)methyl]-6,7-dihydropyrazolo[1,5-a]pyrazin-4(5H)-one, 7-methyl-2-(phenoxymethyl)-6,7-dihydropyrazolo[1,5-a]pyrazin-4(5H)-one, 6-methyl-2-(phenoxymethyl)-6,7-dihydropyrazolo[1,5-a]pyrazin-4(5H)-one, (7*R)-7-methyl-2-(phenoxymethyl)-6,7-dihydropyrazolo[1,5-a]pyrazin-4(5H)-one, (7*S)-7-methyl-2-(phenoxymethyl)-6,7-dihydropyrazolo[1,5-a]pyrazin-4(5H)-one, (6R)-6-methyl-2-(phenoxymethyl)-6,7-dihydropyrazolo[1,5-a]pyrazin-4(5H)-one, (6S)-6-methyl-2-(phenoxymethyl)-6,7-dihydropyrazolo[1,5-a]pyrazin-4(5H)-one, 2-(1-phenoxyethyl)-6,7-dihydropyrazolo[1,5-a]pyrazin-4(5H)-one, 5-(cyclopropylmethyl)-2-(1-phenoxyethyl)-6,7-dihydropyrazolo[1,5-a]pyrazin-4(5H)-one, 5-(4-fluorophenyl)-2-(1-phenoxyethyl)-6,7-dihydropyrazolo[1,5-a]pyrazin-4(5H)-one, 3-chloro-5-(cyclopropylmethyl)-2-(phenoxymethyl)-6,7-dihydropyrazolo[1,5-a]pyrazin-4(5H)-one, 3-chloro-5-(4-fluorophenyl)-2-(phenoxymethyl)-6,7-dihydropyrazolo[1,5-a]pyrazin-4(5H)-one, 5-(cyclopropylmethyl)-3-methyl-2-(phenoxymethyl)-6,7-dihydropyrazolo[1,5-a]pyrazin-4(5H)-one, 5-(4-fluorophenyl)-3-methyl-2-(phenoxymethyl)-6,7-dihydropyrazolo[1,5-a]pyrazin-4(5H)-one, 5-(4-fluorophenyl)-7-(hydroxymethyl)-2-(phenoxymethyl)-6,7-dihydropyrazolo[1,5-a]pyrazin-4(5H)-one, 7-(fluoromethyl)-5-(4-fluorophenyl)-2-(phenoxymethyl)-6,7-dihydropyrazolo[1,5-a]pyrazin-4(5H)-one, (6R)-5-(4-fluorophenyl)-6-(hydroxymethyl)-2-(phenoxymethyl)-6,7-dihydropyrazolo[1,5-a]pyrazin-4(5H)-one, (6R)-6-(fluoromethyl)-5-(4-fluorophenyl)-2-(phenoxymethyl)-6,7-dihydropyrazolo[1,5-a]pyrazin-4(5H)-one, (6R)-5-(4-fluorophenyl)-6-(methoxymethyl)-2-(phenoxymethyl)-6,7-dihydropyrazolo[1,5-a]pyrazin-4(5H)-one, (6S)-5-(4-fluorophenyl)-6-(hydroxymethyl)-2-(phenoxymethyl)-6,7-dihydropyrazolo[1,5-a]pyrazin-4(5H)-one, (6S)-6-(fluoromethyl)-5-(4-fluorophenyl)-2-(phenoxymethyl)-6,7-dihydropyrazolo[1,5-a]pyrazin-4(5H)-one, (6S)-5-(4-fluorophenyl)-6-(methoxymethyl)-2-(phenoxymethyl)-6,7-dihydropyrazolo[1,5-a]pyrazin-4(5H)-one, 7-fluoro-5-(4-fluorophenyl)-2-(phenoxymethyl)-6,7-dihydropyrazolo[1,5-a]pyrazin-4(5H)-one, (7*R)-7-fluoro-5-(4-fluorophenyl)-2-(phenoxymethyl)-6,7-dihydropyrazolo[1,5-a]pyrazin-4(5H)-one, (7*S)-7-fluoro-5-(4-fluorophenyl)-2-(phenoxymethyl)-6,7-dihydropyrazolo[1,5-a]pyrazin-4(5H)-one, 2-(phenoxymethyl)-5-[6-(tetrahydro-2H-pyran-4-yl)pyridin-2-yl]-6,7-dihydropyrazolo[1,5-a]pyrazin-4(5H)-one, 2-(phenoxymethyl)-5-(6-piperidin-4-ylpyridin-2-yl)-6,7-dihydropyrazolo[1,5-a]pyrazin-4(5H)-one, 5-[4-(dimethylamino)pyrimidin-2-yl]-2-(phenoxymethyl)-6,7-dihydropyrazolo[1,5-a]pyrazin-4(5H)-one, 5-[4-(methylamino)pyrimidin-2-yl]-2-(phenoxymethyl)-6,7-dihydropyrazolo[1,5-a]pyrazin-4(5H)-one, 5-[6-(methylamino)pyridin-2-yl]-2-(phenoxymethyl)-6,7-dihydropyrazolo[1,5-a]pyrazin-4(5H)-one, 5-[5-fluoro-4-(methylamino)pyrimidin-2-yl]-2-(phenoxymethyl)-6,7-dihydropyrazolo[1,5-a]pyrazin-4(5H)-one, 5-[6-(dimethylamino)pyrazin-2-yl]-2-(phenoxymethyl)-6,7-dihydropyrazolo[1,5-a]pyrazin-4(5H)-one, 2-(phenoxymethyl)-5-(6-pyrrolidin-1-ylpyridin-2-yl)-6,7-dihydropyrazolo[1,5-a]pyrazin-4(5H)-one, 5-[4-(dimethylamino)pyridin-2-yl]-2-(phenoxymethyl)-6,7-dihydropyrazolo[1,5-a]pyrazin-4(5H)-one, 5-[6-(dimethylamino)-3-fluoropyridin-2-yl]-2-(phenoxymethyl)-6,7-dihydropyrazolo[1,5-a]pyrazin-4(5H)-one, 5-[6-(dimethylamino)pyridazin-3-yl]-2-(phenoxymethyl)-6,7-dihydropyrazolo[1,5-a]pyrazin-4(5H)-one, 5-(6-Aminopyridin-2-yl)-2-(phenoxymethyl)-6,7-dihydropyrazolo[1,5-a]pyrazin-4(5H)-one, 5-[6-(dimethylamino)pyridin-2-yl]-2-(phenoxymethyl)-6,7-dihydropyrazolo[1,5-a]pyrazin-4(5H)-one, 5-[5-(dimethylamino)pyridin-2-yl]-2-(phenoxymethyl)-6,7-dihydropyrazolo[1,5-a]pyrazin-4(5H)-one, 5-[3-(dimethylamino)pyrazin-2-yl]-2-(phenoxymethyl)-6,7-dihydropyrazolo[1,5-a]pyrazin-4(5H)-one, 5-[3-(dimethylamino)pyridin-2-yl]-2-(phenoxymethyl)-6,7-dihydropyrazolo[1,5-a]pyrazin-4(5H)-one, 5-[6-(dimethylamino)-4-methylpyridin-2-yl]-2-(phenoxymethyl)-6,7-dihydropyrazolo[1,5-a]pyrazin-4(5H)-one, 5-[6-(dimethylamino)-3-methylpyridin-2-yl]-2-(phenoxymethyl)-6,7-dihydropyrazolo[1,5-a]pyrazin-4(5H)-one, 5-[6-(dimethylamino)-5-methylpyridin-2-yl]-2-(phenoxymethyl)-6,7-dihydropyrazolo[1,5-a]pyrazin-4(5H)-one, 5-[5-(dimethylamino)pyrazin-2-yl]-2-(phenoxymethyl)-6,7-dihydropyrazolo[1,5-a]pyrazin-4(5H)-one, 5-(2-methoxy-6-methylpyridin-3-yl)-2-

(phenoxymethyl)-6,7-dihydropyrazolo[1,5-a]pyrazin-4(5H)-one, 5-(5-chloro-4-methoxypyrimidin-2-yl)-2-(phenoxymethyl)-6,7-dihydropyrazolo[1,5-a]pyrazin-4(5H)-one, 5-(6-chloro-5-methoxypyridin-3-yl)-2-(phenoxymethyl)-6,7-dihydropyrazolo[1,5-a]pyrazin-4(5H)-one, 5-(3-fluoro-5-methylphenyl)-2-(phenoxymethyl)-6,7-dihydropyrazolo[1,5-a]pyrazin-4(5H)-one, 5-(2-methoxy-5-methylpyridin-3-yl)-2-(phenoxymethyl)-6,7-dihydropyrazolo[1,5-a]pyrazin-4(5H)-one, 5-(3-fluoro-5-methoxyphenyl)-2-(phenoxymethyl)-6,7-dihydropyrazolo[1,5-a]pyrazin-4(5H)-one, 5-(3-methoxy-5-methylpyrazin-2-yl)-2-(phenoxymethyl)-6,7-dihydropyrazolo[1,5-a]pyrazin-4(5H)-one, 5-(5,6-dimethoxypyridin-2-yl)-2-(phenoxymethyl)-6,7-dihydropyrazolo[1,5-a]pyrazin-4(5H)-one, 5-(6-methoxy-5-methylpyrazin-2-yl)-2-(phenoxymethyl)-6,7-dihydropyrazolo[1,5-a]pyrazin-4(5H)-one, 5-(6-chloro-4-methoxypyridazin-3-yl)-2-(phenoxymethyl)-6,7-dihydropyrazolo[1,5-a]pyrazin-4(5H)-one, 5-[4-fluoro-2-(methoxymethyl)phenyl]-2-(phenoxymethyl)-6,7-dihydropyrazolo[1,5-a]pyrazin-4(5H)-one, 5-[6-(dimethylamino)-5-fluoropyridin-2-yl]-2-(phenoxymethyl)-6,7-dihydropyrazolo[1,5-a]pyrazin-4(5H)-one, 5-(4-methoxypyridin-3-yl)-2-(phenoxymethyl)-6,7-dihydropyrazolo[1,5-a]pyrazin-4(5H)-one, 5-(4-methylpyrimidin-5-yl)-2-(phenoxymethyl)-6,7-dihydropyrazolo[1,5-a]pyrazin-4(5H)-one, 5-(5-fluoro-2-methoxypyrimidin-4-yl)-2-(phenoxymethyl)-6,7-dihydropyrazolo[1,5-a]pyrazin-4(5H)-one, 2-(phenoxymethyl)-5-(4-pyrrolidin-1-ylpyrimidin-2-yl)-6,7-dihydropyrazolo[1,5-a]pyrazin-4(5H)-one, 2-({[6-(dimethylamino)pyridin-2-yl]oxy}methyl)-5-(4-fluorophenyl)-6,7-dihydropyrazolo[1,5-a]pyrazin-4(5H)-one, 5-(4-fluorophenyl)-2-({[6-(methylamino)pyridin-2-yl]oxy}methyl)-6,7-dihydropyrazolo[1,5-a]pyrazin-4(5H)-one, 2-({[4-(dimethylamino)pyridin-2-yl]oxy}methyl)-5-(4-fluorophenyl)-6,7-dihydropyrazolo[1,5-a]pyrazin-4(5H)-one, 5-[6-(dimethylamino)pyridin-2-yl]-2-[(pyridin-2-yloxy)methyl]-6,7-dihydropyrazolo[1,5-a]pyrazin-4(5H)-one, 5-[6-(dimethylamino)-3-fluoropyridin-2-yl]-2-[(pyridin-2-yloxy)methyl]-6,7-dihydropyrazolo[1,5-a]pyrazin-4(5H)-one, 5-(3-methoxyphenyl)-2-[(pyridin-2-yloxy)methyl]-6,7-dihydropyrazolo[1,5-a]pyrazin-4(5H)-one, 5-[6-(dimethylamino)pyridin-2-yl]-2-[(3-fluorophenoxy)methyl]-6,7-dihydropyrazolo[1,5-a]pyrazin-4(5H)-one, 5-[6-(dimethylamino)pyridin-2-yl]-2-[(4-fluorophenoxy)methyl]-6,7-dihydropyrazolo[1,5-a]pyrazin-4(5H)-one, 5-(5-fluoro-4-methoxypyrimidin-2-yl)-2-[(4-fluorophenoxy)methyl]-6,7-dihydropyrazolo[1,5-a]pyrazin-4(5H)-one, 5-(5-methylthiophen-2-yl)-2-(phenoxymethyl)-6,7-dihydropyrazolo[1,5-a]pyrazin-4(5H)-one, 5-(1-methyl-1H-pyrazol-4-yl)-2-(phenoxymethyl)-6,7-dihydropyrazolo[1,5-a]pyrazin-4(5H)-one, 5-(1-methyl-1H-imidazol-4-yl)-2-(phenoxymethyl)-6,7-dihydropyrazolo[1,5-a]pyrazin-4(5H)-one, 5-(5-methyl-1H-pyrazol-4-yl)-2-(phenoxymethyl)-6,7-dihydropyrazolo[1,5-a]pyrazin-4(5H)-one, 5-(5-methoxythiophen-2-yl)-2-(phenoxymethyl)-6,7-dihydropyrazolo[1,5-a]pyrazin-4(5H)-one, 5-(1,3-benzoxazol-2-yl)-2-(phenoxymethyl)-6,7-dihydropyrazolo[1,5-a]pyrazin-4(5H)-one, 7-Hydroxy-2-(phenoxymethyl)-6,7-dihydropyrazolo[1,5-a]pyrazin-4(5H)-one, 7,7-dimethyl-2-(phenoxymethyl)-6,7-dihydropyrazolo[1,5-a]pyrazin-4(5H)-one, 2-[(4-chlorophenoxy)methyl]-5-(cyclopropylmethyl)-6,7-dihydropyrazolo[1,5-a]pyrazin-4(5H)-one, 5-(6-Bromopyridin-2-yl)-2-(phenoxymethyl)-6,7-dihydropyrazolo[1,5-a]pyrazin-4(5H)-one, 2-[(4-chlorophenoxy)methyl]-6,7-dihydropyrazolo[1,5-a]pyrazin-4(5H)-one, 2-[(4-fluorophenoxy)methyl]-7-methyl-6,7-dihydropyrazolo[1,5-a]pyrazin-4(5H)-one, 2-[(3-methylphenoxy)methyl]-6,7-dihydropyrazolo[1,5-a]pyrazin-4(5H)-one, 2-[(4-chlorophenoxy)methyl]-5-(4-fluorophenyl)-6,7-dihydropyrazolo[1,5-a]pyrazin-4(5H)-one, 3-chloro-2-(phenoxymethyl)-6,7-dihydropyrazolo[1,5-a]pyrazin-4(5H)-one, 5-(2-hydroxy-1-methylethyl)-2-(phenoxymethyl)-6,7-dihydropyrazolo[1,5-a]pyrazin-4(5H)-one, 3-methyl-2-(phenoxymethyl)-6,7-dihydropyrazolo[1,5-a]pyrazin-4(5H)-one, 7-fluoro-2-(phenoxymethyl)-6,7-dihydropyrazolo[1,5-a]pyrazin-4(5H)-one, 3-[(4-oxo-4,5,6,7-tetrahydropyrazolo[1,5-a]pyrazin-2-yl)methoxy]benzonitrile, (6R)-6-(hydroxymethyl)-2-(phenoxymethyl)-6,7-dihydropyrazolo[1,5-a]pyrazin-4(5H)-one, 2-{[(2,6-dimethylpyridin-4-yl)oxy]methyl}-6,7-dihydropyrazolo[1,5-a]pyrazin-4(5H)-one, 2-[(pyridin-2-yloxy)methyl]-6,7-dihydropyrazolo[1,5-a]pyrazin-4(5H)-one, 2-{[(6-methylpyridin-2-yl)oxy]methyl}-6,7-dihydropyrazolo[1,5-a]pyrazin-4(5H)-one, 2-{[(4-methylpyridin-2-yl)oxy]methyl}-6,7-dihydropyrazolo[1,5-a]pyrazin-4(5H)-one, (6S)-6-(hydroxymethyl)-2-(phenoxymethyl)-6,7-dihydropyrazolo[1,5-a]pyrazin-4(5H)-one, 7-methoxy-2-(phenoxymethyl)-6,7-dihydropyrazolo[1,5-a]pyrazin-4(5H)-one, 2-{[(2-methylpyridin-4-yl)oxy]methyl}-6,7-dihydropyrazolo[1,5-a]pyrazin-4(5H)-one, 5-[6-(hydroxymethyl)pyridin-2-yl]-2-(phenoxymethyl)-6,7-dihydropyrazolo[1,5-a]pyrazin-4(5H)-one, 2-[(pyridin-4-yloxy)methyl]-6,7-dihydropyrazolo[1,5-a]pyrazin-4(5H)-one, 2-{[(6-chloropyridazin-3-yl)oxy]methyl}-5-(4-fluorophenyl)-6,7-dihydropyrazolo[1,5-a]pyrazin-4(5H)-one, 2-{[(6-chloropyrimidin-4-yl)oxy]methyl}-5-(4-fluorophenyl)-6,7-dihydropyrazolo[1,5-a]pyrazin-4(5H)-one, 2-{[(6-chloropyridazin-4-yl)oxy]methyl}-5-(4-fluorophenyl)-6,7-dihydropyrazolo[1,5-a]pyrazin-4(5H)-one, 5-(6-methoxypyrimidin-4-yl)-2-(phenoxymethyl)-6,7-dihydropyrazolo[1,5-a]pyrazin-4(5H)-one, 5-(1-methyl-1H-imidazol-5-yl)-2-(phenoxymethyl)-6,7-dihydropyrazolo[1,5-a]pyrazin-4(5H)-one, 5-(5-methoxypyrimidin-2-yl)-2-(phenoxymethyl)-6,7-dihydropyrazolo[1,5-a]pyrazin-4(5H)-one, 5-[6-(chloromethyl)pyridin-2-yl]-2-(phenoxymethyl)-6,7-dihydropyrazolo[1,5-a]pyrazin-4(5H)-one, 5-(5-fluoropyridin-2-yl)-2-[(4-hydroxyphenoxy)methyl]-6,7-dihydropyrazolo[1,5-a]pyrazin-4(5H)-one, 5-(5,6-dimethylpyrazin-2-yl)-2-(phenoxymethyl)-6,7-dihydropyrazolo[1,5-a]pyrazin-4(5H)-one, 5-(4-methylpyrimidin-5-yl)-2-(phenoxymethyl)-6,7-dihydropyrazolo[1,5-a]pyrazin-4(5H)-one, 5-(2-Hydroxy-1-methylethyl)-2-(phenoxymethyl)-6,7-dihydropyrazolo[1,5-a]pyrazin-4(5H)-one, 5-(6-oxo-1,6-dihydropyridin-2-yl)-2-(phenoxymethyl)-6,7-dihydropyrazolo[1,5-a]pyrazin-4(5H)-one, 2-(phenoxymethyl)-5-(quinolin-7-yl)-6,7-dihydropyrazolo[1,5-a]pyrazin-4(5H)-one, 5-(benzo[d]thiazol-5-yl)-2-(phenoxymethyl)-6,7-dihydropyrazolo[1,5-a]pyrazin-4(5H)-one, 2-(phenoxymethyl)-5-(quinolin-3-yl)-6,7-dihydropyrazolo[1,5-a]pyrazin-4(5H)-one, 2-(phenoxymethyl)-5-(quinazolin-6-yl)-6,7-dihydropyrazolo[1,5-a]pyrazin-4(5H)-one, 5-(4-chloroquinolin-6-yl)-2-(phenoxymethyl)-6,7-dihydropyrazolo[1,5-a]pyrazin-4(5H)-one, 5-(6-chloropyridin-2-yl)-2-(phenoxymethyl)-6,7-dihydropyrazolo[1,5-a]pyrazin-4(5H)-one, 5-(2-methyl-2H-indazol-6-yl)-2-(phenoxymethyl)-6,7-dihydropyrazolo[1,5-a]pyrazin-4(5H)-one, 5-(2-methylbenzo[d]thiazol-5-yl)-2-(phenoxymethyl)-6,7-dihydropyrazolo[1,5-a]pyrazin-4(5H)-one, 5-(4-fluoronaphthalen-1-yl)-2-(phenoxymethyl)-6,7-dihydropyrazolo[1,5-a]pyrazin-4(5H)-one, 5-(2-methylquinolin-7-yl)-2-(phenoxymethyl)-6,7-dihydropyrazolo[1,5-a]pyrazin-4(5H)-one, 5-(imidazo[1,2- b]pyridazin-3-yl)-2-(phenoxymethyl)-6,7-dihydropyrazolo[1,5-a]pyrazin-4(5H)-one, 5-(benzo[c][1,2,5]thiadiazol-5-yl)-2-(phenoxymethyl)-6,7-dihydropyrazolo[1,5-a]pyrazin-4(5H)-one, 5-(6-fluoroquinolin-8-yl)-2-(phenoxymethyl)-6,7-dihydropyrazolo[1,5-a]pyrazin-4(5H)-one, 2-(phenoxymethyl)-5-(pyrido[2,3-b]pyrazin-6-yl)-6,7-dihydropyrazolo[1,5-a]pyrazin-4(5H)-one, 5-(imidazo[1,2-a]pyrazin-3-yl)-2-(phenoxymethyl)-6,7-dihydropyrazolo[1,5-a]pyrazin-4(5H)-one, 5-(benzo[c][1,2,5]oxadiazol-5-yl)-2-(phenoxymethyl)-6,7-dihydropyrazolo[1,5-a]pyrazin-4(5H)-one, (*S)-7-methyl-5-(2-methylbenzo[d]thiazol-5-yl)-2-(phenoxymethyl)-6,7-dihydropyrazolo[1,5-a]pyrazin-4(5H)-one, 5-(5-fluoropyridin-2-yl)-2-((2-hydroxyphenoxy)methyl)-6,7-dihydropyrazolo[1,5-a]pyrazin-4(5H)-one, and 2-(phenoxymethyl)pyrazolo[1,5-a]pyrazin-4(5H)-one, or a subgroup thereof. Included within the scope of this list are stereoisomeric forms, the acid addition salts and the solvates thereof. In a further aspect, within the scope of this list are pharmaceutically acceptable salts, hydrates, solvates, and polymorphs thereof.

In one aspect, a compound can be present as: (6R)-5-(2-methoxyphenyl)-6-methyl-2-(phenoxymethyl)-6,7-dihydropyrazolo[1,5-a]pyrazin-4(5H)-one, (6R)-5-(3-methoxyphenyl)-6-methyl-2-(phenoxymethyl)-6,7-dihydropyrazolo[1,5-a]pyrazin-4(5H)-one, (6R)-6-(hydroxymethyl)-2-(phenoxymethyl)-6,7-dihydropyrazolo[1,5-a]pyrazin-4(5H)-one, (6R)-6-methyl-2-(phenoxymethyl)-6,7-dihydropyrazolo[1,5-a]pyrazin-4(5H)-one, (6R)-6-methyl-5-(4-methylphenyl)-2-(phenoxymethyl)-6,7-dihydropyrazolo[1,5-a]pyrazin-4(5H)-one, (6S)-6-(hydroxymethyl)-2-(phenoxymethyl)-6,7-dihydropyrazolo[1,5-a]pyrazin-4(5H)-one, (7*R)-7-methyl-2-(phenoxymethyl)-6,7-dihydropyrazolo[1,5-a]pyrazin-4(5H)-one, (7*S)-7-methyl-2-(phenoxymethyl)-6,7-dihydropyrazolo[1,5-a]pyrazin-4(5H)-one, 2-(1-phenoxyethyl)-6,7-dihydropyrazolo[1,5-a]pyrazin-4(5H)-one, 2-(phenoxymethyl)-5-(4-pyrrolidin-1-ylpyrimidin-2-yl)-6,7-dihydropyrazolo[1,5-a]pyrazin-4(5H)-one, 2-[(3-fluorophenoxy)methyl]-6,7-dihydropyrazolo[1,5-a]pyrazin-4(5H)-one, 2-[(3-methylphenoxy)methyl]-6,7-dihydropyrazolo[1,5-a]pyrazin-4(5H)-one, 2-[(4-chlorophenoxy)methyl]-5-(4-fluorophenyl)-6,7-dihydropyrazolo[1,5-a]pyrazin-4(5H)-one, 2-[(4-chlorophenoxy)methyl]-5-(cyclopropylmethyl)-6,7-dihydropyrazolo[1,5-a]pyrazin-4(5H)-one, 2-[(4-chlorophenoxy)methyl]-6,7-dihydropyrazolo[1,5-a]pyrazin-4(5H)-one, 2-[(4-fluorophenoxy)methyl]-6,7-dihydropyrazolo[1,5-a]pyrazin-4(5H)-one, 2-[(4-fluorophenoxy)methyl]-7-methyl-6,7-dihydropyrazolo[1,5-a]pyrazin-4(5H)-one, 2-[(pyridin-2-yloxy)methyl]-6,7-dihydropyrazolo[1,5-a]pyrazin-4(5H)-one, 2-[(pyridin-4-yloxy)methyl]-6,7-dihydropyrazolo[1,5-a]pyrazin-4(5H)-one, 2-{[(2,6-dimethylpyridin-4-yl)oxy]methyl}-6,7-dihydropyrazolo[1,5-a]pyrazin-4(5H)-one, 2-{[(2-methylpyridin-4-yl)oxy]methyl}-6,7-dihydropyrazolo[1,5-a]pyrazin-4(5H)-one, 2-{[(4-methylpyridin-2-yl)oxy]methyl}-6,7-dihydropyrazolo[1,5-a]pyrazin-4(5H)-one, 2-{[(6-chloropyridazin-3-yl)oxy]methyl}-5-(4-fluorophenyl)-6,7-dihydropyrazolo[1,5-a]pyrazin-4(5H)-one, 2-{[(6-chloropyridazin-4-yl)oxy]methyl}-5-(4-fluorophenyl)-6,7-dihydropyrazolo[1,5-a]pyrazin-4(5H)-one, 2-{[(6-chloropyrimidin-4-yl)oxy]methyl}-5-(4-fluorophenyl)-6,7-dihydropyrazolo[1,5-a]pyrazin-4(5H)-one, 2-{[(6-methylpyridin-2-yl)oxy]methyl}-6,7-dihydropyrazolo[1,5-a]pyrazin-4(5H)-one, 3-[(4-oxo-4,5,6,7-tetrahydropyrazolo[1,5-a]pyrazin-2-yl)methoxy]benzonitrile, 3-chloro-2-(phenoxymethyl)-6,7-dihydropyrazolo[1,5-a]pyrazin-4(5H)-one, 3-methyl-2-(phenoxymethyl)-6,7-dihydropyrazolo[1,5-a]pyrazin-4(5H)-one, 5-(1,3-benzoxazol-2-yl)-2-(phenoxymethyl)-6,7-dihydropyrazolo[1,5-a]pyrazin-4(5H)-one, 5-(2-hydroxy-1-methylethyl)-2-(phenoxymethyl)-6,7-dihydropyrazolo[1,5-a]pyrazin-4(5H)-one, 5-(2-Hydroxy-1-methylethyl)-2-(phenoxymethyl)-6,7-dihydropyrazolo[1,5-a]pyrazin-4(5H)-one, 5-(2-methoxy-6-methylpyridin-3-yl)-2-(phenoxymethyl)-6,7-dihydropyrazolo[1,5-a]pyrazin-4(5H)-one, 5-(2-methoxypyridin-3-yl)-2-[(pyridin-2-yloxy)methyl]-6,7-dihydropyrazolo[1,5-a]pyrazin-4(5H)-one, 5-(3-methoxypyrazin-2-yl)-2-[(pyridin-2-yloxy)methyl]-6,7-dihydropyrazolo[1,5-a]pyrazin-4(5H)-one, 5-(3-methylpyrazin-2-yl)-2-(phenoxymethyl)-6,7-dihydropyrazolo[1,5-a]pyrazin-4(5H)-one, 5-(4-methoxy-5-methylpyrimidin-2-yl)-2-[(pyridin-2-yloxy)methyl]-6,7-dihydropyrazolo[1,5-a]pyrazin-4(5H)-one, 5-(4-methylpyrimidin-5-yl)-2-(phenoxymethyl)-6,7-dihydropyrazolo[1,5-a]pyrazin-4(5H)-one, 5-(5,6-dimethoxypyridin-2-yl)-2-(phenoxymethyl)-6,7-dihydropyrazolo[1,5-a]pyrazin-4(5H)-one, 5-(5-chloro-4-methoxypyrimidin-2-yl)-2-(phenoxymethyl)-6,7-dihydropyrazolo[1,5-a]pyrazin-4(5H)-one, 5-(5-chloropyrimidin-2-yl)-2-(phenoxymethyl)-6,7-dihydropyrazolo[1,5-a]pyrazin-4(5H)-one, 5-(5-fluoro-2-methoxypyrimidin-4-yl)-2-(phenoxymethyl)-6,7-dihydropyrazolo[1,5-a]pyrazin-4(5H)-one, 5-(5-fluoro-4-methylpyridin-2-yl)-2-[(4-fluorophenoxy)methyl]-6,7-dihydropyrazolo[1,5-a]pyrazin-4(5H)-one, 5-(5-fluoro-4-methylpyridin-2-yl)-2-[(pyridin-2-yloxy)methyl]-6,7-dihydropyrazolo[1,5-a]pyrazin-4(5H)-one, 5-(5-fluoropyridin-2-yl)-2-[(4-hydroxyphenoxy)methyl]-6,7-dihydropyrazolo[1,5-a]pyrazin-4(5H)-one, 5-(6-Bromopyridin-2-yl)-2-(phenoxymethyl)-6,7-dihydropyrazolo[1,5-a]pyrazin-4(5H)-one, 5-(6-chloro-4-methoxypyridazin-3-yl)-2-(phenoxymethyl)-6,7-dihydropyrazolo[1,5-a]pyrazin-4(5H)-one, 5-(6-chloro-4-methoxypyridazin-3-yl)-2-(phenoxymethyl)-6,7-dihydropyrazolo[1,5-a]pyrazin-4(5H)-one, 5-(6-methoxypyrimidin-4-yl)-2-(phenoxymethyl)-6,7-dihydropyrazolo[1,5-a]pyrazin-4(5H)-one, 5-(6-oxo-1,6-dihydropyridin-2-yl)-2-(phenoxymethyl)-6,7-dihydropyrazolo[1,5-a]pyrazin-4(5H)-one, 5-[4-fluoro-2-(methoxymethyl)phenyl]-2-(phenoxymethyl)-6,7-dihydropyrazolo[1,5-a]pyrazin-4(5H)-one, 5-[6-(dimethylamino)pyridin-2-yl]-2-[(3-fluorophenoxy)methyl]-6,7-dihydropyrazolo[1,5-a]pyrazin-4(5H)-one, 5-[6-(hydroxymethyl)pyridin-2-yl]-2-(phenoxymethyl)-6,7-dihydropyrazolo[1,5-a]pyrazin-4(5H)-one, 5-[6-(methoxymethyl)pyridin-2-yl]-2-(phenoxymethyl)-6,7-dihydropyrazolo[1,5-a]pyrazin-4(5H)-one, 6-methyl-2-(phenoxymethyl)-6,7-dihydropyrazolo[1,5-a]pyrazin-4(5H)-one, 7,7-dimethyl-2-(phenoxymethyl)-6,7-dihydropyrazolo[1,5-a]pyrazin-4(5H)-one, 7-fluoro-2-(phenoxymethyl)-6,7-dihydropyrazolo[1,5-a]pyrazin-4(5H)-one, and 7-methoxy-2-(phenoxymethyl)-6,7-dihydropyrazolo[1,5-a]pyrazin-4(5H)-one, or a subgroup thereof. Included within the scope of this list are stereoisomeric forms, the acid addition salts and the solvates thereof. In a further aspect, within the scope of this list are pharmaceutically acceptable salts, hydrates, solvates, and polymorphs thereof.

In one aspect, a compound can be present as: 5-(2-methylquinolin-7-yl)-2-(phenoxymethyl)-6,7-dihydropyrazolo[1,5-a]pyrazin-4(5H)-one, 5-(6-methoxy-5-methylpyridin-2-yl)-2-(phenoxymethyl)-6,7-dihydropyrazolo[1,5-a]pyrazin-4(5H)-one, 5-(5-fluoro-6-methoxypyridin-2-yl)-2-(phenoxymethyl)-6,7-dihydropyrazolo[1,5-a]pyrazin-4

(5H)-one, 5-(2,3-dimethylphenyl)-2-(phenoxymethyl)-6,7-dihydropyrazolo[1,5-a]pyrazin-4(5H)-one, 5-(4-fluoro-3-methylphenyl)-2-(phenoxymethyl)-6,7-dihydropyrazolo[1,5-a]pyrazin-4(5H)-one, 5-(6-chloro-5-methoxypyridazin-3-yl)-2-(phenoxymethyl)-6,7-dihydropyrazolo[1,5-a]pyrazin-4(5H)-one, (6R)-6-methyl-5-(2-methylphenyl)-2-(phenoxymethyl)-6,7-dihydropyrazolo[1,5-a]pyrazin-4(5H)-one, 5-(1-methyl-1H-pyrazol-4-yl)-2-(phenoxymethyl)-6,7-dihydropyrazolo[1,5-a]pyrazin-4(5H)-one, 5-[5-(dimethylamino)pyridin-2-yl]-2-(phenoxymethyl)-6,7-dihydropyrazolo[1,5-a]pyrazin-4(5H)-one, (6R)-5-(4-fluoro-3-methylphenyl)-6-methyl-2-(phenoxymethyl)-6,7-dihydropyrazolo[1,5-a]pyrazin-4(5H)-one, 5-(6-fluoroquinolin-8-yl)-2-(phenoxymethyl)-6,7-dihydropyrazolo[1,5-a]pyrazin-4(5H)-one, 5-(6-methoxypyridin-2-yl)-2-(phenoxymethyl)-6,7-dihydropyrazolo[1,5-a]pyrazin-4(5H)-one, 5-[5-(dimethylamino)pyrazin-2-yl]-2-(phenoxymethyl)-6,7-dihydropyrazolo[1,5-a]pyrazin-4(5H)-one, 5-[6-(dimethylamino)pyridin-2-yl]-2-(phenoxymethyl)-6,7-dihydropyrazolo[1,5-a]pyrazin-4(5H)-one, 5-(2-methyl-2H-indazol-6-yl)-2-(phenoxymethyl)-6,7-dihydropyrazolo[1,5-a]pyrazin-4(5H)-one, 5-(4-fluoro-2-methylphenyl)-2-(phenoxymethyl)-6,7-dihydropyrazolo[1,5-a]pyrazin-4(5H)-one, 5-(4-methoxypyridin-3-yl)-2-(phenoxymethyl)-6,7-dihydropyrazolo[1,5-a]pyrazin-4(5H)-one, 5-[6-(dimethylamino)-3-fluoropyridin-2-yl]-2-(phenoxymethyl)-6,7-dihydropyrazolo[1,5-a]pyrazin-4(5H)-one, 5-[6-(dimethylamino)pyridin-2-yl]-2-[(4-fluorophenoxy)methyl]-6,7-dihydropyrazolo[1,5-a]pyrazin-4(5H)-one, 5-(5-fluoro-4-methoxypyrimidin-2-yl)-2-[(4-fluorophenoxy)methyl]-6,7-dihydropyrazolo[1,5-a]pyrazin-4(5H)-one, 5-(2-methylphenyl)-2-(phenoxymethyl)-6,7-dihydropyrazolo[1,5-a]pyrazin-4(5H)-one, 5-(6-chloropyridin-2-yl)-2-(phenoxymethyl)-6,7-dihydropyrazolo[1,5-a]pyrazin-4(5H)-one, 5-[6-(dimethylamino)-3-methylpyridin-2-yl]-2-(phenoxymethyl)-6,7-dihydropyrazolo[1,5-a]pyrazin-4(5H)-one, 5-(4-fluorophenyl)-7,7-dimethyl-2-(phenoxymethyl)-6,7-dihydropyrazolo[1,5-a]pyrazin-4(5H)-one, 5-(3-fluoro-4-methylphenyl)-2-(phenoxymethyl)-6,7-dihydropyrazolo[1,5-a]pyrazin-4(5H)-one, 2-(phenoxymethyl)-5-(quinazolin-6-yl)-6,7-dihydropyrazolo[1,5-a]pyrazin-4(5H)-one, 5-(6-methoxy-4-methylpyridin-2-yl)-2-(phenoxymethyl)-6,7-dihydropyrazolo[1,5-a]pyrazin-4(5H)-one, 5-[6-(dimethylamino)-5-methylpyridin-2-yl]-2-(phenoxymethyl)-6,7-dihydropyrazolo[1,5-a]pyrazin-4(5H)-one, 5-(4-fluoro-3-methoxyphenyl)-2-(phenoxymethyl)-6,7-dihydropyrazolo[1,5-a]pyrazin-4(5H)-one, (6R)-2-[(3-fluorophenoxy)methyl]-5-(4-fluorophenyl)-6-methyl-6,7-dihydropyrazolo[1,5-a]pyrazin-4(5H)-one, 7-Hydroxy-2-(phenoxymethyl)-6,7-dihydropyrazolo[1,5-a]pyrazin-4(5H)-one, (6R)-6-methyl-5-(3-methylphenyl)-2-(phenoxymethyl)-6,7-dihydropyrazolo[1,5-a]pyrazin-4(5H)-one, 5-(4-fluoro-3-methylphenyl)-2-[(4-fluorophenoxy)methyl]-6,7-dihydropyrazolo[1,5-a]pyrazin-4(5H)-one, (7*S)-2-[(3-fluorophenoxy)methyl]-5-(4-fluorophenyl)-7-methyl-6,7-dihydropyrazolo[1,5-a]pyrazin-4(5H)-one, 5-(4-fluoro-2-methoxyphenyl)-2-(phenoxymethyl)-6,7-dihydropyrazolo[1,5-a]pyrazin-4(5H)-one, (7*S)-5-(5-fluoro-6-methylpyridin-2-yl)-7-methyl-2-(phenoxymethyl)-6,7-dihydropyrazolo[1,5-a]pyrazin-4(5H)-one, 5-(5-fluoro-6-methylpyridin-2-yl)-2-(phenoxymethyl)-6,7-dihydropyrazolo[1,5-a]pyrazin-4(5H)-one, (6R)-5-(4-fluorophenyl)-6-methyl-2-(phenoxymethyl)-6,7-dihydropyrazolo[1,5-a]pyrazin-4(5H)-one, 5-(5-fluoro-2-methylphenyl)-2-(phenoxymethyl)-6,7-dihydropyrazolo[1,5-a]pyrazin-4(5H)-one, 5-(5-fluoro-4-methoxypyrimidin-2-yl)-2-(phenoxymethyl)-6,7-dihydropyrazolo[1,5-a]pyrazin-4(5H)-one, 5-[6-(fluoromethyl)pyridin-2-yl]-2-(phenoxymethyl)-6,7-dihydropyrazolo[1,5-a]pyrazin-4(5H)-one, 5-(4-fluorophenyl)-7-methyl-2-(phenoxymethyl)-6,7-dihydropyrazolo[1,5-a]pyrazin-4(5H)-one, (*S)-7-methyl-5-(2-methylbenzo[d]thiazol-5-yl)-2-(phenoxymethyl)-6,7-dihydropyrazolo[1,5-a]pyrazin-4(5H)-one, 2-(phenoxymethyl)-5-(quinolin-3-yl)-6,7-dihydropyrazolo[1,5-a]pyrazin-4(5H)-one, 5-(4-fluorophenyl)-2-(phenoxymethyl)-6,7-dihydropyrazolo[1,5-a]pyrazin-4(5H)-one, 5-(6-methoxy-3-methylpyridin-2-yl)-2-(phenoxymethyl)-6,7-dihydropyrazolo[1,5-a]pyrazin-4(5H)-one, 5-(5-fluoropyridin-2-yl)-2-((2-hydroxyphenoxy)methyl)-6,7-dihydropyrazolo[1,5-a]pyrazin-4(5H)-one, 2-[(4-fluorophenoxy)methyl]-5-(4-methylphenyl)-6,7-dihydropyrazolo[1,5-a]pyrazin-4(5H)-one, 5-(2-methoxy-5-methylpyridin-3-yl)-2-(phenoxymethyl)-6,7-dihydropyrazolo[1,5-a]pyrazin-4(5H)-one, (6R)-5-(4-fluoro-3-methoxyphenyl)-6-methyl-2-(phenoxymethyl)-6,7-dihydropyrazolo[1,5-a]pyrazin-4(5H)-one, 5-(3-methylphenyl)-2-(phenoxymethyl)-6,7-dihydropyrazolo[1,5-a]pyrazin-4(5H)-one, 5-(4-methylphenyl)-2-(phenoxymethyl)-6,7-dihydropyrazolo[1,5-a]pyrazin-4(5H)-one, (7*S)-5-(4-fluorophenyl)-7-methyl-2-(phenoxymethyl)-6,7-dihydropyrazolo[1,5-a]pyrazin-4(5H)-one, 5-(4-fluoronaphthalen-1-yl)-2-(phenoxymethyl)-6,7-dihydropyrazolo[1,5-a]pyrazin-4(5H)-one, (6R)-5-(4-fluorophenyl)-6-methyl-2-[(3-methylphenoxy)methyl]-6,7-dihydropyrazolo[1,5-a]pyrazin-4(5H)-one, 7-fluoro-5-(4-fluorophenyl)-2-(phenoxymethyl)-6,7-dihydropyrazolo[1,5-a]pyrazin-4(5H)-one, (7*R)-7-fluoro-5-(4-fluorophenyl)-2-(phenoxymethyl)-6,7-dihydropyrazolo[1,5-a]pyrazin-4(5H)-one, 5-(5-fluoro-4-methylpyridin-2-yl)-2-(phenoxymethyl)-6,7-dihydropyrazolo[1,5-a]pyrazin-4(5H)-one, 5-(cyclobutylmethyl)-2-(phenoxymethyl)-6,7-dihydropyrazolo[1,5-a]pyrazin-4(5H)-one, (7*R)-5-(4-fluorophenyl)-7-methyl-2-(phenoxymethyl)-6,7-dihydropyrazolo[1,5-a]pyrazin-4(5H)-one, 5-(2-methoxyphenyl)-2-(phenoxymethyl)-6,7-dihydropyrazolo[1,5-a]pyrazin-4(5H)-one, 5-(3-methoxypyrazin-2-yl)-2-(phenoxymethyl)-6,7-dihydropyrazolo[1,5-a]pyrazin-4(5H)-one, 5-(6-cyclopropylpyridin-2-yl)-2-(phenoxymethyl)-6,7-dihydropyrazolo[1,5-a]pyrazin-4(5H)-one, 5-[6-(1-methylethyl)pyridin-2-yl]-2-(phenoxymethyl)-6,7-dihydropyrazolo[1,5-a]pyrazin-4(5H)-one, 2-[(4-fluorophenoxy)methyl]-5-(3-methylphenyl)-6,7-dihydropyrazolo[1,5-a]pyrazin-4(5H)-one, 5-(4-fluorophenyl)-2-[(3-methylphenoxy)methyl]-6,7-dihydropyrazolo[1,5-a]pyrazin-4(5H)-one, 5-(6-ethylpyridin-2-yl)-2-(phenoxymethyl)-6,7-dihydropyrazolo[1,5-a]pyrazin-4(5H)-one, 5-(6-methoxy-5-methylpyrazin-2-yl)-2-(phenoxymethyl)-6,7-dihydropyrazolo[1,5-a]pyrazin-4(5H)-one, 2-[(4-fluorophenoxy)methyl]-5-(2-methylphenyl)-6,7-dihydropyrazolo[1,5-a]pyrazin-4(5H)-one, 5-(3,4-difluorophenyl)-2-(phenoxymethyl)-6,7-dihydropyrazolo[1,5-a]pyrazin-4(5H)-one, 5-(4-methoxy-5-methylpyrimidin-2-yl)-2-(phenoxymethyl)-6,7-dihydropyrazolo[1,5-a]pyrazin-4(5H)-one, (7*R)-5-(5-fluoro-6-methylpyridin-2-yl)-7-methyl-2-(phenoxymethyl)-6,7-dihydropyrazolo[1,5-a]pyrazin-4(5H)-one, (7*S)-5-(5-fluoropyridin-2-yl)-7-methyl-2-(phenoxymethyl)-6,7-dihydropyrazolo[1,5-a]pyrazin-4(5H)-one, and 5-(6-methoxy-2-methylpyridin-3-yl)-2-(phenoxymethyl)-6,7-dihydropyrazolo[1,5-a]pyrazin-4(5H)-one, or a subgroup thereof. Included within the scope of this list are stereoisomeric forms, the acid addition salts and the solvates thereof.

In a further aspect, within the scope of this list are pharmaceutically acceptable salts, hydrates, solvates, and polymorphs thereof.

In one aspect, a compound can be present as: 2-[(4-fluorophenoxy)methyl]-5-(4-fluorophenyl)-6,7-dihydropyrazolo[1,5-a]pyrazin-4(5H)-one, 5-(2-methylpropyl)-2-(phenoxymethyl)-6,7-dihydropyrazolo[1,5-a]pyrazin-4(5H)-one, 5-(6-methoxypyrazin-2-yl)-2-(phenoxymethyl)-6,7-dihydropyrazolo[1,5-a]pyrazin-4(5H)-one, (7*S)-7-fluoro-5-(4-fluorophenyl)-2-(phenoxymethyl)-6,7-dihydropyrazolo[1,5-a]pyrazin-4(5H)-one, 2-[(4-fluorophenoxy)methyl]-5-(6-methoxypyrazin-2-yl)-6,7-dihydropyrazolo[1,5-a]pyrazin-4(5H)-one, 5-(3-methoxy-5-methylpyrazin-2-yl)-2-(phenoxymethyl)-6,7-dihydropyrazolo[1,5-a]pyrazin-4(5H)-one, 7-(fluoromethyl)-5-(4-fluorophenyl)-2-(phenoxymethyl)-6,7-dihydropyrazolo[1,5-a]pyrazin-4(5H)-one, (6R)-6-(fluoromethyl)-5-(4-fluorophenyl)-2-(phenoxymethyl)-6,7-dihydropyrazolo[1,5-a]pyrazin-4(5H)-one, 2-[(3-fluorophenoxy)methyl]-5-(5-fluoropyridin-2-yl)-6,7-dihydropyrazolo[1,5-a]pyrazin-4(5H)-one, 5-(2,4-difluorophenyl)-2-(phenoxymethyl)-6,7-dihydropyrazolo[1,5-a]pyrazin-4(5H)-one, 5-(2,6-dimethoxypyrimidin-4-yl)-2-(phenoxymethyl)-6,7-dihydropyrazolo[1,5-a]pyrazin-4(5H)-one, 5-(3-fluoro-4-methoxyphenyl)-2-(phenoxymethyl)-6,7-dihydropyrazolo[1,5-a]pyrazin-4(5H)-one, 5-(4-fluoro-3-methoxyphenyl)-2-[(4-fluorophenoxy)methyl]-6,7-dihydropyrazolo[1,5-a]pyrazin-4(5H)-one, 5-(4-methoxyphenyl)-2-(phenoxymethyl)-6,7-dihydropyrazolo[1,5-a]pyrazin-4(5H)-one, 5-(5-methoxy-6-methylpyrazin-2-yl)-2-(phenoxymethyl)-6,7-dihydropyrazolo[1,5-a]pyrazin-4(5H)-one, 5-[6-(2-fluoroethoxy)pyridin-2-yl]-2-(phenoxymethyl)-6,7-dihydropyrazolo[1,5-a]pyrazin-4(5H)-one, (6R)-5-(5-fluoro-4-methylpyridin-2-yl)-6-methyl-2-(phenoxymethyl)-6,7-dihydropyrazolo[1,5-a]pyrazin-4(5H)-one, 2-(phenoxymethyl)-5-(pyrido[2,3-b]pyrazin-6-yl)-6,7-dihydropyrazolo[1,5-a]pyrazin-4(5H)-one, 5-(3-ethoxyphenyl)-2-(phenoxymethyl)-6,7-dihydropyrazolo[1,5-a]pyrazin-4(5H)-one, 5-(3-fluorophenyl)-2-(phenoxymethyl)-6,7-dihydropyrazolo[1,5-a]pyrazin-4(5H)-one, (7*S)-2-[(4-fluorophenoxy)methyl]-5-(4-fluorophenyl)-7-methyl-6,7-dihydropyrazolo[1,5-a]pyrazin-4(5H)-one, (6R)-2-[(4-fluorophenoxy)methyl]-5-(4-fluorophenyl)-6-methyl-6,7-dihydropyrazolo[1,5-a]pyrazin-4(5H)-one, (7*S)-5-(cyclopropylmethyl)-7-methyl-2-(phenoxymethyl)-6,7-dihydropyrazolo[1,5-a]pyrazin-4(5H)-one, 2-[(4-fluorophenoxy)methyl]-5-(4-fluorophenyl)-7-methyl-6,7-dihydropyrazolo[1,5-a]pyrazin-4(5H)-one, 2-[(2-fluorophenoxy)methyl]-5-(4-fluorophenyl)-6,7-dihydropyrazolo[1,5-a]pyrazin-4(5H)-one, 5-(3-methoxyphenyl)-2-(phenoxymethyl)-6,7-dihydropyrazolo[1,5-a]pyrazin-4(5H)-one, 2-[(3-fluorophenoxy)methyl]-5-(4-fluorophenyl)-6,7-dihydropyrazolo[1,5-a]pyrazin-4(5H)-one, 5-(2-ethoxyphenyl)-2-(phenoxymethyl)-6,7-dihydropyrazolo[1,5-a]pyrazin-4(5H)-one, 6-[4-Oxo-2-(phenoxymethyl)-6,7-dihydropyrazolo[1,5-a]pyrazin-5(4H)-yl]pyridine-2-carbonitrile, 2-[(4-fluorophenoxy)methyl]-5-(5-fluoropyridin-2-yl)-6,7-dihydropyrazolo[1,5-a]pyrazin-4(5H)-one, 5-(5-fluoro-6-methylpyridin-2-yl)-2-[(4-fluorophenoxy)methyl]-7-methyl-6,7-dihydropyrazolo[1,5-a]pyrazin-4(5H)-one, 5-[6-(2-methylpropyl)pyridin-2-yl]-2-(phenoxymethyl)-6,7-dihydropyrazolo[1,5-a]pyrazin-4(5H)-one, 5-(5-fluoropyridin-2-yl)-2-(phenoxymethyl)-6,7-dihydropyrazolo[1,5-a]pyrazin-4(5H)-one, 5-(2-fluorophenyl)-2-(phenoxymethyl)-6,7-dihydropyrazolo[1,5-a]pyrazin-4(5H)-one, 5-(4-fluorophenyl)-6-methyl-2-(phenoxymethyl)-6,7-dihydropyrazolo[1,5-a]pyrazin-4(5H)-one, 5-(6-methylpyridin-2-yl)-2-(phenoxymethyl)-6,7-dihydropyrazolo[1,5-a]pyrazin-4(5H)-one, 5-(4-fluoro-3-methylphenyl)-2-[(pyridin-2-yloxy)methyl]-6,7-dihydropyrazolo[1,5-a]pyrazin-4(5H)-one, (6R)-5-(5-fluoro-6-methylpyridin-2-yl)-6-methyl-2-(phenoxymethyl)-6,7-dihydropyrazolo[1,5-a]pyrazin-4(5H)-one, 2-[(4-fluorophenoxy)methyl]-5-(3-fluorophenyl)-7-methyl-6,7-dihydropyrazolo[1,5-a]pyrazin-4(5H)-one, 2-[(4-fluorophenoxy)methyl]-5-(4-methoxy-5-methylpyrimidin-2-yl)-6,7-dihydropyrazolo[1,5-a]pyrazin-4(5H)-one, (6R)-5-(2-methoxypyridin-3-yl)-6-methyl-2-(phenoxymethyl)-6,7-dihydropyrazolo[1,5-a]pyrazin-4(5H)-one, 5-[(2,2-difluorocyclopropyl)methyl]-2-(phenoxymethyl)-6,7-dihydropyrazolo[1,5-a]pyrazin-4(5H)-one, 2-(phenoxymethyl)-5-[(1R)-1,2,2-trimethylpropyl]-6,7-dihydropyrazolo[1,5-a]pyrazin-4(5H)-one, 5-(3-fluoro-6-methylpyridin-2-yl)-2-(phenoxymethyl)-6,7-dihydropyrazolo[1,5-a]pyrazin-4(5H)-one, 5-[6-(dimethylamino)-3-fluoropyridin-2-yl]-2-[(pyridin-2-yloxy)methyl]-6,7-dihydropyrazolo[1,5-a]pyrazin-4(5H)-one, 2-[(4-fluorophenoxy)methyl]-5-(2-methoxyphenyl)-6,7-dihydropyrazolo[1,5-a]pyrazin-4(5H)-one, 5-(benzo[d]thiazol-5-yl)-2-(phenoxymethyl)-6,7-dihydropyrazolo[1,5-a]pyrazin-4(5H)-one, 5-[6-(dimethylamino)-5-fluoropyridin-2-yl]-2-(phenoxymethyl)-6,7-dihydropyrazolo[1,5-a]pyrazin-4(5H)-one, (6R)-5-(5-fluoropyridin-2-yl)-6-methyl-2-(phenoxymethyl)-6,7-dihydropyrazolo[1,5-a]pyrazin-4(5H)-one, 5-(2-methoxypyridin-3-yl)-2-(phenoxymethyl)-6,7-dihydropyrazolo[1,5-a]pyrazin-4(5H)-one, 2-[(4-fluorophenoxy)methyl]-5-(5-fluoropyridin-2-yl)-7-methyl-6,7-dihydropyrazolo[1,5-a]pyrazin-4(5H)-one, 5-(2-methoxypyrimidin-4-yl)-2-(phenoxymethyl)-6,7-dihydropyrazolo[1,5-a]pyrazin-4(5H)-one, 5-[(1R)-1-cyclopropylethyl]-2-(phenoxymethyl)-6,7-dihydropyrazolo[1,5-a]pyrazin-4(5H)-one, 5-(3-methoxyphenyl)-2-[(pyridin-2-yloxy)methyl]-6,7-dihydropyrazolo[1,5-a]pyrazin-4(5H)-one, 5-(5-fluoro-3-methylpyridin-2-yl)-2-(phenoxymethyl)-6,7-dihydropyrazolo[1,5-a]pyrazin-4(5H)-one, 5-[6-(2-fluoroethyl)pyridin-2-yl]-2-(phenoxymethyl)-6,7-dihydropyrazolo[1,5-a]pyrazin-4(5H)-one, 5-(5-methylpyridin-2-yl)-2-(phenoxymethyl)-6,7-dihydropyrazolo[1,5-a]pyrazin-4(5H)-one, 5-(4,6-dimethoxypyrimidin-2-yl)-2-(phenoxymethyl)-6,7-dihydropyrazolo[1,5-a]pyrazin-4(5H)-one, 3-{[(6R)-5-(4-fluorophenyl)-6-methyl-4-oxo-4,5,6,7-tetrahydropyrazolo[1,5-a]pyrazin-2-yl]methoxy}benzonitrile, 5-(6-methoxy-2-methylpyrimidin-4-yl)-2-(phenoxymethyl)-6,7-dihydropyrazolo[1,5-a]pyrazin-4(5H)-one, 5-[5-fluoro-4-(methylamino)pyrimidin-2-yl]-2-(phenoxymethyl)-6,7-dihydropyrazolo[1,5-a]pyrazin-4(5H)-one, 5-[(1S)-1-cyclopropylethyl]-2-(phenoxymethyl)-6,7-dihydropyrazolo[1,5-a]pyrazin-4(5H)-one, 5-(imidazo[1,2-b]pyridazin-3-yl)-2-(phenoxymethyl)-6,7-dihydropyrazolo[1,5-a]pyrazin-4(5H)-one, (6R)-5-(cyclopropylmethyl)-6-methyl-2-(phenoxymethyl)-6,7-dihydropyrazolo[1,5-a]pyrazin-4(5H)-one, 5-(4-fluorophenyl)-2-[(4-methylphenoxy)methyl]-6,7-dihydropyrazolo[1,5-a]pyrazin-4(5H)-one, 5-(5-methylthiophen-2-yl)-2-(phenoxymethyl)-6,7-dihydropyrazolo[1,5-a]pyrazin-4(5H)-one, (7*R)-5-(5-fluoropyridin-2-yl)-7-methyl-2-(phenoxymethyl)-6,7-dihydropyrazolo[1,5-a]pyrazin-4(5H)-one, 2-[(4-fluorophenoxy)methyl]-5-(2-methoxypyrimidin-4-yl)-6,7-dihydropyrazolo[1,5-a]pyrazin-4(5H)-one, 5-(1-methyl-1H-imidazol-5-yl)-2-(phenoxymethyl)-6,7-dihydropyrazolo[1,5-a]pyrazin-4(5H)-one, 5-(2-methylphenyl)-2-[(pyridin-2-yloxy)methyl]-

6,7-dihydropyrazolo[1,5-a]pyrazin-4(5H)-one, 5-(3-fluoro-5-methoxyphenyl)-2-(phenoxymethyl)-6,7-dihydropyrazolo[1,5-a]pyrazin-4(5H)-one, 2-(phenoxymethyl)-5-(6-pyrrolidin-1-ylpyridin-2-yl)-6,7-dihydropyrazolo[1,5-a]pyrazin-4(5H)-one, 5-(cyclopropylmethyl)-2-(phenoxymethyl)-6,7-dihydropyrazolo[1,5-a]pyrazin-4(5H)-one, 5-(cyclopropylmethyl)-2-[(4-fluorophenoxy)methyl]-6,7-dihydropyrazolo[1,5-a]pyrazin-4(5H)-one, 5-[6-(methylamino)pyridin-2-yl]-2-(phenoxymethyl)-6,7-dihydropyrazolo[1,5-a]pyrazin-4(5H)-one, 5-[6-(chloromethyl)pyridin-2-yl]-2-(phenoxymethyl)-6,7-dihydropyrazolo[1,5-a]pyrazin-4(5H)-one, 5-(5-methoxypyrazin-2-yl)-2-(phenoxymethyl)-6,7-dihydropyrazolo[1,5-a]pyrazin-4(5H)-one, 3-{[5-(4-fluorophenyl)-4-oxo-4,5,6,7-tetrahydropyrazolo[1,5-a]pyrazin-2-yl]methoxy}benzonitrile, 5-(6-methylpyrazin-2-yl)-2-(phenoxymethyl)-6,7-dihydropyrazolo[1,5-a]pyrazin-4(5H)-one, 5-(2,6-dimethylpyridin-3-yl)-2-(phenoxymethyl)-6,7-dihydropyrazolo[1,5-a]pyrazin-4(5H)-one, (6S)-5-(5-fluoro-6-methylpyridin-2-yl)-6-methyl-2-(phenoxymethyl)-6,7-dihydropyrazolo[1,5-a]pyrazin-4(5H)-one, 5-(3-chloropyridin-2-yl)-2-(phenoxymethyl)-6,7-dihydropyrazolo[1,5-a]pyrazin-4(5H)-one, 5-(3-fluoro-6-methoxypyridin-2-yl)-2-[(pyridin-2-yloxy)methyl]-6,7-dihydropyrazolo[1,5-a]pyrazin-4(5H)-one, 5-(4,5-dimethoxypyrimidin-2-yl)-2-(phenoxymethyl)-6,7-dihydropyrazolo[1,5-a]pyrazin-4(5H)-one, 2-[(4-fluorophenoxy)methyl]-5-(3-methoxyphenyl)-6,7-dihydropyrazolo[1,5-a]pyrazin-4(5H)-one, 5-(4-fluorophenyl)-2-{[(4-methylpyridin-2-yl)oxy]methyl}-6,7-dihydropyrazolo[1,5-a]pyrazin-4(5H)-one, 5-[6-(dimethylamino)pyrazin-2-yl]-2-(phenoxymethyl)-6,7-dihydropyrazolo[1,5-a]pyrazin-4(5H)-one, 5-(4-methylpyrimidin-5-yl)-2-(phenoxymethyl)-6,7-dihydropyrazolo[1,5-a]pyrazin-4(5H)-one, 5-[6-(3-methylbutyl)pyridin-2-yl]-2-(phenoxymethyl)-6,7-dihydropyrazolo[1,5-a]pyrazin-4(5H)-one, 2-[(4-fluorophenoxy)methyl]-5-(2-methoxypyridin-3-yl)-6,7-dihydropyrazolo[1,5-a]pyrazin-4(5H)-one, 5-(5-fluoropyridin-2-yl)-2-[(3-methylphenoxy)methyl]-6,7-dihydropyrazolo[1,5-a]pyrazin-4(5H)-one, 5-(2-methoxy-5-methylpyrimidin-4-yl)-2-(phenoxymethyl)-6,7-dihydropyrazolo[1,5-a]pyrazin-4(5H)-one, 5-(5-fluoro-6-methylpyridin-2-yl)-2-[(pyridin-2-yloxy)methyl]-6,7-dihydropyrazolo[1,5-a]pyrazin-4(5H)-one, 5-[3-(dimethylamino)pyridin-2-yl]-2-(phenoxymethyl)-6,7-dihydropyrazolo[1,5-a]pyrazin-4(5H)-one, 5-(4-fluoro-3-methoxyphenyl)-2-[(pyridin-2-yloxy)methyl]-6,7-dihydropyrazolo[1,5-a]pyrazin-4(5H)-one, 5-(3-methylphenyl)-2-[(pyridin-2-yloxy)methyl]-6,7-dihydropyrazolo[1,5-a]pyrazin-4(5H)-one, 2-(phenoxymethyl)-5-(quinolin-7-yl)-6,7-dihydropyrazolo[1,5-a]pyrazin-4(5H)-one, 5-(4-fluorophenyl)-2-[(2-methylphenoxy)methyl]-6,7-dihydropyrazolo[1,5-a]pyrazin-4(5H)-one, 5-[2-(methoxymethyl)phenyl]-2-(phenoxymethyl)-6,7-dihydropyrazolo[1,5-a]pyrazin-4(5H)-one, 2-{[5-(4-fluorophenyl)-4-oxo-4,5,6,7-tetrahydropyrazolo[1,5-a]pyrazin-2-yl]methoxy}pyridine-4-carbonitrile, 5-[6-(1-methylethyl)pyridin-2-yl]-2-[(pyridin-2-yloxy)methyl]-6,7-dihydropyrazolo[1,5-a]pyrazin-4(5H)-one, 5-[6-(2-methoxyethoxy)pyridin-2-yl]-2-(phenoxymethyl)-6,7-dihydropyrazolo[1,5-a]pyrazin-4(5H)-one, 5-(4-methylphenyl)-2-[(pyridin-2-yloxy)methyl]-6,7-dihydropyrazolo[1,5-a]pyrazin-4(5H)-one, (6R)-5-(6-methoxypyrazin-2-yl)-6-methyl-2-(phenoxymethyl)-6,7-dihydropyrazolo[1,5-a]pyrazin-4(5H)-one, 5-(4-fluorophenyl)-2-[(pyridin-2-yloxy)methyl]-6,7-dihydropyrazolo[1,5-a]pyrazin-4(5H)-one, 5-(4-methoxypyrimidin-2-yl)-2-(phenoxymethyl)-6,7-dihydropyrazolo[1,5-a]pyrazin-4(5H)-one, and 5-(4-methylpyridin-2-yl)-2-(phenoxymethyl)-6,7-dihydropyrazolo[1,5-a]pyrazin-4(5H)-one, or a subgroup thereof. Included within the scope of this list are stereoisomeric forms, the acid addition salts and the solvates thereof. In a further aspect, within the scope of this list are pharmaceutically acceptable salts, hydrates, solvates, and polymorphs thereof.

In one aspect, a compound can be present as: 5-(2-methylpyrimidin-4-yl)-2-(phenoxymethyl)-6,7-dihydropyrazolo[1,5-a]pyrazin-4(5H)-one, 3-{[5-(5-fluoropyridin-2-yl)-4-oxo-4,5,6,7-tetrahydropyrazolo[1,5-a]pyrazin-2-yl]methoxy}benzonitrile, 5-(5-fluoro-4-methoxypyrimidin-2-yl)-2-[(pyridin-2-yloxy)methyl]-6,7-dihydropyrazolo[1,5-a]pyrazin-4(5H)-one, (6R)-5-(5-fluoro-4-methoxypyrimidin-2-yl)-6-methyl-2-(phenoxymethyl)-6,7-dihydropyrazolo[1,5-a]pyrazin-4(5H)-one, 5-(3-methylpyridin-2-yl)-2-(phenoxymethyl)-6,7-dihydropyrazolo[1,5-a]pyrazin-4(5H)-one, (6R)-5-(4-methoxy-5-methylpyrimidin-2-yl)-6-methyl-2-(phenoxymethyl)-6,7-dihydropyrazolo[1,5-a]pyrazin-4(5H)-one, 5-(3-fluoropyridin-2-yl)-2-(phenoxymethyl)-6,7-dihydropyrazolo[1,5-a]pyrazin-4(5H)-one, (6S)-5-(4-fluorophenyl)-6-methyl-2-(phenoxymethyl)-6,7-dihydropyrazolo[1,5-a]pyrazin-4(5H)-one, 5-(3-fluoropyridin-4-yl)-2-(phenoxymethyl)-6,7-dihydropyrazolo[1,5-a]pyrazin-4(5H)-one, 5-(5-fluoro-4-methylpyrimidin-2-yl)-2-(phenoxymethyl)-6,7-dihydropyrazolo[1,5-a]pyrazin-4(5H)-one, (6R)-5-(4-fluorophenyl)-6-methyl-2-[(pyridin-2-yloxy)methyl]-6,7-dihydropyrazolo[1,5-a]pyrazin-4(5H)-one, 5-(2-methylpyridin-3-yl)-2-(phenoxymethyl)-6,7-dihydropyrazolo[1,5-a]pyrazin-4(5H)-one, 5-[3-(dimethylamino)pyrazin-2-yl]-2-(phenoxymethyl)-6,7-dihydropyrazolo[1,5-a]pyrazin-4(5H)-one, 5-[6-(2-methoxyethyl)pyridin-2-yl]-2-(phenoxymethyl)-6,7-dihydropyrazolo[1,5-a]pyrazin-4(5H)-one, 7-(4-fluorophenyl)-2-(phenoxymethyl)[1,2,4]triazolo[1,5-a]pyrazin-8(7H)-one, 5-(3-fluoro-5-methylphenyl)-2-(phenoxymethyl)-6,7-dihydropyrazolo[1,5-a]pyrazin-4(5H)-one, 5-(4-fluorophenyl)-2-[(pyridin-4-yloxy)methyl]-6,7-dihydropyrazolo[1,5-a]pyrazin-4(5H)-one, 5-(5-fluoropyridin-3-yl)-2-(phenoxymethyl)-6,7-dihydropyrazolo[1,5-a]pyrazin-4(5H)-one, 5-(4-methoxy-6-methylpyridin-2-yl)-2-(phenoxymethyl)-6,7-dihydropyrazolo[1,5-a]pyrazin-4(5H)-one, 5-(6-methoxypyrazin-2-yl)-2-[(pyridin-2-yloxy)methyl]-6,7-dihydropyrazolo[1,5-a]pyrazin-4(5H)-one, (6S)-6-(fluoromethyl)-5-(4-fluorophenyl)-2-(phenoxymethyl)-6,7-dihydropyrazolo[1,5-a]pyrazin-4(5H)-one, 5-(5-methoxypyridin-2-yl)-2-(phenoxymethyl)-6,7-dihydropyrazolo[1,5-a]pyrazin-4(5H)-one, 5-(4-methoxypyrimidin-5-yl)-2-(phenoxymethyl)-6,7-dihydropyrazolo[1,5-a]pyrazin-4(5H)-one, (68)-5-(cyclopropylmethyl)-6-methyl-2-(phenoxymethyl)-6,7-dihydropyrazolo[1,5-a]pyrazin-4(5H)-one, 5-(2-methoxy-6-methylpyrimidin-4-yl)-2-(phenoxymethyl)-6,7-dihydropyrazolo[1,5-a]pyrazin-4(5H)-one, 5-(4-methylpyridin-3-yl)-2-(phenoxymethyl)-6,7-dihydropyrazolo[1,5-a]pyrazin-4(5H)-one, 5-(6-Aminopyridin-2-yl)-2-(phenoxymethyl)-6,7-dihydropyrazolo[1,5-a]pyrazin-4(5H)-one, 5-(3,6-dimethylpyrazin-2-yl)-2-(phenoxymethyl)-6,7-dihydropyrazolo[1,5-a]pyrazin-4(5H)-one, 5-(2-methoxypropyl)-2-(phenoxymethyl)-6,7-dihydropyrazolo[1,5-a]pyrazin-4(5H)-one, 5-(5-fluoropyrimidin-2-yl)-2-(phenoxymethyl)-6,7-dihydropyrazolo[1,5-a]pyrazin-4

(5H)-one, (6R)-5-(3-methoxypyrazin-2-yl)-6-methyl-2-(phenoxymethyl)-6,7-dihydropyrazolo[1,5-a]pyrazin-4(5H)-one, 2-(phenoxymethyl)-5-pyrazin-2-yl-6,7-dihydropyrazolo[1,5-a]pyrazin-4(5H)-one, 2-[(4-fluorophenoxy)methyl]-5-(3-methoxypyrazin-2-yl)-6,7-dihydropyrazolo[1,5-a]pyrazin-4(5H)-one, 5-(2-methylbenzo[d]thiazol-5-yl)-2-(phenoxymethyl)-6,7-dihydropyrazolo[1,5-a]pyrazin-4(5H)-one, 2-(phenoxymethyl)-5-pyridin-2-yl-6,7-dihydropyrazolo[1,5-a]pyrazin-4(5H)-one, (6S)-5-(5-fluoropyridin-2-yl)-6-methyl-2-(phenoxymethyl)-6,7-dihydropyrazolo[1,5-a]pyrazin-4(5H)-one, 5-(2-fluoropropyl)-2-(phenoxymethyl)-6,7-dihydropyrazolo[1,5-a]pyrazin-4(5H)-one, 5-(4-fluorophenyl)-3-methyl-2-(phenoxymethyl)-6,7-dihydropyrazolo[1,5-a]pyrazin-4(5H)-one, 5-(6-methylpyrimidin-4-yl)-2-(phenoxymethyl)-6,7-dihydropyrazolo[1,5-a]pyrazin-4(5H)-one, (6R)-5-(4-fluorophenyl)-6-(methoxymethyl)-2-(phenoxymethyl)-6,7-dihydropyrazolo[1,5-a]pyrazin-4(5H)-one, 5-[4-(methylamino)pyrimidin-2-yl]-2-(phenoxymethyl)-6,7-dihydropyrazolo[1,5-a]pyrazin-4(5H)-one, 5-(5-methylpyrazin-2-yl)-2-(phenoxymethyl)-6,7-dihydropyrazolo[1,5-a]pyrazin-4(5H)-one, 5-(5-fluoropyridin-2-yl)-2-[(pyridin-2-yloxy)methyl]-6,7-dihydropyrazolo[1,5-a]pyrazin-4(5H)-one, or a subgroup thereof. Included within the scope of this list are stereoisomeric forms, the acid addition salts and the solvates thereof. In a further aspect, within the scope of this list are pharmaceutically acceptable salts, hydrates, solvates, and polymorphs thereof.

In one aspect, a compound can be present as: 5-[4-(dimethylamino)pyridin-2-yl]-2-(phenoxymethyl)-6,7-dihydropyrazolo[1,5-a]pyrazin-4(5H)-one, 5-(2-methoxyphenyl)-2-[(pyridin-2-yloxy)methyl]-6,7-dihydropyrazolo[1,5-a]pyrazin-4(5H)-one, 5-(4-methoxypyridin-2-yl)-2-(phenoxymethyl)-6,7-dihydropyrazolo[1,5-a]pyrazin-4(5H)-one, 5-(benzo[c][1,2,5]thiadiazol-5-yl)-2-(phenoxymethyl)-6,7-dihydropyrazolo[1,5-a]pyrazin-4(5H)-one, 5-(5-methylpyridin-3-yl)-2-(phenoxymethyl)-6,7-dihydropyrazolo[1,5-a]pyrazin-4(5H)-one, 5-(6-methylpyridin-3-yl)-2-(phenoxymethyl)-6,7-dihydropyrazolo[1,5-a]pyrazin-4(5H)-one, 5-(4-fluorophenyl)-7-(hydroxymethyl)-2-(phenoxymethyl)-6,7-dihydropyrazolo[1,5-a]pyrazin-4(5H)-one, 5-[6-(dimethylamino)-4-methylpyridin-2-yl]-2-(phenoxymethyl)-6,7-dihydropyrazolo[1,5-a]pyrazin-4(5H)-one, 5-(4-fluorophenyl)-2-{[(2-methylpyridin-4-yl)oxy]methyl}-6,7-dihydropyrazolo[1,5-a]pyrazin-4(5H)-one, 5-[4-(dimethylamino)pyrimidin-2-yl]-2-(phenoxymethyl)-6,7-dihydropyrazolo[1,5-a]pyrazin-4(5H)-one, 2-(phenoxymethyl)-5-pyrimidin-4-yl-6,7-dihydropyrazolo[1,5-a]pyrazin-4(5H)-one, 5-(4-chloroquinolin-6-yl)-2-(phenoxymethyl)-6,7-dihydropyrazolo[1,5-a]pyrazin-4(5H)-one, 5-(4-fluorophenyl)-2-{[(5-fluoropyridin-3-yl)oxy]methyl}-6,7-dihydropyrazolo[1,5-a]pyrazin-4(5H)-one, 5-methyl-2-(phenoxymethyl)-6,7-dihydropyrazolo[1,5-a]pyrazin-4(5H)-one, 5-cyclopropyl-2-(phenoxymethyl)-6,7-dihydropyrazolo[1,5-a]pyrazin-4(5H)-one, (6R)-5-(2-methoxypyrimidin-4-yl)-6-methyl-2-(phenoxymethyl)-6,7-dihydropyrazolo[1,5-a]pyrazin-4(5H)-one, 2-(phenoxymethyl)-5-pyridin-4-yl-6,7-dihydropyrazolo[1,5-a]pyrazin-4(5H)-one, 5-(6-methylpyridin-2-yl)-2-[(pyridin-2-yloxy)methyl]-6,7-dihydropyrazolo[1,5-a]pyrazin-4(5H)-one, 5-(4-methylpyrimidin-2-yl)-2-(phenoxymethyl)-6,7-dihydropyrazolo[1,5-a]pyrazin-4(5H)-one, 5-tert-Butyl-2-(phenoxymethyl)-6,7-dihydropyrazolo[1,5-a]pyrazin-4(5H)-one, 2-{[(5-fluoro-4-methylpyridin-2-yl)oxy]methyl}-5-(4-fluorophenyl)-6,7-dihydropyrazolo[1,5-a]pyrazin-4(5H)-one, 2-{[(3-fluoro-4-methylpyridin-2-yl)oxy]methyl}-5-(4-fluorophenyl)-6,7-dihydropyrazolo[1,5-a]pyrazin-4(5H)-one, 5-(5-fluoropyridin-2-yl)-2-[(pyridin-4-yloxy)methyl]-6,7-dihydropyrazolo[1,5-a]pyrazin-4(5H)-one, 2-(phenoxymethyl)-5-pyridin-3-yl-6,7-dihydropyrazolo[1,5-a]pyrazin-4(5H)-one, 5-(1-methylethyl)-2-(phenoxymethyl)-6,7-dihydropyrazolo[1,5-a]pyrazin-4(5H)-one, 5-(5-methoxypyrimidin-4-yl)-2-(phenoxymethyl)-6,7-dihydropyrazolo[1,5-a]pyrazin-4(5H)-one, 5-methyl-2-(phenoxymethyl)pyrazolo[1,5-a]pyrazin-4(5H)-one, 5-(2-methoxypyrimidin-4-yl)-2-[(pyridin-2-yloxy)methyl]-6,7-dihydropyrazolo[1,5-a]pyrazin-4(5H)-one, 5-(3-methoxypyridin-2-yl)-2-(phenoxymethyl)-6,7-dihydropyrazolo[1,5-a]pyrazin-4(5H)-one, 5-(4-fluorophenyl)-2-{[(3-fluoropyridin-2-yl)oxy]methyl}-6,7-dihydropyrazolo[1,5-a]pyrazin-4(5H)-one, (6R)-5-(4-fluorophenyl)-6-(hydroxymethyl)-2-(phenoxymethyl)-6,7-dihydropyrazolo[1,5-a]pyrazin-4(5H)-one, 2-(phenoxymethyl)-6,7-dihydropyrazolo[1,5-a]pyrazin-4(5H)-one, 5-(cyclopropylmethyl)-2-[(pyridin-4-yloxy)methyl]-6,7-dihydropyrazolo[1,5-a]pyrazin-4(5H)-one, 5-(5-methoxy-2-methylpyrimidin-4-yl)-2-(phenoxymethyl)-6,7-dihydropyrazolo[1,5-a]pyrazin-4(5H)-one, 5-(cyclopropylmethyl)-2-[(pyridin-2-yloxy)methyl]-6,7-dihydropyrazolo[1,5-a]pyrazin-4(5H)-one, 2-(phenoxymethyl)-5-[6-(tetrahydro-2H-pyran-4-yl)pyridin-2-yl]-6,7-dihydropyrazolo[1,5-a]pyrazin-4(5H)-one, 7-(4-fluorophenyl)-2-(phenoxymethyl)-6,7-dihydro[1,2,4]triazolo[1,5-a]pyrazin-8(5H)-one, 5-[6-(dimethylamino)pyridazin-3-yl]-2-(phenoxymethyl)-6,7-dihydropyrazolo[1,5-a]pyrazin-4(5H)-one, 2-(phenoxymethyl)-5-(2,2,2-trifluoroethyl)-6,7-dihydropyrazolo[1,5-a]pyrazin-4(5H)-one, 5-(4-fluorophenyl)-2-[(pyridin-3-yloxy)methyl]-6,7-dihydropyrazolo[1,5-a]pyrazin-4(5H)-one, 5-(4-fluorophenyl)-2-{[(2-methylpyrimidin-4-yl)oxy]methyl}-6,7-dihydropyrazolo[1,5-a]pyrazin-4(5H)-one, 5-(benzo[c][1,2,5]oxadiazol-5-yl)-2-(phenoxymethyl)-6,7-dihydropyrazolo[1,5-a]pyrazin-4(5H)-one, 2-({[6-(dimethylamino)pyridin-2-yl]oxy}methyl)-5-(4-fluorophenyl)-6,7-dihydropyrazolo[1,5-a]pyrazin-4(5H)-one, 5-(5,6-dimethylpyrazin-2-yl)-2-(phenoxymethyl)-6,7-dihydropyrazolo[1,5-a]pyrazin-4(5H)-one, 5-(4-fluorophenyl)-2-[(pyrimidin-4-yloxy)methyl]-6,7-dihydropyrazolo[1,5-a]pyrazin-4(5H)-one, 5-(2-methoxy-1-methylethyl)-2-(phenoxymethyl)-6,7-dihydropyrazolo[1,5-a]pyrazin-4(5H)-one, 5-(4-fluorophenyl)-2-{[(3-methylpyridin-4-yl)oxy]methyl}-6,7-dihydropyrazolo[1,5-a]pyrazin-4(5H)-one, and 5-(cyclopropylmethyl)-2-[(3-methylphenoxy)methyl]-6,7-dihydropyrazolo[1,5-a]pyrazin-4(5H)-one, or a subgroup thereof. Included within the scope of this list are stereoisomeric forms, the acid addition salts and the solvates thereof. In a further aspect, within the scope of this list are pharmaceutically acceptable salts, hydrates, solvates, and polymorphs thereof.

In one aspect, a compound can be present as: (6S)-5-(4-fluorophenyl)-6-(hydroxymethyl)-2-(phenoxymethyl)-6,7-dihydropyrazolo[1,5-a]pyrazin-4(5H)-one, (6S)-5-(4-fluorophenyl)-6-(methoxymethyl)-2-(phenoxymethyl)-6,7-dihydropyrazolo[1,5-a]pyrazin-4(5H)-one, (6S)-6-methyl-2-(phenoxymethyl)-6,7-dihydropyrazolo[1,5-a]pyrazin-4(5H)-one, 2-(phenoxymethyl)-5-pyrimidin-2-yl-6,7-dihydropyrazolo[1,5-a]pyrazin-4(5H)-one, 2-(phenoxymethyl)-5-pyrimidin-5-yl-6,7-dihydropyrazolo[1,5-a]pyrazin-4(5H)-one, 2-(phenoxymethyl)pyrazolo[1,5-a]pyrazin-4(5H)-one, 5-(1-methyl-1H-imidazol-4-yl)-2-

(phenoxymethyl)-6,7-dihydropyrazolo[1,5-a]pyrazin-4 (5H)-one, 5-(2-fluoro-1-methylethyl)-2-(phenoxymethyl)-6,7-dihydropyrazolo[1,5-a]pyrazin-4(5H)-one, 5-(2-methylpyrimidin-5-yl)-2-(phenoxymethyl)-6,7-dihydropyrazolo[1,5-a]pyrazin-4(5H)-one, 5-(4-fluorophenyl)-2-(1-phenoxyethyl)-6,7-dihydropyrazolo[1,5-a]pyrazin-4(5H)-one, 5-(4-fluorophenyl)-2-[(pyrazin-2-yloxy)methyl]-6,7-dihydropyrazolo[1,5-a]pyrazin-4(5H)-one, 5-(4-fluorophenyl)-2-[(pyridazin-3-yloxy)methyl]-6,7-dihydropyrazolo[1,5-a]pyrazin-4(5H)-one, 5-(4-fluorophenyl)-2-[(pyridazin-4-yloxy)methyl]-6,7-dihydropyrazolo[1,5-a]pyrazin-4(5H)-one, 5-(4-fluorophenyl)-2-[(pyrimidin-2-yloxy)methyl]-6,7-dihydropyrazolo[1,5-a]pyrazin-4(5H)-one, 5-(4-fluorophenyl)-2-{[(3-methylpyridin-2-yl)oxy]methyl}-6,7-dihydropyrazolo[1,5-a]pyrazin-4(5H)-one, 5-(4-fluorophenyl)-2-{[(4-methoxypyridin-2-yl)oxy]methyl}-6,7-dihydropyrazolo[1,5-a]pyrazin-4(5H)-one, 5-(4-fluorophenyl)-2-{[(5-fluoropyridin-2-yl)oxy]methyl}-6,7-dihydropyrazolo[1,5-a]pyrazin-4(5H)-one, 5-(4-fluorophenyl)-2-{[(6-methylpyridin-2-yl)oxy]methyl}-6,7-dihydropyrazolo[1,5-a]pyrazin-4(5H)-one, 5-(4-fluorophenyl)-2-{[(6-methylpyrimidin-4-yl)oxy]methyl}-6,7-dihydropyrazolo[1,5-a]pyrazin-4(5H)-one, 5-(5-methoxypyridazin-3-yl)-2-(phenoxymethyl)-6,7-dihydropyrazolo[1,5-a]pyrazin-4(5H)-one, 5-(5-methoxypyrimidin-2-yl)-2-(phenoxymethyl)-6,7-dihydropyrazolo[1,5-a]pyrazin-4(5H)-one, 5-(5-methoxythiophen-2-yl)-2-(phenoxymethyl)-6,7-dihydropyrazolo[1,5-a]pyrazin-4(5H)-one, 5-(6-methoxypyridazin-3-yl)-2-(phenoxymethyl)-6,7-dihydropyrazolo[1,5-a]pyrazin-4(5H)-one, 5-(6-methylpyridazin-3-yl)-2-(phenoxymethyl)-6,7-dihydropyrazolo[1,5-a]pyrazin-4(5H)-one, 5-(cyclopropylmethyl)-2-[(pyridin-3-yloxy)methyl]-6,7-dihydropyrazolo[1,5-a]pyrazin-4(5H)-one, 5-(cyclopropylmethyl)-2-{[(5-fluoropyridin-3-yl)oxy]methyl}-6,7-dihydropyrazolo[1,5-a]pyrazin-4(5H)-one, 5-(imidazo[1,2-a]pyrazin-3-yl)-2-(phenoxymethyl)-6,7-dihydropyrazolo[1,5-a]pyrazin-4(5H)-one, 7-methyl-2-(phenoxymethyl)-6,7-dihydropyrazolo[1,5-a]pyrazin-4(5H)-one, (7*R)-5-(4-fluorophenyl)-7-methyl-2-[(3-methylphenoxy)methyl]-6,7-dihydropyrazolo[1,5-a]pyrazin-4(5H)-one, (7*R)-5-(4-fluorophenyl)-7-methyl-2-[(pyridin-2-yloxy)methyl]-6,7-dihydropyrazolo[1,5-a]pyrazin-4(5H)-one, (7*R)-5-(cyclopropylmethyl)-7-methyl-2-(phenoxymethyl)-6,7-dihydropyrazolo[1,5-a]pyrazin-4(5H)-one, 2-({[4-(dimethylamino)pyridin-2-yl]oxy}methyl)-5-(4-fluorophenyl)-6,7-dihydropyrazolo[1,5-a]pyrazin-4(5H)-one, 2-(phenoxymethyl)-5-(6-piperidin-4-ylpyridin-2-yl)-6,7-dihydropyrazolo[1,5-a]pyrazin-4(5H)-one, 2-(phenoxymethyl)-5-[(1S)-1,2,2-trimethylpropyl]-6,7-dihydropyrazolo[1,5-a]pyrazin-4(5H)-one, 2-{[(2,6-dimethylpyridin-4-yl)oxy]methyl}-5-(4-fluorophenyl)-6,7-dihydropyrazolo[1,5-a]pyrazin-4(5H)-one, 3-{[(7*R)-5-(4-fluorophenyl)-7-methyl-4-oxo-4,5,6,7-tetrahydropyrazolo[1,5-a]pyrazin-2-yl]methoxy}benzonitrile, 3-{[5-(cyclopropylmethyl)-4-oxo-4,5,6,7-tetrahydropyrazolo[1,5-a]pyrazin-2-yl]methoxy}benzonitrile, 3-chloro-5-(4-fluorophenyl)-2-(phenoxymethyl)-6,7-dihydropyrazolo[1,5-a]pyrazin-4(5H)-one, 3-chloro-5-(cyclopropylmethyl)-2-(phenoxymethyl)-6,7-dihydropyrazolo[1,5-a]pyrazin-4(5H)-one, 5-(4-fluorophenyl)-2-({[6-(methylamino)pyridin-2-yl]oxy}methyl)-6,7-dihydropyrazolo[1,5-a]pyrazin-4(5H)-one, 5-(4-fluorophenyl)-2-{[(4-methylpyrimidin-2-yl)oxy]methyl}-6,7-dihydropyrazolo[1,5-a]pyrazin-4(5H)-one, 5-(4-fluorophenyl)-2-{[(5-methylpyridin-2-yl)oxy]methyl}-6,7-dihydropyrazolo[1,5-a]pyrazin-4(5H)-one, 5-(4-fluorophenyl)-2-{[(6-methylpyrazin-2-yl)oxy]methyl}-6,7-dihydropyrazolo[1,5-a]pyrazin-4(5H)-one, 5-(5-methyl-1H-pyrazol-4-yl)-2-(phenoxymethyl)-6,7-dihydropyrazolo[1,5-a]pyrazin-4(5H)-one, 5-(5-methylpyridazin-3-yl)-2-(phenoxymethyl)-6,7-dihydropyrazolo[1,5-a]pyrazin-4(5H)-one, 5-(cyclopropylmethyl)-2-(1-phenoxyethyl)-6,7-dihydropyrazolo[1,5-a]pyrazin-4(5H)-one, 5-(cyclopropylmethyl)-3-methyl-2-(phenoxymethyl)-6,7-dihydropyrazolo[1,5-a]pyrazin-4(5H)-one, and 5-[6-(dimethylamino)pyridin-2-yl]-2-[(pyridin-2-yloxy)methyl]-6,7-dihydropyrazolo[1,5-a]pyrazin-4(5H)-one, or a subgroup thereof. Included within the scope of this list are stereoisomeric forms, the acid addition salts and the solvates thereof. In a further aspect, within the scope of this list are pharmaceutically acceptable salts, hydrates, solvates, and polymorphs thereof.

It is contemplated that one or more compounds can optionally be omitted from the disclosed invention.

3. Positive Allosteric Modulation of mGluR5 Response

Generally, the disclosed compounds exhibit potentiation of mGluR5 response to glutamate as an increase in response to non-maximal concentrations of glutamate in human embryonic kidney cells transfected with mGluR5 in the presence of the compound, compared to the response to glutamate in the absence of the compound. For example, a compound can exhibit positive allosteric modulation of mGluR5 with an $EC_{50}$ of less than about 10,000 nM, of less than about 5,000 nM. of less than about 1,000 nM, of less than about 500 nM, or of less than about 100 nM. In a further aspect, the mGluR5 is rat mGluR5. In a still further aspect, the mGluR5 is human mGluR5.

In one aspect, the disclosed compounds exhibit potentiation of mGluR5 response to glutamate as an increase in response to non-maximal concentrations of glutamate in human embryonic kidney cells transfected with human mGluR5 in the presence of the compound, compared to the response to glutamate in the absence of the compound. In a further aspect, the transfected cell line is the H10H cell line. In a yet further aspect, the transfected cell line is the H12H cell line. For example, a compound can exhibit positive allosteric modulation of transfected human mGluR5 ith an $EC_{50}$ of less than about 10,000 nM, of less than about 5,000 nM. of less than about 1,000 nM, of less than about 500 nM, or of less than about 100 nM.

In one aspect, the disclosed compounds exhibit potentiation of mGluR5 response to glutamate as an increase in response to non-maximal concentrations of glutamate in human embryonic kidney cells transfected with rat mGluR5 in the presence of the compound, compared to the response to glutamate in the absence of the compound. For example, a compound can exhibit positive allosteric modulation of transfected rat mGluR5 with an $EC_{50}$ of less than about 10,000 nM, of less than about 5,000 nM. of less than about 1,000 nM, of less than about 500 nM, or of less than about 100 nM.

C. METABOTROPIC GLUTAMATE RECEPTOR ACTIVITY

The utility of the compounds in accordance with the present invention as potentiators of metabotropic glutamate receptor activity, in particular mGluR5 activity, can be demonstrated by methodology known in the art. Human embryonic kidney (HEK) cells transfected with rat mGluR5 were plated in clear bottom assay plates for assay in a Functional Drug Screening System (FDSS). In the alternative assay, HEK cells transfected with human mGluR5 were plated for assay in the FDSS. In some cases the HEK cells transfected with human mGluR5 were the H10H cell line. Alternatively, the HEK cells transfected with human mGluR5 were the H12H cell line. Rat assay results were found to correlate well with human assay results. The cells were loaded with a $Ca^{2+}$-sensitive fluorescent dye (e.g., Fluo-4), and the plates were washed and placed in the FDSS instrument. After establishment of a fluorescence baseline for twelve seconds, the compounds of the present invention were added to the cells, and the response in cells was measured. Alternatively, in various further aspects, after establishment of a fluorescence baseline for about three seconds, the compounds of the present invention were added to the cells, and the response in cells was measured. Five minutes later, an mGluR5 agonist (e.g., glutamate, 3,5-dihydroxyphenylglycine, or quisqualate) was added to the cells, and the response of the cells was measured. Potentiation of the agonist response of mGluR5 by the compounds in the present invention was observed as an increase in response to non-maximal concentrations of agonist (here, glutamate) in the presence of compound compared to the response to agonist in the absence of compound.

The above described assay operated in two modes. In the first mode, a range of concentrations of the present compounds were added to cells, followed by a single fixed concentration of agonist. If a compound acted as a potentiator, an $EC_{50}$ value for potentiation and a maximum extent of potentiation by the compound at this concentration of agonist was determined by non-linear curve fitting. In the second mode, several fixed concentrations of the present compounds were added to various wells on a plate, followed by a range of concentrations of agonist for each concentration of present compound; the $EC_{50}$ values for the agonist at each concentration of compound were determined by non-linear curve fitting. A decrease in the $EC_{50}$ value of the agonist with increasing concentrations of the present compounds (a leftward shift of the agonist concentration-response curve) is an indication of the degree of mGluR5 potentiation at a given concentration of the present compound. An increase in the $EC_{50}$ value of the agonist with increasing concentrations of the present compounds (a rightward shift of the agonist concentration-response curve) is an indication of the degree of mGluR5 antagonism at a given concentration of the present compound. The second mode also indicates whether the present compounds also affect the maximum response to mGluR5 to agonists.

In one aspect, the disclosed compounds exhibit potentiation of mGluR5 response to glutamate as an increase in response to non-maximal concentrations of glutamate in human embryonic kidney cells transfected with a mammalian mGluR5 in the presence of the compound, compared to the response to glutamate in the absence of the compound. For example, human embryonic kidney cells can be transfected with human mGluR5. For example, human embryonic kidney cells can be transfected with rat mGluR5. For example, a compound can exhibit positive allosteric modulation of mGluR5 (e.g., rmGluR5) with an $EC_{50}$ of less than about 10,000 nM, of less than about 5,000 nM. of less than about 1,000 nM, of less than about 500 nM, or of less than about 100 nM. Alternatively, the disclosed compounds exhibit potentiation of mGluR5 response to glutamate as an increase in response to non-maximal concentrations of glutamate in human embryonic kidney cells transfected with human mGluR5 in the presence of the compound, compared to the response to glutamate in the absence of the compound. In a further aspect, the transfected cell line is the H10H cell line. In a yet further aspect, the transfected cell line is the H12H cell line. For example, a compound can exhibit positive allosteric modulation of mGluR5 (e.g., hmGluR5) with an $EC_{50}$ of less than about 10,000 nM, of less than about 5,000 nM. of less than about 1,000 nM, of less than about 500 nM, or of less than about 100 nM.

In particular, the disclosed compounds exhibit activity in potentiating the mGluR5 receptor in the aforementioned assays, generally with an $EC_{50}$ for potentiation of less than about 10 µM. Preferred compounds within the present invention had activity in potentiating the mGluR5 receptor with an $EC_{50}$ for potentiation of less than about 500 nM. Preferred compounds further caused a leftward shift of the agonist $EC_{50}$ by greater than 3-fold. These compounds did not cause mGluR5 to respond in the absence of agonist, and they did not elicit a significant increase in the maximal response of mGluR5 to agonists. These compounds are positive allosteric modulators (potentiators) of human and rat mGluR5. In various aspects, the compounds can be selective for mGluR5 compared to the other seven subtypes of metabotropic glutamate receptors.

In vivo efficacy for disclosed compounds can be measured in a number of preclinical rat behavioral model where known, clinically useful antipsychotics display similar positive responses. For example, disclosed compounds can reverse amphetamine-induced hyperlocomotion in male Sprague-Dawley rats at doses ranging from 1 to 100 mg/kg p.o.

D. METHODS OF MAKING THE COMPOUNDS

In one aspect, the invention relates to methods of making compounds useful as positive allosteric modulators of the metabotropic glutamate receptor subtype 5 (mGluR5), which can be useful in the treatment neurological and psychiatric disorders associated with glutamate dysfunction and other diseases in which metabotropic glutamate receptors are involved.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In a further aspect, a compound comprises the product of the disclosed methods. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

In one aspect, the invention relates to a synthetic method comprising the steps of: (a) providing a compound having a structure represented by a formula:

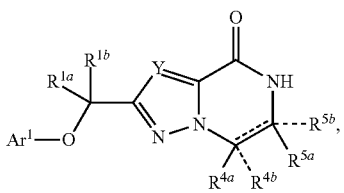

wherein each ____ is independently an optional covalent bond, wherein valence is satisfied; wherein Ar$^1$ is phenyl with 0-3 substituents selected from halogen, cyano, C1-C4 alkyl, C1-C4 alkyloxy, monohalo C1-C4 alkyl, and polyhalo C1-C4 alkyl, or Ar$^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of R$^{1a}$ and R$^{1b}$ is independently selected from hydrogen and C1-C4 alkyl; wherein Y is N or C—R$^3$, wherein R$^3$, when present, is selected from hydrogen, halogen, cyano, and C1-C4 alkyl; wherein R$^{4a}$ is selected from hydrogen and C1-C4 alkyl; wherein R$^{4b}$, when present, is selected from hydrogen and C1-C4 alkyl, or R$^{4a}$ and R$^{4b}$ are covalently bonded and, together with the intermediate carbon, comprise an optionally substituted 3- to 7-membered spirocycloalkyl; wherein R$^{5a}$ is selected from hydrogen and C1-C4 alkyl; and wherein R$^{5b}$, when present, is selected from hydrogen and C1-C4 alkyl, or R$^{5a}$ and R$^{5b}$ are covalently bonded and, together with the intermediate carbon, comprise an optionally substituted 3- to 7-membered spirocycloalkyl, and (b) reacting the compound with R$^2$X, wherein X is a leaving group, and wherein R$^2$ is selected from C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; and C2-C5 heterocyclyl; thereby alkylating the amide.

In one aspect, the invention relates to a synthetic method comprising the steps of: (a) providing a compound having a structure represented by a formula:

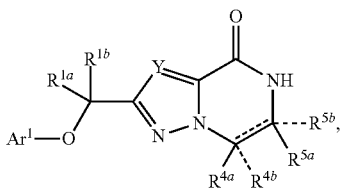

wherein each ____ is independently an optional covalent bond, wherein valence is satisfied; wherein Ar$^1$ is phenyl with 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or Ar$^1$ is pyridinyl, pyridazinyl, pyrimidinyl, or pyrazinyl and has 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of R$^{1a}$ and R$^{1b}$ is independently selected from hydrogen and C1-C4 alkyl; wherein Y is N or C—R$^3$, wherein R$^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein R$^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein R$^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or R$^{4a}$ and R$^{4b}$ are covalently bonded and, together with the intermediate carbon, comprise an optionally substituted 3- to 7-membered spirocycloalkyl; wherein R$^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein R$^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or R$^{5a}$ and R$^{5b}$ are covalently bonded and, together with the intermediate carbon, comprise an optionally substituted 3- to 7-membered spirocycloalkyl; and (b) reacting the compound with R$^2$X, wherein X is a leaving group, and wherein R$^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl, and C3-C6 cycloalkyl; thereby alkylating the amide.

In a further aspect, X is halogen. In a still further aspect, the alkylated amine formed has a structure represented by a formula:

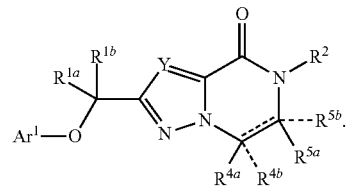

In one aspect, the invention relates to a synthetic method comprising the steps of: (a) providing a compound having a structure represented by a formula:

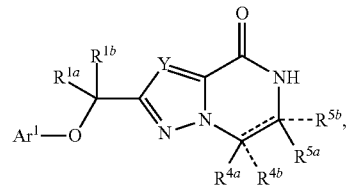

wherein each ____ is independently an optional covalent bond, wherein valence is satisfied; wherein Ar$^1$ is phenyl with 0-3 substituents selected from halogen, cyano, C1-C4 alkyl, C1-C4 alkyloxy, monohalo C1-C4 alkyl, and polyhalo C1-C4 alkyl, or Ar$^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of R$^{1a}$ and R$^{1b}$ is independently selected from hydrogen and C1-C4 alkyl; wherein Y is N or C—R$^3$, wherein R$^3$, when present, is selected from hydrogen, halogen, cyano, and C1-C4 alkyl; wherein R$^{4a}$ is selected from hydrogen and C1-C4 alkyl; wherein R$^{4b}$, when present, is selected from hydrogen and C1-C4 alkyl, or R$^{4a}$ and R$^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl, and (b) coupling the compound with $R^2X$, in the presence of a coupling reagent, wherein X is bromo or iodo, and wherein $R^2$ is selected from C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; thereby substituting at the amide.

In one aspect, the invention relates to a synthetic method comprising the steps of: (a) providing a compound having a structure represented by a formula:

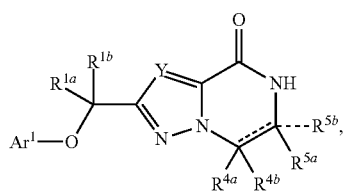

wherein each _____ is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; and (b) coupling the compound with $R^2X$, in the presence of a coupling reagent, wherein X is bromo or iodo, and wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; thereby substituting at the amide.

In a further aspect, $R^2$ is selected from phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl. In a yet further aspect, the coupling reagent is copper (I) iodide. In a still further aspect, the alkylated amide formed has a structure represented by a formula:

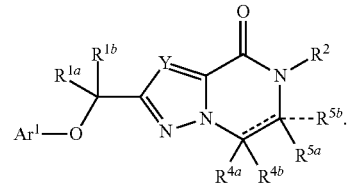

In one aspect, the invention relates to a synthetic method comprising the steps of: (a) providing a compound having a structure represented by a formula:

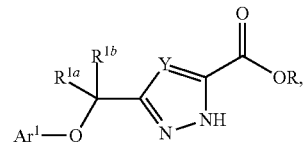

wherein R is hydrogen or alkyl; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein Y is N or C—$R^3$, wherein $R^3$, when present, is selected from hydrogen, halogen, cyano, and C1-C4 alkyl; and (b) reacting the compound with:

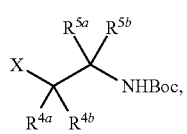

wherein X is a leaving group; wherein each of $R^{4a}$ and $R^{4b}$ is independently selected from hydrogen and C1-C4 alkyl, or are covalently bonded and, together with the intermediate carbon, comprise an optionally substituted 3- to 7-membered spirocycloalkyl; and wherein each of $R^{5a}$ and $R^{5b}$ is independently selected from hydrogen and C1-C4 alkyl, or are covalently bonded and, together with the intermediate carbon, comprise an optionally substituted 3- to 7-membered spirocycloalkyl, thereby forming:

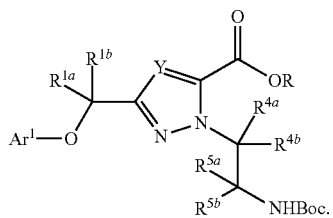

In one aspect, the invention relates to a synthetic method comprising the steps of: (a) providing a compound having a structure represented by a formula:

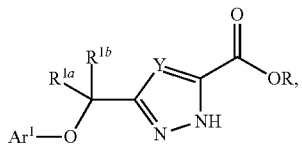

wherein R is hydrogen or alkyl; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein Y is N or C—$R^3$, wherein $R^3$, when present, is selected from hydrogen, halogen, cyano, and C1-C4 alkyl; and (b) reacting the compound with:

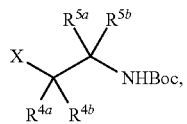

wherein X is a leaving group; wherein each of $R^{4a}$ and $R^{4b}$ is independently selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl, or are covalently bonded and, together with the intermediate carbon, comprise an optionally substituted 3- to 7-membered spirocycloalkyl; and wherein each of $R^{5a}$ and $R^{5b}$ is independently selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl, or are covalently bonded and, together with the intermediate carbon, comprise an optionally substituted 3- to 7-membered spirocycloalkyl, thereby forming:

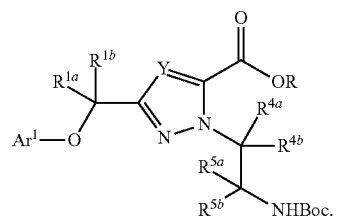

In a further aspect, the reaction is a substitution reaction, and the leaving group is halogen. In a yet further aspect, the reaction is performed in the presence of a base. In a still further aspect, the reaction is a Mitsunobu type reaction, and the leaving group is hydroxyl. In a even further aspect, the providing step comprises reacting hydrazine with a compound having a structure represented by a formula:

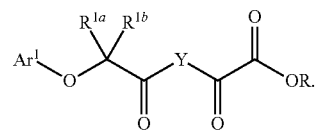

In a further aspect, the reaction further comprises the steps of deprotecting the amine and cyclizing to form a compound having a structure represented by a formula:

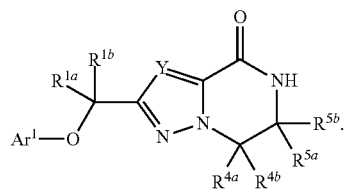

In a still further aspect, the reaction further comprises the step of reacting with $R^2X$, wherein X is a leaving group, and wherein $R^2$ is selected from C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; and C2-C5 heterocyclyl; thereby alkylating the amide.

In a further aspect, the reaction further comprises the step of reacting with $R^2X$, in the presence of a coupling reagent, wherein X is bromo or iodo, and wherein $R^2$ is selected from C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; thereby substituting at the amide. In a still further aspect, $R^2$ is selected from phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl. In a yet further aspect, the coupling reagent is copper (I) iodide. In an even further aspect, the amide formed has a structure represented by a formula:

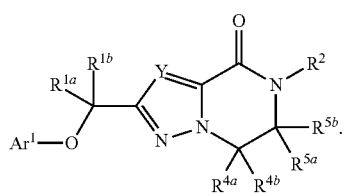

In a further aspect, the reaction further comprises the step of reacting with $R^2X$, in the presence of a coupling reagent, wherein X is bromo or iodo, and wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; thereby substituting at the amide. In a still further aspect, phenyl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl. In a yet further aspect, the coupling reagent is copper (I) iodide. In an even further aspect, the amide formed has a structure represented by a formula:

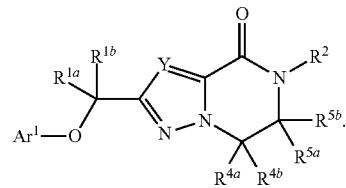

In one aspect, the invention relates to a synthetic method comprising the steps of: (a) providing a compound having a structure represented by a formula:

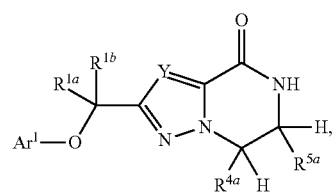

wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; and wherein $R^{5a}$ is selected from hydrogen and C1-C4 alkyl, and (b) oxidizing the compound with an oxidating reagent, thereby yielding a compound having a structure represented by a formula:

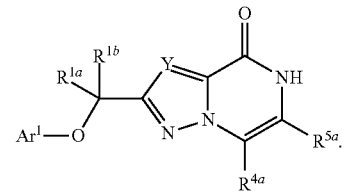

In one aspect, the invention relates to a synthetic method comprising the steps of: (a) providing a compound having a structure represented by a formula:

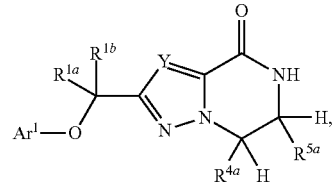

wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; and wherein $R^{5a}$ is selected from hydrogen and C1-C4 alkyl, and (b) oxidizing the compound with an oxidating reagent, thereby yielding a compound having a structure represented by a formula:

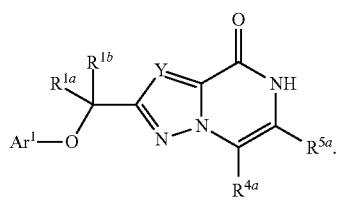

In a further aspect, the oxidating reagent is manganese(IV) oxide.

In one aspect, the invention relates to a synthetic method comprising the steps of: (a) providing a compound having a structure represented by a formula:

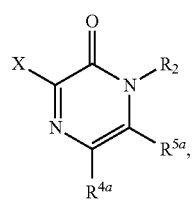

wherein X is halogen or pseudohalogen; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein $R^{4a}$ is selected from hydrogen and C1-C4 alkyl; and wherein $R^{5a}$ is selected from hydrogen and C1-C4 alkyl; and (b) coupling, in the presence of a coupling reagent, the compound with an aryloxyacetamide having a structure represented by a formula:

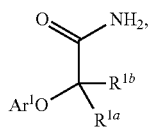

wherein Ar$^1$ is phenyl with 0-3 substituents selected from halogen, cyano, C1-C4 alkyl, C1-C4 alkyloxy, monohalo C1-C4 alkyl, and polyhalo C1-C4 alkyl, or Ar$^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; and wherein each of $R^{1a}$ and $R^{1b}$ is independently selected from hydrogen and C1-C4 alkyl; thereby yielding a compound having a structure represented by a formula:

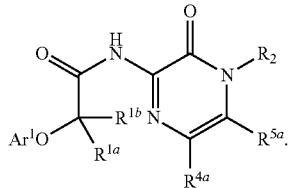

In one aspect, the invention relates to a synthetic method comprising the steps of: (a) providing a compound having a structure represented by a formula:

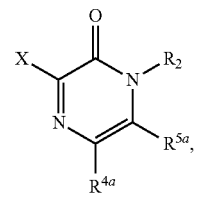

wherein X is halogen or pseudohalogen; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein $R^{4a}$ is selected from hydrogen and C1-C4 alkyl; and wherein $R^{5a}$ is selected from hydrogen and C1-C4 alkyl; and (b) coupling, in the presence of a coupling reagent, the compound with an aryloxyacetamide having a structure represented by a formula:

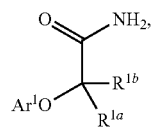

wherein Ar$^1$ is phenyl with 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or Ar$^1$ is pyridinyl, pyridazinyl, pyrimidinyl, or pyrazinyl and has 0-3 substituents selected from halogen, cyano, hydroxyl, —NH$_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; and wherein each of R$^{1a}$ and R$^{1b}$ is independently selected from hydrogen and C1-C4 alkyl; thereby yielding a compound having a structure represented by a formula:

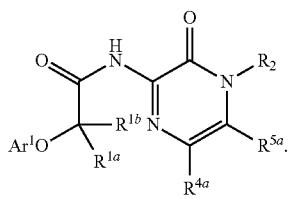

In a further aspect, the coupling reagent is palladium (II) acetate. In a yet further aspect, X is chloro. In a still further aspect, the method further comprises the steps of: reaction of the resultant compound with a dialkyl chlorophosphate, in the presence of a base; and treatment with hydroxylamine; thereby yielding a compound having a structure represented by a formula:

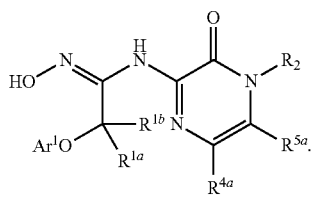

In an even further aspect, the method further comprises the step of reacting the resultant compound represented with a dehydrating reagent, thereby yielding a compound having a structure represented by a formula:

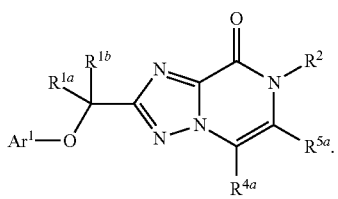

In a further aspect, the method further comprises the step of reducing the resultant compound represented above to yield a compound represented by the formula:

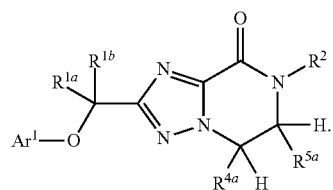

In one aspect, the disclosed compounds comprise the products of the synthetic methods described herein. In a further aspect, the disclosed compounds comprise a compound produced by a synthetic method described herein.

In a further aspect, the compound produced exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In a further aspect, the invention relates to a pharmaceutical composition comprising a therapeutically effective amount of a compound produced by one the synthetic methods described herein and a pharmaceutically acceptable carrier.

1. Reaction Scheme I

In one aspect, compounds of the present invention can be prepared as shown below. Compounds are represented in generic form, with substituents as noted in compound descriptions elsewhere herein.

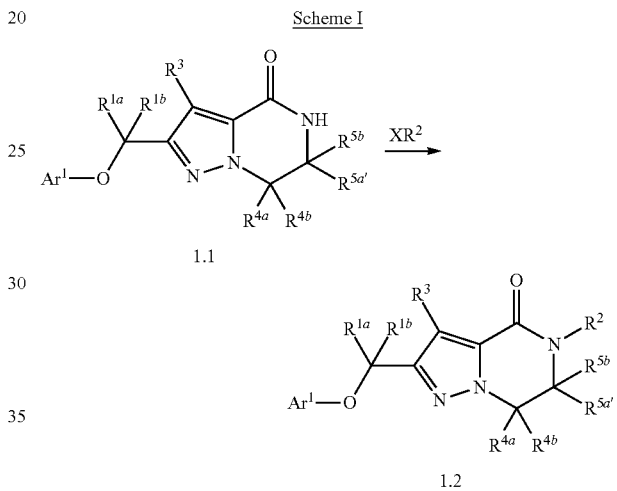

Scheme I

In one aspect, compounds of type 1.2 can be prepared starting with the compound of type 1.1 as outlined in Scheme I. Briefly, a compound represented by formula 1.2 in Scheme I can be prepared by a coupling reaction of a compound of type 1.1 with an aryl or heteroaryl halide (XR$^2$ in Scheme I, wherein X is a halogen and R$^2$ is aryl or heteroaryl) with a coupling reagent in the presence of a ligand in the presence of a base in a solvent at a convenient temperature for a period of time to ensure the completion of the reaction. In one aspect, X is Cl, Br or I. In a further aspect, the coupling reagent is copper (I) iodide or palladium (II) acetate. In a still further aspect, the ligand is N,N'-dimethylethylenediamine or 2-dicyclohexylphosphino-2',4',6'-triisopropylbiphenyl. In an even further aspect, the base is potassium phosphate or cesium carbonate. In a further aspect, the solvent is toluene or 1,4-dioxane. In a yet further aspect, the temperature is about 100° C. to 140° C. Suitable compounds of type XR$^2$ as shown in Scheme I are commercially available or can be prepared by methods described in the literature.

Alternatively, compounds of type 1.2 can be prepared by reaction of a compound of type 1.1 with a suitable boronic acid (XR$^2$ in Scheme I, wherein X is B(OH)$_2$ and R$^2$ is cycloalkyl) in the presence of an appropriate catalyst and a base in an inert solvent at a convenient temperature for a period of time to ensure the completion of the reaction. In one aspect, the boronic acid is cyclopropylboronic acid. In a further aspect, the catalyst is copper (II) acetate monohydrate. In a still further aspect, the base is 4-(dimethylamino)pyridine and the inert solvent is toluene. In a yet further aspect, the temperature is about 80° C. to 110° C.

Alternatively, compounds of type 1.2 can be prepared starting with the compound of type 1.1 as outlined in Scheme I. Briefly, a compound represented by formula 1.2 in Scheme I can be prepared by reacting a compound of type 1.1 with an alkylating reagent ($XR^2$ in Scheme I, wherein X is chlorine or bromine and $R^2$ is an alkyl) in the presence of base in an inert solvent at a convenient reaction temperature for a period of time to ensure the completion of the reaction. In a further aspect, the base is sodium hydride. In a yet further aspect, the inert solvent is tetrahydrofuran. In a still further aspect, the temperature is about 0° C. to 40° C. Suitable compounds of type $XR^2$ as shown in Scheme I are commercially available.

2. Reaction Scheme II

Alternatively, one can prepare the intermediate (compound type 1.1 in Scheme I) by reaction shown in Scheme II below. For example, a compound represented by compound 2.5 can be reacted with an acid in an inert solvent at a convenient reaction temperature for a period of time to ensure the completion of the reaction followed by reaction with a base in an inert solvent at a convenient reaction temperature for a period of time to ensure the completion of the reaction. In one aspect, the acid is hydrochloric acid and the inert solvent is 1,4-dioxane. In a still further aspect, the temperature is about 0° C. to 40° C. In one aspect, the base is sodium carbonate and the inert solvent is 1,4-dioxane. In a still further aspect, the temperature is about 0° C. to 40° C. The reaction scheme shown below in Scheme II outlines a synthetic method to prepare suitable compounds of the type represented by compound 2.5.

Briefly, a compound of type 2.3 can be prepared by reaction of a compound of type 2.1 with a compound of type 2.2 in presence of a base in an inert solvent by heating at a convenient temperature for a period of time that allows completion of the reaction. In one aspect, the base is sodium ethoxide. In a further aspect, the inert solvent is ethanol. In a yet further aspect, the temperature is about 70° C. to 110° C. Compounds of type 2.1 and type 2.2 can be obtained commercially.

A compound of type 2.4 as shown in Scheme II can be prepared by procedures similar to those described in US 2005143443 A1 20050630 by reaction of a compound of type 2.3 with hydrazine in an inert solvent by heating at a convenient temperature for a period of time to ensure completion of the reaction. In one aspect, the inert solvent is ethanol. In a further aspect, the temperature is 70° C. to 110° C. Alternatively, compounds of type 2.4 can be obtained commercially.

A compound of type 2.5 as shown in Scheme II can be prepared by a Mitsunobu type reaction between a compound of type 2.4 with an alcohol of the type as shown in Scheme II wherein X is OH in the presence of a triarylphosphine and a dialkyl azodicarboxylate reagent in an inert solvent at a convenient temperature for a period of time to ensure completion of the reaction. In one aspect, the triarylphosphine is triphenylphosphine. In a further aspect, the dialkyl azodicarboxylate reagent is di-tert-butyl azodicarboxylate (DTBAD). In a still further aspect, the inert solvent is tetrahydrofuran. In a yet further aspect, the convenient temperature is achieved by conventional heating or under microwave irradiation.

Alternatively, a compound of type 2.5 can be prepared by reacting a compound of type 2.4 with an alkylating reagent of the type as shown in Scheme II wherein X is a leaving group in the presence of base in an inert solvent at a convenient temperature for a period of time to ensure completion of the reaction. In one aspect, the base is potassium carbonate. In a further aspect, the inert solvent is N,N-dimethylformamide.

In a still further aspect, the temperature is about 0° C. to 40° C. In an even further aspect, the leaving group, X, is a halogen. In a further aspect, the halogen is bromine.

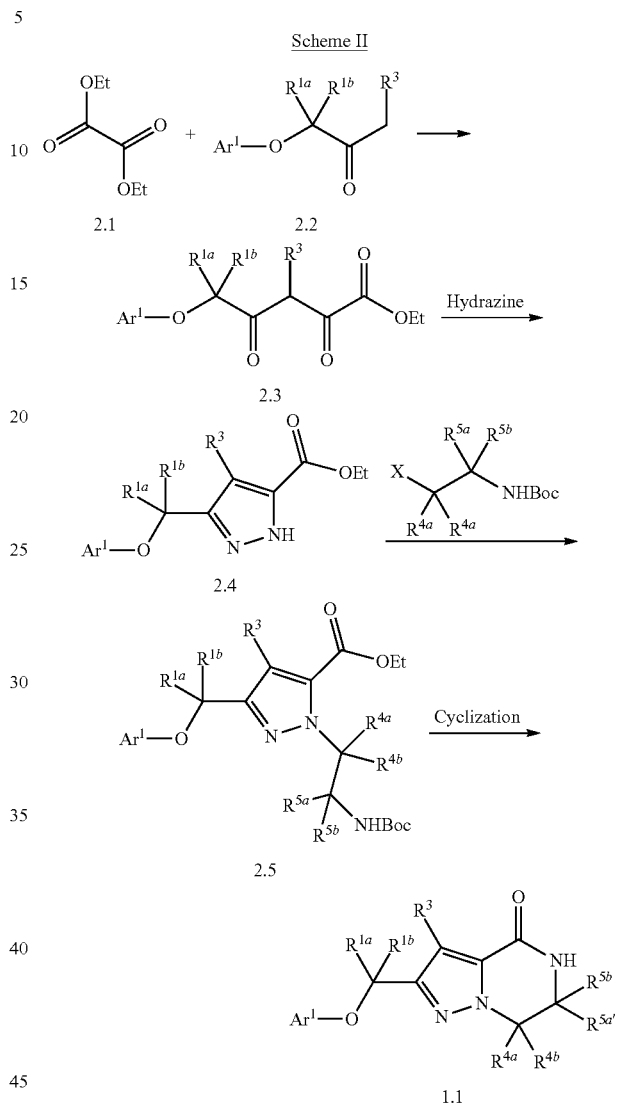

3. Reaction Scheme III

Alternatively, one can prepare compounds of the present invention by methods shown in Scheme III below. A compound represented by type 3.2 in the scheme can be prepared by a coupling reaction of a compound of type 3.1 with a compound of type $XR^2$ (as shown in Scheme III, wherein X is a halogen and $R^2$ is aryl or heteroaryl) with a coupling reagent in the presence of a ligand and a base in a solvent at a convenient temperature to ensure completion of the reaction. In one aspect, the halogen is Br or I. In a further aspect, the coupling reagent is copper (I) iodide. In a yet further aspect, the ligand is N,N'-dimethylethylenediamine. In a still further aspect, the base is potassium carbonate. In an even further aspect, the solvent is toluene. In a further aspect, the temperature is about 100° C. to 140° C. A compound of type $XR^2$ as described in the foregoing can be obtained commercially or can be prepared by methods described in the literature.

In one aspect, a compound of type 3.2 can be prepared by reacting a compound of type 3.1 with an alkylating reagent of type $XR^2$, wherein X is a halogen and $R^2$ is alkyl, in the presence of a base in an inert solvent at a convenient temperature to ensure completion of the reaction. In a further aspect, the halogen is Cl or Br. In a still further aspect, the base is sodium hydride. In a yet further aspect, the temperature is about −10° C. to 25° C. A compound of type $XR^2$ as described in the foregoing can be obtained commercially.

A compound of type 3.1 can be prepared by reacting a compound of type 1.1 with an oxidation reagent in an inert solvent at a convenient temperature for a period of time that allows completion of the reaction. In one aspect, the oxidation reagent is manganese oxide. In a further aspect, the temperature is about 80° C. to 140° C. In a yet further aspect, the inert solvent is toluene.

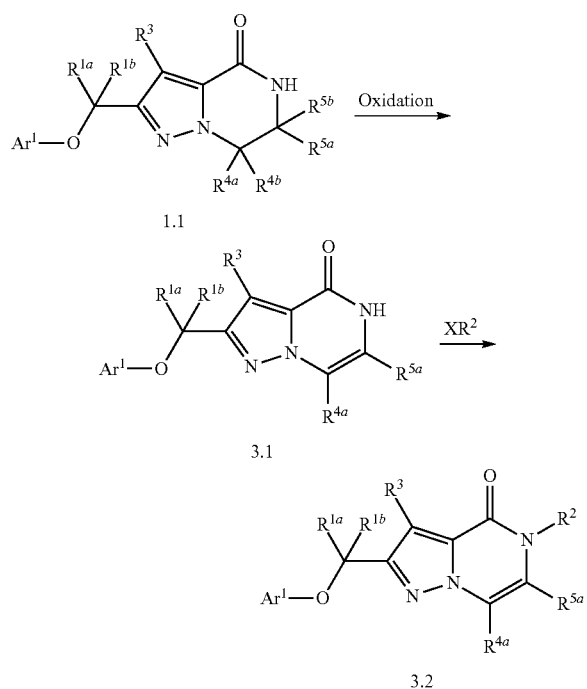

4. Reaction Scheme IV

In one aspect, compounds of the present invention can be prepared by the methods shown in Scheme W. A compound represented by type 4.7 as shown in Scheme IV can be prepared by reaction of a compound of type 4.6 with hydrogen in the presence of catalyst in an inert solvent at a convenient temperature for a period of time that allows completion of the reaction. In a further aspect, the catalyst is 10% palladium on charcoal. In a still further aspect, the inert solvent is a mixture of methanol and dichloromethane. In a yet further aspect, the temperature is about 80° C. to 120° C.

A compound of type 4.6 can be prepared by reaction of a compound of type 4.5 with a dehydrating reagent in an inert solvent and heating at a convenient temperature for a period of time to ensure completion of the reaction. In one aspect, the dehydrating reagent is phosphorus oxychloride. In a still further aspect, the inert solvent is tetrahydrofuran. In a yet further aspect, heating is carried out by conventional means or under microwave irradiation.

A compound of type 4.5 can be prepared by reaction of a compound of type 4.4 with diethyl chlorophosphate in the presence of a base in an inert solvent at a convenient temperature for a period of time to allow completion of the reaction. In one aspect, the base is sodium hydride. In a yet further aspect, the inert solvent is tetrahydrofuran. In a further aspect, the temperature is about −10° C. to 25° C. The reaction is followed by treatment with hydroxylamine at temperature of about −10° C. to 25° C. for a period of time to ensure the completion of the reaction.

A compound of type 4.4 can be prepared by a coupling reaction of a compound of type 4.3 with an aryloxyacetamide and a coupling reagent in the presence of ligand and base in a solvent at a convenient temperature for a period of time to ensure completion of the reaction. In one aspect, the coupling reagent is palladium (II) acetate. In a still further aspect, the ligand is 4,5-bis(diphenylphosphino)-9,9-dimethylxanthene. In a still further aspect, the base is cesium carbonate. In a yet further aspect, the solvent is 1,4-dioxane. In an even further aspect, the temperature is about 80° C. to 120° C.

A compound of type 4.3 can be prepared by reaction of a compound of type 4.2 with a chlorinating reagent in an inert solvent by heating at a convenient temperature for a period of time to ensure completion of the reaction. In one aspect, the chlorinating reagent is phosphorus oxychloride. In a further aspect, the inert solvent is 1,2-dichloroethane. Heating may be carried out by conventional heating or under microwave irradiation.

A compound of type 4.2 can be prepared by reaction of a compound of type 4.1 with a compound of type $XR^2$, wherein X is a halogen and $R^2$ is aryl or heteroaryl, with a coupling reagent in the presence of ligand and base in an inert solvent at a convenient temperature to allow for completion of the reaction. In one aspect, the halogen is Br or I. In a further aspect, the coupling reagent is copper (I) iodide. In a still further aspect, the ligand is N,N'-dimethylethylenediamine. In a yet further aspect, the base is potassium phosphate. In a further aspect, the inert solvent is a mixture of N,N-dimethylformamide and 1,4-dioxane. Heating may be carried out by conventional heating or under microwave irradiation.

A compound of type 4.1 can be prepared by procedures similar to those described in *Journal of Medicinal Chemistry* 2009, 52(7), 2076-2089.

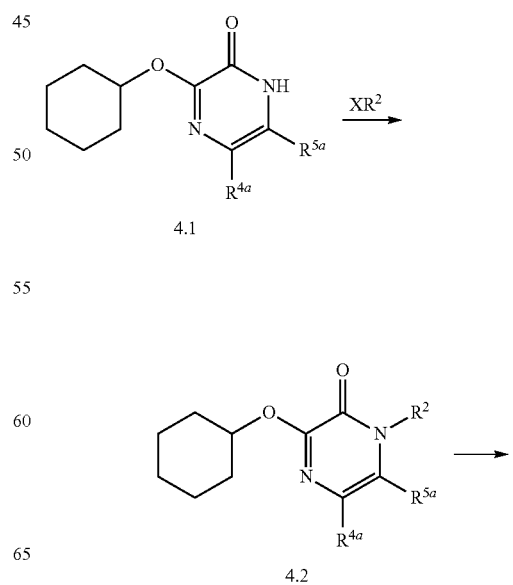

151

-continued

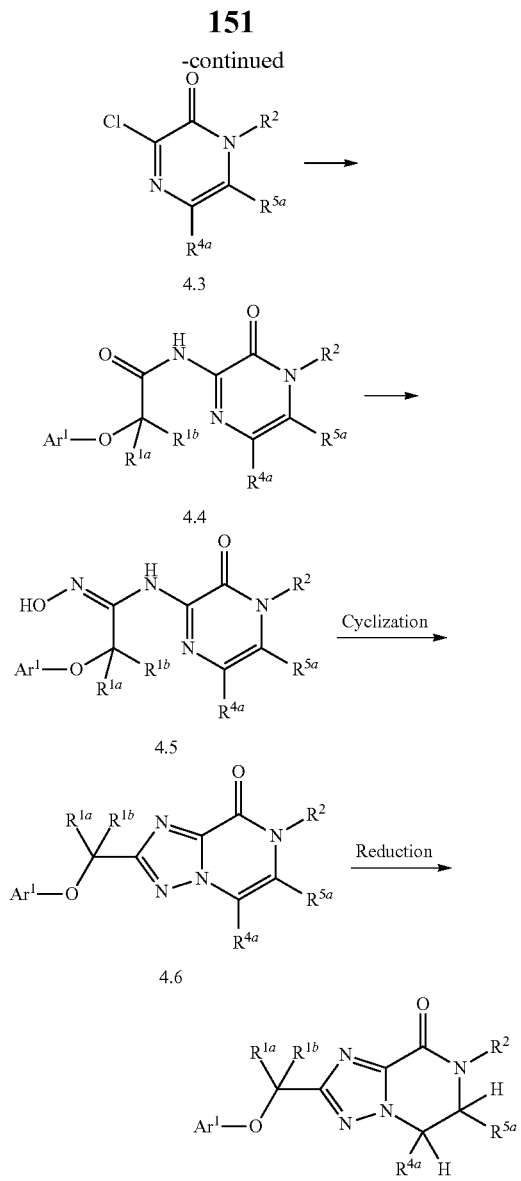

5. Reaction Scheme V

In various aspects, one can prepare compounds of the present invention by methods described in Scheme V below. For example, a compound represented by compound 5.2 can be prepared by a coupling reaction of a compound of type 5.1 with a suitable boronic acid in the presence of an appropriate catalyst and a base in an inert solvent by heating at a convenient temperature for a period of time to ensure the completion of the reaction. In one aspect, the boronic acid can be cyclopropylboronic acid. In a further aspect, the catalyst can be tetrakis(triphenylphosphine)palladium(0). In a yet further aspect, the base is potassium carbonate. In an even further aspect, the solvent can be a mixture of 1,4-dioxane and N,N-dimethylformamide. In a further aspect, the convenient temperature is achieved by conventional heating or under microwave irradiation.

Briefly, a compound of type 5.1 can be prepared by a coupling reaction of a compound of type 1.1 with a 2,6-dibromopyridine with a coupling reagent in the presence of a ligand and a base in an inert solvent at a convenient temperature for a period of time to ensure the completion of the reaction. In one aspect, the coupling reagent is copper (I) iodide. In a further aspect, the ligand is N,N'-dimethylethylenediamine. In a still further aspect, the base is potassium carbonate. In an even further aspect, the solvent is toluene. In a yet further aspect, the temperature is about 100° C. to 140° C.

152

Compound 1.1 can be prepared following the reaction conditions shown above in Scheme II.

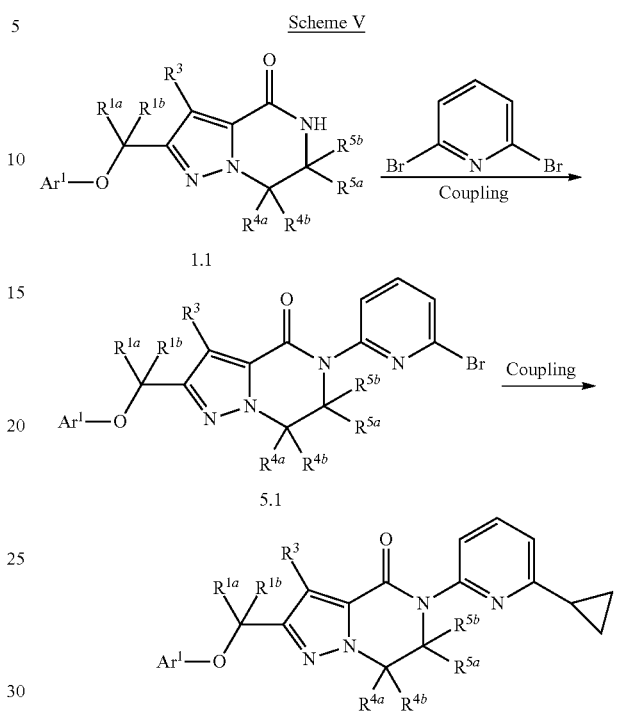

6. Reaction Scheme VI

In various aspects, a compound of type 6.5 can be prepared by deprotection of a compound of type 6.4 as outlined in Scheme VI below with an acid in an inert solvent at a convenient temperature for a period of time to ensure the completion of the reaction. In one aspect, the acid is trifluoroacetic acid. In a further aspect, the solvent is dichloromethane. In a still further aspect, the temperature is about 0° C. to 40° C.

A compound of type 6.2 can be prepared by hydrogenation of a compound type 6.3 in the presence of a catalyst and ammonium formate in an inert solvent at a convenient temperature for a period of time to ensure the completion of the reaction. In one aspect, the catalyst is 10% palladium on charcoal. In a further aspect, the solvent is methanol. In a yet further aspect, the temperature is about 60° C. to 100° C.

Similarly, a compound of type 6.2 can be prepared starting with a compound of type 6.1 following the reaction conditions shown above for compound 6.4.

A compound of type 6.3 can be prepared by reaction of a compound of type 5.1 with (N-tert-butoxycarbonyl)-1,2,3,6-tetrahydropyridine-4-boronic acid pinacol ester and a coupling reagent in the presence of a base in an inert solvent at a convenient temperature for a period of time to ensure the completion of the reaction. In one aspect, the coupling reagent is tetrakis(triphenylphosphine)palladium(0). In a further aspect, the base is potassium carbonate. In a still further aspect, the solvent is a mixture of 1,4-dioxane and N,N-dimethylformamide. In a yet further aspect, the convenient temperature is achieved by conventional heating or under microwave irradiation.

Similarly, a compound of type 6.1 can be prepared by reaction of a compound of type 5.1 with 4-(4,4,5,5-tetramethyl-1,3,2-dioxaborolan-2-yl)-3,6-dihydro-2H-pyran following the reaction conditions shown above for compound 6.3.

Compound 5.1 can be prepared following the reaction conditions shown above in Scheme V.

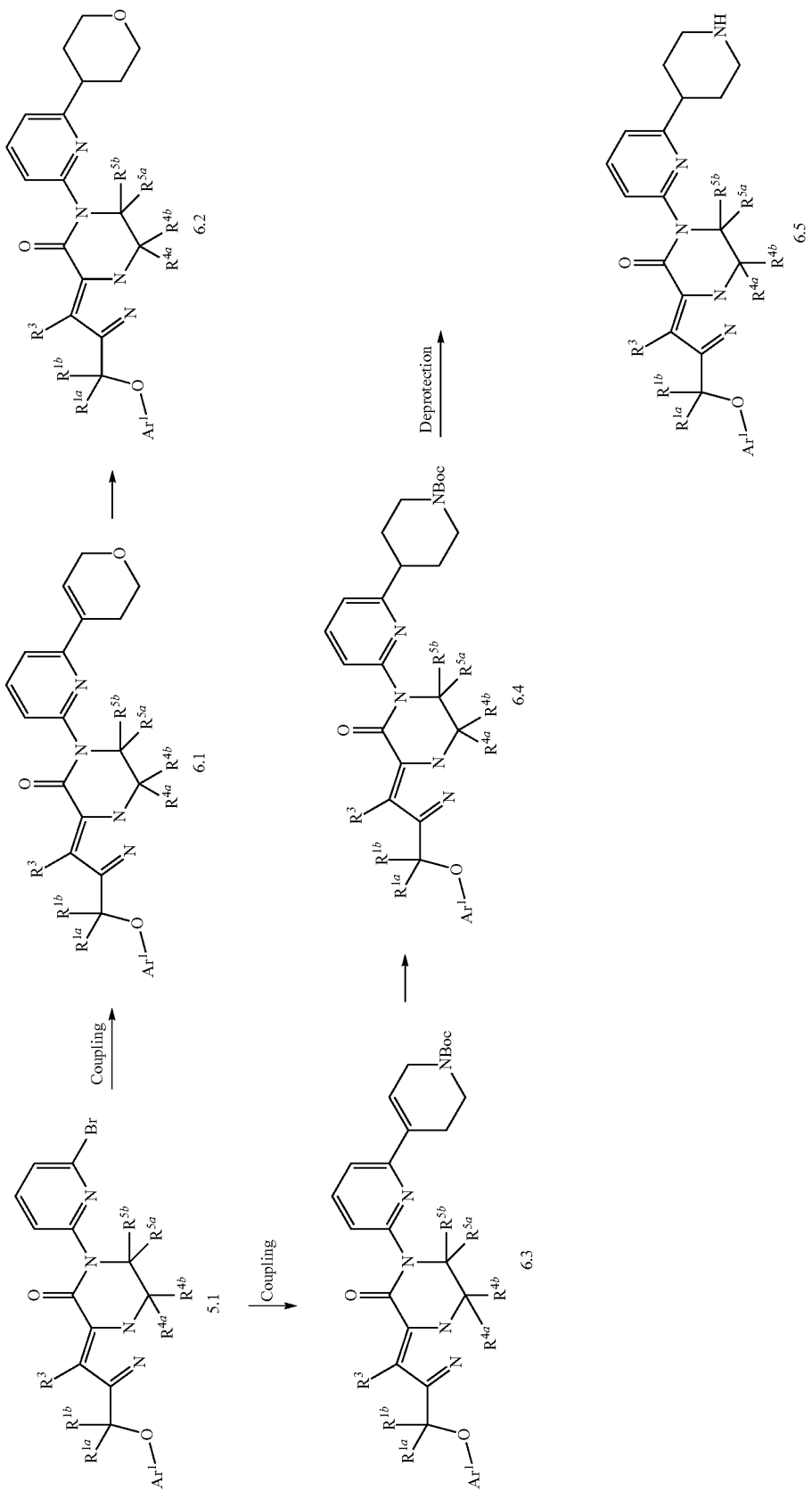

7. Reaction Scheme VII

In various aspects, a compound of type 7.2 can be prepared starting with the compound of type 7.1 as outlined in Scheme VII below, wherein the substituent group "Het" is a heteroaryl and X is a halogen. Briefly, a compound represented by formula 7.2 can be prepared by dehalogenation of a compound type 7.1 in the presence of hydrogen with a catalyst and a base in an inert solvent at a convenient temperature for a period of time to ensure the completion of the reaction. In one aspect, the catalyst is 10% palladium on charcoal. In a further aspect, the base is triethylamine. In a still further aspect, the solvent is tetrahydrofuran. In a yet further aspect, the temperature is about 0° C. to 40° C.

A compound of type 7.1 can be prepared by reaction of a compound of type 1.1 with a dihalo-heteroaryl with a coupling reagent in the presence of a ligand and a base in an inert solvent at a convenient temperature for a period of time to ensure the completion of the reaction. In one aspect, the coupling reagent is palladium (II) acetate. In a further aspect, the ligand is 2-dicyclohexylphosphino-2',4',6'-triisopropylbiphenyl. In a still further aspect, the base is cessium carbonate. In an even further aspect, the solvent is 1,4-dioxane. In a yet further aspect, the temperature is about 100° C. to 140° C. In a further aspect, X is Cl. A dihalo-heteroaryl can be obtained commercially.

Compound 1.1 can be prepared following the reaction conditions shown above in Scheme II.

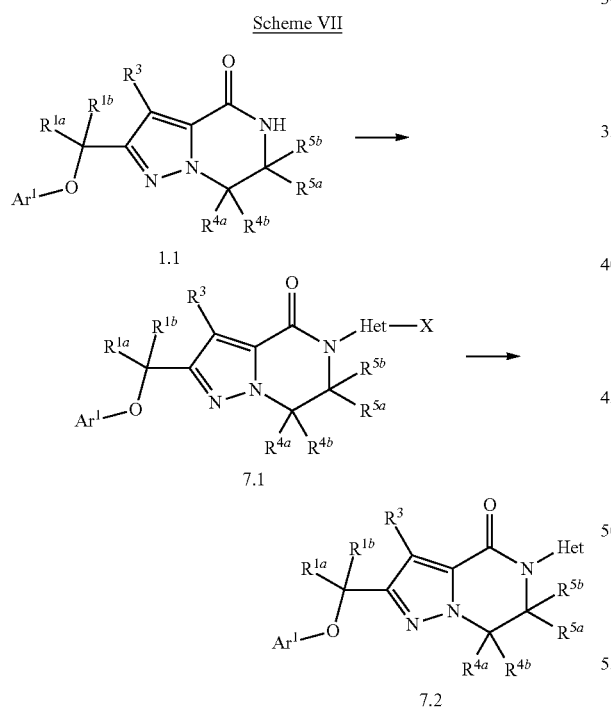

8. Reaction Scheme VIII

In various aspects, a compound of type 8.3 can be prepared starting with the compound of type 8.2 as outlined in Scheme VIII below. Briefly, a compound represented by formula 8.3 can be prepared by reaction of a compound of type 8.2 with a fluorinating reagent in an inert solvent at a convenient temperature for a period of time to ensure the completion of the reaction. In one aspect, the halogenating reagent is (diethylamino)sulfur trifluoride (DAST). In a further aspect, the solvent is dichloromethane. In a yet further aspect, the convenient temperature is achieved by conventional heating or under microwave irradiation.

A compound of type 8.2 can be prepared by deprotection of a compound of type 8.1 with tetrabutylammonium fluoride (TBAF) in a suitable inert solvent at a convenient temperature for a period of time to ensure the completion of the reaction. In one aspect, the inert solvent is tetrahydrofuran. In a further aspect, the temperature is about 0° C. to 40° C.

A compound of type 8.1 can be prepared by reacting a compound of type 1.1 with an alkylating reagent as shown in Scheme VIII, in the presence of a base in an inert solvent at a convenient temperature to ensure completion of the reaction. In one aspect, the alkylating reagent can be (rac) (2-bromo-1-methyl-ethoxy)-tert-butyl-diphenyl-silane. In a further aspect, the base is sodium hydride and the inert solvent is tetrahydrofuran. In a yet further aspect, the convenient temperature is achieved by conventional heating or under microwave irradiation. The alkylating reagent can be obtained commercially.

Compound 1.1 can be synthesized following the reaction conditions shown above in Scheme II.

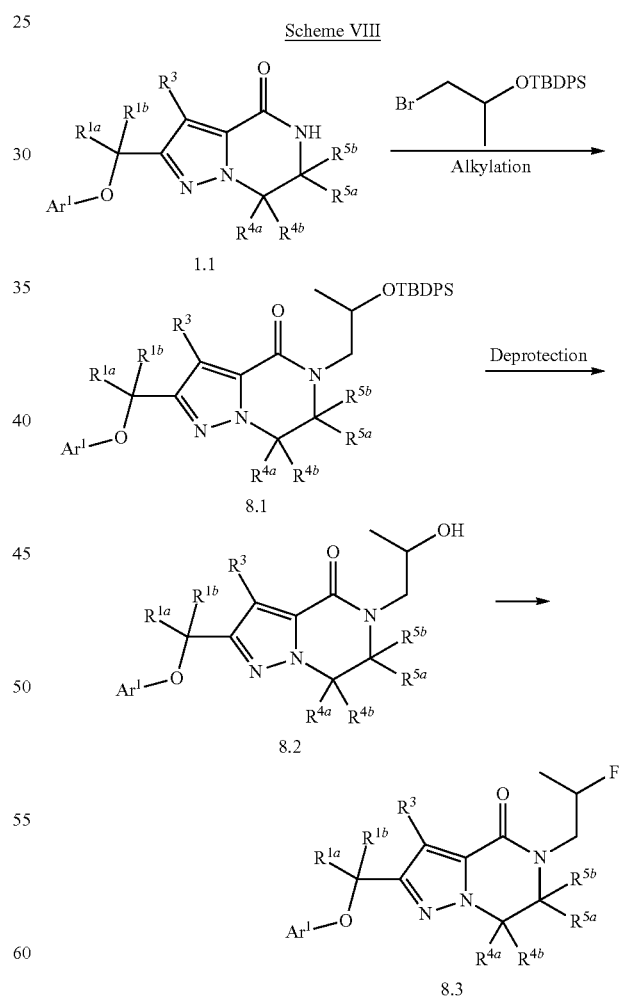

9. Reaction Scheme IX

In various aspects, compounds of type 1.2 can be prepared starting with the compound of type 9.1 as outlined in Scheme IX below. For example, a compound represented by compound 1.2 can be prepared by reacting a compound of type 9.1 with an amine of the type shown in Scheme IX (wherein $R^2$ can be an alkyl), in the presence of potassium iodide in an inert solvent at a convenient temperature to ensure completion of the reaction. In one aspect, the inert solvent is acetonitrile. In a yet further aspect, the temperature is about 70° C. to 110° C. Suitable compounds of type $NH_2R^2$ as shown in Scheme IX are commercially available.

Alternatively, a compound of type 1.2 can be prepared starting with the compound of type 9.3 by methods shown in Scheme IX below. Briefly, a compound represented by formula 9.3 is cyclized in the presence of a coupling reagent and a base in the presence of an inert solvent at a convenient temperature to ensure completion of the reaction. In one aspect, the coupling reagent can be 2-(7-aza-1H-benzotriazole-1-yl)-1,1,3,3-tetramethyluronium hexafluorophosphate (HATU) and the base can be N,N-diisopropylethylamine. Solvents suitable for this reaction can be N,N-dimethylformamide. In a further aspect, the reaction is carried out at a temperature of about 0° C. to 40° C.

A compound of type 9.3 can be prepared by reacting a compound of type 9.2 with a base in the presence of an inert solvent at a convenient temperature to ensure completion of the reaction. In one aspect, the base can be lithium hydroxide. In a further aspect, the solvent can be a mixture of water and tetrahydrofuran. In a yet further aspect, the convenient temperature is about 0° C. to 40° C.

A compound of type 9.2 can be prepared by reaction of a compound of type 9.1 with an amine of the type shown in Scheme IX (wherein $R^2$ can be an alkyl), in the presence of potassium iodide and an inert solvent at a convenient temperature to ensure completion of the reaction. In one aspect, the solvent can be acetonitrile. In a further aspect, the convenient temperature is about 70° C. to 110° C. Suitable compounds of type $NH_2R^2$ as shown in Scheme IX are commercially available.

A compound of type 9.1 can be prepared by a Mitsunobu type reaction between a compound of type 2.4 with an alcohol of the type as shown in Scheme IX in the presence of a triarylphosphine and a dialkyl azodicarboxylate reagent in an inert solvent at a convenient temperature for a period of time to ensure completion of the reaction. In one aspect, the triarylphosphine is triphenylphosphine. In a further aspect, the dialkyl azodicarboxylate reagent is di-tert-butyl azodicarboxylate (DTBAD). In a still further aspect, the inert solvent is tetrahydrofuran. In a yet further aspect, the convenient temperature is achieved by conventional heating or under microwave irradiation. The alcohol shown in Scheme IX can be obtained commercially or can be prepared by methods described in the literature.

Compound 2.4 can be synthesized following the reaction conditions shown above in Scheme II.

Scheme IX

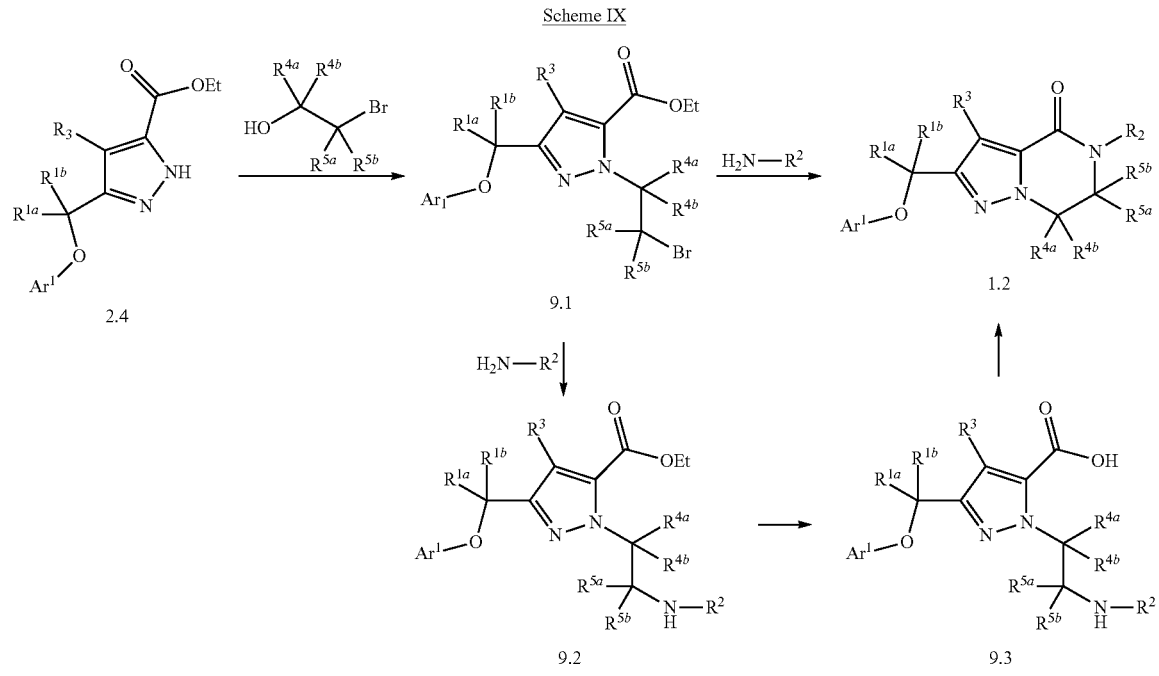

10. Reaction Scheme X

An intermediate of type 10.3 can be prepared starting with the compound of type 10.2 as outlined in Scheme X below. Briefly, a compound represented by formula 10.3 can be prepared by reaction of a compound of type 10.2 with a fluorinating reagent in an inert solvent at a convenient temperature for a period of time to ensure the completion of the reaction. In one aspect, the halogenating reagent is (diethylamino)sulfur trifluoride (DAST). In a further aspect, the solvent is dichloromethane. In a yet further aspect, the temperature is about −30° C. to 10° C.

A compound of type 10.2 can be prepared by reaction of a compound of type 10.1 with an acid in an inert solvent at a convenient reaction temperature for a period of time to ensure the completion of the reaction. In one aspect, the acid is hydrochloric acid. In a further aspect, the inert solvent is acetone. In a still further aspect, the temperature is about 80° C. to 120° C.

A compound of type 10.1 can be prepared by reaction of a compound of type 2.4 with an acetal of the type shown in Scheme X in the presence of a Lewis acid in an inert solvent at a convenient temperature for a period of time to ensure the completion of the reaction. In one aspect, the acetal is aminoacetaldehyde dimethyl acetal. In a further aspect, the Lewis acid is trimethylaluminium. In a still further aspect, the inert solvent is tetrahydrofuran. In a yet further aspect, the convenient temperature is achieved by conventional heating or under microwave irradiation.

Compound 2.4 can be synthesized following the reaction conditions shown above in Scheme II.

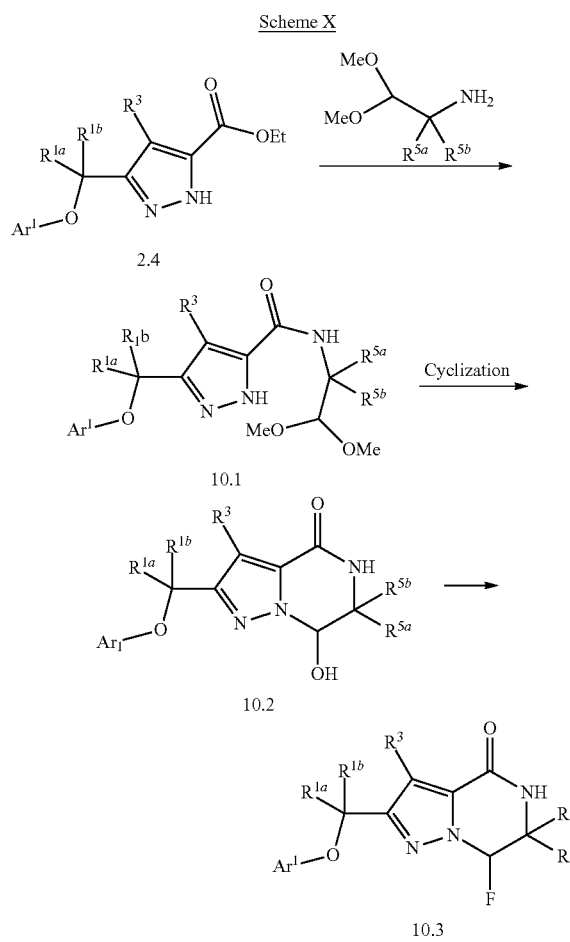

11. Reaction Scheme XI

In various aspects, compounds of type 1.2 can be prepared starting with the compound of type 11.5 as outlined in Scheme XI below, wherein $R^3$ is H or Cl. Briefly, a compound represented by formula 1.2 in Scheme XI can be prepared by reaction of a compound of type 11.5 with an aryl or heteroaryl halide ($XAr^1$ in Scheme XI, wherein X is a halogen and $Ar^1$ is aryl or heteroaryl) with a coupling reagent in the presence of a ligand and a base in a solvent at a convenient temperature for a period of time to ensure the completion of the reaction. In one aspect, X is Br or Cl. In a further aspect, the coupling reagent is copper (I) iodide or palladium (II) acetate. In a still further aspect, the ligand is N,N'-dimethylglycine or 2-(di-tert-butylphosphino)biphenyl. In an even further aspect, the base is cessium carbonate. In a further aspect, the solvent is toluene or 1,4-dioxane. In a yet further aspect, the temperature is about 100° C. to 150° C. Suitable compounds of type $XAr^1$ as shown in Scheme XI are commercially available or can be prepared by methods described in the literature.

Alternatively, a compound of type 1.2 can be prepared by a Mitsunobu type reaction between a compound of type 11.5 (wherein $R^3$ is H or Cl) with an alcohol ($XAr^1$ in Scheme XI, wherein X is OH and $Ar^1$ is aryl or heteroaryl) in the presence of a triarylphosphine and a dialkyl azodicarboxylate reagent in an inert solvent at a convenient temperature for a period of time to ensure completion of the reaction. In one aspect, the triarylphosphine is triphenylphosphine. In a further aspect, the dialkyl azodicarboxylate reagent is di-tert-butyl azodicarboxylate (DTBAD). In a still further aspect, the inert solvent is tetrahydrofuran. In a yet further aspect, the convenient temperature is about 0° C. to 40° C. or 110° C. to 150° C. Suitable compounds of type $XAr^1$ as shown in Scheme XI are commercially available.

A compound of type 11.5 can be prepared by reaction of a compound of type 11.4 with a suitable reducing reagent in a suitable inert solvent at a temperature of about 10° C. and 25° C. for a period of time to ensure the completion of the reaction. In one aspect, the reducing agent is sodium borohydride or lithium aluminum hydride. In a further aspect, the inert solvent is tetrahydrofuran or a mixture of dichloromethane and methanol.

A compound represented by type 11.4 can be prepared by a coupling reaction of a compound of type 11.3 with a compound of type $XR^2$ (as shown in Scheme XI, wherein X is a halogen and $R^2$ is aryl or heteroaryl) with a coupling reagent in the presence of a ligand and a base in a solvent at a convenient temperature to ensure completion of the reaction. In one aspect, the halogen is Br, Cl or I. In a further aspect, the coupling reagent is copper (I) iodide. In a yet further aspect, the ligand is N,N'-dimethylethylenediamine. In a still further aspect, the base is potassium carbonate. In an even further aspect, the solvent is toluene. In a further aspect, the temperature is about 100° C. to 140° C. A compound of type $XR^2$ as described in the foregoing can be obtained commercially or can be prepared by methods described in the literature.

Alternatively, a compound of type 11.4 can be prepared by reacting a compound of type 11.3 with an alkylating reagent of type $XR^2$, wherein X is a halogen and $R^2$ is alkyl, in the presence of a base in an inert solvent at a convenient temperature to ensure completion of the reaction. In a further aspect, the halogen is Cl or Br. In a still further aspect, the base is sodium hydride. In a yet further aspect, the temperature is about −10° C. to 25° C. A compound of type $XR^2$ as described in the foregoing can be obtained commercially.

A compound represented by compound 11.2 can be reacted with an acid in an inert solvent at a convenient reaction temperature for a period of time to ensure the completion of the reaction followed by reaction with a base in an inert solvent at a convenient reaction temperature for a period of time to ensure the completion of the reaction. In one aspect, the acid is hydrochloric acid and the inert solvent is 1,4-dioxane. In a still further aspect, the temperature is about 0° C. to 40° C. In one aspect, the base is sodium carbonate and the inert solvent is 1,4-dioxane. In a still further aspect, the temperature is about 0° C. to 40° C.

A compound of type 11.2 can be prepared by reacting a compound of type 11.1 or 11.7 with an alkylating reagent of the type as shown in Scheme XI in the presence of a base in an inert solvent at a convenient temperature for a period of time to ensure completion of the reaction. In one aspect, the base is cessium carbonate or potassium carbonate. In a further aspect, the inert solvent is N,N-dimethylformamide or acetonitrile. In a still further aspect, the temperature is about 0° C. to 40° C. In an even further aspect, the alkylating reagent can be obtained commercially.

A compound of type 11.7 can be prepared by reaction of a compound of type 11.6 with a chlorinating reagent in acidic conditions at a convenient temperature for a period of time to ensure completion of the reaction. In one aspect, a compound of type 11.1 can be reacted with sodium hypochlorite. In a further aspect, the inert solvent is acetic acid. In a still further aspect, the temperature is about 0° C. to 40° C.

Compounds 11.1 and 11.6 can be obtained commercially.

Scheme XII, wherein X is OH and $Ar^1$ is aryl) in the presence of a triarylphosphine and a dialkyl azodicarboxylate reagent in an inert solvent at a convenient temperature for a period of time to ensure completion of the reaction. In one aspect, the triarylphosphine is triphenylphosphine. In a further aspect, the dialkyl azodicarboxylate reagent is di-tert-butyl azodicarboxylate (DTBAD). In a still further aspect, the inert solvent is tetrahydrofuran. In a yet further aspect, the convenient

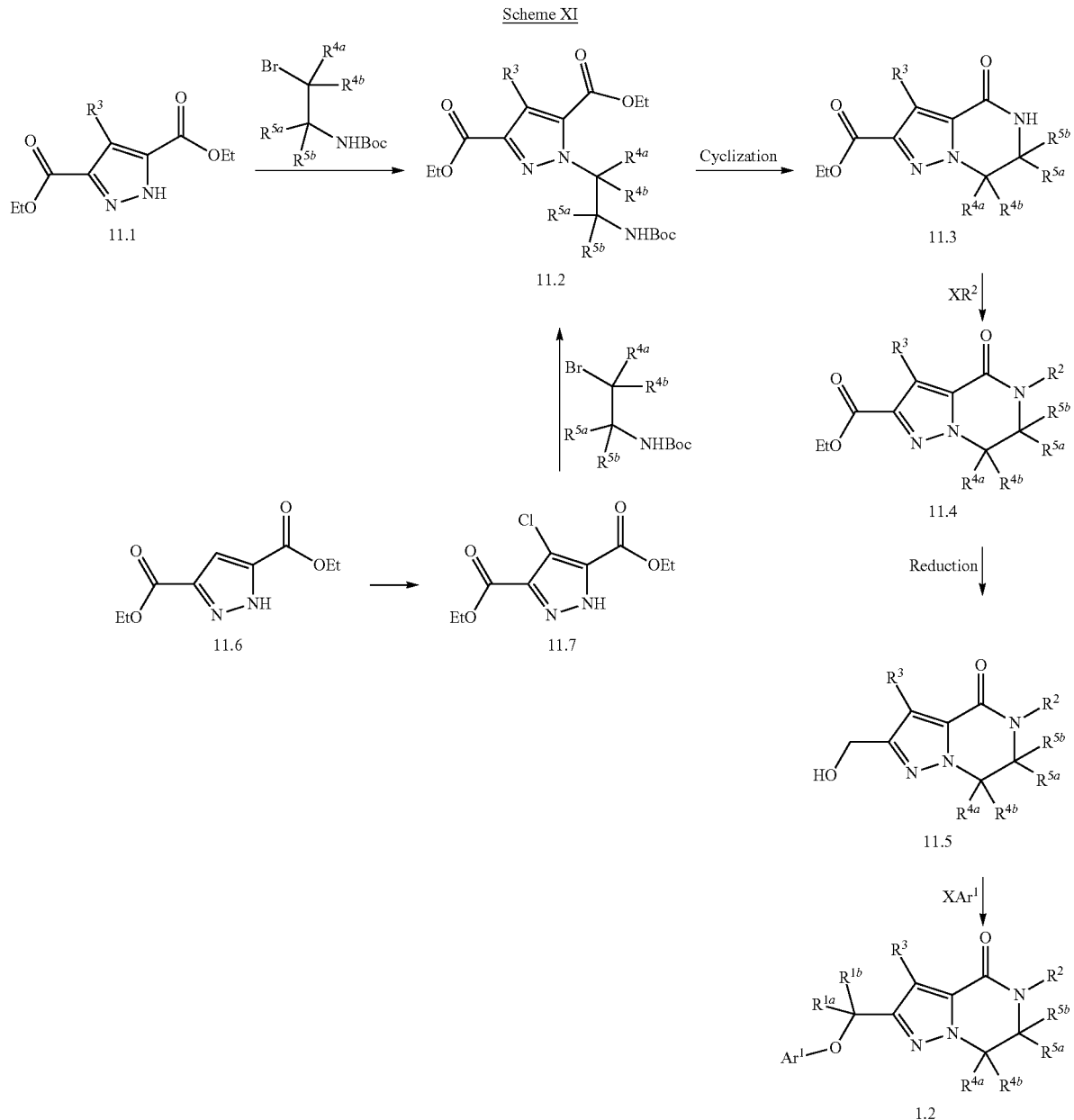

12. Reaction Scheme XII

In various aspects, an intermediate of type 12.6 can be prepared starting with the compound of type 12.5 as outlined in Scheme XII below. Briefly, a compound represented by formula 12.6 can be prepared by a Mitsunobu type reaction between a compound of type 12.5 with an alcohol ($XAr^1$ in temperature is about 60° C. to 100° C. Suitable compounds of type $XAr^1$ as shown in Scheme XII are commercially available.

A compound of type 12.5 can be prepared by reaction of a compound of type 12.4 with a suitable reducing reagent in a suitable inert solvent at a temperature of about 10° C. and 25° C. for a period of time to ensure the completion of the reaction. In one aspect, the reducing agent is lithium aluminum hydride. In a further aspect, the inert solvent is a tetrahydrofuran.

A compound represented by type 12.4 can be prepared by a coupling reaction of a compound of type 12.3 with methylboronic acid in the presence of a coupling reagent, a ligand and a base in a solvent at a convenient temperature to ensure completion of the reaction. In one aspect, the coupling reagent is palladium(II) acetate. In a yet further aspect, the ligand is 2-dicyclohexylphosphino-2',4',6'-triisopropylbiphenyl. In a still further aspect, the base is potassium carbonate and the solvent is toluene. In an even further aspect, the temperature is about 80° C. to 110° C.

A compound represented by compound 12.2 can be reacted with an acid in an inert solvent at a convenient reaction temperature for a period of time to ensure the completion of the reaction followed by reaction with a base in an inert solvent at a convenient reaction temperature for a period of time to ensure the completion of the reaction. In one aspect, the acid is hydrochloric acid and the inert solvent is 1,4-dioxane. In a still further aspect, the temperature is about 0° C. to 40° C. In one aspect, the base is sodium carbonate and the inert solvent is 1,4-dioxane. In a still further aspect, the temperature is about 0° C. to 40° C.

A compound of type 12.2 can be prepared by reacting a compound of type 12.1 with an alkylating reagent of the type as shown in Scheme XII in the presence of a base in an inert solvent at a convenient temperature for a period of time to ensure completion of the reaction. In one aspect, the base is potassium carbonate. In a further aspect, the inert solvent is acetonitrile. In a still further aspect, the temperature is about 0° C. to 40° C. In an even further aspect, the alkylating reagent can be obtained commercially.

A compound of type 12.1 can be prepared by reaction of a compound of type 11.1 with N-iodosuccinimide in the presence of an inert solvent at a convenient temperature for a period of time to ensure the completion of the reaction. In one aspect, the inert solvent is chloroform. In a further aspect, the temperature is about 80° C. to 120° C.

Compound 11.1 can be obtained commercially.

Scheme XII

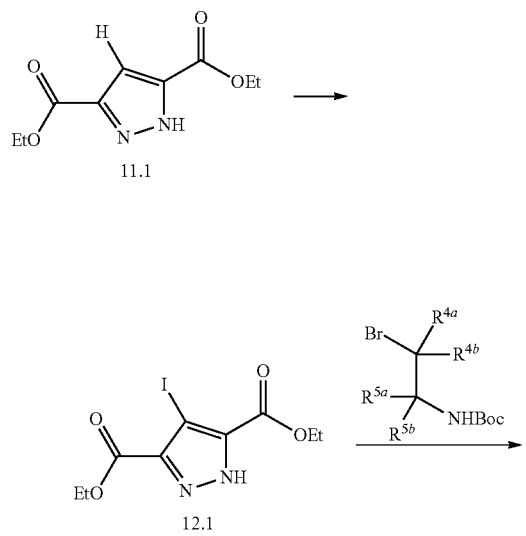

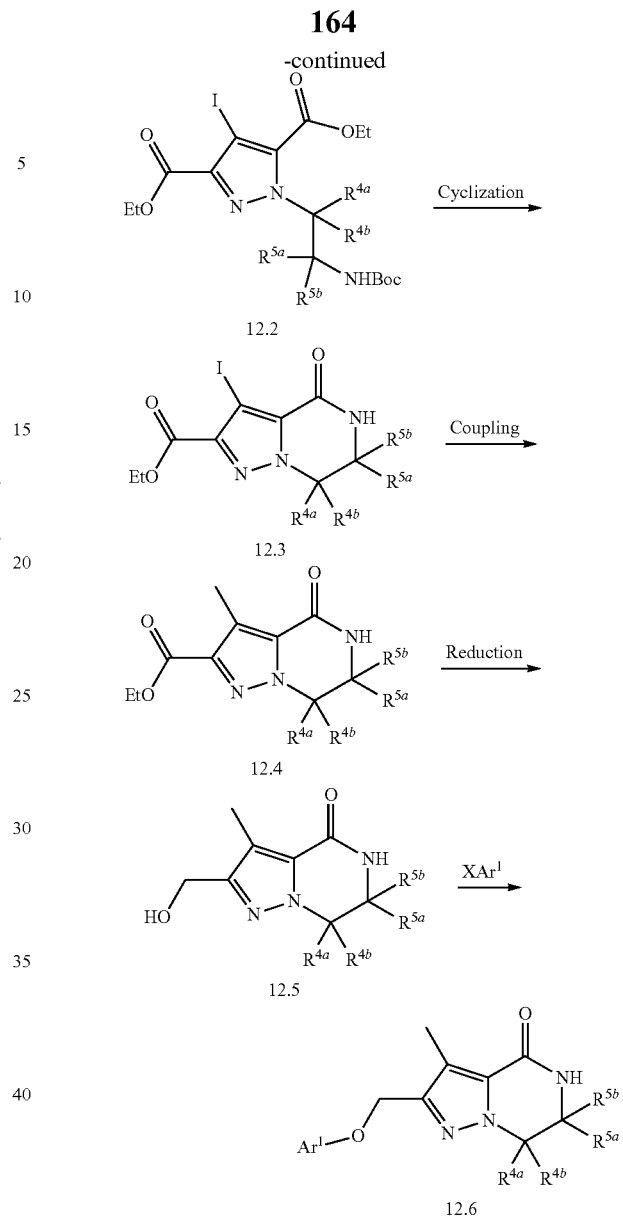

13. Reaction Scheme XIII

In various aspects, an intermediate of type 11.6 can be prepared starting with the compound of type 13.5 as outlined in Scheme XIII below. Briefly, a compound represented by formula 11.6 can be prepared by reaction of a compound of type 13.5 with a base in an inert solvent at a convenient temperature for a period of time to ensure the completion of the reaction. In one aspect, the base is potassium carbonate. In a further aspect, the solvent is methanol. In a yet further aspect, the temperature is about 0° C. to 40° C.

A compound of type 13.5 can be prepared by a coupling reaction of a compound of type 13.4 with a compound of type $XR^2$ (as shown in Scheme XIII, wherein X is halogen and $R^2$ is heteroaryl) with a coupling reagent in the presence of a ligand and a base in a solvent at a convenient temperature to ensure completion of the reaction. In one aspect, the halogen is Cl. In a further aspect, the coupling reagent is copper (I) iodide. In a yet further aspect, the ligand is N,N'-dimethylethylenediamine. In a still further aspect, the base is potassium carbonate. In an even further aspect, the solvent is toluene. In a further aspect, the temperature is about 100° C. to 140° C. A compound of type XR² as described in the foregoing can be obtained commercially.

A compound of type 13.4 can be prepared by reaction of a compound of type 13.3 with ammonium cerium (IV) nitrate (CAN) in the presence of an inert solvent at a convenient temperature to ensure completion of the reaction. In one aspect, the inert solvent is acetonitrile. In a further aspect, the temperature is about 0° C. to 40° C.

A compound of type 13.3 can be prepared by reacting a compound of type 13.2 with acetyl chloride in the presence of a base in a solvent at a convenient temperature to ensure completion of the reaction. In one aspect, the base is a mixture of triethylamine and 4-dimethylaminopyridine. In a further aspect, the solvent is dichloromethane. In a still further aspect, the temperature is about –10° C. to 40° C.

A compound of type 13.2 can be prepared by reaction of a compound of type 13.1 with a suitable reducing reagent in a suitable inert solvent at a temperature of about 10° C. and 25° C. for a period of time to ensure the completion of the reaction. In one aspect, the reducing agent is sodium borohydride. In a further aspect, the inert solvent is a mixture of tetrahydrofuran and methanol.

A compound of type 13.1 can be prepared by reacting a compound of type 11.4 with p-methoxybenzyl bromide in the presence of a base in an inert solvent at a convenient temperature to ensure completion of the reaction. In one aspect, the base is sodium hydride. In a further aspect, the solvent is N,N-dimethylformamide. In a yet further aspect, the temperature is about –10° C. to 40° C.

Compound 11.4 can be synthesized following the reaction conditions shown above in Scheme XI.

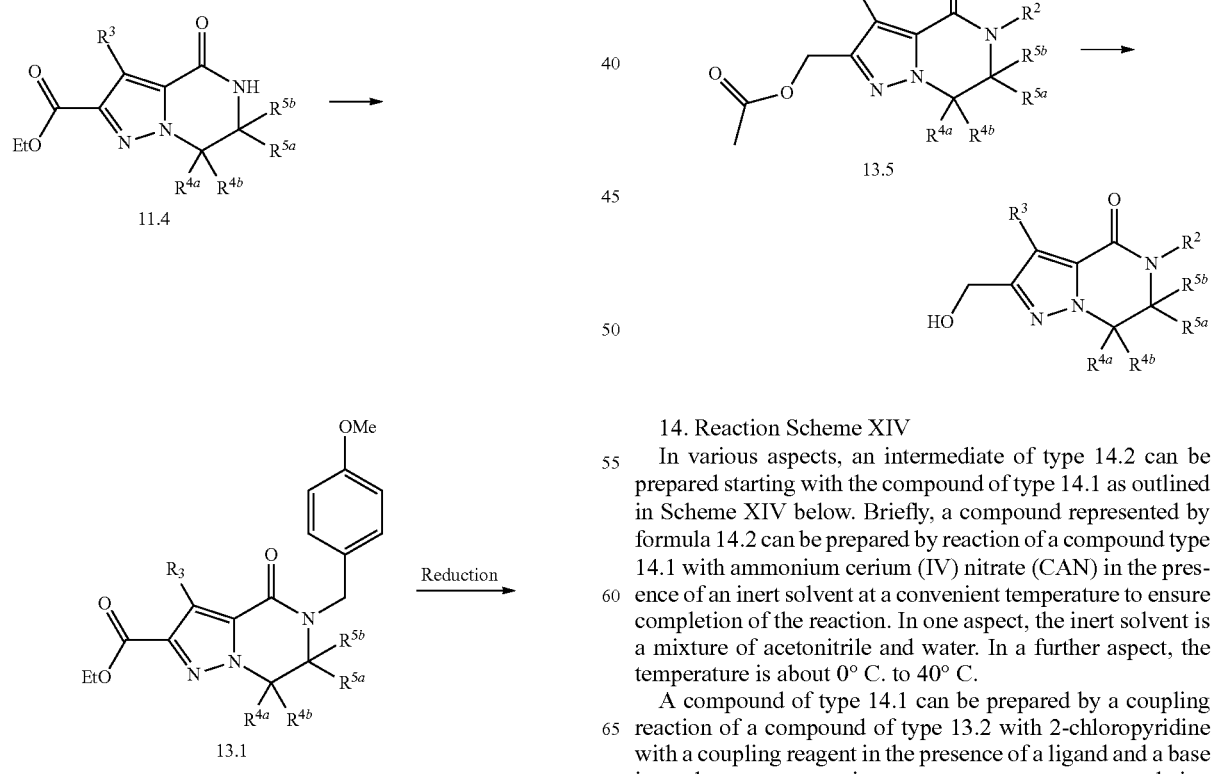

14. Reaction Scheme XIV

In various aspects, an intermediate of type 14.2 can be prepared starting with the compound of type 14.1 as outlined in Scheme XIV below. Briefly, a compound represented by formula 14.2 can be prepared by reaction of a compound type 14.1 with ammonium cerium (IV) nitrate (CAN) in the presence of an inert solvent at a convenient temperature to ensure completion of the reaction. In one aspect, the inert solvent is a mixture of acetonitrile and water. In a further aspect, the temperature is about 0° C. to 40° C.

A compound of type 14.1 can be prepared by a coupling reaction of a compound of type 13.2 with 2-chloropyridine with a coupling reagent in the presence of a ligand and a base in a solvent at a convenient temperature to ensure completion of the reaction. In one aspect, the coupling reagent is palladium (II) acetate. In a further aspect, the ligand is (2-biphenylyl)di-tert-butylphosphine. In a still further aspect, the base is cessium carbonate. In an even further aspect, the solvent is toluene. In a further aspect, the temperature is about 100° C. to 140° C.

Compound 13.2 can be synthesized following the reaction conditions shown above in Scheme XIII.

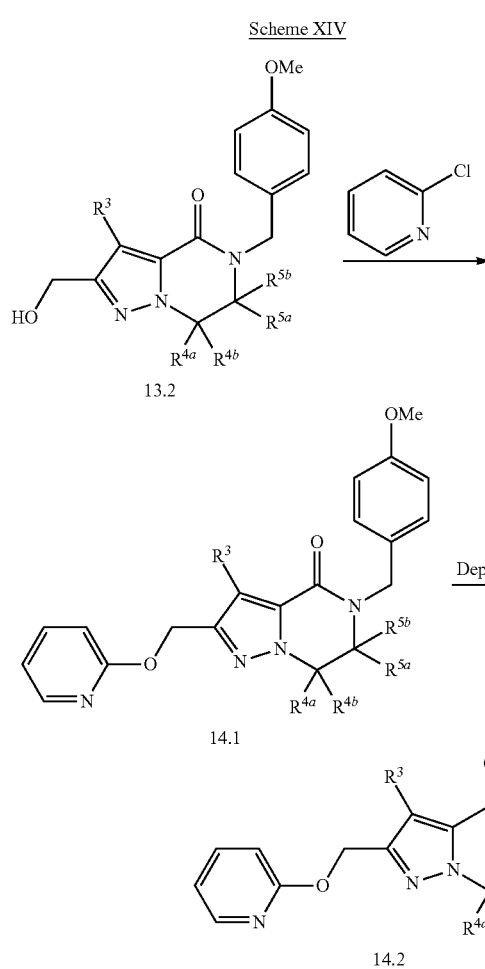

14.2

15. Reaction Scheme XV

A compound of type 15.2 can be prepared starting with the compound of type 15.1 as outlined in Scheme XV below. Briefly, a compound represented by formula 15.2 can be prepared by deprotection of a compound of type 15.1 with tetrabutylammonium fluoride (TBAF) in an inert solvent at a convenient temperature for a period of time to ensure the completion of the reaction. In one aspect, the inert solvent is tetrahydrofuran. In a further aspect, the temperature is about 0° C. to 40° C.

A compound of type 15.1 can be prepared starting with the compound of type 11.6 by a Mitsunobu type reaction with 4-{[tert-butyl(dimethyl)silyl]oxy}phenol in the presence of a triarylphosphine and a dialkyl azodicarboxylate reagent in an inert solvent at a convenient temperature for a period of time to ensure completion of the reaction. In one aspect, the triarylphosphine is triphenylphosphine. In a further aspect, the dialkyl azodicarboxylate reagent is di-tert-butyl azodicarboxylate (DTBAD). In a still further aspect, the inert solvent is tetrahydrofuran. In a yet further aspect, the convenient temperature is achieved by conventional heating or under microwave irradiation.

Compound 11.6 can be synthesized following the reaction conditions shown above in Scheme XI.

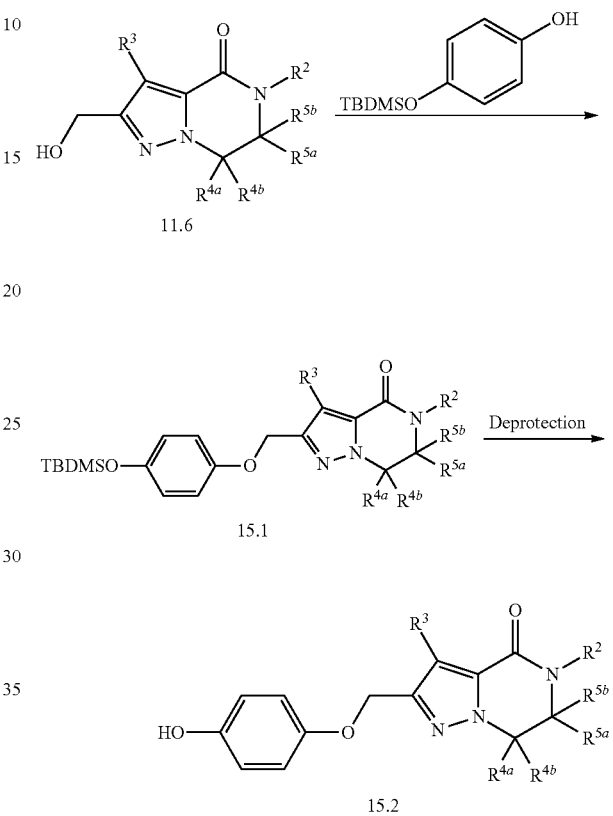

16. Reaction Scheme XVI

Alternatively, a compound of type 16.2 can be prepared starting with the compound of type 16.1 as outlined in Scheme XVI below, wherein the substituent group "Het" is heteroaryl. Briefly, a compound represented by formula 16.2 can be prepared by hydrogenation of a compound type 16.1 in the presence of a catalyst and a base in an inert solvent at a convenient temperature for a period of time to ensure the completion of the reaction. In one aspect, the catalyst is 10% palladium on charcoal. In a further aspect, the base is triethylamine. In a still further aspect, the solvent is a mixture of tetrahydrofuran and methanol. In a yet further aspect, the temperature is about 20° C. to 60° C.

A compound of type 16.1 can be prepared by reaction of a compound of type 11.6 with a dihalo-heteroaryl with a coupling reagent in the presence of a ligand in the presence of a base in a solvent at a convenient temperature for a period of time to ensure the completion of the reaction. In one aspect, the coupling reagent is palladium (II) acetate. In a further aspect, the ligand is (2-biphenylyl)di-tert-butylphosphine. In a still further aspect, the base is cessium carbonate. In an even further aspect, the solvent is toluene. In a yet further aspect, the temperature is about 100° C. to 140° C. A dihalo-heteroaryl can be obtained commercially.

Compound 11.6 can be synthesized following the reaction conditions shown above in Scheme XI.

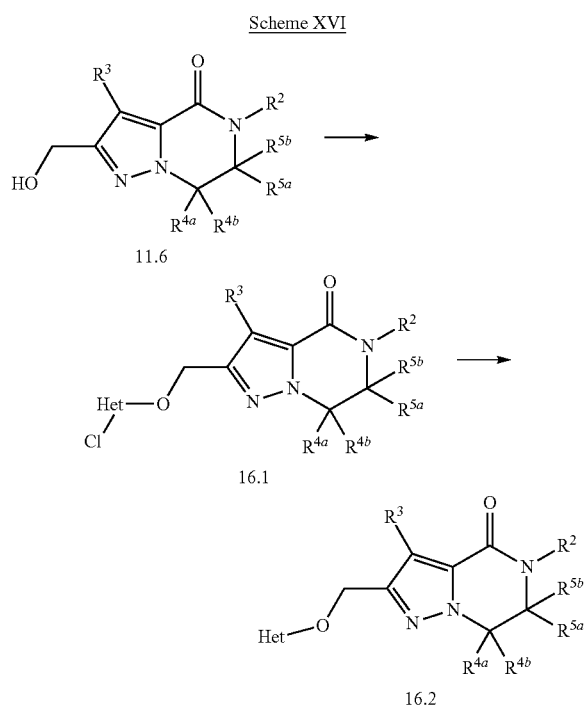

17. Reaction Scheme XVII

In one aspect, a compound of type 17.6 can be prepared starting with the compound of type 17.4 as outlined in Scheme XVII below. Briefly, a compound represented by formula 17.6 can be prepared by reaction of a compound type 17.4 with (diethylamino)sulfur trifluoride (DAST) in an inert solvent at a convenient temperature for a period of time to ensure the completion of the reaction. In one aspect, the solvent is dichloromethane. In a further aspect, the temperature is about −30° C. to 40° C.

A compound of type 17.5 can be prepared starting with the compound of type 17.4 as outlined in Scheme XVII below. Briefly, a compound represented by formula 17.5 can be prepared by reaction of a compound type 17.4 with iodomethane in the presence of a base and an inert solvent at a convenient temperature for a period of time to ensure the completion of the reaction. In one aspect, the base is sodium hydride. In a further aspect, the solvent is tetrahydrofuran. In a still further aspect, the convenient temperature is achieved by conventional heating or under microwave irradiation.

A compound represented by type 17.4 can be prepared by a coupling reaction of a compound of type 17.3 with a compound of type $XR^2$ (wherein X is a halogen and $R^2$ is aryl) with a coupling reagent in the presence of a ligand and a base in a solvent at a convenient temperature to ensure completion of the reaction, followed by in situ deprotection reaction carried out by heating in a suitable solvent at a convenient reaction temperature for a period of time to ensure the completion of the reaction. In one aspect, the halogen is Br, the coupling reagent is copper (I) iodide, the ligand is N,N'-dimethylethylenediamine, the base is potassium carbonate, the solvent is toluene and the temperature is about 120° C. to 160° C. In a further aspect, the suitable solvent is methanol and the convenient temperature is achieved by conventional heating or under microwave irradiation. A compound of type $XR^2$ as described in the foregoing can be obtained commercially or can be prepared by methods described in the literature.

A compound of type 17.3 can be prepared by reacting a compound of type 17.2 with chlorotrimethylsilane in the presence of a base in an inert solvent at a convenient temperature for a period of time to ensure completion of the reaction. In one aspect, the base is triethylamine. In a further aspect, the inert solvent is acetonitrile. In a still further aspect, the temperature is about 0° C. to 40° C.

A compound represented by compound 17.1 can be reacted with an acid in an inert solvent at a convenient reaction temperature for a period of time to ensure the completion of the reaction followed by reaction with a base in an inert solvent at a convenient reaction temperature for a period of time to ensure the completion of the reaction. In one aspect, the acid is hydrochloric acid and the inert solvent is 1,4-dioxane. In a still further aspect, the temperature is about 0° C. to 40° C. In one aspect, the base is potassium carbonate and the inert solvent is methanol. In a still further aspect, the convenient temperature is achieved by conventional heating or under microwave irradiation.

A compound of type 17.1 can be prepared by a Mitsunobu type reaction between a compound of type 2.4 with an alcohol in the presence of a triarylphosphine and a dialkyl azodicarboxylate reagent in an inert solvent at a convenient temperature for a period of time to ensure completion of the reaction. In one aspect, the alcohol is (R)-1-boc-2,2-dimethyl-4-hydroxymethyl-oxazolidine or (S)-1-boc-2,2-dimethyl-4-hydroxymethyl-oxazolidine. In a further aspect, the triarylphosphine is triphenylphosphine. In a still further aspect, the dialkyl azodicarboxylate reagent is di-tert-butyl azodicarboxylate (DTBAD). In a yet further aspect, the inert solvent is tetrahydrofuran. In a further aspect, the temperature is about 0° C. to 40° C.

Compound 2.4 can be synthesized following the reaction conditions shown above in Scheme II.

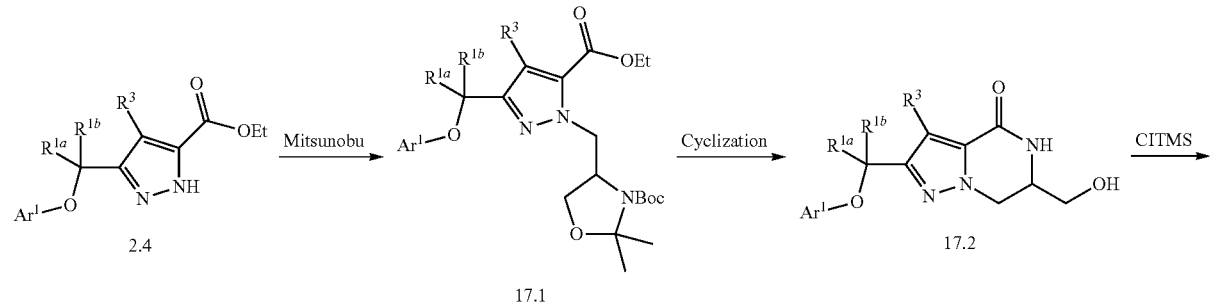

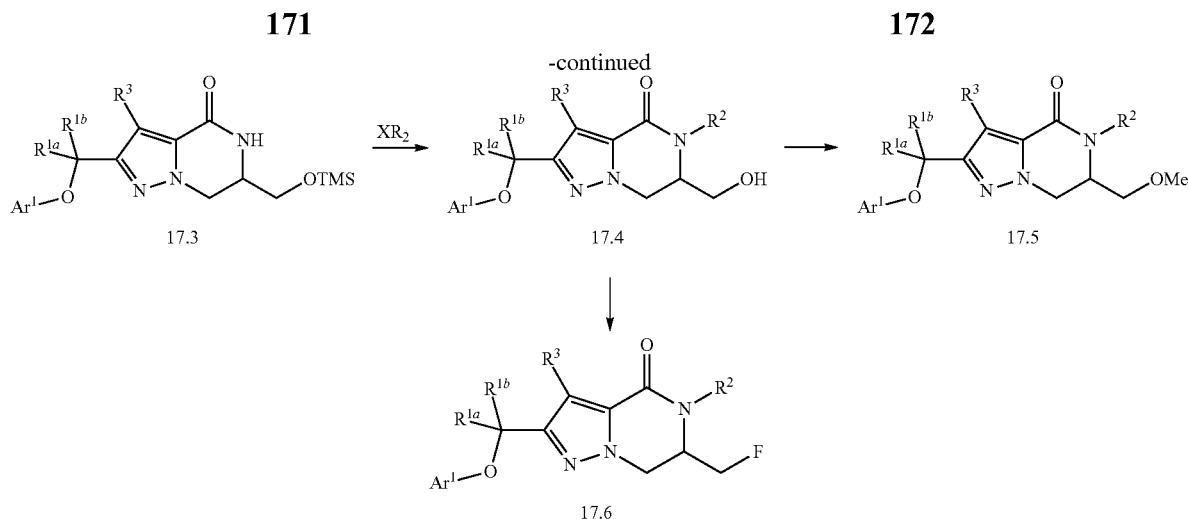

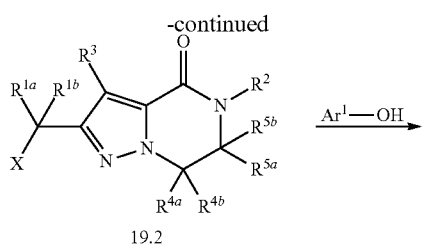

18. Reaction Scheme XVIII

In one aspect, a compound of type 18.2 can be prepared starting with the compound of type 18.1 as outlined in Scheme XVIII below. Briefly, a compound represented by formula 18.2 can be prepared by reaction of a compound type 18.1 with N-chlorosuccinimide in an inert solvent at a convenient temperature for a period of time to ensure the completion of the reaction. In one aspect, the solvent is chloroform. In a further aspect, the temperature is about 60° C. to 100° C. A compound of type 18.1 can be prepared following the reaction conditions shown above in Scheme II, wherein Ar¹ is phenyl.

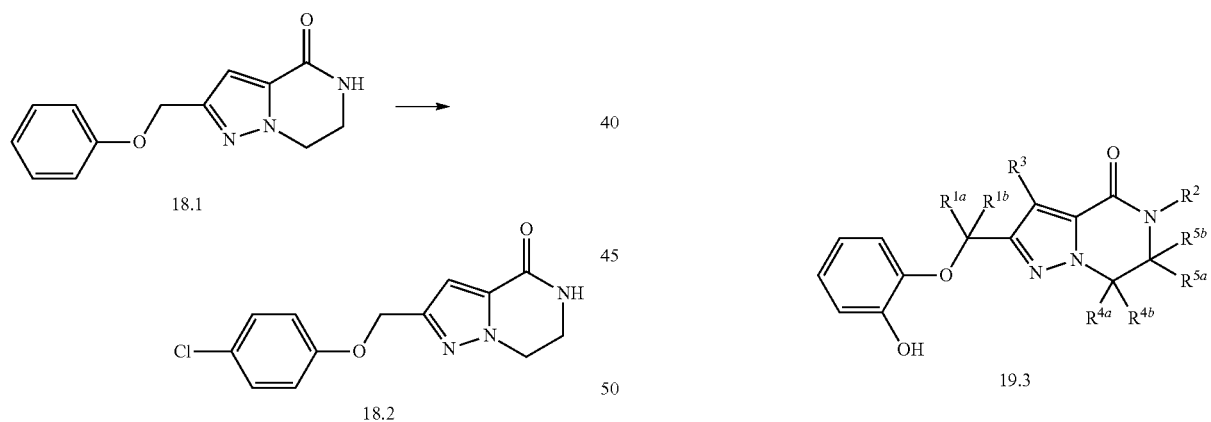

19. Reaction Scheme XIX

In one aspect, compounds of type 19.3 can be prepared generically by the synthetic scheme as shown below in Scheme XIX(a).

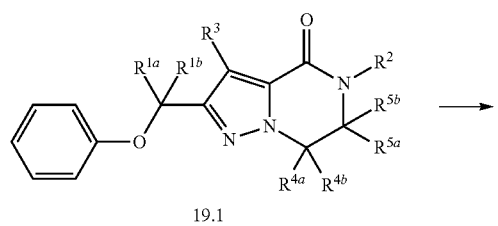

Compounds are represented in generic form, with substituents as noted in compound descriptions elsewhere herein. A more specific example is set forth below in Scheme XIX(b).

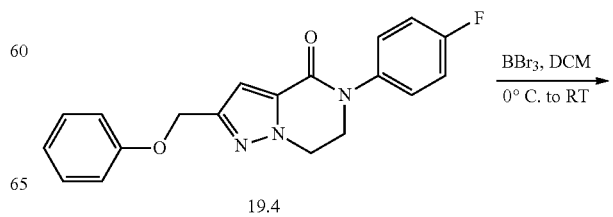

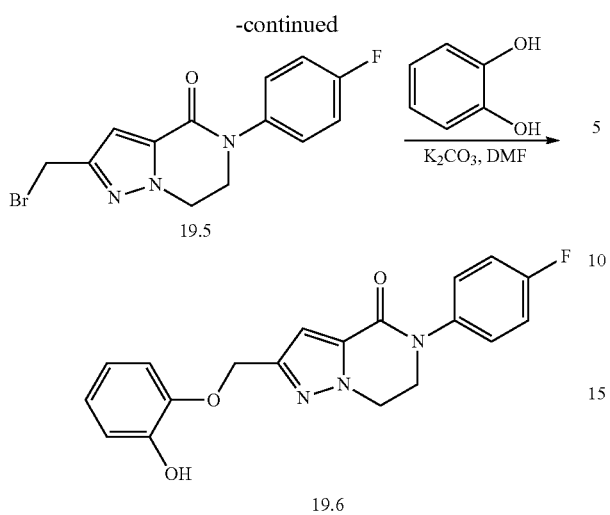

Briefly, a compound of type 19.6 can be prepared from a compound of type 19.5, i.e. a aryl alcohol, by reaction in a suitable solvent, e.g. DMF, in the presence of a suitable base, e.g. K$_2$CO$_3$, at a suitable temperature (about 10° C. to about 30° C.) for a period of time to ensure the completion of the reaction (about 10 hr to about 24 hr). A compound of type 19.5 can be prepared from the corresponding aryl ether, i.e. a compound of type 19.4. Briefly, a compound of type 19.4 is dissolved in a suitable solvent, e.g. DCM, cooled to an appropriate temperature (about −10° C. to about 10° C.) and treated with a suitable cleavage agent such as BBr$_3$ as shown in Scheme XIX(b). The reaction is allowed to gradually warm to room temperature and stirred for a suitable period of time to ensure completion of the reaction (about 2 hr to about 8 hr). Various modifications of the reaction as outlined herein can be made by one skilled in the art as appropriate for the target compound (19.3) and the initial aryl ether (19.1). For example, alternative reagents are available for cleavage of the aryl ether (19.1). Furthermore, base, solvent, temperature and reaction time can be modified to facilitate reaction of alkyl halide (19.2) with Ar$^1$—OH to yield the desired product (19.3).

In a further aspect, the compound produced exhibits positive allosteric modulation of mGluR5 response to glutamate as an increase in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5.

In a further aspect, the compound produced exhibits positive allosteric modulation of mGluR5 (e.g., rmGluR5) with an EC$_{50}$ of less than about 10,000 nM, of less than about 5,000 nM. of less than about 1,000 nM, of less than about 500 nM, or of less than about 100 nM. In a still further aspect, the compound produced exhibits potentiation of mGluR5 response to glutamate as an increase in response to non-maximal concentrations of glutamate in human embryonic kidney cells transfected with human mGluR5 in the presence of the compound, compared to the response to glutamate in the absence of the compound. In a further aspect, the transfected cell line is the H10H cell line. In a still further aspect, the transfected cell line is the H12H cell line. In a yet further aspect, the compound produced exhibits positive allosteric modulation of mGluR5 (e.g., hmGluR5) with an EC$_{50}$ of less than about 10,000 nM, of less than about 5,000 nM. of less than about 1,000 nM, of less than about 500 nM, or of less than about 100 nM.

In particular, the compound produced exhibits activity in potentiating the mGluR5 receptor in the disclosed assays, generally with an EC$_{50}$ for potentiation of less than about 10 µM. Preferred compounds within the present invention had activity in potentiating the mGluR5 receptor with an EC$_{50}$ for potentiation of less than about 500 nM. Preferred compounds further caused a leftward shift of the agonist EC$_{50}$ by greater than 3-fold. These compounds did not cause mGluR5 to respond in the absence of agonist, and they did not elicit a significant increase in the maximal response of mGluR5 to agonists. These compounds are positive allosteric modulators (potentiators) of human and rat mGluR5. In various aspects, the compounds can be selective for mGluR5 compared to the other seven subtypes of metabotropic glutamate receptors.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

Table 1 below lists specific compounds as well as experimentally determined mGluR5 activity determined in a cell-based assay. The mGluR5 activity was determined using the metabotropic glutamate receptor activity assays in human embryonic kidney cells as described herein, wherein the human embryonic kidney cells were transfected with human mGluR5. The compounds in Table 1 were synthesized with methods identical or analogous to those shown herein. The requisite starting materials were commercially available, described in the literature, or readily synthesized by one skilled in the art of organic synthesis. The compound number given in Table I corresponds to the compound number in Table II and the structure given therein.

TABLE I*

| No. | pEC50 | EC$_{50}$ (nM) | E$_{max}$ (%) |
|---|---|---|---|
| 1 | 5.65 | 2239 | 69 |
| 2 | 5.87 | 1349 | 72 |
| 3 | 6.94 | 115 | 101 |
| 4 | 6.21 | 617 | 52 |
| 5 | 5.59 | 2570 | 73 |
| 6 | 7.14 | 72 | 82 |
| 7 | 7.01 | 98 | 80 |
| 8 | 6.88 | 132 | 81 |
| 9 | 6.79 | 162 | 82 |
| 10 | 6.79 | 162 | 84 |
| 11 | 6.81 | 155 | 79 |
| 12 | 6.06 | 871 | 69 |
| 13 | 5.73 | 1862 | 64 |
| 14 | 5.83 | 1479 | 72 |
| 15 | 6.20 | 631 | 69 |
| 16 | 6.68 | 209 | 76 |
| 17 | 6.31 | 490 | 72 |
| 18 | 6.79 | 162 | 70 |
| 19 | 7.15 | 71 | 68 |
| 20 | 7.30 | 50 | 64 |
| 21 | 6.58 | 263 | 74 |
| 22 | 5.92 | 1200 | 74 |
| 23 | 5.92 | 1200 | 81 |
| 24 | 5.78 | 2820 | 78 |
| 25 | 5.73 | 1862 | 53 |
| 26 | 6.98 | 105 | 75 |
| 27 | 7.04 | 92 | 80 |
| 28 | 6.76 | 174 | 60 |

TABLE I*-continued

| No. | pEC50 | EC$_{50}$ (nM) | E$_{max}$ (%) |
|---|---|---|---|
| 29 | 6.24 | 575 | 80 |
| 30 | 6.27 | 537 | 75 |
| 31 | <5.00 | >10000 | 58 |
| 32 | 6.13 | 741 | 74 |
| 33 | <5.00 | >10000 | 67 |
| 34 | 7.20 | 63 | 74 |
| 35 | 5.86 | 1365 | 66 |
| 36 | 7.01 | 96 | 76 |
| 37 | 5.68 | 2069 | 74 |
| 38 | 6.70 | 200 | 60 |
| 39 | 6.75 | 178 | 61 |
| 40 | 5.37 | 4266 | 56 |
| 41 | 6.64 | 229 | 41 |
| 42 | <4.52 | >30200 | 14 |
| 43 | 6.12 | 759 | 58 |
| 44 | 6.05 | 891 | 64 |
| 45 | <5.00 | >10000 | 52 |
| 46 | 5.80 | 1585 | 51 |
| 47 | 7.03 | 93 | 65 |
| 48 | 7.09 | 81 | 65 |
| 49 | 7.09 | 81 | 64 |
| 50 | 6.92 | 120 | 58 |
| 51 | 7.26 | 55 | 61 |
| 52 | 7.58 | 26 | 68 |
| 53 | 6.84 | 145 | 65 |
| 54 | 7.21 | 62 | 63 |
| 55 | 7.34 | 45 | 64 |
| 56 | 7.62 | 24 | 69 |
| 57 | 6.82 | 150 | 67 |
| 58 | 6.92 | 120 | 58 |
| 59 | 6.89 | 130 | 57 |
| 60 | 7.40 | 40 | 66 |
| 61 | 7.19 | 65 | 68 |
| 62 | 7.27 | 53 | 60 |
| 63 | 6.37 | 430 | 68 |
| 64 | 6.22 | 603 | 74 |
| 65 | 6.44 | 363 | 74 |
| 66 | 7.03 | 93 | 72 |
| 67 | 6.82 | 151 | 70 |
| 68 | 6.49 | 324 | 68 |
| 69 | 6.22 | 603 | 70 |
| 70 | 7.47 | 34 | 73 |
| 71 | 6.15 | 708 | 74 |
| 72 | 7.04 | 91 | 72 |
| 73 | 7.64 | 23 | 67 |
| 74 | 6.90 | 126 | 74 |
| 75 | 6.69 | 204 | 68 |
| 76 | 7.18 | 66 | 69 |
| 77 | <5.00 | >10000 | 42 |
| 78 | 6.31 | 490 | 69 |
| 79 | 5.66 | 2188 | 48 |
| 80 | 5.89 | 1288 | 71 |
| 81 | 6.26 | 550 | 67 |
| 82 | 5.81 | 1549 | 61 |
| 83 | 6.05 | 891 | 65 |
| 84 | <5.00 | >10000 | 53 |
| 85 | 6.36 | 437 | 72 |
| 86 | 6.69 | 204 | 73 |
| 87 | 6.09 | 813 | 56 |
| 88 | 6.75 | 178 | 72 |
| 89 | <5.00 | >10000 | 75 |
| 90 | 6.24 | 575 | 67 |
| 91 | 7.19 | 65 | 71 |
| 92 | 6.51 | 309 | 71 |
| 93 | <4.52 | >30200 | 29 |
| 94 | 6.29 | 513 | 65 |
| 95 | 6.82 | 150 | 54 |
| 96 | 6.71 | 195 | 68 |
| 97 | 7.01 | 98 | 68 |
| 98 | 6.13 | 741 | 63 |
| 99 | 6.19 | 646 | 67 |
| 100 | 6.02 | 955 | 67 |
| 101 | 6.53 | 295 | 78 |
| 102 | 6.92 | 120 | 69 |
| 103 | 7.03 | 93 | 72 |
| 104 | 7.27 | 54 | 67 |
| 105 | 6.66 | 219 | 53 |
| 106 | 6.41 | 389 | 53 |
| 107 | 6.46 | 347 | 63 |
| 108 | 7.75 | 18 | 64 |
| 109 | 7.13 | 74 | 63 |
| 110 | 6.70 | 200 | 68 |
| 111 | 7.03 | 93 | 68 |
| 112 | 6.98 | 105 | 69 |
| 113 | 6.14 | 724 | 57 |
| 114 | 7.00 | 100 | 68 |
| 115 | 5.96 | 1100 | 66 |
| 116 | 6.51 | 310 | 62 |
| 117 | n.d. | n.d. | n.d. |
| 118 | 5.69 | 2000 | 67 |
| 119 | 5.64 | 2300 | 72 |
| 120 | 6.12 | 750 | 67 |
| 121 | n.d. | n.d. | n.d. |
| 122 | 6.91 | 120. | 61 |
| 123 | n.d. | n.d. | n.d. |
| 124 | n.d. | n.d. | n.d. |
| 125 | <5.00 | >10000 | 48 |
| 126 | 6.11 | 780 | 71 |
| 127 | 6.68 | 210 | 63 |
| 128 | 6.85 | 141 | 66 |
| 129 | <4.52 | >30200 | 21 |
| 130 | 7.08 | 83 | 71 |
| 131 | 7.03 | 93 | 62 |
| 132 | 7.00 | 100 | 68 |
| 133 | 6.59 | 257 | 43 |
| 134 | 7.20 | 63 | 70 |
| 135 | 7.00 | 100 | 56 |
| 136 | 6.13 | 741 | 56 |
| 137 | 6.62 | 240 | 66 |
| 138 | 6.50 | 316 | 59 |
| 139 | 6.05 | 891 | 43 |
| 140 | 6.77 | 170 | 68 |
| 141 | 6.71 | 195 | 66 |
| 142 | 7.19 | 65 | 68 |
| 143 | 7.09 | 81 | 62 |
| 144 | 7.49 | 32 | 70 |
| 145 | 5.85 | 1413 | 59 |
| 146 | 6.32 | 479 | 72 |
| 147 | 6.27 | 537 | 72 |
| 148 | 6.76 | 174 | 71 |
| 149 | 6.10 | 794 | 64 |
| 150 | n.d. | n.d. | n.d. |
| 151 | n.d. | n.d. | n.d. |
| 152 | n.d. | n.d. | n.d. |
| 153 | 7.22 | 60 | 71 |
| 154 | 7.53 | 29 | 72 |
| 155 | 6.89 | 130 | 62 |
| 156 | 6.27 | 540 | 79 |
| 157 | 6.24 | 575 | 63 |
| 158 | 5.51 | 3090 | 69 |
| 159 | 6.32 | 479 | 69 |
| 160 | 6.20 | 631 | 68 |
| 161 | 5.88 | 1318 | 68 |
| 162 | 5.60 | 2512 | 47 |
| 163 | 5.65 | 2239 | 63 |
| 164 | <4.52 | >30200 | 28 |
| 165 | 6.98 | 105 | 71 |
| 166 | 7.02 | 95 | 64 |
| 167 | 6.58 | 263 | 64 |
| 168 | 5.18 | 6607 | 30 |
| 169 | 6.51 | 309 | 62 |
| 170 | <5.00 | >10000 | 45 |
| 171 | <5.00 | >10000 | 51 |
| 172 | 5.99 | 1023 | 64 |
| 173 | <5.00 | >10000 | 31 |
| 174 | 5.90 | 1259 | 34 |
| 175 | <4.52 | >30200 | 22 |
| 176 | 5.75 | 1778 | 64 |
| 177 | 6.42 | 380 | 61 |
| 178 | 6.94 | 115 | 61 |
| 179 | 6.82 | 151 | 60 |
| 180 | 5.77 | 1698 | 53 |
| 181 | <5.00 | >10000 | 52 |
| 182 | 5.49 | 3236 | 36 |

TABLE I*-continued

| No. | pEC50 | EC$_{50}$ (nM) | E$_{max}$ (%) |
|---|---|---|---|
| 183 | <4.52 | >30200 | 15 |
| 184 | 6.45 | 355 | 61 |
| 185 | <5.00 | >10000 | 51 |
| 186 | <4.52 | >30200 | 30 |
| 187 | 5.66 | 2188 | 60 |
| 188 | 6.83 | 148 | 66 |
| 189 | 5.31 | 4898 | 45 |
| 190 | 6.84 | 145 | 66 |
| 191 | 6.37 | 427 | 57 |
| 192 | 6.62 | 240 | 57 |
| 193 | 6.36 | 437 | 53 |
| 194 | <5.00 | >10000 | 50 |
| 195 | <5.00 | >10000 | 40 |
| 196 | <5.00 | >10000 | 37 |
| 197 | <5.00 | >10000 | 58 |
| 198 | 5.76 | 1738 | 61 |
| 199 | 5.43 | 3715 | 60 |
| 200 | <4.52 | >30200 | 21 |
| 201 | <5.00 | >10000 | 46 |
| 202 | <5.00 | >10000 | 39 |
| 203 | 6.78 | 166 | 66 |
| 204 | 6.39 | 407 | 69 |
| 205 | 6.41 | 389 | 55 |
| 206 | 5.82 | 1514 | 67 |
| 207 | 6.36 | 437 | 69 |
| 208 | 6.46 | 347 | 69 |
| 209 | 6.28 | 525 | 62 |
| 210 | 5.67 | 2138 | 50 |
| 211 | n.d. | n.d. | n.d. |
| 212 | n.d. | n.d. | n.d. |
| 213 | 6.18 | 660 | 56 |
| 214 | 5.97 | 1100 | 54 |
| 215 | n.d. | n.d. | n.d. |
| 216 | 6.39 | 410 | 63 |
| 217 | n.d. | n.d. | n.d. |
| 218 | 6.33 | 470 | 69 |
| 219 | 6.59 | 260 | 67 |
| 220 | 6.45 | 350 | 63 |
| 221 | 6.72 | 190 | 66 |
| 222 | 7.11 | 76 | 64 |
| 223 | 7.00 | 98 | 63 |
| 224 | 7.02 | 95 | 72 |
| 225 | 7.21 | 61 | 58 |
| 226 | 6.08 | 830 | 57 |
| 227 | 6.59 | 260 | 62 |
| 228 | 6.92 | 120 | 65 |
| 229 | 6.42 | 380 | 66 |
| 230 | 6.78 | 170 | 72 |
| 231 | 6.92 | 110 | 67 |
| 232 | n.d. | n.d. | n.d. |
| 233 | 6.28 | 525 | 54 |
| 234 | 6.85 | 141 | 69 |
| 235 | 6.77 | 170 | 64 |
| 236 | 6.82 | 151 | 64 |
| 237 | 6.70 | 200 | 52 |
| 238 | 6.87 | 135 | 67 |
| 239 | 7.21 | 62 | 72 |
| 240 | <4.52 | >30200 | 23 |
| 241 | <4.52 | >30200 | 21 |
| 242 | <4.52 | >30200 | 21 |
| 243 | 7.05 | 89 | 68 |
| 244 | 7.25 | 56 | 78 |
| 245 | 6.86 | 138 | 74 |
| 246 | 6.67 | 214 | 69 |
| 247 | 6.23 | 589 | 73 |
| 248 | n.d. | n.d. | n.d. |
| 249 | n.d. | n.d. | n.d. |
| 250 | <5.00 | >10000 | 52 |
| 251 | n.d. | n.d. | n.d. |
| 252 | n.d. | n.d. | n.d. |
| 253 | n.d. | n.d. | n.d. |
| 254 | n.d. | n.d. | n.d. |
| 255 | <5.00 | >10000 | 46 |
| 256 | n.d. | n.d. | n.d. |
| 257 | <4.52 | >30200 | 25 |
| 258 | <5.00 | >10000 | 65 |
| 259 | <4.52 | >30200 | 14 |
| 260 | <4.52 | >30200 | 17 |
| 261 | <4.52 | >30200 | 23 |
| 262 | 6.05 | 891 | 32 |
| 263 | 5.92 | 1202 | 87 |
| 264 | 6.95 | 112 | 63 |
| 265 | 5.65 | 2239 | 60 |
| 266 | 6.94 | 115 | 65 |
| 267 | 6.03 | 933 | 70 |
| 268 | <5.00 | >10000 | 27 |
| 269 | 6.16 | 692 | 58 |
| 270 | <5.00 | >10000 | 39 |
| 271 | 7.05 | 89 | 66 |
| 272 | 7.04 | 91 | 69 |
| 273 | 6.97 | 107 | 68 |
| 274 | 5.59 | 2570 | 65 |
| 275 | <4.52 | >30200 | 36 |
| 276 | 5.90 | 1259 | 68 |
| 277 | 6.03 | 933 | 63 |
| 278 | 6.56 | 275 | 56 |
| 279 | 6.65 | 224 | 69 |
| 280 | 6.45 | 355 | 70 |
| 281 | 6.58 | 263 | 68 |
| 282 | 5.96 | 1096 | 64 |
| 283 | 7.39 | 41 | 77 |
| 284 | 5.55 | 2818 | 53 |
| 285 | 6.13 | 741 | 68 |
| 286 | 7.44 | 36 | 76 |
| 286** | 7.53 | 30 | 69 |
| 287 | 6.22 | 603 | 67 |
| 288 | 6.40 | 398 | 69 |
| 289 | 5.92 | 1202 | 65 |
| 290 | 7.33 | 47 | 56 |
| 291 | 7.27 | 54 | 63 |
| 292 | 7.47 | 34 | 66 |
| 293 | n.d. | n.d. | n.d. |
| 294 | n.d. | n.d. | n.d. |
| 295 | 7.56 | 28 | 69 |
| 296 | 6.21 | 620 | 50 |
| 297 | 7.12 | 76 | 71 |
| 298 | 6.58 | 260 | 73 |
| 299 | 6.96 | 110 | 64 |
| 300 | n.d. | n.d. | n.d. |
| 301 | 7.02 | 96 | 58 |
| 302 | n.d. | n.d. | n.d. |
| 303 | n.d. | n.d. | n.d. |
| 304 | 6.72 | 190 | 77 |
| 305 | 7.40 | 40 | 71 |
| 306 | n.d. | n.d. | n.d. |
| 307 | n.d. | n.d. | n.d. |
| 308 | n.d. | n.d. | n.d. |
| 309 | 5.45 | 3548 | 56 |
| 310 | <4.52 | >30200 | 26 |
| 311 | <4.52 | >30200 | 28 |
| 312 | <4.52 | >30200 | 25 |
| 313 | 6.75 | 178 | 74 |
| 314 | 6.69 | 204 | 70 |
| 315 | n.d. | n.d. | n.d. |
| 316 | 7.39 | 41 | 74 |
| 317 | 7.38 | 42 | 66 |
| 318 | 6.62 | 240 | 72 |
| 319 | 7.54 | 29 | 68 |
| 320 | <5.00 | >10000 | 61 |
| 321 | <4.52 | >30200 | 23 |
| 322 | <5.00 | >10000 | 44 |
| 323 | n.d. | n.d. | n.d. |
| 324 | 7.24 | 58 | 71 |
| 325 | n.d. | n.d. | n.d. |
| 326 | n.d. | n.d. | n.d. |
| 327 | n.d. | n.d. | n.d. |
| 328 | n.d. | n.d. | n.d. |
| 329 | n.d. | n.d. | n.d. |
| 330 | n.d. | n.d. | n.d. |
| 331 | n.d. | n.d. | n.d. |
| 332 | n.d. | n.d. | n.d. |
| 333 | n.d. | n.d. | n.d. |
| 334 | n.d. | n.d. | n.d. |
| 335 | n.d. | n.d. | n.d. |

TABLE I*-continued

| No. | pEC50 | EC$_{50}$ (nM) | E$_{max}$ (%) |
|---|---|---|---|
| 336 | n.d. | n.d. | n.d. |
| 337 | n.d. | n.d. | n.d. |
| 338 | n.d. | n.d. | n.d. |
| 339 | n.d. | n.d. | n.d. |
| 340 | n.d. | n.d. | n.d. |
| 341 | n.d. | n.d. | n.d. |
| 342 | n.d. | n.d. | n.d. |
| 343 | n.d. | n.d. | n.d. |
| 344 | n.d. | n.d. | n.d. |
| 345 | n.d. | n.d. | n.d. |
| 346 | n.d. | n.d. | n.d. |
| 347 | n.d. | n.d. | n.d. |
| 348 | n.d. | n.d. | n.d. |
| 349 | n.d. | n.d. | n.d. |
| 350 | n.d. | n.d. | n.d. |
| 351 | 6.59 | 260 | 66 |
| 352 | <5.00 | >10000 | 55 |
| 353 | 6.55 | 280 | 61 |
| 354 | n.d. | n.d. | n.d. |
| 355 | 5.44 | 3631 | 55 |
| 356 | 6.44 | 360 | 69 |
| 357 | n.d. | n.d. | n.d. |
| 358 | n.d. | n.d. | n.d. |
| 359 | 6.38 | 420 | 64 |
| 360 | 6.72 | 190 | 66 |
| 361 | 7.14 | 72 | 66 |
| 362 | 7.27 | 54 | 71 |
| 363 | 5.89 | 1300 | 65 |
| 364 | 7.34 | 46 | 75 |
| 365 | 7.40 | 40 | 73 |
| 366 | 6.07 | 850 | 62 |
| 367 | 7.06 | 88 | 60 |
| 368 | 7.89 | 13 | 69 |
| 369 | 6.64 | 230 | 68 |
| 370 | 5.96 | 1100 | 68 |
| 371 | 7.49 | 32 | 68 |
| 372 | 6.89 | 130 | 67 |
| 373 | <5.00 | >10000 | 55 |
| 374 | 5.47 | 3400 | 72 |
| 375 | 7.14 | 72 | 70 |
| 376 | 7.12 | 75 | 60 |
| 377 | <5.00 | >10000 | 71 |
| 378 | <4.52 | >30200 | 29 |

*"n.d." indicates that the parameter was not determined.
**HCl salt of Compound No. 286.

E. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require negative allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 miligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

F. METHODS OF USING THE COMPOUNDS AND COMPOSITIONS

The amino acid L-glutamate (referred to herein simply as glutamate) is the principal excitatory neurotransmitter in the mammalian central nervous system (CNS). Within the CNS, glutamate plays a key role in synaptic plasticity (e.g., long term potentiation (the basis of learning and memory)), motor control and sensory perception. It is now well understood that a variety of neurological and psychiatric disorders, including, but not limited to, schizophrenia general psychosis and cognitive deficits, are associated with dysfunctions in the glutamatergic system. Thus, modulation of the glutamatergic system is an important therapeutic goal. Glutamate acts through two distinct receptors: ionotropic and metabotropic glutamate receptors. The first class, the ionotropic glutamate receptors, is comprised of multi-subunit ligand-gated ion channels that mediate excitatory post-synaptic currents. Three subtypes of ionotropic glutamate receptors have been identified, and despite glutamate serving as agonist for all three receptor subtypes, selective ligands have been discovered that activate each subtype. The ionotropic glutamate receptors are named after their respective selective ligands: kainite receptors, AMPA receptors and NMDA receptors.

The second class of glutamate receptor, termed metabotropic glutamate receptors, (mGluRs), are G-protein coupled receptors (GPCRs) that modulate neurotransmitter release or the strength of synaptic transmission, based on their location (pre- or post-synaptic). The mGluRs are family C GPCR, characterized by a large (~560 amino acid) "venus fly trap" agonist binding domain in the amino-terminal domain of the receptor. This unique agonist binding domain distinguishes family C GPCRs from family A and B GPCRs wherein the agonist binding domains are located within the 7-strand transmembrane spanning (7TM) region or within the extracellular loops that connect the strands to this region. To date, eight distinct mGluRs have been identified, cloned and sequenced. Based on structural similarity, primary coupling to intracellular signaling pathways and pharmacology, the mGluRs have been assigned to three groups: Group I (mGluR1 and mGluR5), Group II (mGluR2 and mGluR3) and Group III (mGluR4, mGluR6, mGluR7 and mGluR8). Group I mGluRs are coupled through $G\alpha q/11$ to increase inositol phosphate and metabolism and resultant increases in intracellular calcium. Group I mGluRs are primarily located post-synaptically and have a modualtory effect on ion channel activity and neuronal excitability. Group II (mGluR2 and mGluR3) and Group III (mGluR4, mGluR6, mGluR7 and mGluR8) mGluRs are primarily located pre-synaptically where they regulate the release of neurotransmitters, such as glutamate. Group II and Group III mGluRs are coupled to Gori and its associated effectors such as adenylate cyclase.

Post-synaptic mGluRs are known to functionally interact with post-synaptic ionotropic glutamate receptors, such as the NMDA receptor. For example, activation of mGluR5 by a selective agonist has been shown to increase post-synaptic NMDA currents (Mannaioni et. al. J. Neurosci. 21:5925-5934 (2001)). Therefore, modulation of mGluRs is an approach to modulating glutamatergic transmission. Numerous reports indicate that mGluR5 plays a role in a number of disease states including anxiety (Spooren et. al. J. Pharmacol. Exp. Therapeut. 295:1267-1275 (2000), Tatarczynska et al. Br. J. Pharmaol. 132:1423-1430 (2001)), schizophrenia (reviewed in Chavez-Noriega et al. Curr. Drug Targets: CNS & Neurological Disorders 1:261-281 (2002), Kinney, G. G. et al. J. Pharmacol. Exp. Therapeut. 313:199-206 (2005)), addiction to cocaine (Chiamulera et al. Nature Neurosci. 4:873-874 (2001), Parkinson's disease (Awad et al. J. Neurosci. 20:7871-7879 (2000), Ossowska et al. Neuropharmacol. 41: 413-420 (2001), and pain (Salt and Binns Neurosci. 100: 375-380 (2001).

Figure 2:
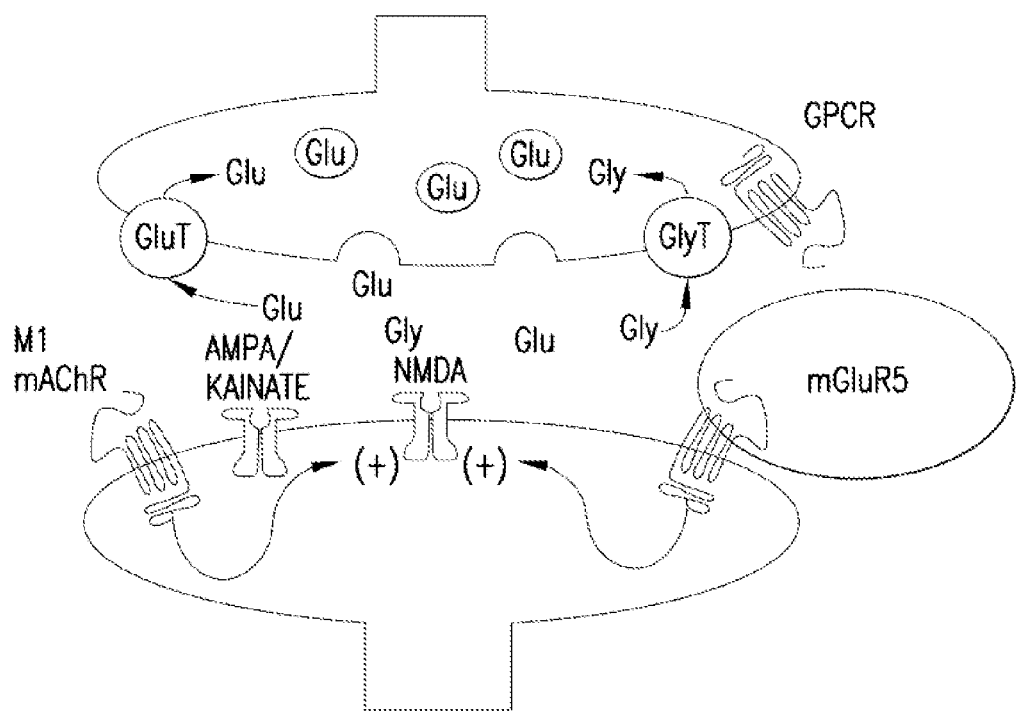
FIG. 2 shows a schematic illustrating that activation of mGluR5 potentiates NMDA receptor function.
Figure 3:
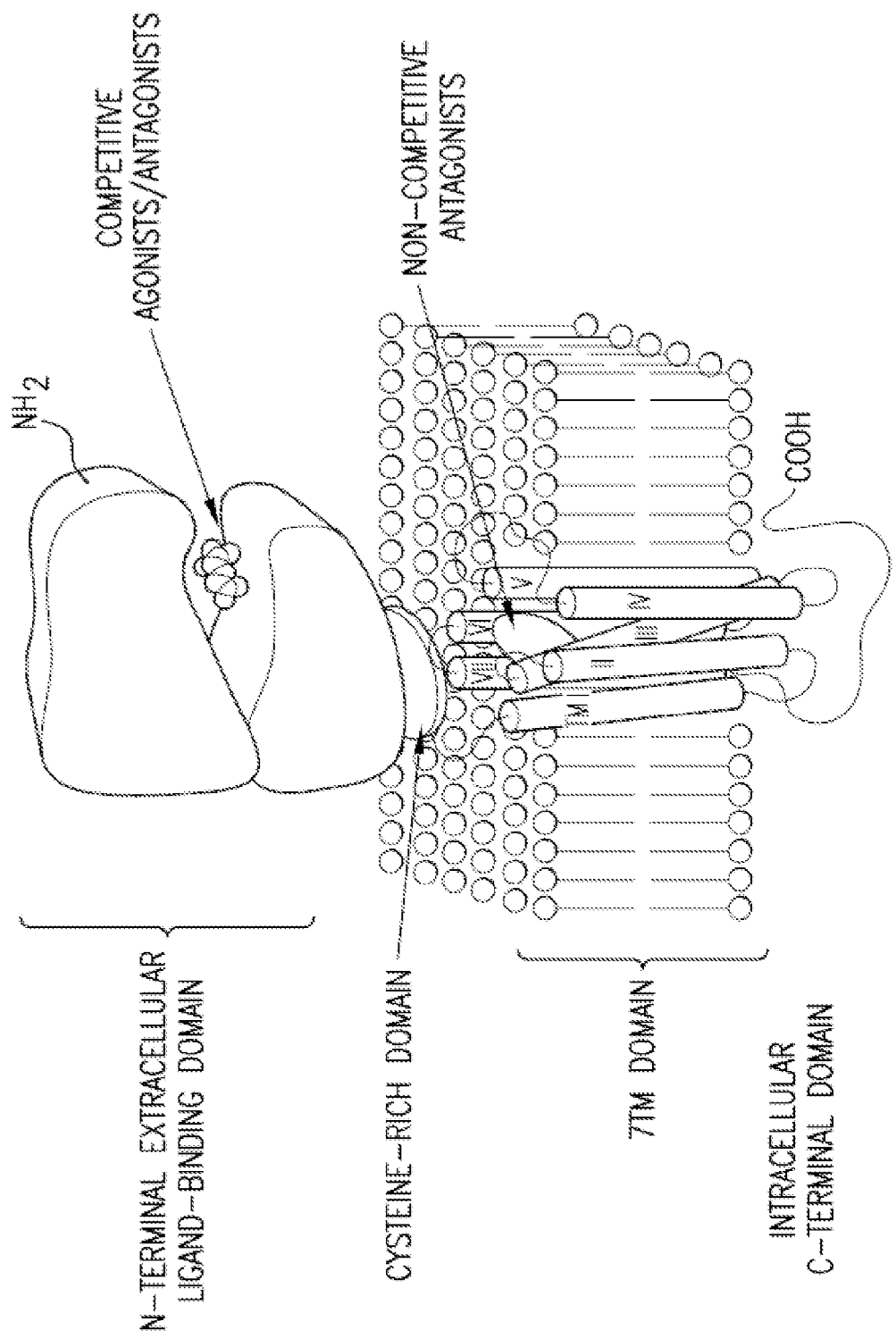
FIG. 3 illustrates allosteric modulation of mGluR5.

Phencyclidine (PCP) and other NMDA receptor antagonists induce a psychotic state in humans similar to schizophrenia. In schizophrenia patients, PCP and ketamine exacerbate/precipitate preexisting positive and negative symptoms in stable patients. Treatment with NMDA receptor co-agonists can improve positive and negative symptoms. A schematic of the NMDA receptor is shown in FIG. 1. Activation of mGluR5 potentiates NMDA receptor function as shown in FIG. 2. Orthosteric ligands lack subtype selectivity and can cause unwanted side effects. Allosteric modulators (see FIG. 3) that can target transmembrane domains offer a pharmacologically attractive alternative. In one aspect, transmembrane domains can be significantly less conserved than extracellular loop regions.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the subject compounds can be coadministered with ant-Alzheimer's agents, beta-secretase inhibitors, gamma-secretase inhibitors, muscarinic agonists, muscarinic potentiatorsHMG-CoA reductase inhibitors, NSAIDs and anti-amyloid antibodies.

In another aspect, the subject compounds can be administered in combination with sedatives, hypnotics, anxiolytics, antipsychotics, selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

In another aspect, the subject compound can be used in combination with levodopa (with or without a selective extracerebral decarboxylase inhibitor), anitcholinergics such as biperiden, COMT inhibitors such as entacapone, A2a adenosine antagonists, cholinergic agonists, NMDA receptor antagonists and dopamine agonists.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of neurological and psychiatric disorders associated with glutamate dysfunction.

Examples of disorders associated with glutamate dysfunction include: autism, acute and chronic neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, addictive behavior, including addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.), obesity, psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Epilepsy can be treated or prevented by the compositions disclosed herein, including absence epilepsy. In various aspects, the compositions disclosed herein can have a protective role for spike and wave discharges associated with absence seizures. Metabotropic glutamate (mGlu) receptors positioned at synapses of the cortico-thalamo-cortical circuitry that generates spike-and-wave discharges (SWDs) associated with absence seizures. Thus, without wishing to be bound by a particular theory, mGluR receptors are therapeutic targets for the treatment of absence epilepsy (e.g. see Epilepsia, 52(7):1211-1222, 2011; Neuropharmacology 60 (2011) 1281e1291; and abstract from 7th International conference on metabotropic glutamate receptors, Oct. 2-6, 2011 Taormina, Italy, "Pharmacological activation of metabotropic glutamate receptor subtype reduces Spike and Wave Discharges in the WAG/Rij rat model of absence epilepsy," I. Santolini, V. D'Amore, C. M. van Rijn, A. Simonyi, A, Prete, P. J. Conn, C. Lindsley, S. Zhou, P. N. Vinson, A. L. Rodriguez, C. K. Jones, S. R. Stauffer, F. Nicoletti, G. van Luijtelaar and R. T. Ngomba).

Anxiety disorders that can be treated or prevented by the compositions disclosed herein include generalized anxiety disorder, panic disorder, and obsessive compulsive disorder. Addictive behaviors include addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

Thus, in some aspects of the disclosed method, the disorder is dementia, delirium, amnestic disorders, age-related cognitive decline, schizophrenia, including positive and negative symptoms thereof and cognitive dysfunction related to schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

Thus, provided is a method for treating or prevention schizophrenia, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including schizophrenia and related disorders.

Also provided is a method for treating or prevention anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

a. Treatment of a Neurological and/or Psychiatric Disorder Associated with Glutamate Dysfunction In one aspect, the invention relates to a method for the treatment of a disorder associated with mGluR5 activity in a mammal comprising the step of administering to the mammal at least one disclosed compound or at least one disclosed product in a dosage and amount effective to treat the disorder in the mammal. In a further aspect, the mammal is a human. In a further aspect, the mammal has been diagnosed with a need for treatment of the disorder prior to the administering step. In a further aspect, the method further comprises the step of identifying a mammal in need of treatment of the disorder.

In one aspect, the invention relates to a method for the treatment of a neurological and/or psychiatric disorder associated with glutamate dysfunction in a mammal comprising the step of administering to the mammal a therapeutically effective amount of at least one compound having a structure represented by a formula:

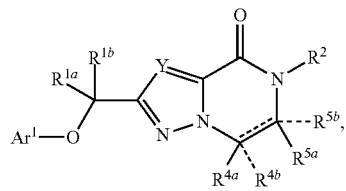

wherein each ____ is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various further aspects, the invention relates to a method for the treatment of a neurological and/or psychiatric disorder associated with glutamate dysfunction in a mammal comprising the step of administering to the mammal a therapeutically effective amount of at least one compound having a structure represented by a formula:

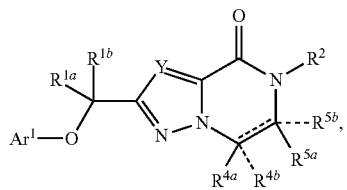

wherein each ____ is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, the mammal is a human. In a further aspect, the mammal has been diagnosed with a need for treatment of the disorder prior to the administering step. In a further aspect, the method further comprises the step of identifying a mammal in need of treatment of the disorder.

In a further aspect, the disorder is a neurological and/or psychiatric disorder associated with mGluR5 dysfunction. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

b. Treatment of a Disorder of Uncontrolled Cellular Proliferation

In one aspect, the invention relates to a method for the treatment of a disorder of uncontrolled cellular proliferation in a mammal comprising the step of administering to the mammal a therapeutically effective amount of at least one compound having a structure represented by a formula:

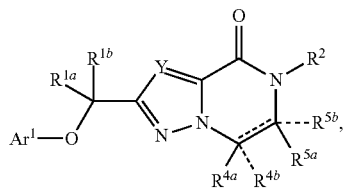

wherein each ____ is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various further aspects, the invention relates to a method for the treatment of a disorder of uncontrolled cellular proliferation in a mammal comprising the step of administering to the mammal a therapeutically effective amount of at least one compound having a structure represented by a formula:

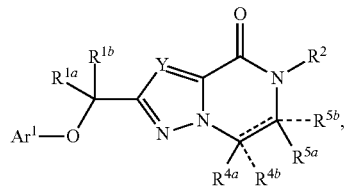

wherein each ____ is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl;

wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In a further aspect, the compound administered is a disclosed compound or a product of a disclosed method of making a compound.

In one aspect, the mammal is human. In a further aspect, the mammal has been diagnosed with a need for treatment of a disorder of uncontrolled cellular proliferation prior to the administering step. In a still further aspect, the method further comprises the step of identifying a mammal in need of treatment of a disorder of uncontrolled cellular proliferation. In a yet further aspect, the disorder of uncontrolled cellular proliferation is associated with mGluR5 dysfunction.

In a further aspect, the disorder of uncontrolled cellular proliferation is cancer. In a still further aspect, the cancer is selected from breast cancer, renal cancer, gastric cancer, and colorectal cancer. In a yet further aspect, the disorder is selected from lymphoma, cancers of the brain, genitourinary tract cancer, lymphatic system cancer, stomach cancer, larynx cancer, lung, pancreatic cancer, breast cancer, and malignant melanoma. In an even further aspect, the disorder is selected from breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma.

c. Potentiation of Metabotropic Glutamate Receptor Activity

In one aspect, the invention relates to a method for potentiation of mGluR5 activity in a mammal comprising the step of administering to the mammal at least one disclosed compound or at least one disclosed product in a dosage and amount effective to increase mGluR5 activity in the mammal either in the presence or absence of the endogenous ligand. In a further aspect, the mammal is a human. In a further aspect, the mammal has been diagnosed with a need for increasing mGluR5 activity prior to the administering step. In a further aspect, the mammal has been diagnosed with a need for treatment of a disorder related to mGluR5 activity prior to the administering step. In a further aspect, the method further comprises the step of identifying a mammal in need of increasing mGluR5 activity.

In one aspect, the invention relates to a method for potentiation of metabotropic glutamate receptor activity in a mammal comprising the step of administering to the mammal a therapeutically effective amount of at least one compound having a structure represented by a formula:

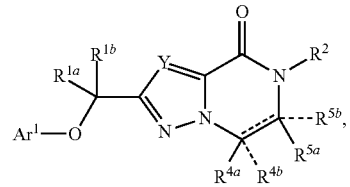

wherein each ____ is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various further aspects, the invention relates to a method for potentiation of metabotropic glutamate receptor activity in a mammal comprising the step of administering to the mammal a therapeutically effective amount of at least one compound having a structure represented by a formula:

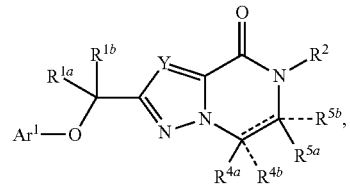

wherein each ____ is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —NH$_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In a further aspect, the compound administered is a disclosed compound or a product of a disclosed method of making a compound.

In a further aspect, the compound exhibits positive allosteric modulation of mGluR5 with an EC$_{50}$ of less than about 10,000 nM. In a still further aspect, the compound exhibits positive allosteric modulation of mGluR5 with an EC$_{50}$ of less than about 5,000 nM. In an even further aspect, the compound exhibits positive allosteric modulation of mGluR5 with an EC$_{50}$ of less than about 1,000 nM. In a further aspect, the compound exhibits positive allosteric modulation of mGluR5 with an EC$_{50}$ of less than about 500 nM. In a yet further aspect, the compound exhibits positive allosteric modulation of mGluR5 with an EC$_{50}$ of less than about 100 nM.

In one aspect, the mammal is a human. In a further aspect, the mammal has been diagnosed with a need for potentiation of metabotropic glutamate receptor activity prior to the administering step. In a further aspect, the method further comprises comprising the step of identifying a mammal in need for potentiation of metabotropic glutamate receptor activity. In a further aspect, the metabotropic glutamate receptor is mGluR5.

In a yet further aspect, the potentiation of mGluR5 activity treats a disorder associated with mGluR5 activity in the mammal. In a still further aspect, the mammal has been diagnosed with a need for treatment of the disorder prior to the administering step. In an even further aspect, treatment further comprises the step of identifying a mammal in need of treatment of the disorder.

In a further aspect, potentiation of metabotropic glutamate receptor activity in a mammal is associated with the treatment of a neurological and/or psychiatric disorder associated with mGluR5 dysfunction. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

In a further aspect, potentiation of metabotropic glutamate receptor activity in a mammal is associated with the treatment of a disorder associated with uncontrolled cellular proliferation. In a further aspect, the disorder associated with uncontrolled cellular proliferation is cancer. In a still further aspect, the cancer is selected from breast cancer, renal cancer, gastric cancer, and colorectal cancer. In a yet further aspect, the disorder is selected from lymphoma, cancers of the brain, genitourinary tract cancer, lymphatic system cancer, stomach cancer, larynx cancer, lung, pancreatic cancer, breast cancer, and malignant melanoma. In an even further aspect, the disorder is selected from breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma.

d. Partial Agonism of Metabotropic Glutamate Receptor Activity

In one aspect, the invention relates to a method for partial agonism of metabotropic glutamate receptor activity in a mammal. In a further aspect, the method relates to a method for partial agonism of metabotropic glutamate receptor activity in a mammal by contacting at least one cell in the mammal, comprising the step of contacting the at least one cell with at least one disclosed compound or at least one disclosed product in an amount effective to inhibit mGluR5 activity in the at least one cell.

In one aspect, the invention relates to a method for partial agonism of metabotropic glutamate receptor activity in a mammal comprising the step of administering to the mammal a therapeutically effective amount of at least one compound having a structure represented by a formula:

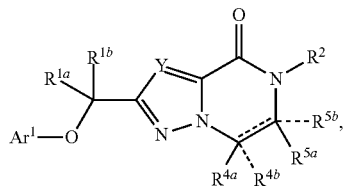

wherein each _____ is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various further aspects, the invention relates to a method for partial agonism of metabotropic glutamate receptor activity in a mammal comprising the step of administering to the mammal a therapeutically effective amount of at least one compound having a structure represented by a formula:

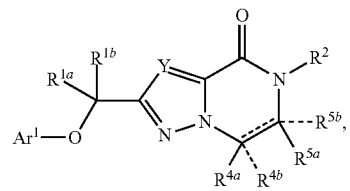

wherein each _____ is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, the mammal is a human. In a further aspect, the mammal has been diagnosed with a need for partial agonism of metabotropic glutamate receptor activity prior to the administering step. In a still further aspect, the method further comprises the step of identifying a mammal in need for partial agonism of metabotropic glutamate receptor activity. In a yet further aspect, the metabotropic glutamate receptor is mGluR5.

In a further aspect, partial agonism of metabotropic glutamate receptor activity in a mammal is associated with the treatment of a neurological and/or psychiatric disorder associated with mGluR5 dysfunction. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

In a further aspect, partial agonism of metabotropic glutamate receptor activity in a mammal is associated with the treatment of a disorder associated with uncontrolled cellular proliferation. In a further aspect, the disorder associated with uncontrolled cellular proliferation is cancer. In a still further aspect, the cancer is selected from breast cancer, renal cancer, gastric cancer, and colorectal cancer. In a yet further aspect, the disorder is selected from lymphoma, cancers of the brain, genitourinary tract cancer, lymphatic system cancer, stomach cancer, larynx cancer, lung, pancreatic cancer, breast cancer, and malignant melanoma. In an even further aspect, the disorder is selected from breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma.

e. Enhancing Cognition

In one aspect, the invention relates to a method for enhancing cognition in a mammal comprising the step of administering to the mammal an effective amount of least one disclosed compound.

In one aspect, the invention relates to a method for enhancing cognition in a mammal comprising the step of administering to the mammal an effective amount of at least one compound having a structure represented by a formula:

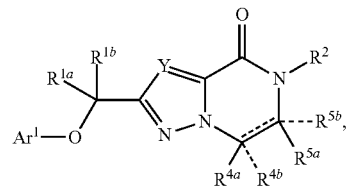

wherein each _____ is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various further aspects, the invention relates to a method for enhancing cognition in a mammal comprising the step of administering to the mammal an effective amount of at least one compound having a structure represented by a formula:

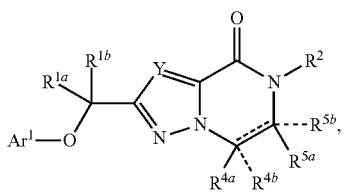

wherein each ____ is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, the mammal is a human. In a further aspect, the cognition enhancement is a statistically significant increase in Novel Object Recognition. In a further aspect, the cognition enhancement is a statistically significant increase in performance of the Wisconsin Card Sorting Test.

f. Modulating mGluR5 Activity in Mammals

In one aspect, the invention relates to a method for modulating mGluR5 activity in a mammal comprising the step of administering to the mammal an effective amount of least one disclosed compound.

In one aspect, the invention relates to a method for modulating mGluR5 activity in a mammal comprising the step of administering to the mammal an effective amount of at least one compound having a structure represented by a formula:

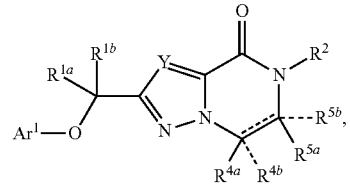

wherein each ____ is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In one aspect, the invention relates to a method for modulating mGluR5 activity in a mammal comprising the step of administering to the mammal an effective amount of at least one compound having a structure represented by a formula:

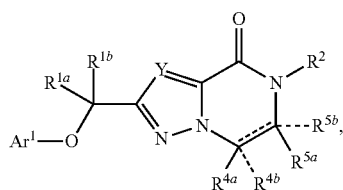

wherein each _____ is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, modulating is increasing. In a further aspect, modulating is potentiation. In a further aspect, modulating is partial agonism.

In one aspect, the mammal is a human. In a further aspect, the mammal has been diagnosed with a need for modulating mGluR5 activity prior to the administering step. In a further aspect, the mammal has been diagnosed with a need for treatment of a disorder related to mGluR5 activity prior to the administering step. In a further aspect, the method further comprises the step of identifying a mammal in need of increasing mGluR5 activity.

In one aspect, an effective amount is a therapeutically effective amount. In a further aspect, an effective amount is a prophylatically effective amount.

In one aspect, modulating mGluR5 activity in a mammal is associated with the treatment of a neurological and/or psychiatric disorder associated with mGluR5 dysfunction. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

In a further aspect, modulating mGluR5 activity in a mammal is associated with the treatment of a disorder associated with uncontrolled cellular proliferation. In a further aspect, the disorder associated with uncontrolled cellular proliferation is cancer. In a still further aspect, the cancer is selected from breast cancer, renal cancer, gastric cancer, and colorectal cancer. In a yet further aspect, the disorder is selected from lymphoma, cancers of the brain, genitourinary tract cancer, lymphatic system cancer, stomach cancer, larynx cancer, lung, pancreatic cancer, breast cancer, and malignant melanoma. In an even further aspect, the disorder is selected from breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma.

g. Modulating mGluR5 Activity in Cells

In one aspect, the invention relates to a method for modulating mGluR5 activity in at least one cell, comprising the step of contacting the at least one cell with an effective amount of at least one disclosed compound.

In one aspect, the invention relates to a method for modulating mGluR5 activity in at least one cell, comprising the step of contacting the at least one cell with an effective amount of at least one compound having a structure represented by a formula:

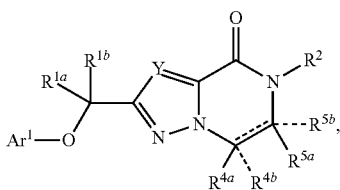

wherein each ____ is independently an optional covalent bond, wherein valence is satisfied; wherein $Ar^1$ is phenyl with 0-3 substituents selected from halogen, cyano, C1-C4 alkyl, C1-C4 alkyloxy, monohalo C1-C4 alkyl, and polyhalo C1-C4 alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl; wherein Y is N or C—$R^3$, wherein $R^3$, when present, is selected from hydrogen, halogen, cyano, and C1-C4 alkyl; wherein $R^{4a}$ is selected from hydrogen and C1-C4 alkyl; wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl; or a pharmaceutically acceptable salt thereof.

In various further aspects, the invention relates to a method for modulating mGluR5 activity in at least one cell, comprising the step of contacting the at least one cell with an effective amount of at least one compound having a structure represented by a formula:

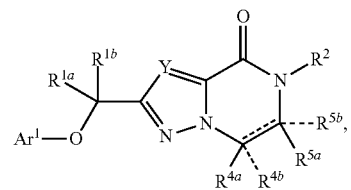

wherein each ____ is independently an optional covalent bond, wherein valence is satisfied; wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; wherein each of $R^{1a}$ and $R^{1b}$ is independently selected from hydrogen and C1-C4 alkyl; wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl; wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl; wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl; or a pharmaceutically acceptable salt thereof, wherein the compound exhibits potentiation of mGluR5 response to glutamate as an increase in response to non-maximal concentrations of glutamate in human embryonic kidney cells transfected with mGluR5 in the presence of the compound, compared to the response to glutamate in the absence of the compound.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, modulating is increasing. In a further aspect, modulating is potentiation. In a further aspect, modulating is partial agonism.

In one aspect, the cell is mammalian. In a further aspect, the cell is human. In a further aspect, the cell has been isolated from a mammal prior to the contacting step.

In a further aspect, contacting is via administration to a mammal. In a further aspect, the mammal has been diagnosed with a need for modulating mGluR5 activity prior to the administering step. In a further aspect, the mammal has been diagnosed with a need for treatment of a disorder related to mGluR5 activity prior to the administering step.

In one aspect, modulating mGluR5 activity in at least one cell treats a neurological and/or psychiatric disorder. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

In a further aspect, modulating mGluR5 activity in at least one cell treats a disorder associated with uncontrolled cellular proliferation. In a further aspect, the disorder associated with uncontrolled cellular proliferation is cancer. In a still further aspect, the cancer is selected from breast cancer, renal cancer, gastric cancer, and colorectal cancer. In a yet further aspect, the disorder is selected from lymphoma, cancers of the brain, genitourinary tract cancer, lymphatic system cancer, stomach cancer, larynx cancer, lung, pancreatic cancer, breast cancer, and malignant melanoma. In an even further aspect, the disorder is selected from breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma.

2. Manufacture of a Medicament

In one aspect, the invention relates to a method for the manufacture of a medicament for potentiation of metabotropic glutamate receptor activity in a mammal comprising combining a therapeutically effective amount of a disclosed compound or product of a disclosed method with a pharmaceutically acceptable carrier or diluent.

3. Use of Compounds

In one aspect, the invention relates to the use of a disclosed compound or a product of a disclosed method. In a further aspect, a use relates to the manufacture of a medicament for the treatment of a disorder associated with glutamate dysfunction in a mammal. In a further aspect, the disorder is a neurological and/or psychiatric disorder. In a further aspect, the disorder is a disease of uncontrolled cellular proliferation. In a further aspect, a use relates to treatment of a neurological and/or psychiatric disorder associated with glutamate dysfunction in a mammal.

In a further aspect, a use relates to potentiation of metabotropic glutamate receptor activity in a mammal. In a further aspect, a use relates to partial agonism of metabotropic glutamate receptor activity in a mammal. In a further aspect, a use relates to enhancing cognition in a mammal. In a further aspect, a use relates to modulating mGluR5 activity in a mammal. In a further aspect, a use relates to modulating mGluR5 activity in a cell.

In one aspect, a use is treatment of a neurological and/or psychiatric disorder associated with mGluR5 dysfunction. In a further aspect, the disorder is selected from autism, dementia, delirium, amnestic disorders, age-related cognitive decline, schizophrenia, including the positive and negative symptoms thereof and cognitive dysfunction related to schizophrena, psychosis including schizophrenia, schizophreniform disorder, schizoaffective disorder, delusional disorder, brief psychotic disorder, substance-related disorder, movement disorders, epilepsy, including absence epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression. In a yet further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression, autism, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, and substance-induced anxiety disorder. In an even further aspect, the disorder is absence epilepsy. In a still further aspect, the disorder is selected from cognitive disorders, age-related cognition decline, learning deficit, intellectual impairment disorders, cognition impairment in schizophrenia, cognition impairment in Alzheimer's disease, and mild cognitive impairment.

In one aspect, a use is associated with the treatment of a disorder associated with uncontrolled cellular proliferation. In a further aspect, the disorder is cancer. In a still further aspect, the cancer is selected from breast cancer, renal cancer, gastric cancer, and colorectal cancer. In a further aspect, the disorder is selected from lymphoma, cancers of the brain, genitourinary tract cancer, lymphatic system cancer, stomach cancer, larynx cancer, lung, pancreatic cancer, breast cancer, and malignant melanoma.

In one aspect, the invention relates to the use of a disclosed compound or a disclosed product in the manufacture of a medicament for the treatment of a disorder associated with glutamate dysfunction in a mammal. In a further aspect, the disorder is a neurological and/or psychiatric disorder. In a further aspect, the disorder is a disease of uncontrolled cellular proliferation.

4. Kits

In one aspect, the invention relates to a kit comprising a disclosed compound or a product of a disclosed method and one or more of at least one agent known to increase mGluR5 activity; at least one agent known to decrease mGluR5 activity; at least one agent known to treat a neurological and/or psychiatric disorder; at least one agent known to treat a disease of uncontrolled cellular proliferation; or instructions for treating a disorder associated with glutamate dysfunction. In a further aspect, the at least one compound or the at least one product and the at least one agent are co-formulated. In a further aspect, the at least one compound or the at least one product and the at least one agent are co-packaged.

In a further aspect, the kit comprises a disclosed compound or a product of a disclosed method.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

5. Non-Medical Uses

Also provided are the uses of the disclosed compounds and products as pharmacological tools in the development and standardization of in vitro and in vivo test systems for the evaluation of the effects of potentiators of mGluR related activity in laboratory animals such as cats, dogs, rabbits, monkeys, rats and mice, as part of the search for new therapeutic agents of mGluR. In a further aspect, the invention relates to the use of a disclosed compound or a disclosed product as pharmacological tools in the development and standardization of in vitro and in vivo test systems for the evaluation of the effects of potentiators of mGluR5 related activity in laboratory animals such as cats, dogs, rabbits, monkeys, rats and mice, as part of the search for new therapeutic agents of mGluR5.

G. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods $^1$H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

Microwave assisted reactions were performed in a single-mode reactor: Emrys™ Optimizer microwave reactor (Personal Chemistry A.B., currently Biotage).

Hydrogenation reactions were performed in a continuous flow hydrogenator H-CUBE® from ThalesNano Nanotechnology Inc.

Thin layer chromatography (TLC) was carried out on silica gel 60 F254 plates (Merck) using reagent grade solvents. Open column chromatography was performed on silica gel, particle size 60 Å, mesh=230-400 (Merck) under standard techniques. Flash column chromatography was performed using ready-to-connect cartridges from Merck, on irregular silica gel, particle size 15-40 μm (normal layer disposable flash columns) on a SPOT or FLASH system from Armen Instrument.

Reverse phase HPLC was performed on C18 XBridge 30×100 5 μm columns.

Melting point values are peak values, and are obtained with experimental uncertainties that are commonly associated with this analytical method. For a number of compounds, melting points were determined in open capillary tubes on a Mettler FP62, a Mettler FT90 or a Mettler FP81HT-FP90 apparatus. Melting points were measured with a temperature gradient of 10° C./minute. Maximum temperature was 300° C. The melting point was read from a digital display.

Optical rotations were measured on a Perkin-Elmer 341 polarimeter with a sodium lamp and reported as follows: $[\alpha]^{T°C.}_{\lambda}$ (λ, c g/100 ml, solvent, T° C.). $[\alpha]^{T}_{\lambda}=(100\alpha)/(l \times c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

2. LCMS Methods a. General Procedure A

The HPLC measurement was performed using an HP 1100 (Agilent Technologies) system comprising a pump (quaternary or binary) with degasser, an autosampler, a column oven, a diode-array detector (DAD) and a column as specified in the respective methods below. Flow from the column was split to the MS spectrometer. The MS detector was configured with either an electrospray ionization source or an ESCI dual ionization source (electrospray combined with atmospheric pressure chemical ionization). The source temperature was maintained at 140° C. Nitrogen was used as the nebulizer gas. Data acquisition was performed with MassLynx-Openlynx software.

b. General Procedure B

The HPLC (Ultra Performance Liquid Chromatography) measurement was performed using an Acquity HPLC (Waters) system comprising a sampler organizer, a binary pump with degasser, a four column's oven, a diode-array detector (DAD) and a column as specified in the respective methods below. Column flow was used without split to the MS detector. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

c. General Procedure C

The HPLC measurement was performed using an HP 1100 (Agilent Technologies) system comprising a binary pump with degasser, an autosampler, a column oven, a diode-array detector (DAD) and a column as specified in the respective methods below. Flow from the column was split to a MS spectrometer. The MS detector was configured with an ESCI dual ionization source (electrospray combined with atmospheric pressure chemical ionization). Nitrogen was used as the nebulizer gas. The source temperature was maintained at 100° C. Data acquisition was performed with Chemsation-Agilent Data Browser software.

d. General Procedure D

The HPLC measurement was performed using an Agilent 1200 system comprising a binary pump with degasser, an autosampler, a column oven, a diode-array detector (DAD) and a column as specified in the respective methods below. Flow from the column was split to a SQ mass spectrometer and Polymer Labs ELSD. The MS detector was configured with an ES ionization source. Nitrogen was used as the nebulizer gas. The source temperature was maintained at 350° C. Data acquisition was performed with Agilent Chemstation software.

e. LCMS Method 1

In addition to the general procedure A: Reversed phase HPLC was carried out on a Eclipse Plus-C18 column (3.5 μm, 2.1×30 mm) from Agilent, with a flow rate of 1.0 ml/min, at 60° C. The gradient conditions used are: 95% A (0.5 g/l ammonium acetate solution+5% acetonitrile), 5% B (acetonitrile:methanol, 1:1) to 100% B in 5.0 minutes, kept till 5.15 minutes and equilibrated to initial conditions at 5.3 minutes until 7.0 minutes. Injection volume 2 μl High-resolution mass spectra (Time of Flight, TOF detector) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

f. LCMS Method 2

In addition to the general procedure A: Reversed phase HPLC was carried out on a Eclipse Plus-C18 column (3.5 μm, 2.1×30 mm) from Agilent, with a flow rate of 1.0 ml/min, at 60° C. The gradient conditions used are: 95% A (0.5 g/l ammonium acetate solution+5% acetonitrile), 5% B (acetonitrile:methanol, 1:1), kept 0.2 minutes, to 100% B in 3.0 minutes, kept till 3.15 minutes and equilibrated to initial conditions at 3.3 minutes until 5.0 minutes. Injection volume 2 High-resolution mass spectra (Time of Flight, TOF detector) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

g. LCMS Method 3

The method utilizes the same HPLC gradent as described by LCMS Method 2. MS: High-resolution mass spectra (Time of Flight, TOF detector) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

h. LCMS Method 4

In addition to the general procedure B: Reversed phase HPLC was carried out on a BEH-C18 column (1.7 µm, 2.1×50 mm) from Waters, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 2.8 minutes, to 5% A, 95% B in 3.6 minutes, kept till 3.8 minutes and equilibrated to initial conditions at 4.0 minutes until 5.0 minutes. Injection volume 0.5 Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

i. LCMS Method 5

In addition to the general procedure B: Reversed phase HPLC was carried out on a BEH-C18 column (1.7 µm, 2.1×50 mm) from Waters, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 3.8 minutes, to 5% A, 95% B in 4.6 minutes, kept till 5.0 minutes. Injection volume 2.0 Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

j. LCMS Method 6

In addition to the general procedure A: Reversed phase HPLC was carried out on an Eclipse Plus-C18 column (3.5 µm, 2.1×30 mm) from Agilent, with a flow rate of 1.0 ml/min, at 60° C. without split to the MS detector. The gradient conditions used are: 95% A (0.5 g/l ammonium acetate solution+5% acetonitrile), 5% B (mixture of acetonitrile/methanol, 1/1), kept 0.2 minutes, to 100% B in 3.0 minutes, kept till 3.15 minutes and equilibrated to initial conditions at 3.30 minutes until 5.0 minutes. Injection volume 2 µl. Low-resolution mass spectra (single quadrupole, SQD detector) were acquired by scanning from 100 to 1000 in 0.1 second using an inter-channel delay of 0.08 second. The capillary needle voltage was 3 kV. The cone voltage was 20 V and 50 V for positive ionization mode and 30 V for negative ionization mode.

k. LCMS Method 7

The method was the same as method 5, but the column used was RRHD Eclipse Plus-C18 (1.8 µm, 2.1×50 mm) from Agilent.

l. LCMS Method 8

In addition to the general procedure B: Reversed phase HPLC was carried out on a RRHD Eclipse Plus-C18 (1.8 µm, 2.1×50 mm) from Agilent, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 1.2 minutes, to 5% A, 95% B in 1.8 minutes, kept till 2.0 minutes. Injection volume 2.0 µl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

m. LCMS Method 9

In addition to the general procedure B: Reversed phase HPLC was carried out on a RRHD Eclipse Plus-C18 (1.8 µm, 2.1×50 mm) from Agilent, with a flow rate of 1.0 ml/min, at 50° C. without split to the MS detector. The gradient conditions used are: 95% A (0.5 g/l ammonium acetate solution+5% acetonitrile), 5% B (acetonitrile), to 5% A, 95% B in 4.6 minutes, kept till 5.0 minutes. Injection volume 2.0 µl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

n. LCMS Method 10

In addition to the general procedure A: Reversed phase HPLC was carried out on an Eclipse Plus-C18 column (3.5 µm, 2.1×30 mm) from Agilent, with a flow rate of 1.0 ml/min, at 60° C. without split to the MS detector. The gradient conditions used are: 95% A (0.5 g/l ammonium acetate solution+5% acetonitrile), 5% B (mixture of acetonitrile/methanol, 1/1), to 100% B in 5.0 minutes, kept till 5.15 minutes and equilibrated to initial conditions at 5.30 minutes until 7.0 minutes. Injection volume 2 Low-resolution mass spectra (single quadrupole, SQD detector) were acquired by scanning from 100 to 1000 in 0.1 second using an inter-channel delay of 0.08 second. The capillary needle voltage was 3 kV. The cone voltage was 20 V for positive ionization mode and 30 V for negative ionization mode.

o. LCMS Method 11

In addition to the general procedure C: Reversed phase HPLC was carried out on an Eclipse Plus-C18 column (3.5 µm, 2.1×30 mm) from Agilent, with a flow rate of 1.0 ml/min, at 60° C. The gradient conditions used are: 95% A (0.5 g/l ammonium acetate solution+5% acetonitrile), 5% B (acetonitrile), kept 0.2 minutes, to 100% B in 3.0 minutes, kept till 3.15 minutes and equilibrated to initial conditions at 3.3 minutes until 5.0 minutes. Injection volume 2 Low-resolution mass spectra (single quadrupole, MSD detector) were acquired in electrospray mode by scanning from 100 to 1000 in 0.99 seconds, step size of 0.30 and peak width of 0.10 minutes. The capillary needle voltage was 1.0 kV and the fragmentor voltage was 70V for both positive and negative ionization modes.

p. LCMS Method 12

In addition to the general procedure C: Reversed phase HPLC was carried out on an Eclipse Plus-C18 column (3.5 µm, 2.1×30 mm) from Agilent, with a flow rate of 1.0 ml/min, at 60° C. The gradient conditions used are: 95% A (0.5 g/l ammonium acetate solution+5% acetonitrile), 5% B (acetonitrile), to 100% B in 5.0 minutes, kept till 5.15 minutes and equilibrated to initial conditions at 5.3 minutes until 7.0 minutes. Injection volume 2 Low-resolution mass spectra (single quadrupole, MSD detector) were acquired in electrospray mode by scanning from 100 to 1000 in 0.99 seconds, step size of 0.30 and peak width of 0.10 minutes. The capillary needle voltage was 1.0 kV and the fragmentor voltage was 70V for both positive and negative ionization modes.

q. LCMS Method 13

In addition to the general procedure C: Reversed phase HPLC was carried out on an Eclipse Plus-C18 column (3.5 µm, 2.1×30 mm) from Agilent, with a flow rate of 1.0 ml/min, at 60° C. The gradient conditions used are: 95% A (0.5 g/l ammonium acetate solution+5% acetonitrile), 5% B (acetonitrile), to 100% B at 6.5 minutes, kept till 7.0 minutes and equilibrated to initial conditions at 7.3 minutes until 9.0 minutes. Injection volume 2 µl. Low-resolution mass spectra (single quadrupole, MSD detector) were acquired in electrospray mode by scanning from 100 to 1000 in 0.99 seconds, step size of 0.30 and peak width of 0.10 minutes. The capillary needle voltage was 1.0 kV and the fragmentor voltage was 70V for both positive and negative ionization modes.

r. LCMS Method 14

In addition to the general procedure A: Reversed phase HPLC was carried out on a Eclipse Plus-C18 column (3.5 μm, 2.1×30 mm) from Agilent, with a flow rate of 1.0 ml/min, at 60° C. The gradient conditions used are: 95% A (0.5 g/l ammonium acetate solution+5% of acetonitrile), 5% B (acetonitrile/methanol, 1/1) to 100% B in 6.5 minutes, kept till 7.0 minutes and equilibrated to initial conditions at 7.3 minutes until 9.0 minutes. Injection volume 2 μl. High-resolution mass spectra (Time of Flight, TOF detector) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephalin was the standard substance used for the lock mass calibration.

s. LCMS Method 15

In addition to the general procedure D: Reversed phase HPLC was carried out on a Kinetex C18 column (2.6 μm, 2.1×30 μm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 μL. Low-resolution mass spectra (single quadrupole MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V.

t. LCMS Method 16

In addition to the general procedure D: Reversed phase HPLC was carried out on a Kinetex C18 column (2.6 μm, 2.1×30 μm) from Phenomenex, with a flow rate of 1.5 mL/min, at 45° C. The gradient conditions used are: 93% A (water+0.1% TFA), 7% B (acetonitrile), to 95% B in 2.1 minutes, returning to initial conditions at 2.11 minutes. Injection volume 1 μL. Low-resolution mass spectra (single quadrupole MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V.

3. 2,4-dioxo-5-phenoxy-pentanoic acid ethyl ester

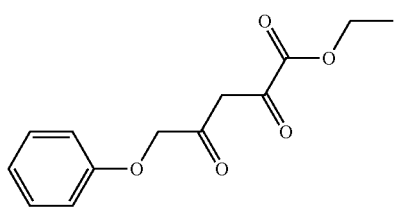 [SMILES: CCOC(=O)C(=O)CC(=O)COc1ccccc1]

Sodium (6.74 g, 293 mmol) was added to EtOH at 0° C. The mixture was stirred at 0° C. until the sodium was completely dissolved. Then phenoxy-2-propanone (53 mL, 266 mmol) was added dropwise. The mixture was stirred at 0° C. for 10 minutes and then diethyl oxalate (36 g, 266 mmol) was added. Then the mixture was stirred at room temperature for 16 hours and the solvent was evaporated in vacuo. The residue was dissolved in H$_2$O and the mixture was acidified with a 1M solution of HCl and extracted with DCM. The organic layer was separated, dried (Na$_2$SO$_4$), filtered and the solvents evaporated in vacuo. The crude product was purified by open column chromatography (silica; DCM) to yield 2,4-dioxo-5-phenoxy-pentanoic acid ethyl ester (35.85 g, 54% yield) as an oil.

4. 5-phenoxymethyl-2H-pyrazole-3-carboxylic acid ethyl ester

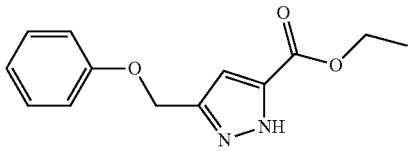 [SMILES: CCOC(=O)c1cc(COc2ccccc2)n[nH]1]

Hydrazine hydrate (0.27 mL, 2.76 mmol) was added to a stirred solution of 2,4-dioxo-5-phenoxy-pentanoic acid ethyl ester (0.69 g, 2.76 mmol in EtOH (3 mL)). The mixture was stirred at 80° C. overnight. The solvent was evaporated in vacuo. The crude product was purified by flash column chromatography (silica; DCM in AcOEt 0/100 to 20/80). The desired fractions were collected and the solvents evaporated in vacuo to yield 5-phenoxymethyl-2H-pyrazole-3-carboxylic acid ethyl ester (0.66 g, 98% yield) as a yellow oil.

5. 2-(2-tert-butoxycarbonylamino-ethyl)-5-phenoxymethyl-2H-pyrazole-3-carboxylic acid ethyl ester

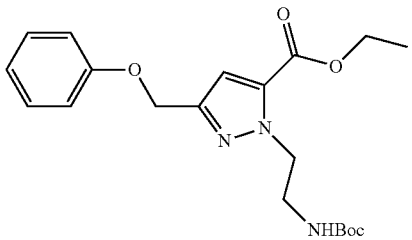 [SMILES: CCOC(=O)c1cc(COc2ccccc2)nn1CCNC(=O)OC(C)(C)C]

2-(2-tert-Butoxycarbonylamino)ethyl bromide (0.78 g, 3.5 mmol) was added to a suspension of 5-phenoxymethyl-2H-pyrazole-3-carboxylic acid ethyl ester and K$_2$CO$_3$ (0.75 g, 5.4 mmol) in DMF (15 mL). The mixture was stirred at room temperature for 16 hours and the solvent evaporated in vacuo. The crude product was purified by flash column chromatography (silica; heptane in AcOEt 0/100 to 50/50). The desired fractions were collected and the solvents evaporated in vacuo to yield 2-(2-tert-butoxycarbonylamino-ethyl)-5-phenoxymethyl-2H-pyrazole-3-carboxylic acid ethyl ester (0.72 g, 69% yield) as a yellow oil.

6. 2-phenoxymethyl-6,7-dihydro-5H-pyrazolo[1,5-a]pyrazin-4-one

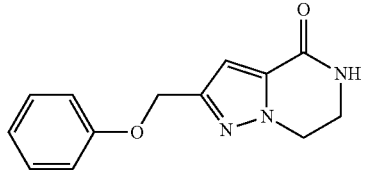 [SMILES: O=C1NCCn2nc(COc3ccccc3)cc21]

2-(2-tert-Butoxycarbonylamino-ethyl)-5-phenoxymethyl-2H-pyrazole-3-carboxylic acid ethyl ester (0.72 g, 1.85 mmol) was dissolved in a 4M solution of HCl in 1,4-dioxane (7 mL) under N₂. The mixture was stirred at room temperature for 1 hour. The mixture was basified with a saturated solution of Na₂CO₃ and stirred at room temperature for 72 hours. Then the mixture was extracted with DCM. The organic layer was separated, dried (Na₂SO₄), filtered and the solvents evaporated in vacuo. The crude product was purified by flash column chromatography (silica; 7 M solution of ammonia in MeOH in DCM 0/100 to 5/95). The desired fractions were collected and the solvents evaporated in vacuo to yield 2-phenoxymethyl-6,7-dihydro-5H-pyrazolo[1,5-a]pyrazin-4-one (0.39 g, 85% yield) as a white solid. ¹H NMR (500 MHz, CDCl₃) δ ppm 3.71-3.86 (m, 2H), 4.32-4.48 (m, 2H), 5.11 (s, 2H), 6.39 (br. s., 1H), 6.91-6.99 (m, 2H), 7.00 (d, J=8.1 Hz, 2H), 7.27-7.34 (m, 2H).

7. rac-2-(2-tert-butoxycarbonylamino-propyl)-5-phenoxymethyl-2H-pyrazole-3-carboxylic acid ethyl ester

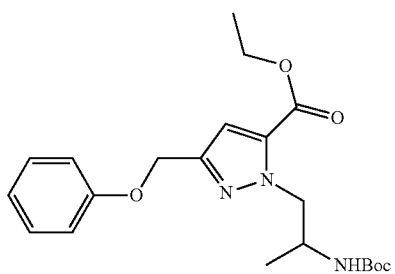 [SMILES: CCOC(=O)c1cc(COc2ccccc2)nn1CC(C)NC(=O)OC(C)(C)C]

Di-tert-butyl azodicarboxylate (2.52 g, 10.96 mmol) was added to a stirred solution of triphenylphosphine (2.87 g, 10.96 mmol), rac-2-hydroxy-1-methyl-ethyl-carbamic acid tert-butyl ester (2.13 g, 12.18 mmol) and 5-phenoxymethyl-2H-pyrazole-3-carboxylic acid ethyl ester (1.5 g, 6.09 mmol) in THF (45 mL). The mixture was stirred at 120° C. for 20 minutes under microwave irradiation and the solvents evaporated in vacuo. The crude product was purified by open column chromatography (silica; AcOEt in DCM 0/100 to 10/90). The desired fractions were collected and the solvents evaporated in vacuo to yield 2-(2-tert-butoxycarbonylamino-propyl)-5-phenoxymethyl-2H-pyrazole-3-carboxylic acid ethyl ester (5.58 g, 91% yield, 40% pure) as a colorless oil that crystallized upon standing in white crystals.

8. (rac)-6-methyl-2-phenoxymethyl-6,7-dihydro-5H-pyrazolo[1,5-a]pyrazin-4-one

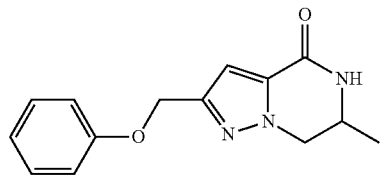 [SMILES: CC1Cn2nc(COc3ccccc3)cc2C(=O)N1]

The compound was prepared from (rac)-2-(2-tert-butoxycarbonylamino-propyl)-5-phenoxymethyl-2H-pyrazole-3-carboxylic acid ethyl ester using the method described in the preceding example 6 (2-phenoxymethyl-6,7-dihydro-5H-pyrazolo[1,5-a]pyrazin-4-one).

9. (R)-6-methyl-2-phenoxymethyl-6,7-dihydro-5H-pyrazolo[1,5-a]pyrazin-4-one

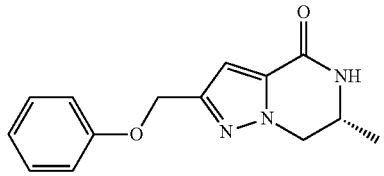 [SMILES: C[C@@H]1Cn2nc(COc3ccccc3)cc2C(=O)N1]

The compound was prepared from (S)-(2-hydroxy-1-methyl-ethyl)-carbamic acid tert-butyl ester and 5-phenoxymethyl-2H-pyrazole-3-carboxylic acid ethyl ester using the methods described in the preceding examples 7 ((rac)-2-(2-tert-butoxycarbonylamino-propyl)-5-phenoxymethyl-2H-pyrazole-3-carboxylic acid ethyl ester) and 6 (2-phenoxymethyl-6,7-dihydro-5H-pyrazolo[1,5-a]pyrazin-4-one).

10. (S)-6-methyl-2-phenoxymethyl-6,7-dihydro-5H-pyrazolo[1,5-a]pyrazin-4-one

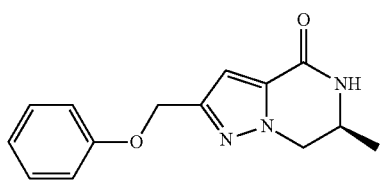 [SMILES: C[C@H]1Cn2nc(COc3ccccc3)cc2C(=O)N1]

The compound was prepared from (R)-(2-hydroxy-1-methyl-ethyl)-carbamic acid tert-butyl ester and 5-phenoxymethyl-2H-pyrazole-3-carboxylic acid ethyl ester using the methods described in the preceding examples 7 ((rac)-2-(2-tert-butoxycarbonylamino-propyl)-5-phenoxymethyl-2H-pyrazole-3-carboxylic acid ethyl ester) and 6 (2-phenoxymethyl-6,7-dihydro-5H-pyrazolo[1,5-a]pyrazin-4-one).

11. rac-7-methyl-2-phenoxymethyl-6,7-dihydro-5H-pyrazolo[1,5-a]pyrazin-4-one

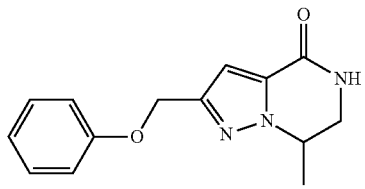 [SMILES: CC1CNC(=O)c2cc(COc3ccccc3)nn21]

The compound was prepared from 5-phenoxymethyl-2H-pyrazole-3-carboxylic acid ethyl ester and rac-2-hydroxy-propyl-carbamic acid tert-butyl ester using the methods described in the preceding examples 7 ((rac)-2-(2-tert-butoxycarbonylamino-propyl)-5-phenoxymethyl-2H-pyrazole-3-carboxylic acid ethyl ester) and 6 (2-phenoxymethyl-6,7-dihydro-5H-pyrazolo[1,5-a]pyrazin-4-one).

12. (*R)-7-methyl-2-phenoxymethyl-6,7-dihydro-5H-pyrazolo[1,5-a]pyrazin-4-one

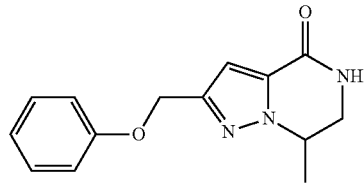 [SMILES: CC1CNC(=O)c2cc(COc3ccccc3)nn21]

The compound was prepared from 5-phenoxymethyl-2H-pyrazole-3-carboxylic acid ethyl ester and (S)-2-hydroxy-propyl-carbamic acid tert-butyl ester using the methods described in the preceding examples 7 ((rac)-2-(2-tert-butoxycarbonylamino-propyl)-5-phenoxymethyl-2H-pyrazole-3-carboxylic acid ethyl ester) and 6 (2-phenoxymethyl-6,7-dihydro-5H-pyrazolo[1,5-a]pyrazin-4-one).

13. (*S)-7-methyl-2-phenoxymethyl-6,7-dihydro-5H-pyrazolo[1,5-a]pyrazin-4-one

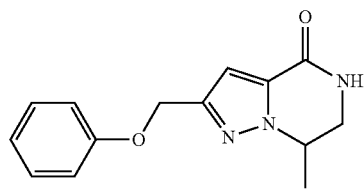 [SMILES: CC1CNC(=O)c2cc(COc3ccccc3)nn21]

The compound was prepared from 5-phenoxymethyl-2H-pyrazole-3-carboxylic acid ethyl ester and (R)-2-hydroxy-propyl-carbamic acid tert-butyl ester using the methods described in the preceding examples 7 ((rac)-2-(2-tert-butoxycarbonylamino-propyl)-5-phenoxymethyl-2H-pyrazole-3-carboxylic acid ethyl ester) and 6 (2-phenoxymethyl-6,7-dihydro-5H-pyrazolo[1,5-a]pyrazin-4-one).

14. 7,7-dimethyl-2-phenoxymethyl-6,7-dihydro-5H-pyrazolo[1,5-a]pyrazin-4-one

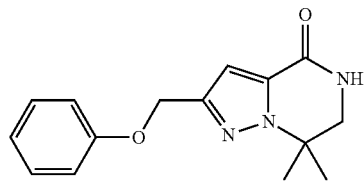 [SMILES: CC1(C)CNC(=O)c2cc(COc3ccccc3)nn21]

The compound was prepared from 5-phenoxymethyl-2H-pyrazole-3-carboxylic acid ethyl ester and tert-butyl (2-hydroxy-2-methylpropyl)carbamate using the methods described in the preceding examples 7 ((rac)-2-(2-tert-butoxycarbonylamino-propyl)-5-phenoxymethyl-2H-pyrazole-3-carboxylic acid ethyl ester) and 6 (2-phenoxymethyl-6,7-dihydro-5H-pyrazolo[1,5-a]pyrazin-4-one).

15. 2-phenoxymethyl-5H-pyrazolo[1,5-a]pyrazin-4-one

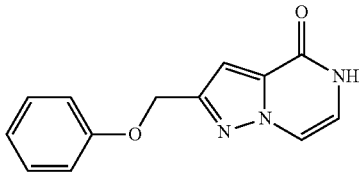 [SMILES: O=c1[nH]ccn2nc(COc3ccccc3)cc12]

Manganese dioxide (0.36 g, 4.1 mmol) was added to a stirred solution of 2-phenoxymethyl-6,7-dihydro-5H-pyrazolo[1,5-a]pyrazin-4-one (0.10 g, 0.41 mmol) in toluene (5 mL). The mixture was stirred at 120° C. for 10 hours and then filtered through a pad of diatomaceous earth and washed with MeOH and AcOEt. The solvents were evaporated in vacuo and the crude product purified by RP HPLC on (C18 XBridge 30×100 5 um). Mobile phase (Gradient from 80% 0.1% $NH_4CO_3H/NH_4OH$ pH 9 solution in $H_2O$, 20% ACN to 0% 0.1% $NH_4CO_3H/NH_4OH$ pH 9 solution in $H_2O$, 100% ACN) to yield 2-phenoxymethyl-5H-pyrazolo[1,5-a]pyrazin-4-one (4.71 mg, 4.6% yield) as a solid.

16. 3-cyclohexyloxy-1-(4-fluoro-phenyl)-1H-pyrazin-2-one

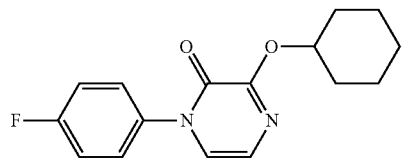 [SMILES: O=c1c(OC2CCCCC2)nccn1-c1ccc(F)cc1]

Copper (I) iodide (0.98 g, 5.1 mmol) was added to a suspension of 3-(cyclohexyloxy)-2(1H)-pyrazinone (1.0 g, 5.1 mmol, prepared according to the method described in the *Journal of Medicinal Chemistry,* 52(7), 2076-2089; 2009), 1-bromo-4-fluorobenzene (0.85 mL, 7.7 mmol), N,N'-dimethylethylenediamine (0.55 mL, 5.1 mmol) and $K_3PO_4$ (2.18 g, 10.3 mmol) in a mixture of DMF (2 mL) and 1,4-dioxane (8 mL). The reaction mixture was stirred at 180° C. for 15 minutes under microwave irradiation. The solid was filtered off and washed with DCM, the filtrate was treated with a 32% solution of $NH_4OH$. The organic layer was separated, dried ($Na_2SO_4$), filtered and the solvent evaporated in vacuo. The crude product was purified by flash column chromatography (silica; AcOEt in DCM 1/99 to 20/80). The desired fractions were collected and the solvents evaporated in vacuo to yield 3-cyclohexyloxy-1-(4-fluoro-phenyl)-1H-pyrazin-2-one (1.13 g, 76% yield).

17. 3-chloro-1-(4-fluoro-phenyl)-1H-pyrazin-2-one

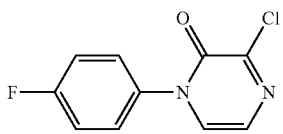 [SMILES: O=c1c(Cl)nccn1-c1ccc(F)cc1]

Phosphorus oxychloride (0.94 mL, 10 mmol) was added to a solution of 3-cyclohexyloxy-1-(4-fluoro-phenyl)-1H-pyrazin-2-one (0.97 g, 3.36 mmol) in DCE (10 mL). The reaction mixture was stirred at 160° C. for 15 minutes under microwave irradiation. The reaction was poured into ice-water, then basified with a saturated solution of Na$_2$CO$_3$ and extracted with DCM. The organic layer was separated, dried (Na$_2$SO$_4$), filtered and the solvents evaporated in vacuo to yield 3-chloro-1-(4-fluoro-phenyl)-1H-pyrazin-2-one (0.71 g, 95% yield) that was used in the next step without further purification.

18. N-[4-(4-fluoro-phenyl)-3-oxo-3,4-dihydro-pyrazin-2-yl]-2-phenoxy-acetamide

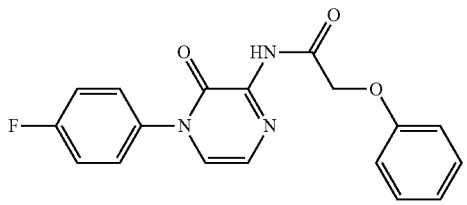 [SMILES: O=C(COc1ccccc1)Nc1nccn(-c2ccc(F)cc2)c1=O]

Palladium (II) acetate (36 mg, 0.16 mmol) was added to a suspension of 3-chloro-1-(4-fluoro-phenyl)-1H-pyrazin-2-one (0.71 g, 3.2 mmol), phenoxyacetamide (0.57 g, 3.8 mmol), 4,5-bis(diphenylphosphino)-9,9-dimethylxanthene (0.138 g, 0.24 mmol) and Cs$_2$CO$_3$ (1.5 g, 4.45 mmol) in 1,4-dioxane (10 mL). The mixture was stirred at 80° C. for 15 minutes. Then DCM was added, the solid was filtered off and washed with more DCM. The filtrate was separated and the solvent evaporated in vacuo and the crude product was purified by flash column chromatography (silica; AcOEt in DCM 1/99 to 1/4). The desired fractions were collected and the solvents evaporated in vacuo to yield N-[4-(4-fluoro-phenyl)-3-oxo-3,4-dihydro-pyrazin-2-yl]-2-phenoxy-acetamide (0.38 g, 84% yield).

19. N-[4-(4-fluoro-phenyl)-3-oxo-3,4-dihydro-pyrazin-2-yl]-N'-hydroxy-2-phenoxy-acetamidine

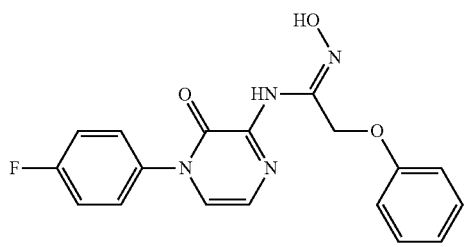 [SMILES: O=c1c(N/C(COc2ccccc2)=N\O)nccn1-c1ccc(F)cc1]

A solution of N-[4-(4-fluoro-phenyl)-3-oxo-3,4-dihydro-pyrazin-2-yl]-2-phenoxy-acetamide (0.51 g, 1.5 mmol) in THF (6 mL) was added to a 60% dispersion of sodium hydride in mineral oils (90 mg, 2.3 mmol) in THF (2 mL) at 0° C. The reaction mixture was stirred at room temperature for 30 minutes. Then diethyl chlorophosphate (0.54 g, 3.7 mmol) was added portionwise at 0° C. and the reaction mixture was stirred for 2 hours at room temperature. Then a 50% solution of hydroxylamine in H$_2$O (5 mL) was added and the reaction stirred at room temperature overnight. Then H$_2$O and a saturated solution of NaHCO$_3$ were added, the organic layer was separated, dried (Na$_2$SO$_4$), filtered and the solvents evaporated in vacuo to yield N-[4-(4-fluoro-phenyl)-3-oxo-3,4-dihydro-pyrazin-2-yl]-N-hydroxy-2-phenoxy-acetamidine (55 mg, 100% yield) that was used in the next step without further purification.

20. 7-(4-fluoro-phenyl)-2-phenoxymethyl-7H-[1,2,4]triazolo[1,5-a]pyrazin-8-one

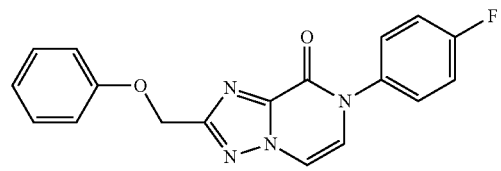 [SMILES: O=c1c2nc(COc3ccccc3)nn2ccn1-c1ccc(F)cc1]

Phosphorus oxychloride (0.28 mL, 3.0 mmol) was added to a solution of N-[4-(4-fluoro-phenyl)-3-oxo-3,4-dihydro-pyrazin-2-yl]-N-hydroxy-2-phenoxy-acetamidine (0.35 g. 1.51 mmol) in THF (8 mL) at 0° C. The reaction was stirred at 100° C. for 5 minutes under microwave irradiation. The reaction mixture was basified with a saturated solution of Na$_2$CO$_3$. The organic layer was separated, dried (Na$_2$SO$_4$), filtered and the solvent evaporated in vacuo. The crude product was purified by flash column chromatography (silica; AcOEt in DCM 1/99 to 10/90). The desired fractions were collected and the solvents evaporated in vacuo and treated with DIPE to yield 7-(4-fluoro-phenyl)-2-phenoxymethyl-7H-[1,2,4]triazolo[1,5-a]pyrazin-8-one (32 mg, 6% yield). $^1$H NMR (500 MHz, DMSO-d$_6$) δ ppm 5.33 (s, 2H), 6.97 (t, J=7.4 Hz, 1H), 7.07 (d, J=7.8 Hz, 2H), 7.26-7.36 (m, 2H), 7.36-7.44 (m, 2H), 7.45 (d, J=6.1 Hz, 1H), 7.50-7.62 (m, 2H), 8.03 (d, J=5.8 Hz, 1H).

21. 7-(4-fluoro-phenyl)-2-phenoxymethyl-6,7-dihydro-5H-[1,2,4]triazolo[1,5-a]pyrazin-8-one

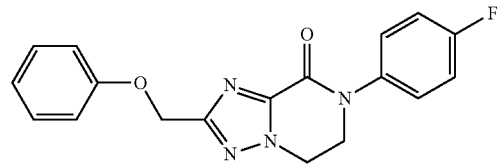 [SMILES: O=C1c2nc(COc3ccccc3)nn2CCN1c1ccc(F)cc1]

A solution of 7-(4-fluoro-phenyl)-2-phenoxymethyl-7H-[1,2,4]triazolo[1,5-a]pyrazin-8-one (26 mg, 0.08 mmol) in a mixture of DCM (1 mL) and MeOH (1 mL) was hydrogenated in a H-Cube reactor (1.0 mL/min, 30 mm Pd/C 10% cartridge, full $H_2$ mode, 100° C., 3 cycles). The solvent was evaporated in vacuo and the residue was purified by RP HPLC, mobile phase (gradient from 80% 0.1% $NH_4CO_3H$ pH=7.8 solution in $H_2O$, 20% MeOH to 0% 0.1% $NH_4CO_3H$ pH=7.8 solution in $H_2O$, 100% MeOH) to yield 7-(4-fluoro-phenyl)-2-phenoxymethyl-6,7-dihydro-5H-[1,2,4]triazolo[1,5-a]pyrazin-8-one (1.7 mg, 6% yield). $^1H$ NMR (400 MHz, $CDCl_3$) δ ppm 4.11-4.24 (m, 2H), 4.44-4.58 (m, 2H), 5.42 (s, 2H), 6.95-7.02 (m, 2H), 7.04 (t, J=7.4 Hz, 1H), 7.13 (t, J=8.6 Hz, 2H), 7.29-7.49 (m, 4H).

22. (rac)-2,4-dioxo-5-phenoxy-hexanoic acid ethyl ester

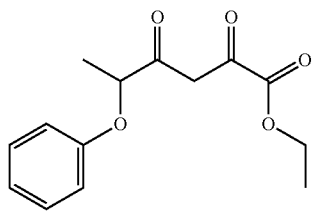 [SMILES: CCOC(=O)C(=O)CC(=O)C(C)Oc1ccccc1]

Sodium (82 mg, 3.55 mmol) was added to EtOH absolute (9.8 mL) at 0° C. The mixture was stirred at 0° C. until the sodium was completely dissolved. Then (rac)-3-phenoxy-butan-2-one (530 mg, 3.23 mmol) was added dropwise. The mixture was stirred at 0° C. for 10 minutes. Then diethyl oxalate (0.44 mL, 3.23 mmol) was added. Then the mixture was stirred at room temperature for 16 hours and the solvent evaporated in vacuo. The residue was diluted with water, the mixture acidified with a 1M solution of HCl and extracted with DCM. The organic layer was separated, dried ($Na_2SO_4$), filtered and the solvents evaporated in vacuo. The crude product was purified by open column chromatography (silica; DCM 100%) to yield (rac)-2,4-dioxo-5-phenoxy-hexanoic acid ethyl ester (566 mg, 58% yield) as an orange oil.

23. (rac)-5-(1-Phenoxy-ethyl)-2H-pyrazole-3-carboxylic acid ethyl ester

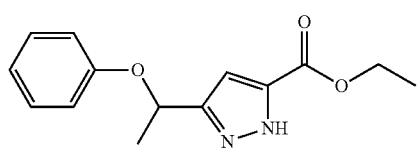 [SMILES: CCOC(=O)c1cc(C(C)Oc2ccccc2)n[nH]1]

Hydrazine hydrate (41.7 µL, 0.4 mmol) was added to a stirred solution of 2,4-dioxo-5-phenoxy-hexanoic acid ethyl ester (566 mg, 2.14 mmol) in EtOH (4.5 mL). The mixture was stirred at 80° C. for 1 hour. Then, the mixture was stirred at room temperature for 16 hours. Hydrazine hydrate (20 µL, 0.2 mmol) was added and the mixture was stirred at 80° C. for 2 hours. More hydrazine hydrate (41.7 µL, 0.4 mmol) was added and the mixture was stirred at 80° C. for 2 hours. The solvent was evaporated in vacuo. The crude product was purified by flash column chromatography (silica, AcOEt in DCM 0/100 to 20/80). The desired fractions were collected and solvents evaporated in vacuo to yield (rac)-5-(1-phenoxy-ethyl)-2H-pyrazole-3-carboxylic acid ethyl ester (467 mg, 78% yield) as a colourless oil.

24. (rac)-2-(1-Phenoxy-ethyl)-6,7-dihydro-5H-pyrazolo[1,5-a]pyrazin-4-one

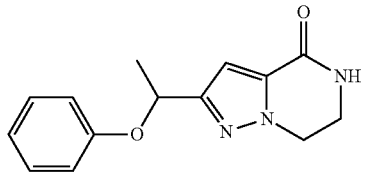 [SMILES: CC(Oc1ccccc1)c1cc2n(n1)CCNC2=O]

The compound was prepared from (rac)-5-(1-phenoxy-ethyl)-2H-pyrazole-3-carboxylic acid ethyl ester and tert-butyl n-(2-hydroxyethyl)carbamate using the methods described in the preceding examples 7 ((rac)-2-(2-tert-butoxycarbonylamino-propyl)-5-phenoxymethyl-2H-pyrazole-3-carboxylic acid ethyl ester) and 6 (2-phenoxymethyl-6,7-dihydro-5H-pyrazolo[1,5-a]pyrazin-4-one).

25. 2-(4-fluoro-phenoxymethyl)-6,7-Dihydro-5H-pyrazolo[1,5-a]pyrazin-4-one

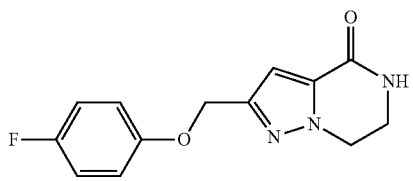 [SMILES: O=C1NCCn2nc(COc3ccc(F)cc3)cc21]

The compound was prepared from 1-(4-fluoro-phenoxy)-propan-2-one and diethyl oxalate using the methods described in the preceding examples 3 (2,4-dioxo-5-phenoxy-pentanoic acid ethyl ester), 4 (5-phenoxymethyl-2H-pyrazole-3-carboxylic acid ethyl ester), 7 ((rac)-2-(2-tert-butoxycarbonylamino-propyl)-5-phenoxymethyl-2H-pyrazole-3-carboxylic acid ethyl ester) and 6 (2-phenoxymethyl-6,7-dihydro-5H-pyrazolo[1,5-a]pyrazin-4-one).

26. 5-Phenoxymethyl-2H-pyrazole-3-carboxylic acid (2,2-dimethoxy-ethyl)-amide

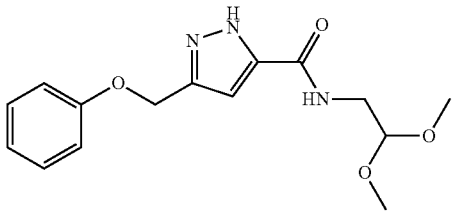 [SMILES: COC(CNC(=O)c1cc(COc2ccccc2)n[nH]1)OC]

Trimethylaluminum (1.7 mL, 3.4 mmol) was added to a stirred solution of aminoacetaldehyde dimethyl acetal (0.37 mL, 3.4 mmol) in THF (2 mL) at 0° C. under nitrogen atmosphere. To this solution 5-phenoxymethyl-2H-pyrazole-3-carboxylic acid ethyl ester (0.7 g, 2.84 mmol) in THF (5 mL)

was added at 0° C. The reaction was heated at 130° C. for 2 minutes under microwave irradiation. Then mixture was quenched with a 2N solution of HCl (pH~3) and diluted with DCM. The organic layer was separated, dried (Na₂SO₄), filtered and the solvent evaporated in vacuo to yield 5-phenoxymethyl-2H-pyrazole-3-carboxylic acid (2,2-dimethoxy-ethyl)-amide (1.25 g, quantitative) as a brown oil that was used in the next step without further purification.

27. (rac)-7-Hydroxy-2-phenoxymethyl-6,7-dihydro-5H-pyrazolo[1,5-a]pyrazin-4-one

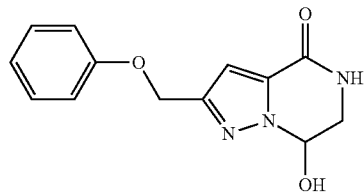 [SMILES: O=C1NCC(O)n2nc(COc3ccccc3)cc21]

A 2M solution of HCl in H₂O was added to a solution of 5-phenoxymethyl-2H-pyrazole-3-carboxylic acid (2,2-dimethoxy-ethyl)-amide (1.25 g, 4.09 mmol) in acetone (7 mL). The mixture was stirred at 100° C. for 5 minutes under microwave irradiation. The solvent was evaporated in vacuo and the residue was supported on silica gel and purified by flash column chromatography (silica; AcOEt in DCM 0/100 to 100/0, then MeOH in AcOEt 0/100 to 10/90). Desired fractions were collected and the solvents evaporated in vacuo. The residue was triturated with diethyl ether to yield (rac)-7-hydroxy-2-phenoxymethyl-6,7-dihydro-5H-pyrazolo[1,5-a]pyrazin-4-one (286 mg, 30% yield) as an off-white solid.

28. (rac)-7-Fluoro-2-phenoxymethyl-6,7-dihydro-5H-pyrazolo[1,5-a]pyrazin-4-one

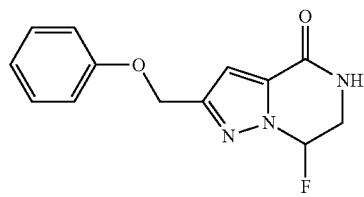 [SMILES: O=C1NCC(F)n2nc(COc3ccccc3)cc21]

DAST (0.035 mL, 0.29 mmol) was added to a solution of (rac)-7-hydroxy-2-phenoxymethyl-6,7-dihydro-5H-pyrazolo[1,5-a]pyrazin-4-one (50 mg, 0.19 mmol) in DCM (0.5 mL) at −10° C. The mixture was stirred at room temperature for 15 minutes. Then quenched with a 1N solution of HCl and extracted with DCM. The organic layer was separated, dried (Na₂SO₄), filtered and the solvent evaporated in vacuo to yield (rac)-7-fluoro-2-phenoxymethyl-6,7-dihydro-5H-pyrazolo[1,5-a]pyrazin-4-one (51 mg, quantitative) as light brown solid that was used without further purification.

29. (R)-4-(5-Ethoxycarbonyl-3-phenoxymethyl-pyrazol-1-ylmethyl)-2,2-dimethyl-oxazolidine-3-carboxylic acid tert-butyl ester

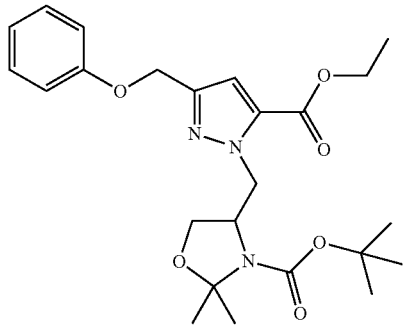 [SMILES: CCOC(=O)c1cc(COc2ccccc2)nn1CC1COC(C)(C)N1C(=O)OC(C)(C)C]

Di-tert-butyl azodicarboxylate (0.56 g, 2.43 mmol) was added portionwise to a mixture of 5-phenoxymethyl-2H-pyrazole-3-carboxylic acid ethyl ester (0.5 g, 2.0 mmol), (R)-1-boc-2,2-dimethyl-4-hydroxymethyl-oxazolidine (0.49 g, 2.1 mmol) and triphenylphosphine (0.64 g, 2.4 mmol) in THF (10 mL) at 0° C. The mixture was stirred at room temperature for 30 minutes. The solvent was evaporated in vacuo and the residue was purified by flash column chromatography (silica; DCM in heptane 50/50 to 100/0). Desired fractions were collected and the solvent evaporated in vacuo to yield (R)-4-(5-ethoxycarbonyl-3-phenoxymethyl-pyrazol-1-ylmethyl)-2,2-dimethyl-oxazolidine-3-carboxylic acid tert-butyl ester (0.91 g, 98% yield) as a clear oil.

30. (S)-4-(5-Ethoxycarbonyl-3-phenoxymethyl-pyrazol-1-ylmethyl)-2,2-dimethyl-oxazolidine-3-carboxylic acid tert-butyl ester

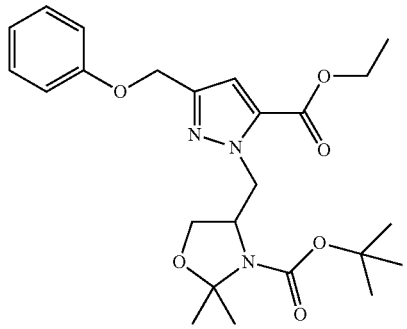 [SMILES: CCOC(=O)c1cc(COc2ccccc2)nn1CC1COC(C)(C)N1C(=O)OC(C)(C)C]

The compound was prepared from 5-phenoxymethyl-2H-pyrazole-3-carboxylic acid ethyl ester and (S)-1-boc-2,2-dimethyl-4-hydroxymethyl-oxazolidine using the method described in the preceding example 29 (R)-4-(5-ethoxycarbonyl-3-phenoxymethyl-pyrazol-1-ylmethyl)-2,2-dimethyl-oxazolidine-3-carboxylic acid tert-butyl ester.

31. (S)-6-Hydroxymethyl-2-phenoxymethyl-6,7-dihydro-5H-pyrazolo[1,5-a]pyrazin-4-one

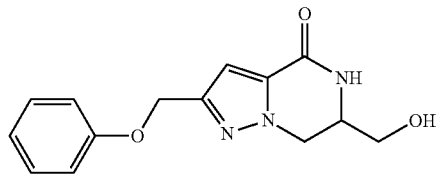 [SMILES: O=C1NC(CO)Cn2nc(COc3ccccc3)cc21]

(S)-4-(5-Ethoxycarbonyl-3-phenoxymethyl-pyrazol-1-ylmethyl)-2,2-dimethyl-oxazolidine-3-carboxylic acid tert-butyl ester (0.91 g, 1.9 mmol) was dissolved in a 4M solution of HCl in dioxane (9.8 mL) and the solution was stirred at room temperature for 1 hour. The solvent was evaporated in vacuo and the residue was taken up in MeOH (10 mL) and $K_2CO_3$ (0.82 g, 5.96 mmol) was added. The mixture was stirred at 100° C. for 5 minutes under microwave irradiation. Then mixture was diluted with DCM. The solid was filtered off and the filtrate solvent was evaporated in vacuo. The residue was purified by flash column chromatography (silica, MeOH in AcOEt 0/100 to 10/90). Desired fractions were collected and the solvents evaporated in vacuo to yield (S)-6-hydroxymethyl-2-phenoxymethyl-6,7-dihydro-5H-pyrazolo[1,5-a]pyrazin-4-one (0.33 g, 61% yield) as an off-white solid. $^1$H NMR (400 MHz, DMSO-$d_6$) δ ppm 3.27-3.33 (m, 1H), 3.46-3.54 (m, 1H), 3.73-3.84 (m, 1H), 4.30 (dd, J=13.4, 5.8 Hz, 1H), 4.38 (dd, J=12.9, 5.3 Hz, 1H), 5.05 (s, 2H), 5.18 (br. s., 1H), 6.77 (s, 1H), 6.91-6.98 (m, 1H), 6.99-7.07 (m, 2H), 7.25-7.35 (m, 2H), 8.26 (d, J=2.5 Hz, 1H).

32. (S)-2-Phenoxymethyl-6-trimethylsilanyloxymethyl-6,7-dihydro-5H-pyrazolo[1,5-a]pyrazin-4-one

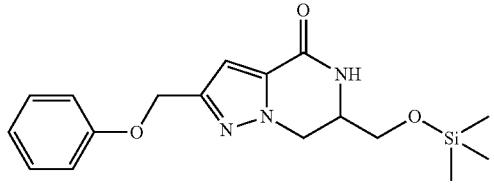 [SMILES: C[Si](C)(C)OCC1Cn2nc(COc3ccccc3)cc2C(=O)N1]

Chlorotrimethylsilane (0.30 mL, 2.41 mmol) was added to a solution of (S)-6-hydroxymethyl-2-phenoxymethyl-6,7-dihydro-5H-pyrazolo[1,5-a]pyrazin-4-one (0.33 g, 2.4 mmol) and TEA (0.33 mL, 2.4 mmol) in ACN (6 mL) at 0° C. The reaction was stirred for 30 minutes at room temperature. Then a 1N solution of HCl was added and the mixture extracted with AcOEt. The organic layer was separated, dried ($Na_2SO_4$), filtered and the solvent evaporated in vacuo to yield (S)-2-phenoxymethyl-6-trimethylsilanyloxymethyl-6,7-dihydro-5H-pyrazolo[1,5-a]pyrazin-4-one (0.375 g, 90% yield) as an off-white solid that was used in the next step without further purification.

33. (R)-2-Phenoxymethyl-6-trimethylsilanyloxymethyl-6,7-dihydro-5H-pyrazolo[1,5-a]pyrazin-4-one

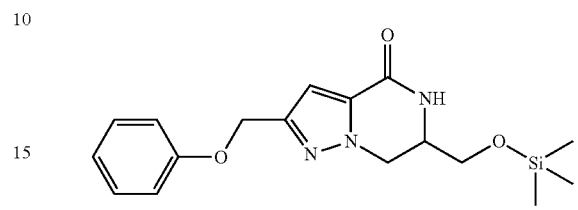

The compound was prepared from (R)-4-(5-ethoxycarbonyl-3-phenoxymethyl-pyrazol-1-ylmethyl)-2,2-dimethyl-oxazolidine-3-carboxylic acid tert-butyl ester using the methods described in the preceding examples 31 ((S)-6-hydroxymethyl-2-phenoxymethyl-6,7-dihydro-5H-pyrazolo[1,5-a]pyrazin-4-one) and 32 ((S)-2-phenoxymethyl-6-trimethylsilanyloxymethyl-6,7-dihydro-5H-pyrazolo[1,5-a]pyrazin-4-one).

34. (S)-5-(4-fluoro-phenyl)-6-hydroxymethyl-2-phenoxymethyl-6,7-dihydro-5H-pyrazolo[1,5-a]pyrazin-4-one

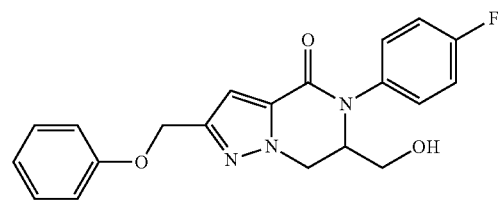 [SMILES: O=C1c2cc(COc3ccccc3)nn2CC(CO)N1c1ccc(F)cc1]

Copper (I) iodide (41 mg, 0.22 mmol) was added to a stirred suspension of 4-bromofluorobenzene (0.24 mL, 2.17 mmol), (S)-2-phenoxymethyl-6-trimethylsilanyloxymethyl-6,7-dihydro-5H-pyrazolo[1,5-a]pyrazin-4-one (0.37 g, 1.08 mmol), $K_2CO_3$ (0.3 g, 2.17 mmol) and N,N'-dimethylethylenediamine (0.070 mL, 0.65 mmol) in toluene (8 mL) in a sealed tube and under nitrogen. The mixture was stirred at 140° C. for 24 hours. The mixture was diluted with AcOEt and washed with a 16% aqueous solution of $NH_4OH$. The organic layer was separated, dried ($MgSO_4$), filtered and the solvents evaporated in vacuo. The residue was dissolved in MeOH (4 mL) and stirred at 100° C. for 10 minutes under microwave irradiation. The solvent was evaporated in vacuo and the residue purified by flash column chromatography (silica; AcOEt in DCM 0/100 to 50/50). Desired fractions were collected and the solvents evaporated in vacuo to yield (S)-5-(4-fluoro-phenyl)-6-hydroxymethyl-2-phenoxymethyl-6,7-dihydro-5H-pyrazolo[1,5-a]pyrazin-4-one (285 mg, 71% yield) as an off-white foam. $^1$H NMR (400 MHz, CDCl$_3$) δ ppm 2.21 (br. s., 1H), 3.57-3.68 (m, 1H), 3.81 (dt, J=10.9, 4.4 Hz, 1H), 4.13-4.20 (m, 1H), 4.61 (dd, J=13.4, 4.9

Hz, 1H), 4.81 (dd, J=13.4, 2.1 Hz, 1H), 5.10 (s, 2H), 6.95-7.03 (m, 4H), 7.09-7.18 (m, 2H), 7.27-7.35 (m, 4H).

35. (S)-5-(4-fluoro-phenyl)-6-methoxymethyl-2-phenoxymethyl-6,7-dihydro-5H-pyrazolo[1,5-a]pyrazin-4-one

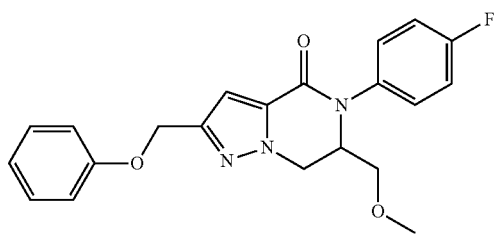 [SMILES: COCC1Cn2nc(COc3ccccc3)cc2C(=O)N1c1ccc(F)cc1]

A solution of (S)-5-(4-fluoro-phenyl)-6-hydroxymethyl-2-phenoxymethyl-6,7-dihydro-5H-pyrazolo[1,5-a]pyrazin-4-one (0.135 g, 0.36 mmol) in THF (0.5 mL) was added to a suspension of a 60% dispersion of sodium hydride in mineral oils (17 mg, 0.44 mmol) in THF (0.5 mL) at 0° C. The mixture was stirred for 10 minutes at 0° C., then iodomethane (0.046 mL, 0.73 mmol) was added. The reaction was heated at 120° C. for 10 minutes under microwave irradiation. Then the mixture was quenched with a saturated solution of NH$_4$Cl and extracted with AcOEt. The organic layer was separated, dried (Na$_2$SO$_4$), filtered and the solvents evaporated in vacuo. The residue was purified by flash column chromatography (silica; AcOEt in DCM 0/100 to 20/80). Desired fractions were collected and the solvents evaporated in vacuo. The residue was triturated with DIPE to yield (S)-5-(4-fluoro-phenyl)-6-methoxymethyl-2-phenoxymethyl-6,7-dihydro-5H-pyrazolo[1,5-a]pyrazin-4-one (90 mg, 64% yield) as an off-white solid. $^1$H NMR (400 MHz, CDCl$_3$) δ ppm 3.26 (s, 3H), 3.36 (t, J=9.2 Hz, 1H), 3.51 (dd, J=9.5, 3.9 Hz, 1H), 4.21 (dtd, J=9.0, 4.5, 4.5, 2.3 Hz, 1H), 4.59 (dd, J=13.3, 4.7 Hz, 1H), 4.74 (dd, J=13.3, 2.2 Hz, 1H), 5.13 (s, 2H), 6.94-7.00 (m, 1H), 7.00-7.04 (m, 3H), 7.10-7.19 (m, 2H), 7.27-7.36 (m, 4H).

36. (S)-6-Fluoromethyl-5-(4-fluoro-phenyl)-2-phenoxymethyl-6,7-dihydro-5H-pyrazolo[1,5-a]pyrazin-4-one

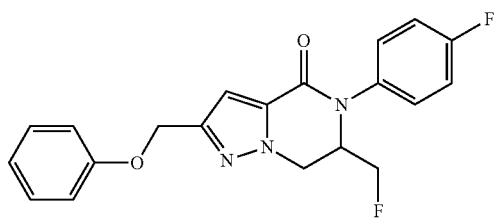 [SMILES: O=C1c2cc(COc3ccccc3)nn2CC(CF)N1c1ccc(F)cc1]

DAST (0.067 mL, 0.55 mmol) was added to a solution of (S)-5-(4-fluoro-phenyl)-6-hydroxymethyl-2-phenoxymethyl-6,7-dihydro-5H-pyrazolo[1,5-a]pyrazin-4-one (135 mg, 0.37 mmol) in DCM (2 mL) at −10° C. The mixture was stirred at room temperature for 15 minutes. Then quenched with a 1N solution of HCl and extracted with AcOEt. The organic layer was separated, dried (Na$_2$SO$_4$), filtered and the solvent evaporated in vacuo. The residue was purified by flash column chromatography (silica; AcOEt in heptane 20/80 to 80/20). Desired fractions were collected and the solvents evaporated in vacuo. The residue was triturated with DIPE to yield (S)-6-fluoromethyl-5-(4-fluoro-phenyl)-2-phenoxymethyl-6,7-dihydro-5H-pyrazolo[1,5-a]pyrazin-4-one (81 mg, 60% yield) as an off-white solid. $^1$H NMR (400 MHz, CDCl$_3$) δ ppm 4.32-4.37 (m, 1H), 4.37-4.42 (m, 0.5H), 4.42-4.52 (m, 1H), 4.59 (dd, J=9.4, 4.5 Hz, 0.5H), 4.66-4.77 (m, 2H), 5.13 (s, 2H), 6.95-7.03 (m, 3H), 7.03 (s, 1H), 7.13-7.20 (m, 2H), 7.27-7.35 (m, 4H).

37. (rac)-5-[2-(tert-butyl-diphenyl-silanyloxy)-propyl]-2-phenoxymethyl-6,7-dihydro-5H-pyrazolo[1,5-a]pyrazin-4-one

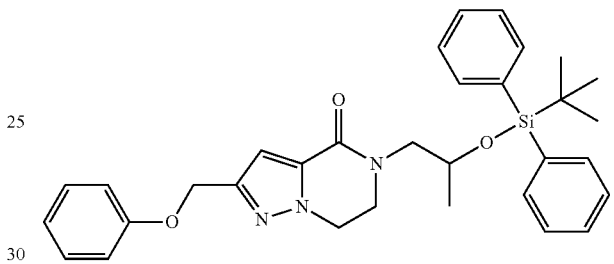

2-Phenoxymethyl-6,7-dihydro-5H-pyrazolo[1,5-a]pyrazin-4-one (60 mg, 0.25 mmol) was added to a suspension of (rac)-(2-bromo-1-methyl-ethoxy)-tert-butyl-diphenyl-silane (0.23 g, 0.62 mmol) and 60% dispersion of sodium hydride in mineral oils (11 mg, 0.29 mmol) in THF (2 mL) at 0° C. The mixture was allowed to reach room temperature and stirred at 150° C. for 15 minutes under microwave irradiation. The mixture was used as such in the next step.

38. (rac)-5-(2-Hydroxy-propyl)-2-phenoxymethyl-6,7-dihydro-5H-pyrazolo[1,5-a]pyrazin-4-one

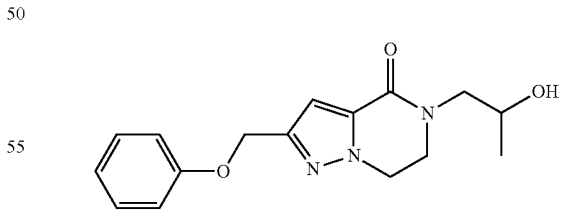

(Rac)-5-[2-(tert-butyl-diphenyl-silanyloxy)-propyl]-2-phenoxymethyl-6,7-dihydro-5H-pyrazolo[1,5-a]pyrazin-4-one (70 mg, 0.13 mmol) was dissolved in a 1M solution of TBAF in THF (0.13 mL, 0.13 mmol). The mixture stirred at room temperature for 16 hours. Then the solvent was evaporated in vacuo to yield a yellow crude that was purified by flash column chromatography (silica; MeOH in DCM from 0/100 to 10/90) to yield (rac)-5-(2-hydroxy-propyl)-2-phenoxymethyl-6,7-dihydro-5H-pyrazolo[1,5-a]pyrazin-4-one (20 mg, 51% yield) as a white solid.

39. (rac)-5-(2-methoxy-propyl)-2-phenoxymethyl-6,7-dihydro-5H-pyrazolo[1,5-a]pyrazin-4-one

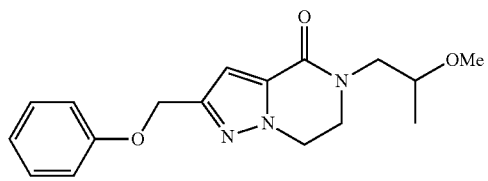 [SMILES: COC(C)CN1CCn2nc(COc3ccccc3)cc2C1=O]

A 60% dispersion of sodium hydride in mineral oils (8.6 mg, 0.21 mmol) was added to a solution of (rac)-5-(2-hydroxy-propyl)-2-phenoxymethyl-6,7-dihydro-5H-pyrazolo[1,5-a]pyrazin-4-one (54 mg, 0.18 mmol) in THF (1 mL) at 0° C. The mixture was stirred at 0° C. for 15 minutes and then iodomethane (0.02 mL, 0.36 mmol) was added and the mixture was allowed to warm to room temperature and stirred for 16 hours. The reaction was quenched with a saturated solution of NH$_4$Cl and extracted with AcOEt, dried with (Na$_2$SO$_4$), filtered and the solvent evaporated in vacuo to yield a yellow oil which was purified by flash column chromatography (silica; AcOEt in heptane from 0:100 to 0:100) to yield a colourless oil which was triturated with DIPE to yield (rac)-5-(2-methoxy-propyl)-2-phenoxymethyl-6,7-dihydro-5H-pyrazolo[1,5-a]pyrazin-4-one (28 mg, 49% yield) as a white solid. $^1$H NMR (500 MHz, CDCl$_3$) δ ppm 1.17 (d, J=6.4 Hz, 3H), 3.27 (dd, J=14.0, 7.9 Hz, 1H), 3.33 (s, 3H), 3.60-3.69 (m, 1H), 3.79-3.85 (m, 1H), 3.85-3.90 (m, 1H), 3.93-4.02 (m, 1H), 4.36 (t, J=6.2 Hz, 2H), 5.09 (s, 2H), 6.93 (s, 1H), 6.96 (t, J=7.4 Hz, 1H), 7.00 (d, J=8.1 Hz, 2H), 7.27-7.32 (m, 2H).

40. (rac)-5-(2-Fluoro-propyl)-2-phenoxymethyl-6,7-dihydro-5H-pyrazolo[1,5-a]pyrazin-4-one

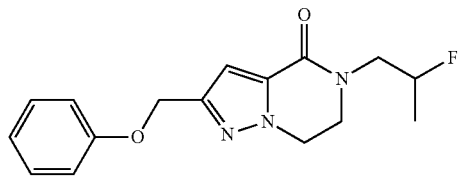 [SMILES: CC(F)CN1CCn2nc(COc3ccccc3)cc2C1=O]

DAST (0.02 mL, 0.15 mmol) was added dropwise to a solution of (rac)-5-(2-hydroxy-propyl)-2-phenoxymethyl-6,7-dihydro-5H-pyrazolo[1,5-a]pyrazin-4-one (30 mg, 0.1 mmol) in DCM (0.6 mL) at 0° C. The mixture was then allowed to warm to room temperature and stirred at 100° C. for 10 minutes under microwave irradiation. The mixture was quenched with a saturated solution of NaHCO$_3$ and extracted with DCM. The organic layer was separated, dried (Na$_2$SO$_4$), filtered and the solvent evaporated in vacuo. The residue was purified by flash column chromatography (silica; AcOEt in heptane 0/100 to 100/0). Desired fractions were collected and solvents evaporated in vacuo. The product was repurified by RP HPLC on (C18 XBridge 30×100 5 um). Mobile phase (Gradient from 80% 0.1% NH$_4$CO$_3$H/NH$_4$OH pH 9 solution in H$_2$O, 20% ACN to 0% 0.1% NH$_4$CO$_3$H/NH$_4$OH pH 9 solution in H$_2$O, 100% ACN) and triturated with DIPE to yield (rac)-5-(2-fluoro-propyl)-2-phenoxymethyl-6,7-dihy-dro-5H-pyrazolo[1,5-a]pyrazin-4-one (8.3 mg, 29% yield) as a white solid. $^1$H NMR (400 MHz, CDCl$_3$) δ ppm 1.38 (dd, J=24.0, 6.5 Hz, 3H), 3.42 (ddd, J=20.1, 14.6, 7.6 Hz, 1H), 3.80-3.91 (m, 1H), 3.91-4.08 (m, 2H), 4.33-4.46 (m, 2H), 4.83-5.05 (m, 1H), 5.10 (s, 2H), 6.90-6.95 (m, 1H), 6.95-7.03 (m, 3H), 7.27-7.33 (m, 2H).

41. 5-(5-Fluoro-4-methoxy-pyrimidin-2-yl)-2-phenoxymethyl-6,7-dihydro-5H-pyrazolo[1,5-a]pyrazin-4-one

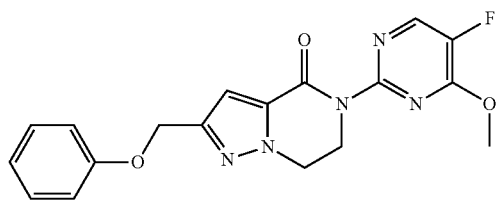 [SMILES: COc1nc(N2CCn3nc(COc4ccccc4)cc3C2=O)ncc1F]

Palladium (II) acetate (2.79 mg, 0.012 mmol) was added to a stirred suspension of 2-phenoxymethyl-6,7-dihydro-5H-pyrazolo[1,5-a]pyrazin-4-one (100 mg, 0.41 mmol), cesium carbonate (0.18 g, 0.57 mmol), 2-dicyclohexylphosphino-2',4',6'-triisopropylbiphenyl (17 mg, 0.037 mmol) and 2-chloro-5-fluoro-4-methoxypyrimidine (0.2 g, 1.23 mmol) in a sealed tube and under nitrogen. The reaction mixture was stirred at 120° C. for 16 hours. The solvent was evaporated in vacuo and the crude product was purified by flash column chromatography (silica; AcOEt in DCM 0/100 to 100/0). The desired fractions were collected and the solvents evaporated in vacuo to yield 5-(5-fluoro-4-methoxy-pyrimidin-2-yl)-2-phenoxymethyl-6,7-dihydro-5H-pyrazolo[1,5-a]pyrazin-4-one (50 mg, 33% yield) as a white solid. $^1$H NMR (500 MHz, CDCl$_3$) δ ppm 4.10 (s, 3H), 4.41-4.57 (m, 4H), 5.12 (s, 2H), 6.93-7.04 (m, 3H), 7.09 (s, 1H), 7.27-7.34 (m, 2H), 8.28 (d, J=2.3 Hz, 1H).

42. 5-methyl-2-phenoxymethyl-6,7-dihydro-5H-pyrazolo[1,5-a]pyrazin-4-one

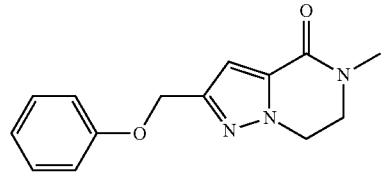 [SMILES: CN1CCn2nc(COc3ccccc3)cc2C1=O]

A 60% dispersion of sodium hydride in mineral oils (9 mg, 0.22 mmol) was added to a stirred solution of 2-phenoxymethyl-6,7-dihydro-5H-pyrazolo[1,5-a]pyrazin-4-one (0.05 g, 0.20 mmol) in DMF (3 mL) at 0° C. The mixture was stirred at 0° C. for 15 minutes. Then iodomethane (15 μL, 0.24 mmol) was added at 0° C., the mixture stirred at 0° C. for 1 hour and allowed to warm to room temperature. Then additional iodomethane (15 μL, 0.24 mmol) was added and the mixture was stirred at room temperature overnight. The mixture was treated with a saturated solution of NH$_4$Cl and the solvents evaporated in vacuo. The crude product was diluted with H$_2$O and extracted with DCM. The organic layer was separated, dried (Na$_2$SO$_4$), filtered and the solvents evaporated in vacuo. The crude product was purified by flash column chromatography (silica; AcOEt in DCM 0/100 to 40/60).

The desired fractions were collected and the solvents evaporated in vacuo to yield 5-methyl-2-phenoxymethyl-6,7-dihydro-5H-pyrazolo[1,5-a]pyrazin-4-one (49 mg, 97% yield) as an oil which solidified upon standing. $^1$H NMR (500 MHz, CDCl$_3$) δ ppm 3.14 (s, 3H), 3.69-3.83 (m, 2H), 4.32-4.49 (m, 2H), 5.09 (s, 2H), 6.93 (s, 1H), 6.96 (t, J=7.2 Hz, 1H), 6.99 (d, J=8.1 Hz, 2H), 7.27-7.32 (m, 2H).

43. 5-(2,4-difluoro-phenyl)-2-phenoxymethyl-6,7-dihydro-5H-pyrazolo[1,5-a]pyrazin-4-one

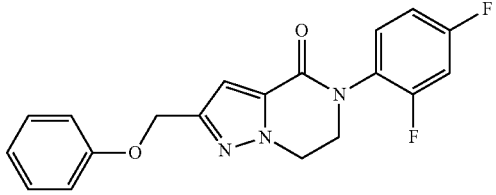 [SMILES: O=C1c2cc(COc3ccccc3)nn2CCN1c1ccc(F)cc1F]

Copper (I) iodide (6.6 mg, 0.033 mmol) was added to a suspension of 2-phenoxymethyl-6,7-dihydro-5H-pyrazolo[1,5-a]pyrazin-4-one (40 mg, 0.16 mmol), 1-bromo-2,4-difluorobenzene (63 mg, 0.033 mmol), N,N'-dimethylethylenediamine (0.01 mL, 0.09 mmol) and K$_2$CO$_3$ (45 mg, 0.033 mmol) in toluene (2 mL). The reaction mixture was stirred at 120° C. for 16 hours. The mixture was filtered through a pad of diatomaceous earth which was washed with AcOEt. The filtrate was evaporated in vacuo. The crude product was purified by flash column chromatography (silica; AcOEt in DCM 0/100 to 20/80). The desired fractions were collected and the solvents evaporated in vacuo to yield 5-(2,4-difluoro-phenyl)-2-phenoxymethyl-6,7-dihydro-5H-pyrazolo[1,5-a]pyrazin-4-one (52 mg, 92% yield) as a white solid. $^1$H NMR (500 MHz, CDCl$_3$) δ ppm 4.02-4.15 (m, 2H), 4.50-4.62 (m, 2H), 5.13 (s, 2H), 6.91-6.99 (m, 3H), 7.01 (d, J=8.4 Hz, 2H), 7.04 (s, 1H), 7.27-7.32 (m, 2H), 7.35 (td, J=8.7, 6.1 Hz, 1H).

44. 5-(6-Bromo-pyridin-2-yl)-2-phenoxymethyl-6,7-dihydro-5H-pyrazolo[1,5-a]pyrazin-4-one

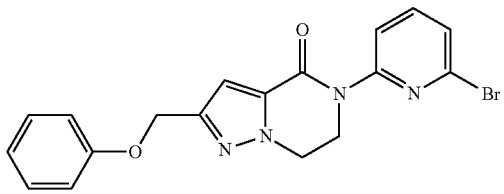 [SMILES: O=C1c2cc(COc3ccccc3)nn2CCN1c1cccc(Br)n1]

The compound was prepared from 2-phenoxymethyl-6,7-dihydro-5H-pyrazolo[1,5-a]pyrazin-4-one and 2,6-dibromopyridine using the method described in the preceding example 43 (5-(2,4-difluoro-phenyl)-2-phenoxymethyl-6,7-dihydro-5H-pyrazolo[1,5-a]pyrazin-4-one). $^1$H NMR (500 MHz, CDCl$_3$) δ ppm 4.48-4.55 (m, 2H), 4.58-4.63 (m, 2H), 5.13 (s, 2H), 6.98 (t, J=7.4 Hz, 1H), 7.01 (d, J=7.8 Hz, 2H), 7.08 (s, 1H), 7.28-7.34 (m, 3H), 7.60 (t, J=7.9 Hz, 1H), 8.09 (d, J=8.1 Hz, 1H).

45. 5-(6-Cyclopropyl-pyridin-2-yl)-2-phenoxymethyl-6,7-dihydro-5H-pyrazolo[1,5-a]pyrazin-4-one

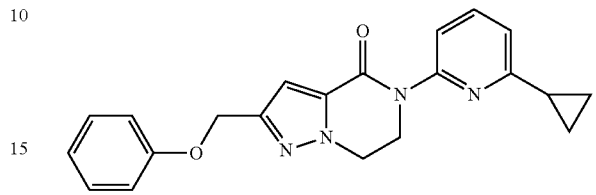

Tetrakis(triphenylphosphine)palladium (0) (7 mg, 0.006 mmol), was added to a stirred suspension of 5-(6-bromo-pyridin-2-yl)-2-phenoxymethyl-6,7-dihydro-5H-pyrazolo[1,5-a]pyrazin-4-one (50 mg, 0.12 mmol), potassium carbonate (52 mg, 0.37 mmol), cyclopropylboronic acid (21.5 mg, 0.25 mmol) in a mixture of DMF (0.5 mL) and 1,4-dioxane (0.5 mL) in a sealed tube and under nitrogen. The mixture was stirred at 150° C. for 15 minutes under microwave irradiation. The mixture was diluted with water and extracted with AcOEt. The organic layer was washed with brine, dried (MgSO$_4$), filtered and the solvents evaporated in vacuo. The crude product was purified by flash column chromatography (silica; AcOEt in DCM 0/100 to 20/80). The desired fractions were collected and the solvents evaporated in vacuo. The product was triturated with heptane to yield 5-(6-cyclopropyl-pyridin-2-yl)-2-phenoxymethyl-6,7-dihydro-5H-pyrazolo[1,5-a]pyrazin-4-one (28 mg, 62% yield) as a white solid. $^1$H NMR (500 MHz, CDCl$_3$) δ ppm 0.93-1.03 (m, 4H), 1.97-2.06 (m, 1H), 4.44-4.58 (m, 4H), 5.12 (s, 2H), 6.93-7.04 (m, 4H), 7.05 (s, 1H), 7.27-7.34 (m, 2H), 7.58 (t, J=7.8 Hz, 1H), 7.74-7.80 (m, 1H).

46. 5-Cyclopropyl-2-phenoxymethyl-6,7-dihydro-5H-pyrazolo[1,5-a]pyrazin-4-one

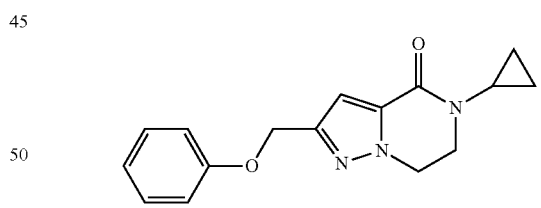

Copper(II) acetate monohydrate (83 mg, 041 mmol) was added to a mixture of 2-phenoxymethyl-6,7-dihydro-5H-pyrazolo[1,5-a]pyrazin-4-one (0.1 g, 0.41 mmol), cyclopropylboronic acid (35 mg, 0.41 mmol) and DMAP (75 mg, 0.617 mmol) in toluene (1 mL). The mixture was stirred at 95° C. for 16 hours. The mixture was stirred at 95° C. for 24 hours more. The reaction was allowed to room temperature and was poured into a 1N solution of HCl and extracted with AcOEt. The organic layer was separated, dried (Na$_2$SO$_4$), filtered and concentrated in vacuo. The crude product was purified by flash column chromatography (silica; AcOEt in DCM 0/100 to 50/50). The desired fractions were collected and the solvents evaporated in vacuo. The desired product was triturated with diethyl ether to yield 5-cyclopropyl-2-phenoxymethyl- 6,7-dihydro-5H-pyrazolo[1,5-a]pyrazin-4-one (19 mg, 16% yield) as a white solid. ¹H NMR (500 MHz, CDCl₃) δ ppm 0.68-0.79 (m, 2H), 0.89-1.00 (m, 2H), 2.74-2.82 (m, 1H), 3.74-3.82 (m, 2H), 4.30-4.37 (m, 2H), 5.08 (s, 2H), 6.93 (s, 1H), 6.94-6.97 (m, 1H), 6.98-7.02 (m, 2H), 7.26-7.31 (m, 2H).

47. 1-(3-tert-butoxycarbonylaminoethyl)-1H-pyrazole-3,5-dicarboxylic acid diethyl ester

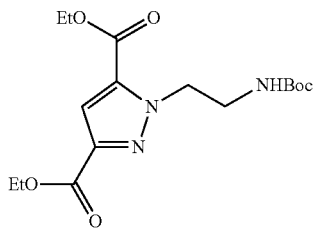 [SMILES: CCOC(=O)c1cc(C(=O)OCC)n(CCNC(=O)OC(C)(C)C)n1]

The compound was prepared from 2-(2-tert-butoxycarbonylamino)ethylbromide and diethyl 3,5-pyrazoledicarboxylate using the methods describe in the preceding example 5 (2-(2-tert-butoxycarbonylamino-ethyl)-5-phenoxymethyl-2H-pyrazole-3-carboxylic acid ethyl ester).

48. 4,5,6,7-tetrahydro-4-oxo-pyrazolo[1,5-a]pyrazine-2-carboxylic acid ethyl ester

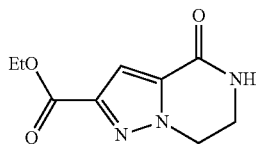 [SMILES: CCOC(=O)c1cc2n(n1)CCNC2=O]

1-(3-tert-Butoxycarbonylaminoethyl)-1H-pyrazole-3,5-dicarboxylic acid diethyl ester (2.4 g, 6.7 mmol) was dissolved in a 4M solution of HCl in dioxane (25 mL) under N₂. The mixture was stirred at room temperature for 1 hour and then basified with a saturated solution of Na₂CO₃ and extracted with DCM. The organic layer was separated, washed with brine, dried (Na₂SO₄), filtered and the solvent evaporated in vacuo. The crude product was purified by flash column chromatography (silica; 7 M solution of ammonia in MeOH in DCM 0/100 to 5/95). The desired fractions were collected and the solvents evaporated in vacuo to yield 4,5,6,7-tetrahydro-4-oxo-pyrazolo[1,5-a]pyrazine-2-carboxylic acid ethyl ester (1.1 g, 79% yield) as a white solid.

49. 5-Cyclopropylmethyl-4-oxo-4,5,6,7-tetrahydro-pyrazolo[1,5-a]pyrazine-2-carboxylic acid ethyl ester

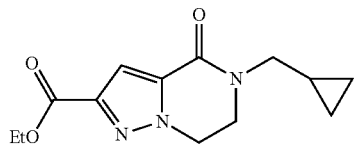 [SMILES: CCOC(=O)c1cc2n(n1)CCN(CC1CC1)C2=O]

A 60% dispersion of sodium hydride in mineral oils (0.11 g, 2.74 mmol) was added to a stirred solution of 4,5,6,7-tetrahydro-4-oxo-pyrazolo[1,5-a]pyrazine-2-carboxylic acid ethyl ester (0.48 g, 2.28 mmol) in DMF (11.4 mL) at 0° C. The mixture was stirred at room temperature for 15 minutes and then bromomethylcyclopropane (0.26 mL, 2.74 mmol) was added. The mixture was stirred at room temperature for 16 hours, diluted with water and extracted with AcOEt. The organic layer was separated, washed with brine, dried (NaSO₄), filtered and the solvents evaporated in vacuo. The crude product was purified by flash column chromatography (silica; AcOEt in DCM 0/100 to 40/60). The desired fractions were collected and the solvents evaporated in vacuo to yield 5-cyclopropylmethyl-4-oxo-4,5,6,7-tetrahydro-pyrazolo[1,5-a]pyrazine-2-carboxylic acid ethyl ester (0.32 g, 54% yield) as a white solid.

50. 5-Cyclopropylmethyl-2-hydroxymethyl-6,7-dihydro-5H-pyrazolo[1,5-a]pyrazin-4-one

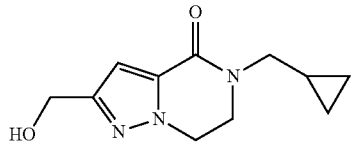 [SMILES: O=C1c2cc(CO)nn2CCN1CC1CC1]

Sodium borohydride (0.23 mL, 6.1 mmol) was added dropwise to a stirred solution of 5-cyclopropylmethyl-4-oxo-4,5,6,7-tetrahydro-pyrazolo[1,5-a]pyrazine-2-carboxylic acid ethyl ester (0.32 g, 1.2 mmol) in a mixture of THF (4 mL) and MeOH (1 mL) under N₂ at 0° C. The reaction mixture was stirred at 80° C. for 30 minutes and then diluted with water and extracted with DCM. The aqueous layer was acidified with a 1N solution of HCl and extracted with DCM. The organic layers were combined, dried (NaSO₄), filtered and the solvents evaporated in vacuo. The crude product was purified by flash column chromatography (silica; 7 M solution of ammonia in methanol in DCM 0/100 to 10/90). The desired fractions were collected and the solvents evaporated in vacuo to yield 5-cyclopropylmethyl-2-hydroxymethyl-6,7-dihydro-5H-pyrazolo[1,5-a]pyrazin-4-one (0.21 g, 78% yield) as a colorless oil.

51. 5-(4-Fluorophenyl)-4-oxo-4,5,6,7-tetrahydro-pyrazolo[1,5-a]pyrazine-2-carboxylic acid ethyl ester

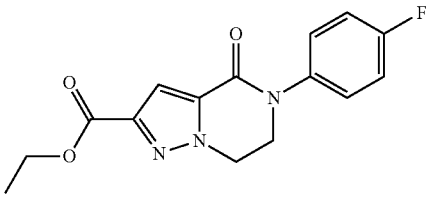 [SMILES: CCOC(=O)c1cc2n(n1)CCN(c1ccc(F)cc1)C2=O]

Copper (I) iodide (0.18 g, 0.95 mmol) was added to a suspension of 4,5,6,7-tetrahydro-4-oxo-pyrazolo[1,5-a]pyrazine-2-carboxylic acid ethyl ester (1.0 g, 4.78 mmol), 1-bromo-4-fluorobenzene (1.0 mL, 9.56 mmol), N,N'-dimethylethylenediamine (0.30 mL, 2.86 mmol) and K₂CO₃ (1.3 g, 9.56 mmol) in toluene (20 mL). The reaction mixture was stirred at 130° C. for 16 hours. The mixture was filtered through a pad of diatomaceous earth which was washed with AcOEt. The mixture was diluted with AcOEt and washed with a 16% aqueous solution of NH$_4$OH. The organic layer was separated, dried (Na$_2$SO$_4$), filtered and the solvents evaporated in vacuo. The crude product was purified by flash column chromatography (silica; AcOEt in DCM 0/100 to 30/70). The desired fractions were collected and the solvents evaporated in vacuo to yield 5-(4-fluorophenyl)-4-oxo-4,5,6,7-tetrahydro-pyrazolo[1,5-a]pyrazine-2-carboxylic acid ethyl ester (1.3 g, 90% yield) as a white solid.

52. 5-(4-Fluoro-phenyl)-2-hydroxymethyl-6,7-dihydro-5H-pyrazolo[1,5-a]pyrazin-4-one

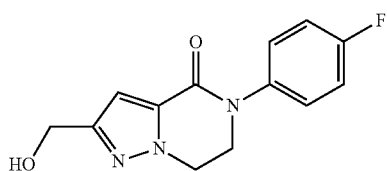 [SMILES: O=C1c2cc(CO)nn2CCN1c1ccc(F)cc1]

The compound was prepared from 5-(4-fluorophenyl)-4-oxo-4,5,6,7-tetrahydro-pyrazolo[1,5-a]pyrazine-2-carboxylic acid ethyl ester using the method described in the preceding example 50 (5-cyclopropylmethyl-2-hydroxymethyl-6,7-dihydro-5H-pyrazolo[1,5-a]pyrazin-4-one.

53. 5-(4-Fluoro-phenyl)-2-(pyridin-2-yloxymethyl)-6,7-dihydro-5H-pyrazolo[1,5-a]pyrazin-4-one

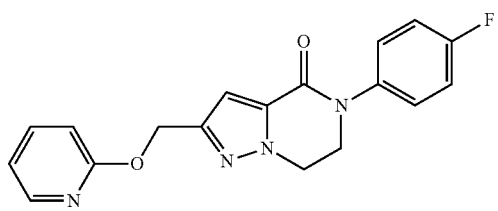 [SMILES: O=C1c2cc(COc3ccccn3)nn2CCN1c1ccc(F)cc1]

Palladium (II) acetate (9 mg, 0.038 mmol) was added to a stirred suspension of 5-(4-fluoro-phenyl)-2-hydroxymethyl-6,7-dihydro-5H-pyrazolo[1,5-a]pyrazin-4-one (0.74 g, 2.83 mmol), 2-chloropyridine (0.4 mL, 4.25 mmol), cesium carbonate (1.84 g, 5.66 mmol) and (2-biphenylyl)di-tert-butylphosphine (0.17 g, 5.66 mmol) in toluene (15 mL) in a sealed tube and under nitrogen. The mixture was stirred at 120° C. for 16 hours, then filtered through a pad of diatomaceous earth and washed with AcOEt. The solvents were evaporated in vacuo and the crude product was purified by flash column chromatography (silica; AcOEt in DCM 0/100 to 100/0). The desired fractions were collected, the solvents evaporated in vacuo and triturated with DIPE to yield 5-(4-fluorophenyl)-2-(pyridin-2-yloxymethyl)-6,7-dihydro-5H-pyrazolo[1,5-a]pyrazin-4-one (620 g, 65% yield) as a white solid. $^1$H NMR (400 MHz, CDCl$_3$) δ ppm 4.12-4.20 (m, 2H), 4.54 (dd, J=6.9, 5.1 Hz, 2H), 5.44 (s, 2H), 6.81 (d, J=8.6 Hz, 1H), 6.90 (ddd, J=7.1, 5.2, 0.7 Hz, 1H), 7.03 (s, 1H), 7.08-7.17 (m, 2H), 7.28-7.35 (m, 2H), 7.55-7.63 (m, 1H), 8.19 (dd, J=5.0, 1.3 Hz, 1H).

54. 5-(4-Fluoro-phenyl)-2-(pyridin-3-yloxymethyl)-6,7-dihydro-5H-pyrazolo[1,5-a]pyrazin-4-one

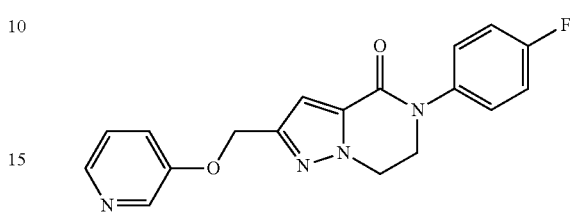

Copper (I) iodide (7.3 mg, 0.038 mmol) was added to a stirred suspension of 5-(4-fluoro-phenyl)-2-hydroxymethyl-6,7-dihydro-5H-pyrazolo[1,5-a]pyrazin-4-one (50 mg, 0.19 mmol), 3-bromopyridine (0.073 mL, 0.76 mmol), cesium carbonate (0.25 g, 0.77 mmol) and N,N-dimethylglycine (7.89 mg, 0.077 mmol) in 1,4-dioxane (1 mL) in a sealed tube and under nitrogen. The mixture was stirred at 100° C. for 16 hours. More copper (I) iodide (7.3 mg, 0.038 mmol) was added, N,N-dimethylglycine (7.89 mg, 0.077 mmol), cesium carbonate (0.25 g, 0.77 mmol) 3-bromopyridine (0.073 mL, 0.76 mmol) were added and the mixture was stirred at 130° C. for another 24 hours. The mixture was diluted with AcOEt and washed with a 16% aqueous solution of NH$_4$OH. The organic layer was separated, dried (MgSO$_4$), filtered and the solvents evaporated in vacuo. The crude product was purified by flash column chromatography (silica; 7 M solution of ammonia in MeOH in DCM 0/100 to 5/95). The desired fractions were collected and the solvents evaporated in vacuo to yield 5-(4-fluorophenyl)-2-(pyridin-3-yloxymethyl)-6,7-dihydro-5H-pyrazolo[1,5-a]pyrazin-4-one (7 mg, 11% yield) as a yellow solid. $^1$H NMR (500 MHz, CDCl$_3$) δ ppm 4.13-4.22 (m, 2H), 4.55 (dd, J=6.8, 5.3 Hz, 2H), 5.17 (s, 2H), 7.03 (s, 1H), 7.10-7.18 (m, 2H), 7.23 (dd, J=8.5, 4.8 Hz, 1H), 7.28-7.36 (m, 3H), 8.25 (dd, J=4.6, 1.2 Hz, 1H), 8.41 (d, J=2.9 Hz, 1H).

55. 5-(4-Fluoro-phenyl)-2-(p-tolyloxymethyl)-6,7-dihydro-5H-pyrazolo[1,5-a]pyrazin-4-one

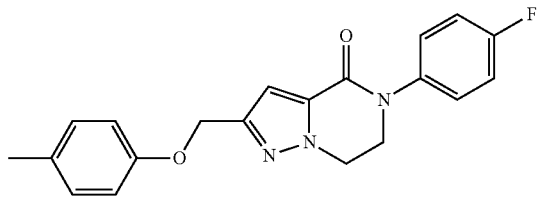 [SMILES: Cc1ccc(OCc2cc3n(n2)CCN(c2ccc(F)cc2)C3=O)cc1]

Di-tert-butyl azodicarboxylate (0.027 g, 1.2 mmol) was added portionwise to a stirred solution of 5-(4-fluoro-phenyl)-2-hydroxymethyl-6,7-dihydro-5H-pyrazolo[1,5-a]pyrazin-4-one (104 mg, 0.4 mmol), p-cresol (0.13 mL, 1.2 mmol) and triphenylphosphine (0.31 g, 1.2 mmol) in THF (2 mL) at 0° C. The mixture was stirred at room temperature for 16 hours. More di-tert-butyl azodicarboxylate (0.027 g, 1.2 mmol), p-cresol (0.13 mL, 1.2 mmol) and triphenylphosphine (0.31 g, 1.2 mmol) were added at 0° C. and the mixture was stirred at 130° C. for 20 minutes. The mixture was diluted with AcOEt and washed with a 10% solution of NaOH. The organic layer was separated, dried (Na₂SO₄), filtered and the solvent was evaporated in vacuo. The crude product was purified by open column chromatography (silica; AcOEt in DCM 0/100 to 20/80). The desired fractions were collected and the solvents evaporated in vacuo. The crude product was dissolved in a mixture of TFA (2.5 mL) and DCM (2.5 mL) and stirred at room temperature for 2 days. The mixture was basified with a saturated solution of Na₂CO₃ and extracted with DCM. The organic layer was separated, dried (MgSO₄), filtered and the solvents evaporated in vacuo. The crude product was purified by flash column chromatography (silica; AcOEt in DCM 0/100 to 100/0). The desired fractions were collected and the solvents evaporated in vacuo. The product was triturated with DIPE to yield 5-(4-fluorophenyl)-2-(p-tolyloxymethyl)-6,7-dihydro-5H-pyrazolo[1,5-a]pyrazin-4-one (54 mg, 38% yield) as a yellow solid. ¹H NMR (500 MHz, CDCl₃) δ ppm 2.29 (s, 3H), 4.16 (dd, J=6.8, 5.3 Hz, 2H), 4.53 (dd, J=6.9, 5.2 Hz, 2H), 5.09 (s, 2H), 6.90 (d, J=8.7 Hz, 2H), 7.01 (s, 1H), 7.09 (d, J=8.4 Hz, 2H), 7.13 (t, J=8.7 Hz, 2H), 7.28-7.35 (m, 2H).

56. 2-Hydroxymethyl-5-(4-methoxy-benzyl)-6,7-dihydro-5H-pyrazolo[1,5-a]pyrazin-4-one

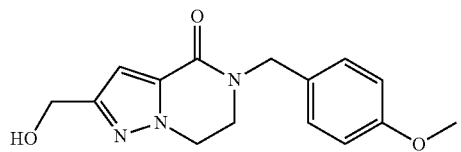 [SMILES: COc1ccc(CN2CCn3nc(CO)cc3C2=O)cc1]

The compound was prepared from 1-(3-tert-butoxycarbonylaminoethyl)-1H-pyrazole-3,5-dicarboxylic acid diethyl ester and 4-methoxybenzyl chloride using the methods described in the preceding examples 49 (5-cyclopropylmethyl-4-oxo-4,5,6,7-tetrahydro-pyrazolo[1,5-a]pyrazine-2-carboxylic acid ethyl ester) and 50 (5-cyclopropylmethyl-2-hydroxymethyl-6,7-dihydro-5H-pyrazolo[1,5-a]pyrazin-4-one).

57. Acetic acid 5-(4-methoxy-benzyl)-4-oxo-4,5,6,7-tetrahydro-pyrazolo[1,5-a]pyrazin-2-ylmethyl ester

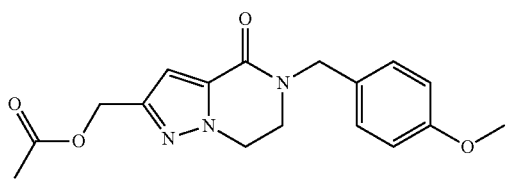 [SMILES: COc1ccc(CN2CCn3nc(COC(C)=O)cc3C2=O)cc1]

Acetyl chloride (0.043 mL, 0.055 mmol) was added to a stirred solution of 5-(4-methoxy-benzyl)-4-oxo-4,5,6,7-tetrahydro-pyrazolo[1,5-a]pyrazine-2-carboxylic acid ethyl ester (3.8 g, 11.5 mmol), TEA (0.1 mL, 0.75 mmol) and DMAP (6.1 mL, 0.05 mmol)) in DCM (2.5 mL) at 0° C. The mixture was stirred at room temperature for 2 hours. Then more acetyl chloride (0.01 mL, 0.01 mmol) was added and the mixture was stirred at room temperature for 2 hours more. The mixture was treated with a saturated solution of Na₂CO₃ and extracted with DCM. The organic layer was separated, dried (MgSO₄), filtered and the solvents evaporated in vacuo to yield acetic acid 5-(4-methoxy-benzyl)-4-oxo-4,5,6,7-tetrahydro-pyrazolo[1,5-a]pyrazin-2-ylmethyl ester (142 mg, 86% yield) as a colourless oil that was used in the next step without further purification.

58. Acetic acid 4-oxo-4,5,6,7-tetrahydro-pyrazolo[1,5-a]pyrazin-2-ylmethyl ester

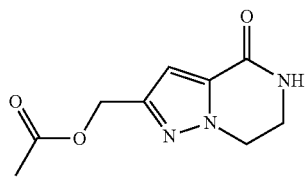

A solution of ammonium cerium (IV) nitrate (0.7 g, 1.29 mmol) in water (1.1 mL) was added to a stirred solution of acetic acid 5-(4-methoxy-benzyl)-4-oxo-4,5,6,7-tetrahydro-pyrazolo[1,5-a]pyrazin-2-ylmethyl ester (142 mg, 0.43 mmol) in ACN (4.3 mL). The mixture was stirred at room temperature for 30 minutes and the solvents evaporated in vacuo. The crude product was purified by flash column chromatography (silica, 7 N solution of ammonia in MeOH in DCM 0/100 to 10/90). The desired fractions were collected and concentrated in vacuo to yield acetic acid 4-oxo-4,5,6,7-tetrahydro-pyrazolo[1,5-a]pyrazin-2-ylmethyl ester (56 mg, 62% yield) as a white solid.

59. Acetic acid 5-(5-fluoro-pyridin-2-yl)-4-oxo-4,5,6,7-tetrahydro-pyrazolo[1,5-a]pyrazin-2-ylmethyl ester

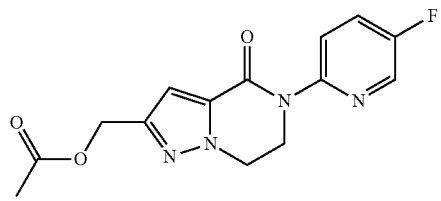 [SMILES: CC(=O)OCc1cc2n(n1)CCN(c1ccc(F)cn1)C2=O]

The compound was prepared from acetic acid 4-oxo-4,5,6,7-tetrahydro-pyrazolo[1,5-a]pyrazin-2-ylmethyl ester and 2-bromo-5-fluoropyridine using the method described in the preceding example 43 (5-(2,4-difluoro-phenyl)-2-phenoxymethyl-6,7-dihydro-5H-pyrazolo[1,5-a]pyrazin-4-one).

60. 5-(5-fluoro-pyridin-2-yl)-2-hydroxymethyl-6,7-dihydro-5H-pyrazolo[1,5-a]pyrazin-4-one

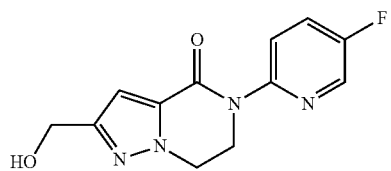 [SMILES: O=C1c2cc(CO)nn2CCN1c1ccc(F)cn1]

Potassium carbonate (63 mg, 0.46 mmol) was added to a stirred suspension of acetic acid 5-(5-fluoro-pyridin-2-yl)-4-oxo-4,5,6,7-tetrahydro-pyrazolo[1,5-a]pyrazin-2-ylmethyl ester (70 mg, 0.23 mmol) in MeOH (1 mL). The mixture was stirred at room temperature for 16 hours. The solvent was evaporated in vacuo. The crude product was purified by flash column chromatography (silica, 7 N solution of ammonia in MeOH in DCM 0/100 to 10/90). The desired fractions were collected and the solvents evaporated in vacuo to yield 5-(5-fluoro-pyridin-2-yl)-2-hydroxymethyl-6,7-dihydro-5H-pyrazolo[1,5-a]pyrazin-4-one (30 mg, 50% yield) as a white solid.

61. 5-(4-Methoxy-benzyl)-2-(pyridin-2-yloxymethyl)-6,7-dihydro-5H-pyrazolo[1,5-a]pyrazin-4-one

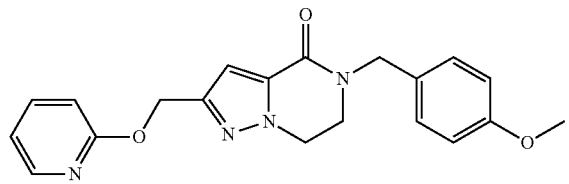 [SMILES: COc1ccc(CN2CCn3nc(COc4ccccn4)cc3C2=O)cc1]

The compound was prepared from 2-hydroxymethyl-5-(4-methoxy-benzyl)-6,7-dihydro-5H-pyrazolo[1,5-a]pyrazin-4-one and 2-chloropyridine using the method described in the preceding example 53 (5-(4-fluoro-phenyl)-2-(pyridin-2-yloxymethyl)-6,7-dihydro-5H-pyrazolo[1,5-a]pyrazin-4-one).

62. 2-(Pyridin-2-yloxymethyl)-6,7-dihydro-5H-pyrazolo[1,5-a]pyrazin-4-one

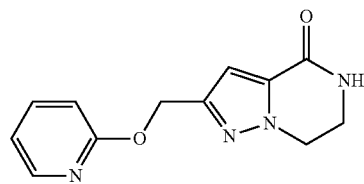 [SMILES: O=C1NCCn2nc(COc3ccccn3)cc21]

The compound was prepared from 5-(4-methoxy-benzyl)-2-(pyridin-2-yloxymethyl)-6,7-dihydro-5H-pyrazolo[1,5-a]pyrazin-4-one using the method described in the preceding example 58 (acetic acid 4-oxo-4,5,6,7-tetrahydro-pyrazolo[1,5-a]pyrazin-2-ylmethyl ester).

63. 2-(2-Bromoethyl)-5-phenoxymethyl-2H-pyrazole-3-carboxylic acid ethyl ester

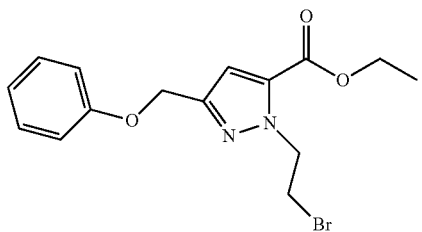 [SMILES: CCOC(=O)c1cc(COc2ccccc2)nn1CCBr]

Di-tert-butyl azodicarboxylate (1.68 g, 7.30 mmol) was added portionwise to a stirred solution of 5-phenoxymethyl-2H-pyrazole-3-carboxylic acid ethyl ester (1.0 g, 4.06 mmol), 2-bromoethanol (0.58 mL, 8.12 mmol) and triphenylphosphine (1.92 g, 7.30 mmol) in THF (24.5 mL) at 0° C. The mixture was stirred at 120° C. for 30 minutes under microwave irradiation and then the solvent was evaporated in vacuo. The crude product was purified by flash column chromatography (silica; DCM). The desired fractions were collected and concentrated in vacuo to yield 2-(2-bromoethyl)-5-phenoxymethyl-2H-pyrazole-3-carboxylic acid ethyl ester (1.08 g, 71% yield) as a yellow oil.

64. (R)-5-(1-cyclopropyl-ethyl)-2-phenoxymethyl-6,7-dihydro-5H-pyrazolo[1,5-a]pyrazin-4-one

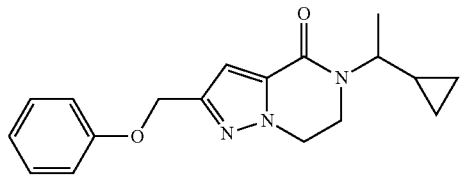 [SMILES: CC(C1CC1)N1CCn2nc(COc3ccccc3)cc2C1=O]

(R)-1-Cyclopropylethylamine (0.3 mL, 2.82 mmol) was added to a suspension of 2-(2-bromo-ethyl)-5-phenoxymethyl-2H-pyrazole-3-carboxylic acid ethyl ester (100 mg, 0.128 mmol) and potassium iodide (9.36 mg, 0.056 mmol) in ACN (1 mL). The mixture was stirred at 90° C. for 20 hours. The solvent was evaporated in vacuo. The crude product was purified by flash column chromatography (silica; AcOEt in DCM 0/100 to 20/80). The desired fractions were collected and the solvents evaporated in vacuo to yield (R)-5-(1-cyclopropyl-ethyl)-2-phenoxymethyl-6,7-dihydro-5H-pyrazolo[1,5-a]pyrazin-4-one as a orange oil. $^1$H NMR (500 MHz, CDCl$_3$) δ ppm 0.29-0.37 (m, 1H), 0.38-0.49 (m, 2H), 0.60-0.70 (m, 1H), 0.86-0.97 (m, 1H), 1.28 (d, J=6.9 Hz, 3H), 3.75 (ddd, J=12.9, 7.6, 4.9 Hz, 1H), 3.87 (ddd, J=12.9, 7.4, 5.2 Hz, 1H), 4.07 (dq, J=9.2, 6.9 Hz, 1H), 4.32-4.44 (m, 2H), 5.09 (s, 2H), 6.92 (s, 1H), 6.96 (t, J=7.4 Hz, 1H), 6.98-7.03 (m, 2H), 7.27-7.32 (m, 2H).

65. (R)-5-Phenoxymethyl-2-[2-(1,2,2-trimethyl-propylamino)-ethyl]-2H-pyrazole-3-carboxylic acid ethyl ester and (1)-5-Phenoxymethyl-2-[2-(1,2,2-trimethyl-propylamino)-ethyl]-2H-pyrazole-3-carboxylic acid

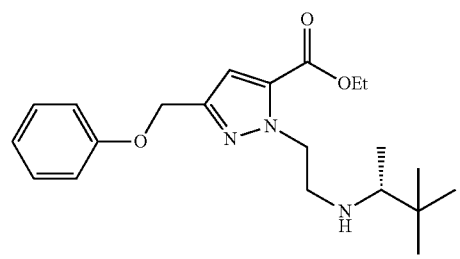

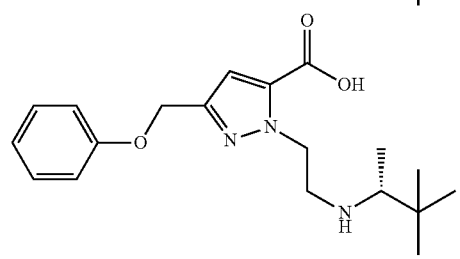

(R)-3,3-Dimethyl-2-aminobutane (0.37 g, 2.86 mmol) was added to a suspension of 2-(2-bromoethyl)-5-phenoxymethyl-2H-pyrazole-3-carboxylic acid ethyl ester (0.1 g, 0.28 mmol) and potassium iodide (9 mg, 0.056 mmol) in ACN (1 mL). The mixture was stirred at 90° C. for 20 hours. Sodium tert-butoxide (41 mg, 0.42 mmol) and DMF (1 mL) was added and the mixture was stirred at 130° C. for 20 minutes under microwave irradiation. The solvent was evaporated in vacuo. The crude product was washed with a 2N solution of HCl until pH 1 and extracted with AcOEt. The organic layer was separated, dried (Na$_2$SO$_4$), filtered and the solvents evaporated in vacuo to yield a 1:1 mixture (R)-5-phenoxymethyl-2-[2-(1,2,2-trimethyl-propylamino)-ethyl]-2H-pyrazole-3-carboxylic acid ethyl ester and (R)-5-phenoxymethyl-2-[2-(1,2,2-trimethyl-propylamino)-ethyl]-2H-pyrazole-3-carboxylic acid (113 mg, 57%) as a yellow oil which was used in the next step without any further purification.

66. (R)-5-Phenoxymethyl-2-[2-(1,2,2-trimethyl-propylamino)-ethyl]-2H-pyrazole-3-carboxylic acid

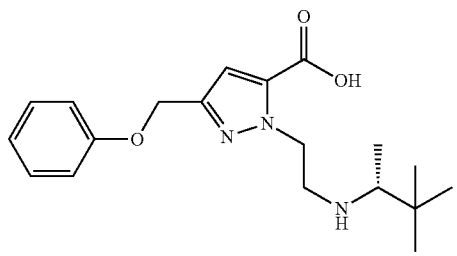 [SMILES: C[C@@H](NCCn1nc(COc2ccccc2)cc1C(=O)O)C(C)(C)C]

A solution of lithium hydroxide (13 mg, 0.55 mmol) in water (1 mL) was added to a solution of a mixture of (R)-5-phenoxymethyl-2-[2-(1,2,2-trimethyl-propylamino)-ethyl]-2H-pyrazole-3-carboxylic acid (55 mg, 0.078 mmol) and (R)-5-phenoxymethyl-2-[2-(1,2,2-trimethyl-propylamino)-ethyl]-2H-pyrazole-3-acid ethyl ester (55 mg, 0.078 mmol) in THF (1 mL). The mixture was stirred at room temperature for 20 hours. The solvents were evaporated in vacuo to yield (R)-5-phenoxymethyl-2-[2-(1,2,2-trimethyl-propylamino)-ethyl]-2H-pyrazole-3-carboxylic acid (130 mg, quantitative) as a yellow solid which was used in the next step without any further purification.

67. (R)-2-Phenoxymethyl-5-(1,2,2-trimethyl-propyl)-6,7-dihydro-5H-pyrazolo[1,5-a]pyrazin-4-one

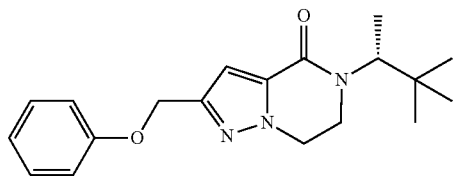 [SMILES: C[C@@H](N1CCn2nc(COc3ccccc3)cc2C1=O)C(C)(C)C]

A mixture of (R)-5-phenoxymethyl-2-[2-(1,2,2-trimethyl-propylamino)-ethyl]-2H-pyrazole-3-carboxylic acid (130 mg, 0.38 mmol) and HATU (143 mg, 0.38 mmol) in DMF (3 mL) was stirred for 5 minutes at room temperature, then DIPEA (0.16 mL, 0.945 mmol) were added. The reaction mixture was stirred at room temperature for 16 hours and then washed with a saturated solution of NH$_4$Cl and extracted with DCM. The organic layer was separated, dried (Na$_2$SO$_4$), filtered and the solvents evaporated in vacuo. The residue was purified by flash column chromatography (silica; AcOEt in DCM 0/100 to 20/80). The desired fractions were collected and the solvents evaporated in vacuo. The desired product was triturated with diethyl ether to yield (R)-2-phenoxymethyl-5-(1,2,2-trimethyl-propyl)-6,7-dihydro-5H-pyrazolo[1,5-a]pyrazin-4-one (21 mg, 17% yield) as a white solid. $^1$H NMR (500 MHz, CDCl$_3$) δ ppm 0.98 (s, 9H), 1.21 (d, J=7.2 Hz, 3H), 3.66-3.79 (m, 2H), 4.27-4.40 (m, 2H), 4.73 (q, J=7.2 Hz, 1H), 5.09 (s, 2H), 6.93 (s, 1H), 6.96 (t, J=7.4 Hz, 1H), 7.00 (d, J=7.8 Hz, 2H), 7.27-7.32 (m, 2H).

68. 2-[4-(tert-Butyl-dimethyl-silanyloxy)-phenoxymethyl]-5-(5-fluoro-pyridin-2-yl)-6,7-dihydro-5H-pyrazolo[1,5-a]pyrazin-4-one

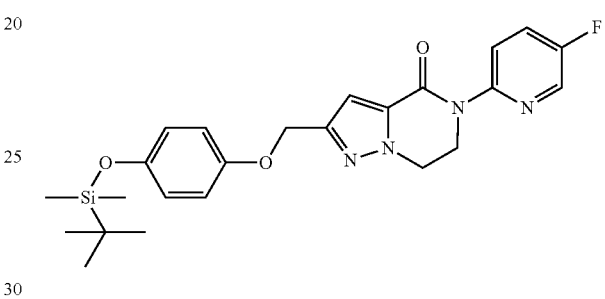

The compound was prepared from 4-(tert-butyldimethyl-siloxy)phenol and 5-(5-fluoro-pyridin-2-yl)-2-hydroxymethyl-6,7-dihydro-5H-pyrazolo[1,5-a]pyrazin-4-one using the method described in the preceding example 55 (5-(4-fluorophenyl)-2-(p-tolyloxymethyl)-6,7-dihydro-5H-pyrazolo[1,5-a]pyrazin-4-one).

69. 5-(5-Fluoro-pyridin-2-yl)-2-(4-hydroxy-phenoxymethyl)-6,7-dihydro-5H-pyrazolo[1,5-a] pyrazin-4-one

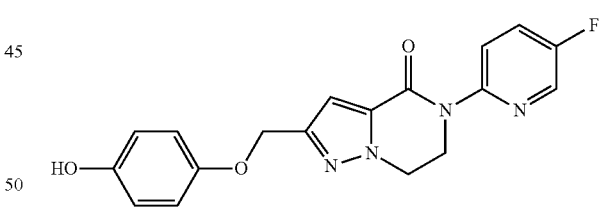

A 1M solution of TBAF in THF (0.14 mL, 0.144 mmol) was added to a stirred solution of 2-[4-(tert-butyl-dimethyl-silanyloxy)-phenoxymethyl]-5-(5-fluoro-pyridin-2-yl)-6,7-dihydro-5H-pyrazolo[1,5-a]pyrazin-4-one (45 mg, 0.096 mmol) in THF (0.5 mL). The mixture was stirred at room temperature for 16 hours. The mixture was treated with water and extracted with AcOEt. The organic layer was separated, dried (MgSO$_4$), filtered and the solvents evaporated in vacuo. The crude product was purified by flash column chromatography (silica; 7 N solution of ammonia in MeOH in DCM 0/100 to 10/90). The desired fractions were collected and the solvents evaporated in vacuo to yield 5-(5-fluoro-pyridin-2-yl)-2-(4-hydroxy-phenoxymethyl)-6,7-dihydro-5H-pyrazolo[1,5-a]pyrazin-4-one as a white solid. $^1$H NMR (500 MHz, DMSO-d$_6$) δ ppm 4.40-4.48 (m, 2H), 4.48-4.55 (m, 2H), 4.99 (s, 2H), 6.65-6.72 (m, 2H), 6.83-6.88 (m, 2H), 6.95 (s, 1H), 7.85 (td, J=8.7, 3.2 Hz, 1H), 7.93 (dd, J=9.1, 4.2 Hz, 1H), 8.50 (d, J=3.2 Hz, 1H), 8.96 (s, 1H).

70. 5-(4-Fluoro-phenyl)-2-(pyridazin-3-yloxymethyl)-6,7-dihydro-5H-pyrazolo[1,5-a]pyrazin-4-one

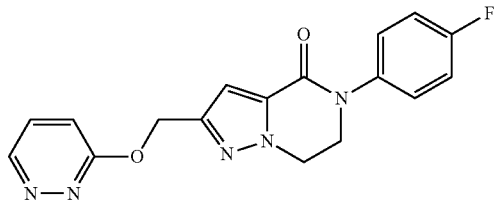 [SMILES: O=C1c2cc(COc3cccnn3)nn2CCN1c1ccc(F)cc1]

2-(6-Chloro-pyridazin-3-yloxymethyl)-5-(4-fluoro-phenyl)-6,7-dihydro-5H-pyrazolo[1,5-a]pyrazin-4-one (74 mg, 0.2 mmol) was dissolved in a mixture of TEA (0.2 mL), MeOH (1.6 mL) and THF (2.4 mL). The solution was hydrogenated in a H-Cube reactor (1 ml/min, 30 mm 10% Pd/C cartridge, full H$_2$ mode, 40° C., 1 cycle). The solvents were evaporated in vacuo. The crude product was purified by flash column chromatography (silica; 7 N solution of ammonia in MeOH in DCM 0/100 to 10/90). The desired fractions were collected and the solvents evaporated in vacuo. The product was repurified by RP HPLC on (C18 XBridge 30×100 5 um). Mobile phase (Gradient from 80% 0.1% NH$_4$CO$_3$H/NH$_4$OH pH 9 solution in H$_2$O, 20% MeOH to 0% 0.1% NH$_4$CO$_3$H/NH$_4$OH pH 9 solution in H$_2$O, 100% MeOH) to yield 5-(4-fluoro-phenyl)-2-(pyridazin-3-yloxymethyl)-6,7-dihydro-5H-pyrazolo[1,5-a]pyrazin-4-one (17 mg, 24% yield) as a white solid. $^1$H NMR (400 MHz, CDCl$_3$) δ ppm 4.18 (dd, J=6.8, 5.2 Hz, 2H), 4.56 (dd, J=6.8, 5.2 Hz, 2H), 5.64 (s, 2H), 7.05 (dd, J=9.0, 1.4 Hz, 1H), 7.08 (s, 1H), 7.09-7.17 (m, 2H), 7.29-7.35 (m, 2H), 7.40 (dd, J=8.9, 4.5 Hz, 1H), 8.88 (dd, J=4.4, 1.4 Hz, 1H).

71. 5-(6-Chloromethyl-pyridin-2-yl)-2-phenoxymethyl-6,7-dihydro-5H-pyrazolo[1,5-a]pyrazin-4-one

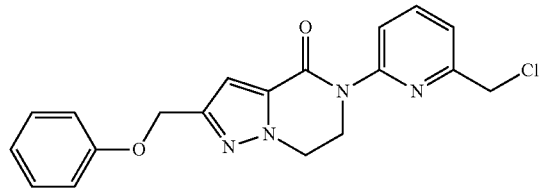 [SMILES: O=C1c2cc(COc3ccccc3)nn2CCN1c1cccc(CCl)n1]

Toluene-4-sulfonyl chloride (73 mg, 0.38 mmol) was added to a solution of 5-(6-hydroxymethyl-pyridin-2-yl)-2-phenoxymethyl-6,7-dihydro-5H-pyrazolo[1,5-a]pyrazin-4-one (67 mg, 0.19 mmol) and TEA (0.06 mL, 0.478 mmol) in DCM (1 mL) at 0° C. The reaction was stirred for 10 minutes at 100° C. under microwave irradiation. The mixture was basified with a saturated solution of NaHCO$_3$, the organic layer was separated, dried (Na$_2$SO$_4$) and the solvent evaporated in vacuo. The residue was purified by flash column chromatography (silica, AcOEt in DCM 0/100 to 10/90). Desired fractions were collected and the solvent evaporated in vacuo. The residue was triturated with DIPE to yield 5-(6-chloromethyl-pyridin-2-yl)-2-phenoxymethyl-6,7-dihydro-5H-pyrazolo[1,5-a]pyrazin-4-one (19 mg, 27% yield) as an off-white solid. $^1$H NMR (400 MHz, CDCl$_3$) δ ppm 4.47-4.56 (m, 2H), 4.62 (s, 2H), 4.62-4.67 (m, 2H), 5.13 (s, 2H), 6.94-7.00 (m, 1H), 7.00-7.05 (m, 2H), 7.08 (s, 1H), 7.27-7.35 (m, 3H), 7.77 (dd, J=8.3, 7.6 Hz, 1H), 8.02 (d, J=8.3 Hz, 1H).

72. 6-(4-Oxo-2-phenoxymethyl-6,7-dihydro-4H-pyrazolo[1,5-a]pyrazin-5-yl)-3',6'-dihydro-2'H-[2,4']bipyridinyl-1'-carboxylic acid tert-butyl ester

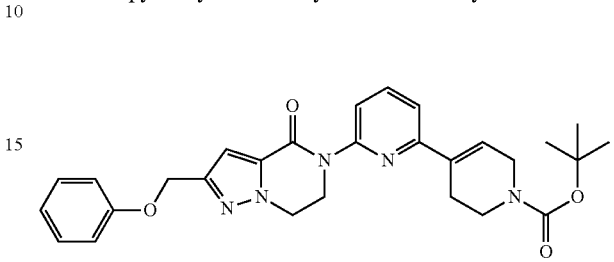

Tetrakis(triphenylphosphine)palladium(0) (7 mg, 0.006 mmol) was added to a stirred suspension of 5-(6-bromo-pyridin-2-yl)-2-phenoxymethyl-6,7-dihydro-5H-pyrazolo[1,5-a]pyrazin-4-one (50 mg, 0.125 mmol), (N-tert-butoxycarbonyl)-1,2,3,6-tetrahydropyridine-4-boronic acid pinacol ester (97 mg, 0.31 mmol) and potassium carbonate in a mixture of 1,4-dioxane (0.5 mL) and DMF (0.5 mL) in a sealed tube and under nitrogen. The mixture was stirred at 150° C. for 15 minutes under microwave irradiation. The mixture was diluted with water and extracted with AcOEt. The organic layer was separated, washed with brine, dried (MgSO$_4$), filtered and the solvents evaporated in vacuo. The crude product was purified by flash column chromatography (silica; AcOEt in DCM 0/100 to 100/0). The desired fractions were collected and the solvents evaporated in vacuo to yield 6-(4-oxo-2-phenoxymethyl-6,7-dihydro-4H-pyrazolo[1,5-a]pyrazin-5-yl)-3',6'-dihydro-2'H-[2,4']bipyridinyl-1'-carboxylic acid tert-butyl ester (51 mg, 81%) as a pale yellow solid.

73. 6-(4-Oxo-2-phenoxymethyl-6,7-dihydro-4H-pyrazolo[1,5-a]pyrazin-5-yl)-3',4',5',6'-tetrahydro-2'H-[2,4']bipyridinyl-1'-carboxylic acid tert-butyl ester

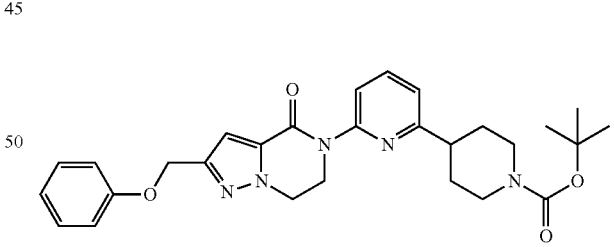

10% Palladium on charcoal (11 mg, 0.01 mmol) was added to a stirred suspension of 6-(4-oxo-2-phenoxymethyl-6,7-dihydro-4H-pyrazolo[1,5-a]pyrazin-5-yl)-3',6'-dihydro-2'H-[2,4']bipyridinyl-1'-carboxylic acid tert-butyl ester (51 mg, 0.10 mmol) and ammonium formate (38 mg, 0.61 mmol) in MeOH (0.5 mL) in a sealed tube and under nitrogen. The mixture was stirred at 80° C. for 30 minutes. The mixture was filtered through a pad of diatomaceous earth and washed with DCM. The filtrate was treated with brine and extracted with more DCM. The organic layer was separated, dried (MgSO$_4$), filtered and the solvents evaporated in vacuo. The crude product was purified by flash column chromatography (silica;

AcOEt in DCM 0/100 to 50/50). The desired fractions were collected and the solvents evaporated in vacuo to yield 6-(4-oxo-2-phenoxymethyl-6,7-dihydro-4H-pyrazolo[1,5-a]pyrazin-5-yl)-3',4',5',6'-tetrahydro-2'H-[2,4']bipyridinyl-1'-carboxylic acid tert-butyl ester (44 mg, 86% yield) as a yellow oil.

74. 5-(1',2',3',4',5',6'-Hexahydro-[2,4']bipyridinyl-6-yl)-2-phenoxymethyl-6,7-dihydro-5H-pyrazolo[1,5-a]pyrazin-4-one

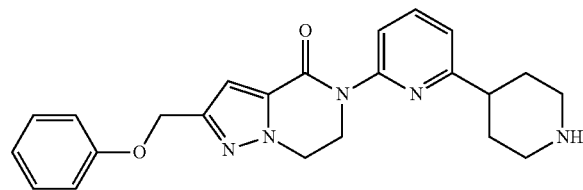 [SMILES: O=C1c2cc(COc3ccccc3)nn2CCN1c1cccc(C2CCNCC2)n1]

Trifluoroacetic acid (0.5 mL) was added to a stirred solution of 6-(4-oxo-2-phenoxymethyl-6,7-dihydro-4H-pyrazolo[1,5-a]pyrazin-5-yl)-3',4',5',6'-tetrahydro-2'H-[2,4']bipyridinyl-1'-carboxylic acid tert-butyl ester (44 mg, 0.087 mmol) in DCM (0.5 mL). The mixture was stirred at room temperature for 16 hours. The mixture was basified with a saturated solution of Na$_2$CO$_3$ and extracted with more DCM. The organic layer was separated, dried (MgSO$_4$), filtered and the solvents evaporated in vacuo. The crude product was purified by flash column chromatography (silica; 7 N solution of ammonia in MeOH in DCM 0/100 to 10/90). The desired fractions were collected and the solvents evaporated in vacuo. The product was repurified by ion exchange chromatography using an ISOLUTE SCX2 cartridge and eluting with MeOH and 7 N solution of ammonia in MeOH. The desired fractions were collected and the solvents evaporated in vacuo. The product was triturated with DIPE and repurified by RP HPLC on (C18 XBridge 30×100 5 um). Mobile phase (Gradient from 80% 0.1% NH$_4$CO$_3$H/NH$_4$OH pH 9 solution in H$_2$O, 20% ACN to 0% 0.1% NH$_4$CO$_3$H/NH$_4$OH pH 9 solution in H$_2$O, 100% ACN) to yield 5-(1',2',3',4',5',6'-hexahydro-[2,4']bipyridinyl-6-yl)-2-phenoxymethyl-6,7-dihydro-5H-pyrazolo[1,5-a]pyrazin-4-one (8 mg, 24% yield) as a white solid. $^1$H NMR (400 MHz, CDCl$_3$d) δ ppm 1.66 (br. s., 1H), 1.70-1.83 (m, 2H), 1.89 (dd, J=12.0, 1.8 Hz, 2H), 2.76 (td, J=12.3, 2.8 Hz, 2H), 2.74-2.83 (m, 1H), 3.21 (dt, J=12.0, 2.8 Hz, 2H), 4.46-4.54 (m, 2H), 4.58-4.68 (m, 2H), 5.13 (s, 2H), 6.93-7.00 (m, 2H), 7.00-7.05 (m, 2H), 7.06 (s, 1H), 7.27-7.34 (m, 2H), 7.66 (t, J=8.0 Hz, 1H), 7.87 (d, J=8.1 Hz, 1H).

75. 4-Chloro-1H-pyrazole-3,5-Dicarboxylic acid diethyl ester

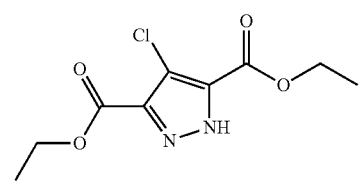 [SMILES: CCOC(=O)c1n[nH]c(C(=O)OCC)c1Cl]

Sodium hypochlorite (2.79 mL, 5.89 mmol) was added to a solution of diethyl 3,5-pyrazoledicarboxylate (0.5 g, 2.36 mmol) in AcOH (10 mL) and the mixture was stirred at room temperature for 16 hours. Then, the solvent was evaporated in vacuo and the mixture was acidified with a 1N solution of HCl and extracted with AcOEt. The organic layer was separated, dried (MgSO$_4$), filtered and the solvents evaporated in vacuo. The crude product was purified by flash column chromatography (silica; MeOH in DCM 0/100 to 05/95). The desired fractions were collected and the solvents evaporated in vacuo to yield 4-chloro-1H-pyrazole-3,5-dicarboxylic acid diethyl ester (450 mg, 66% yield) as a white solid.

76. 3-Chloro-4-oxo-4,5,6,7-tetrahydro-pyrazolo[1,5-a]pyrazine-2-carboxylic acid ethyl ester

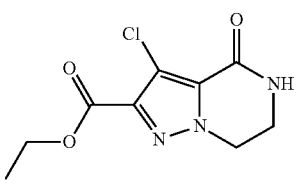

The compound was prepared from 4-chloro-1H-pyrazole-3,5-dicarboxylic acid diethyl ester and 2-(2-tert-butoxycarbonylamino)ethyl bromide using the methods described in the preceding examples 5 (2-(2-tert-butoxycarbonylamino-ethyl)-5-phenoxymethyl-2H-pyrazole-3-carboxylic acid ethyl ester) and 48 (4,5,6,7-tetrahydro-4-oxo-pyrazolo[1,5-a]pyrazine-2-carboxylic acid ethyl ester.

77. 3-Chloro-2-hydroxymethyl-6,7-dihydro-5H-pyrazolo[1,5-a]pyrazin-4-one

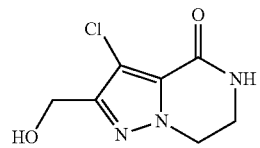 [SMILES: O=C1NCCn2nc(CO)c(Cl)c21]

A 1M solution of lithium aluminum hydride was added to a stirred solution of 3-chloro-4-oxo-4,5,6,7-tetrahydro-pyrazolo[1,5-a]pyrazine-2-carboxylic acid ethyl ester (0.37 g, 1.51 mmol) in THF (15 mL) at 0° C. The mixture was stirred at room temperature for 2 hours and then diluted with AcOEt. Na$_2$SO$_4$.10H$_2$O was added at 0° C. and the mixture stirred for 15 minutes at 0° C., filtered through a pad of diatomaceous earth and then washed with additional THF. The solvents were evaporated in vacuo to yield 3-chloro-2-hydroxymethyl-6,7-dihydro-5H-pyrazolo[1,5-a]pyrazin-4-one (0.24 g, 79% yield) that was used in the next step without further purification.

78. 3-Chloro-2-phenoxymethyl-6,7-dihydro-5H-pyrazolo[1,5-a]pyrazin-4-one

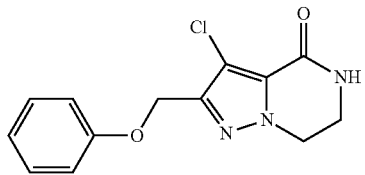 [SMILES: O=C1NCCn2nc(COc3ccccc3)c(Cl)c21]

The compound was prepared from 3-chloro-2-hydroxymethyl-6,7-dihydro-5H-pyrazolo[1,5-a]pyrazin-4-one using the method described in the preceding example 55 (5-(4-fluorophenyl)-2-(p-tolyloxymethyl)-6,7-dihydro-5H-pyrazolo[1,5-a]pyrazin-4-one). $^1$H NMR (500 MHz, CDCl$_3$) δ ppm 3.72-3.84 (m, 2H), 4.39 (dd, J=6.1, 5.5 Hz, 2H), 5.10 (s, 2H), 6.02 (br. s., 1H), 6.99 (t, J=7.4 Hz, 1H), 7.04 (d, J=7.8 Hz, 2H), 7.28-7.35 (m, 2H).

79. 4-Iodo-1H-pyrazole-3,5-dicarboxylic acid diethyl ester

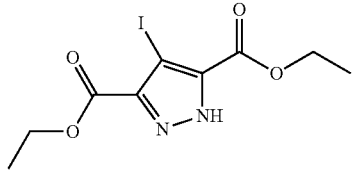 [SMILES: CCOC(=O)c1n[nH]c(C(=O)OCC)c1I]

N-iodosuccinimide (0.6 g, 2.59 mmol) was added to a solution of diethyl 3,5-pyrazoledicarboxylate (0.5 g, 2.35 mmol) in CHCl$_3$ (10 mL) and the mixture was stirred at 80° C. for 24 hours. Then more of N-iodosuccinimide (0.6 g, 2.59 mmol) was added and the mixture was stirred at 100° C. for 48 hours more. Then the mixture was stirred at room temperature for 5 days. Then the mixture was treated with a saturated solution of Na$_2$S$_2$O$_3$ and extracted with DCM. The organic layer was separated, dried (MgSO$_4$), filtered and the solvents evaporated in vacuo. The crude product was purified by flash column chromatography (silica; MeOH in DCM 0/100 to 10/90). The desired fractions were collected and the solvents evaporated in vacuo to yield 4-iodo-1H-pyrazole-3,5-dicarboxylic acid diethyl ester (0.83 g, 90% yield).

80. 1-(2-tert-Butoxycarbonylamino-ethyl)-4-iodo-1H-pyrazole-3,5-dicarboxylic acid diethyl ester

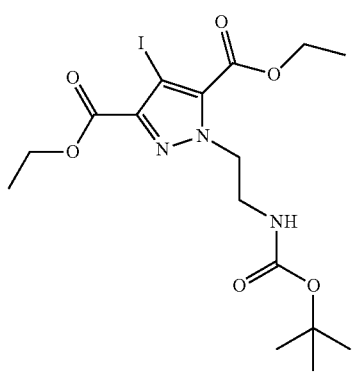 [SMILES: CCOC(=O)c1nn(CCNC(=O)OC(C)(C)C)c(C(=O)OCC)c1I]

The compound was prepared from 4-iodo-1H-pyrazole-3,5-dicarboxylic acid diethyl ester and 2-(2-tert-butoxycarbonylamino)ethyl bromide using the method described in the preceding example 5 (2-(2-tert-butoxycarbonylamino-ethyl)-5-phenoxymethyl-2H-pyrazole-3-carboxylic acid ethyl ester).

81. 3-Iodo-4-oxo-4,5,6,7-tetrahydro-pyrazolo[1,5-a]pyrazine-2-carboxylic acid ethyl ester

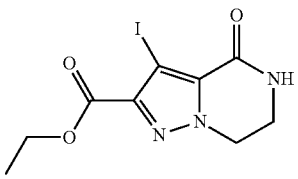

The compound was prepared from 1-(2-tert-butoxycarbonylamino-ethyl)-4-iodo-1H-pyrazole-3,5-dicarboxylic acid diethyl ester using the method described in the preceding example 6 (2-phenoxymethyl-6,7-dihydro-5H-pyrazolo[1,5-a]pyrazin-4-one).

82. 3-methyl-4-oxo-4,5,6,7-tetrahydro-pyrazolo[1,5-a]pyrazine-2-carboxylic acid ethyl ester

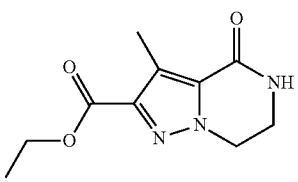 [SMILES: CCOC(=O)c1nn2c(c1C)C(=O)NCC2]

Palladium (II) acetate (38 mg, 0.17 mmol) was added to a solution of 3-iodo-4-oxo-4,5,6,7-tetrahydro-pyrazolo[1,5-a]pyrazine-2-carboxylic acid ethyl ester (0.56 g 1.68 mmol), methylboronic acid (0.75 g, 12.6 mmol), 2-dicyclohexylphosphino-2',4',6'-triiso-propyl-1,1'-biphenyl (0.16 mg, 0.34 mmol) and potassium carbonate (0.69 g, 5.0 mmol) in toluene (15 mL) under nitrogen and the mixture was heated at 90° C. for 16 hours. Then the mixture was heated at 120° C. for 4 hours more. The mixture was diluted with a saturated Na$_2$CO$_3$ solution and extracted with DCM. The organic layer was separated, dried (MgSO$_4$), filtered and the solvent evaporated in vacuo. The crude product was purified by flash column chromatography (silica; MeOH in DCM 0/100 to 10/90). The desired fractions were collected and the solvents evaporated in vacuo to yield 3-methyl-4-oxo-4,5,6,7-tetrahydro-pyrazolo[1,5-a]pyrazine-2-carboxylic acid ethyl ester (0.22 g, 58% yield).

83. 3-Methyl-2-phenoxymethyl-6,7-dihydro-5H-pyrazolo[1,5-a]pyrazin-4-one

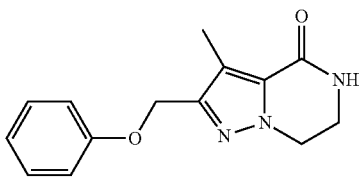

The compound was prepared from 3-methyl-4-oxo-4,5,6,7-tetrahydro-pyrazolo[1,5-a]pyrazine-2-carboxylic acid ethyl ester using the methods described in the preceding examples 77 (3-chloro-2-hydroxymethyl-6,7-dihydro-5H-pyrazolo[1,5-a]pyrazin-4-one) and 78 (3-chloro-2-phenoxymethyl-6,7-dihydro-5H-pyrazolo[1,5-a]pyrazin-4-one).

84. 2-(4-Chloro-phenoxymethyl)-6,7-dihydro-5H-pyrazolo[1,5-a]pyrazin-4-one

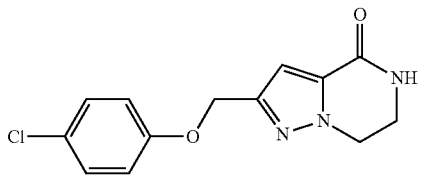 [SMILES: O=C1NCCn2nc(COc3ccc(Cl)cc3)cc21]

N-chlorosuccinimide (61 mg, 0.45 mmol) was added to a solution of 2-phenoxymethyl-6,7-dihydro-5H-pyrazolo[1,5-a]pyrazin-4-one (0.1 g, 0.41 mmol) in $CHCl_3$ (3 mL) and the mixture was stirred at 80° C. for 20 hours. Then the solvent was evaporated in vacuo and the crude product was purified by flash column chromatography (silica; MeOH in DCM 0/100 to 10/90). The desired fractions were collected and the solvents evaporated in vacuo to yield 2-(4-chloro-phenoxymethyl)-6,7-dihydro-5H-pyrazolo[1,5-a]pyrazin-4-one (0.1 g, 90% yield).

85. 2-Bromo-6-(2-methoxy-ethyl)-pyridine

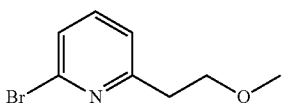

2-Bromo-6-(2-methoxy-ethyl)-pyridine has been prepared as described in WO 2008156726 A1.

86. (6-Chloro-5-methyl-pyridin-2-yl)-dimethyl-amine and (6-chloro-3-methyl-pyridin-2-yl)-dimethyl-amine

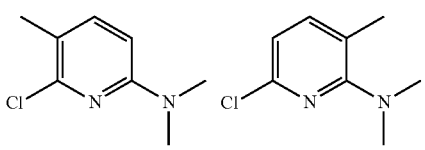

2,6-Dichloro-3-methylpyridine (250 mg, 1.5 mmol) was dissolved in a 40% aqueous solution of dimethylamine (0.2 mL, 1.5 mmol) and stirred at 80° C. in a sealed tube for 16 hours. Then DCM was added. The organic layer was separated, dried ($Na_2SO_4$), filtered and the solvent evaporated in vacuo to yield (6-chloro-5-methyl-pyridin-2-yl)-dimethyl-amine and (6-chloro-3-methyl-pyridin-2-yl)-dimethyl-amine as a colorless oil that was used in the next step without further purification.

87. (6-Chloro-4-methyl-pyridin-2-yl)-dimethyl-amine

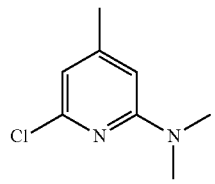

The compound was prepared from 2,6-dichloro-4-methylpyridine and dimethylamine using the method described in the preceding example 86 (6-chloro-5-methyl-pyridin-2-yl)-dimethyl-amine and (6-chloro-3-methyl-pyridin-2-yl)-dimethyl-amine).

88. 2-Bromo-6-fluoromethyl-pyridine

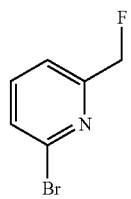

2-Bromo-6-fluoromethyl-pyridine was prepared as described in US 20070037817 A1.

89. 2-Bromo-6-(2-fluoro-ethyl)-pyridine

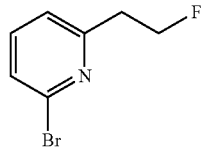

2-Bromo-6-(2-fluoro-ethyl)-pyridine was prepared as described in US 20070037817 A1.

90. 4-Chloro-5-methoxy-2-methyl-pyrimidine

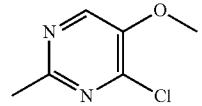

4-Chloro-5-methoxy-2-methyl-pyrimidine was prepared following the method described in *European Journal of Medicinal Chemistry* 2009, 44, 4179.

91. -Bromo-3,6-difluoro-pyridine

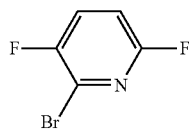

Bromine (0.30 mL, 6 mmol) was added dropwise to a stirred solution of (3,6-difluoro-pyridin-2-yl)-hydrazine (435 mg, 3 mmol) in CHCl₃ (6 mL) at room temperature. The mixture was stirred at 60° C. for 1 hour. The mixture was cooled at 0° C. and a saturated solution of NaHCO₃ was added dropwise. DCM was added, the organic layer was separated, dried (MgSO₄), filtered and the solvents evaporated in vacuo to yield 2-bromo-3,6-difluoro-pyridine (600 mg, 88% yield) as a dark oil.

92. (6-Bromo-5-fluoro-pyridin-2-yl)-dimethyl-amine

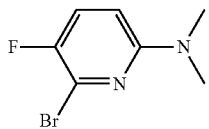

2-Bromo-3,6-difluoro-pyridine (300 mg, 1.5 mmol) was dissolved in a 2M solution of dimethylamine in MeOH (7.8 mL, 15.56 mmol) and stirred at 80° C. in a sealed tube for 16 hours. The mixture was treated with brine and extracted with DCM. The organic layer was separated, dried (MgSO₄), filtered and the solvents evaporated in vacuo to yield (6-bromo-5-fluoro-pyridin-2-yl)-dimethyl-amine as a dark oil that was used in the next step without further purification.

93. 2-Chloro-4,5-dimethoxy-pyrimidine

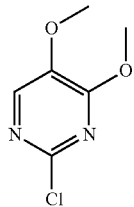

2-Chloro-4,5-dimethoxy-pyrimidine was prepared as described in WO2011109267 A1.

94. 2-Bromo-6-(3-methyl-butyl)-pyridine

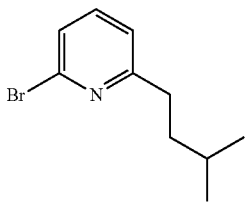

A 2.5M solution of n-buthyllithium (0.44 mL, 1.1 mmol) was added dropwise to a stirred solution of diisopropylamine (0.16 mL, 1.15 mmol) in THF (2 mL) at −78° C. The mixture was stirred for 15 minutes and 2-bromo-6-methylpyridine (0.11 mL, 1 mmol) was added dropwise. The mixture was stirred for 15 minutes and 1-bromo-2-methylpropane (0.21 mL, 2 mmol) was added dropwise. The mixture was stirred for 1 hour at this temperature and at room temperature for 60 hours. The mixture was treated with water and extracted with AcOEt. The organic layer was separated, dried (MgSO₄), filtered and the solvents evaporated in vacuo. The crude product was purified by flash column chromatography (silica; AcOEt in heptane 0/100 to 10/90). The desired fractions were collected and the solvents evaporated in vacuo to yield 2-bromo-6-(3-methyl-butyl)-pyridine (82 mg, 36% yield) as a colourless oil.

95. 2-(bromomethyl)-5-(5-fluoropyridin-2-yl)-6,7-dihydropyrazolo[1,5-a]pyrazin-4(5H)-one

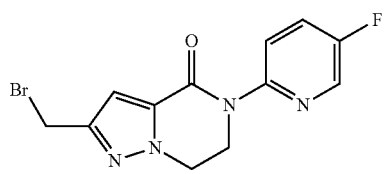 [SMILES: O=C1c2cc(CBr)nn2CCN1c1ccc(F)cn1]

5-(5-fluoropyridin-2-yl)-2-(phenoxymethyl)-6,7-dihydropyrazolo[1,5-a]pyrazin-4(5H)-one (100 mg, 0.296 mmol) was dissolved in DCM (2 mL), cooled to 0° C. and treated with 1M BBr₃ in DCM (1.18 mmol, 1.18 mL). The reaction was allowed to warm to room temperature and stirred for 4 h. The reaction was diluted with DCM (5 mL) and then washed sequentially with 1M HCl (2 mL), saturated aq. NaHCO₃ (2 mL) and 1N NaOH (2 ml). The organic layer was dried over Na₂SO₄, filtered and concentrated under vacuum to give A (82 mg, 85%) as an oil: LC-MS (215 nm)>98%, 324.8 (M+H).

96. 5-(5-fluoropyridin-2-yl)-2-((2-hydroxyphenoxy)methyl)-6,7-duhydropyrazolo[1,5-a]pyrazin-4(5H)-one

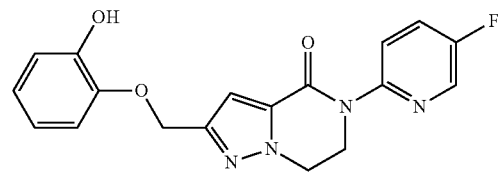 [SMILES: O=C1c2cc(COc3ccccc3O)nn2CCN1c1ccc(F)cn1]

To a solution of 2-(bromomethyl)-5-(5-fluoropyridin-2-yl)-6,7-dihydropyrazolo[1,5-a]pyrazin-4(5H)-one (prepared as described in Example 95; 0.123 mmol, 40 mg) in DMF (2 mL), catechol (0.135 mmol, 15 mg) and K₂CO₃ (0.492 mmol, 68 mg) were added. The reaction was stirred at room temperature for 16 h. The reaction was diluted with EtOAc (5 mL) and then washed sequentially with H₂O and saturated aq. LiCl. The organic layer was dried over Na₂SO₄, filtered, concentrated under vacuum and purified by automated flash chromatography (silica gel) using 40% to 100% EtOAc/hexanes to afford title compound (11.7 mg, 27%) as a white powder: ¹H-NMR (400 MHz, CDCl₃) δ 8.28 (d, J=3.2 Hz, 1H), 8.02 (dd, J=9.2 Hz, 4 Hz, 1H), 7.48 (ddd, J=10.8 Hz, 7.6 Hz, 3.2 Hz, 1H), 7.02 (dd, J=8 Hz, 1.2 HZ, 1H), 7.00 (s, 1H), 6.96-6.89 (m, 2H), 6.84 (ddd, 8 Hz, 8 Hz, 2.4 Hz, 1H), 5.17 (s. 2H), 4.57-4.49 (m, 4H); LC-MS (220 nm)>98%, 355.0 (M+H).

97. Additional Compounds

Compounds were synthesized having the structure:

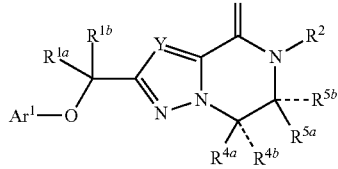

wherein Y and $Ar^1$ were as described in Table II below. $R^{1a}$, $R^{1b}$, $R^2$, $R^3$, $R^{4a}$, $R^{4b}$, $R^{5a}$, and $R^{5b}$ were H unless as otherwise noted under "Other Substitutions" in Table II. The methods were as described in the preceding examples with a reference example method as noted in Table II (see column labeled "Ref. Ex.").

Compounds were synthesized having the structure:

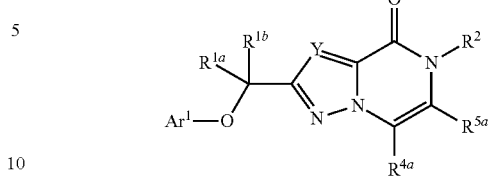

wherein Y, $R^2$ and $Ar^1$ were as described in Table III below. $R^{1a}$, $R^{1b}$, $R^3$, $R^{4a}$, and $R^{5a}$ were H unless as otherwise noted under "Other Substitutions" in Table III. The methods were as described in the preceding examples with a reference example method as noted in the table (see column labeled "Ref. Ex.").

Analytical data for the numbered compound in Table IV corresponds to the number given in the first column of either Table II or Table III, and optical rotation values are given in Table V. LCMS: $[M+H]^+$ means the protonated mass of the free base of the compound; $R_t$ means retention time (in minutes); and Method refers to the LCMS method used.

TABLE II

| No. | $Ar^1$ | $R^2$ | Y | Other Substitutions* | Ref. Ex.** |
|---|---|---|---|---|---|
| 1 | phenyl | H | CH | | 6 |
| 2 | phenyl | Me | CH | | 42 |
| 3 | phenyl | 2,4-difluorophenyl | CH | | 43 |
| 5 | phenyl | 4-fluorophenyl | N | | 21 |
| 6 | phenyl | 4-fluorophenyl | CH | | 43 |
| 7 | phenyl | 2,3-difluorophenyl | CH | | 43 |
| 8 | phenyl | 3-fluorophenyl | CH | | 43 |

TABLE II-continued

| No. | Ar¹ | R² | Y | Other Substitutions* | Ref. Ex.** |
|---|---|---|---|---|---|
| 9 | phenyl | 2-fluorophenyl | CH | | 43 |
| 10 | phenyl | 6-methylpyridin-2-yl | CH | | 43 |
| 11 | phenyl | 5-fluoropyridin-2-yl | CH | | 43 |
| 12 | phenyl | pyridin-2-yl | CH | | 43 |
| 13 | phenyl | pyridin-3-yl | CH | | 43 |
| 14 | phenyl | pyridin-4-yl | CH | | 43 |
| 15 | phenyl | 5-fluoropyridin-3-yl | CH | | 43 |
| 16 | phenyl | 5-methylpyridin-2-yl | CH | | 43 |
| 17 | phenyl | 4-methylpyridin-2-yl | CH | | 43 |
| 18 | phenyl | 4-fluorophenyl | CH | $R^{5a}$ = rac-$CH_3$ | 43 |
| 19 | phenyl | 4-fluorophenyl | | $R^{4a}$ = rac-$CH_3$ | 43 |
| 20 | phenyl | 4-fluorophenyl | CH | $R^{4a} = R^{4b} = $—$CH_3$ | 43 |

TABLE II-continued
| No. | Ar¹ | R² | Y | Other Substitutions* | Ref. Ex.** |
|---|---|---|---|---|---|
| 21 | 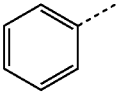 | 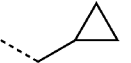 | CH | | 42 |
| 22 | 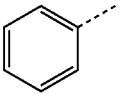 | 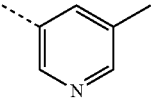 | CH | | 43 |
| 23 | 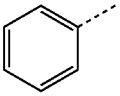 | 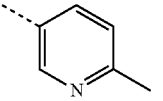 | CH | | 43 |
| 24 | 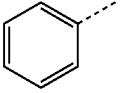 | 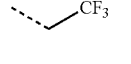 | CH | | 42 |
| 25 | 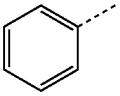 |  | CH | | 42 |
| 26 | 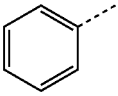 |  | CH | | 42 |
| 27 | 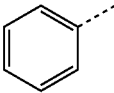 | 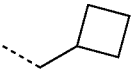 | CH | | 42 |
| 28 | 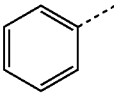 | 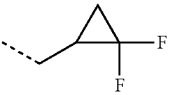 | CH | | 42 |
| 29 | 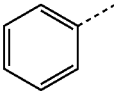 | 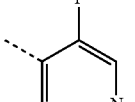 | CH | | 43 |
| 30 | 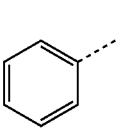 |  | CH | | 43 |
| 31 |  | 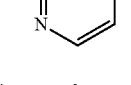 | CH | | 43 |
| 32 | 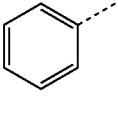 | 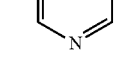 | CH | | 43 |

TABLE II-continued
| No. | Ar¹ | R² | Y | Other Substitutions* | Ref. Ex.** |
|---|---|---|---|---|---|
| 33 | 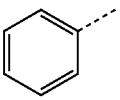 | 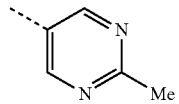 | CH | | 43 |
| 34 | 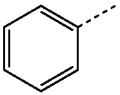 | 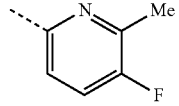 | CH | | 43 |
| 35 | 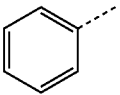 |  | CH | | 46 |
| 36 | 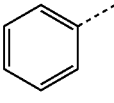 | 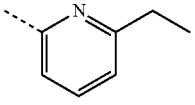 | CH | | 43 |
| 38 | 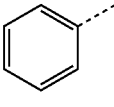 | 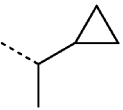<br>(R configuration) | CH | | 64 |
| 39 | 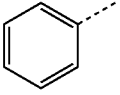 | 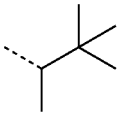<br>(R configuration) | CH | | 67 |
| 40 | 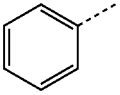 | 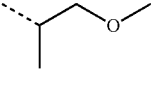<br>(racemic) | CH | | 67 |
| 41 | 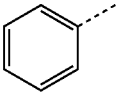 | <br>(S configuration) | CH | | 64 |
| 42 | 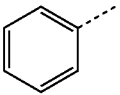 | 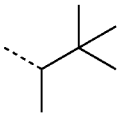<br>(S configuration) | CH | | 67 |
| 43 | 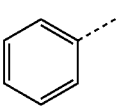 | 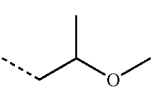<br>(racemic) | CH | | 39 |

TABLE II-continued
| No. | Ar¹ | R² | Y | Other Substitutions* | Ref. Ex.** |
|---|---|---|---|---|---|
| 44 | 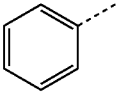 | 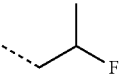 (racemic) | CH | | 40 |
| 45 | 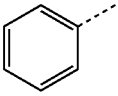 | 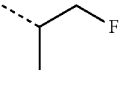 (racemic) | CH | | 40 |
| 46 | 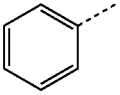 |  | CH | | 67 |
| 47 | 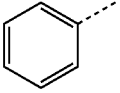 | 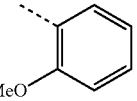 | CH | | 43 |
| 48 | 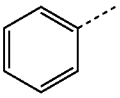 | 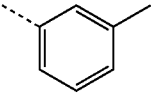 | CH | | 43 |
| 49 | 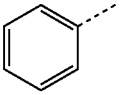 | 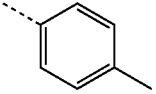 | CH | | 43 |
| 50 | 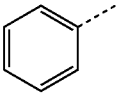 | 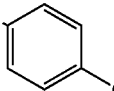 | CH | | 43 |
| 51 | 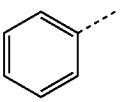 | 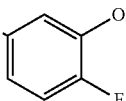 | CH | | 43 |
| 52 | 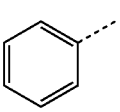 | 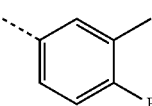 | CH | | 43 |
| 53 | 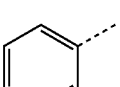 | 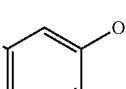 | CH | | 43 |
| 54 | 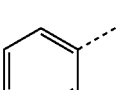 | 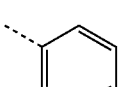 | CH | | 43 |
| 55 | 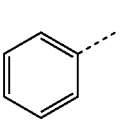 | 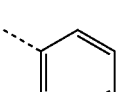 | CH | | 43 |

TABLE II-continued

| No. | Ar¹ | R² | Y | Other Substitutions* | Ref. Ex.** |
|---|---|---|---|---|---|
| 56 | phenyl | 2,3-dimethylphenyl | CH | | 43 |
| 57 | phenyl | 2-ethoxyphenyl | CH | | 43 |
| 58 | phenyl | 3-fluoro-4-methoxyphenyl | CH | | 43 |
| 59 | phenyl | 3-ethoxyphenyl | CH | | 43 |
| 60 | phenyl | 2-methyl-5-fluorophenyl | CH | | 43 |
| 61 | phenyl | 4-fluoro-2-methylphenyl | CH | | 43 |
| 62 | phenyl | 3-fluoro-4-methylphenyl | CH | | 43 |
| 63 | phenyl | 2-(methoxymethyl)phenyl | CH | | 43 |
| 64 | phenyl | 2-methylpyridin-3-yl | CH | | 43 |
| 65 | phenyl | 6-isopentylpyridin-2-yl | CH | | 43 |
| 66 | phenyl | 6-cyclopropylpyridin-2-yl | CH | | 45 |
| 67 | phenyl | 6-isobutylpyridin-2-yl | CH | | 43 |

TABLE II-continued
| No. | Ar¹ | R² | Y | Other Substitutions* | Ref. Ex.** |
|---|---|---|---|---|---|
| 68 | 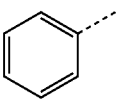 | 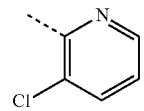 | CH | | 43 |
| 69 | 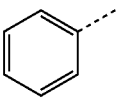 | 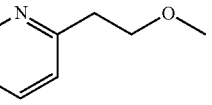 | CH | | 43 |
| 70 | 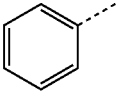 | 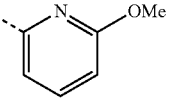 | CH | | 43 |
| 71 | 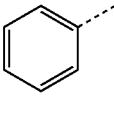 | 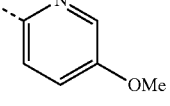 | CH | | 43 |
| 72 | 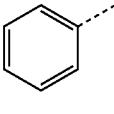 | 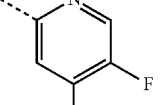 | CH | | 43 |
| 73 | 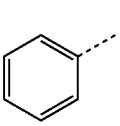 | 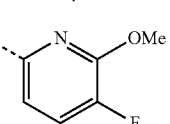 | CH | | 43 |
| 74 | 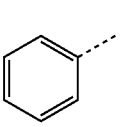 | 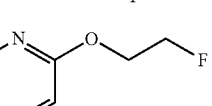 | CH | | 43 |
| 75 | 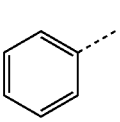 | 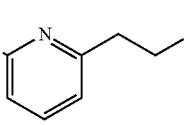 | CH | | 43 |
| 76 | 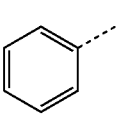 | 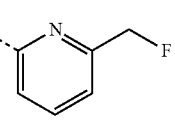 | CH | | 43 |
| 77 | 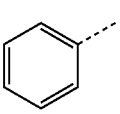 | 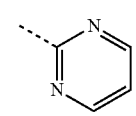 | CH | | 41 |
| 78 | 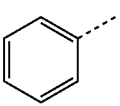 | 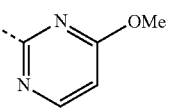 | CH | | 41 |
| 79 | 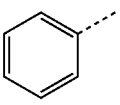 | 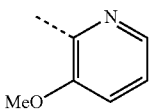 | CH | | 43 |
| 80 | 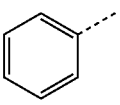 | 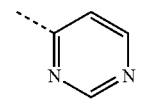 | CH | | 41 |

TABLE II-continued
| No. | Ar¹ | R² | Y | Other Substitutions* | Ref. Ex.** |
|---|---|---|---|---|---|
| 81 | 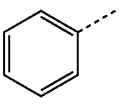 | 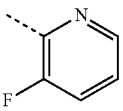 | CH | | 43 |
| 82 | 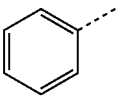 | 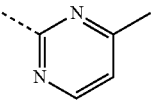 | CH | | 41 |
| 83 | 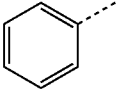 | 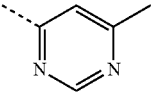 | CH | | 41 |
| 84 | 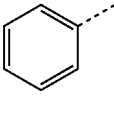 | 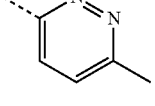 | CH | | 41 |
| 85 | 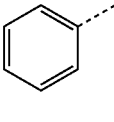 | 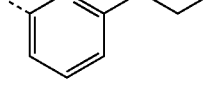 | CH | | 43 |
| 86 | 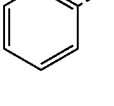 | 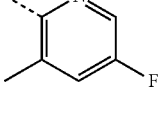 | CH | | 43 |
| 87 | 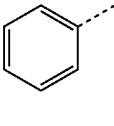 | 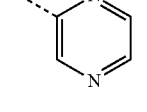 | CH | | 43 |
| 88 | 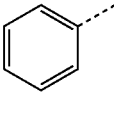 | 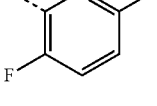 | CH | | 43 |
| 89 | 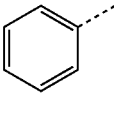 | 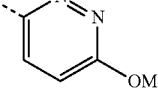 | CH | | 41 |
| 90 | 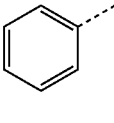 | 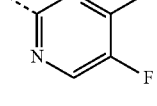 | CH | | 41 |
| 91 | 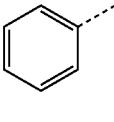 | 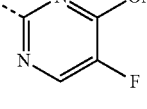 | CH | | 41 |
| 92 | 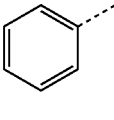 | 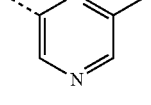 | CH | | 41 |
| 93 | 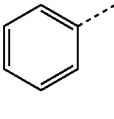 | 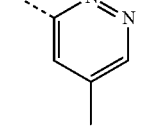 | CH | | 41 |

TABLE II-continued
| No. | Ar¹ | R² | Y | Other Substitutions* | Ref. Ex.** |
|---|---|---|---|---|---|
| 94 | 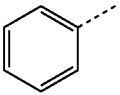 | 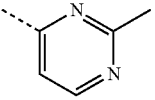 | CH | | 41 |
| 95 | 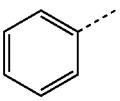 | 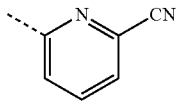 | CH | | 43 |
| 96 | 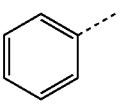 | 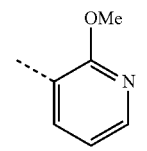 | CH | | 43 |
| 97 | 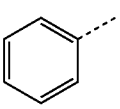 | 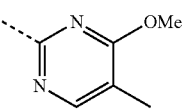 | CH | | 41 |
| 98 | 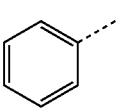 | 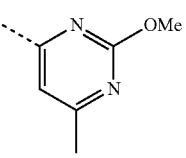 | CH | | 41 |
| 99 | 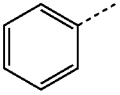 | 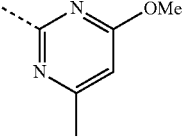 | CH | | 41 |
| 100 | 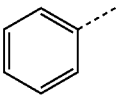 | 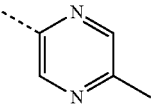 | CH | | 41 |
| 101 | 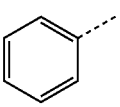 | 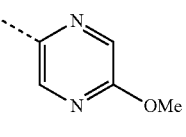 | CH | | 41 |
| 102 | 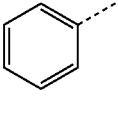 | 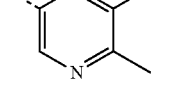 | CH | | 41 |
| 103 | 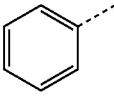 | 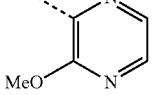 | CH | | 41 |
| 104 | 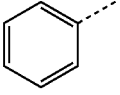 | 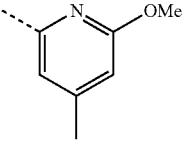 | CH | | 43 |

TABLE II-continued
| No. | Ar¹ | R² | Y | Other Substitutions* | Ref. Ex.** |
|---|---|---|---|---|---|
| 105 | 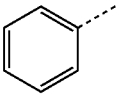 | 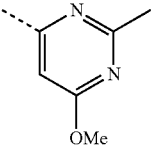 | CH | | 41 |
| 106 | 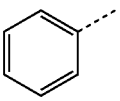 | 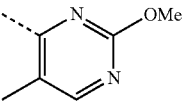 | CH | | 41 |
| 107 | 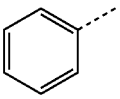 | 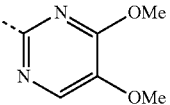 | CH | | 41 |
| 108 | 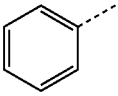 | 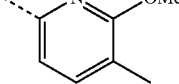 | CH | | 43 |
| 109 | 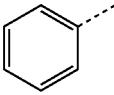 | 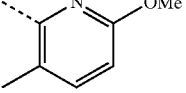 | CH | | 43 |
| 110 | 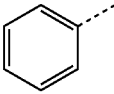 | 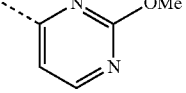 | CH | | 41 |
| 111 | 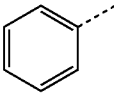 | 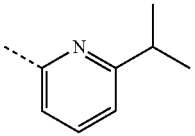 | CH | | 43 |
| 112 | 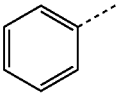 | 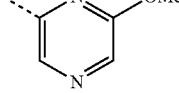 | CH | | 41 |
| 113 | 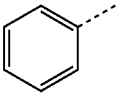 | 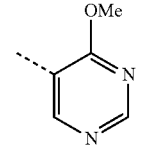 | CH | | 41 |
| 114 | 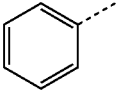 | 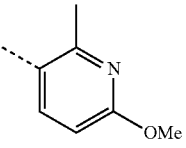 | CH | | 43 |
| 115 | 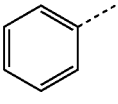 | 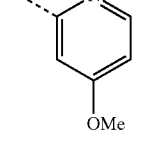 | CH | | 43 |

TABLE II-continued
| No. | Ar¹ | R² | Y | Other Substitutions* | Ref. Ex.** |
|---|---|---|---|---|---|
| 116 | 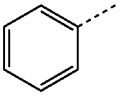 | 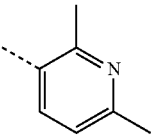 | CH | | 43 |
| 117 | 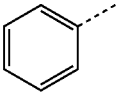 | 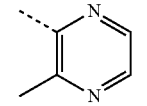 | CH | | 41 |
| 118 | 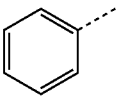 | 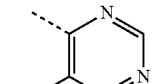 | CH | | 41 |
| 119 | 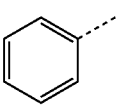 | 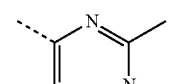 | CH | | 41 |
| 120 | 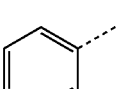 | 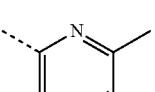 | CH | | 43 |
| 121 | 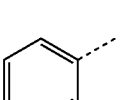 | 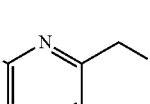 | CH | | 43 |
| 122 | 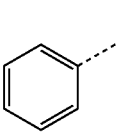 | 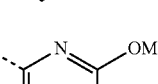 | CH | | 41 |
| 123 |  | 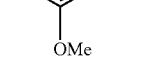 | CH | | 41 |
| 124 | 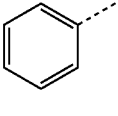 | 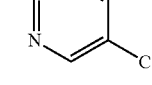 | CH | | 41 |
| 125 | 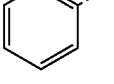 | 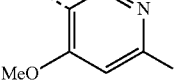 | CH | | 70 |
| 126 | 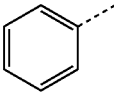 | 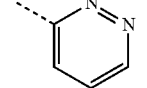 | CH | | 41 |

TABLE II-continued

| No. | Ar¹ | R² | Y | Other Substitutions* | Ref. Ex.** |
|---|---|---|---|---|---|
| 127 | 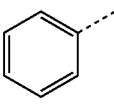 | 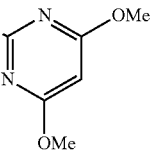 | CH | | 41 |
| 128 | 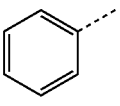 | 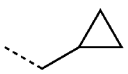 | CH | $R^{4a}$ = —$CH_3$ (*S configuration) | 42 |
| 129 | 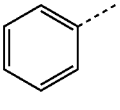 | 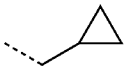 | CH | $R^{4a}$ = —$CH_3$ (*R configuration) | 42 |
| 130 | 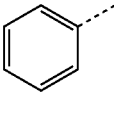 | 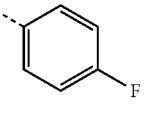 | CH | $R^{4a}$ = —$CH_3$ (*S configuration) | 43 |
| 131 | 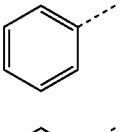 | 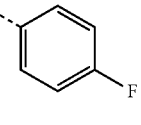 | CH | $R^{4a}$ = —$CH_3$ (*R configuration) | 43 |
| 132 | 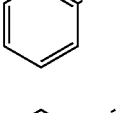 | 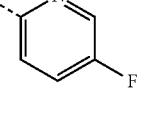 | CH | $R^{4a}$ = —$CH_3$ (*S configuration) | 43 |
| 133 | 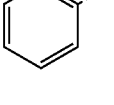 | 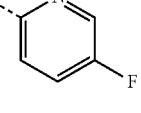 | CH | $R^{4a}$ = —$CH_3$ (*R configuration) | 43 |
| 134 | 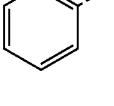 | 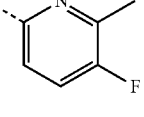 | CH | $R^{4a}$ = —$CH_3$ (*S configuration) | 43 |
| 135 | 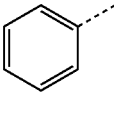 | 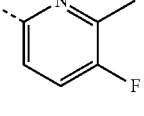 | CH | $R^{4a}$ = —$CH_3$ (*R configuration) | 43 |
| 136 | 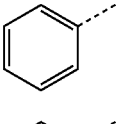 |  | CH | $R^{5a}$ = —$CH_3$ (S configuration) | 42 |
| 137 | 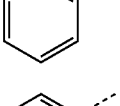 | 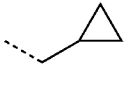 | CH | $R^{5a}$ = —$CH_3$ (R configuration) | 42 |
| 138 | 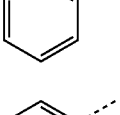 | 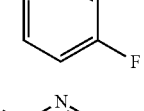 | CH | $R^{5a}$ = —$CH_3$ (S configuration) | 43 |
| 139 | 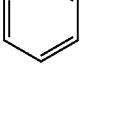 | 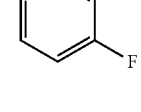 | CH | $R^{5a}$ = —$CH_3$ (S configuration) | 43 |

TABLE II-continued

| No. | Ar¹ | R² | Y | Other Substitutions* | Ref. Ex.** |
|---|---|---|---|---|---|
| 140 | 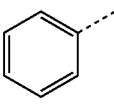 | 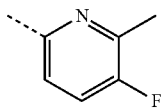 | CH | $R^{5a}$ = —CH₃ (R configuration) | 43 |
| 141 | 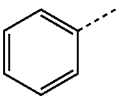 | 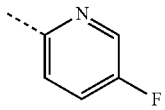 | CH | $R^{5a}$ = —CH₃ (R configuration) | 43 |
| 142 | 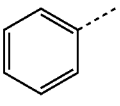 | 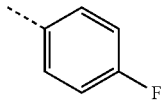 | CH | $R^{5a}$ = —CH₃ (R configuration) | 43 |
| 143 | 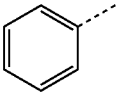 | 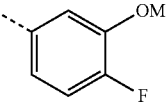 | CH | $R^{5a}$ = —CH₃ (R configuration) | 43 |
| 144 | 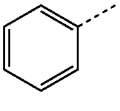 | 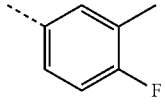 | CH | $R^{5a}$ = —CH₃ (R configuration) | 43 |
| 145 | 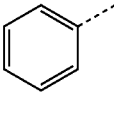 | 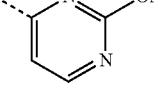 | CH | $R^{5a}$ = —CH₃ (R configuration) | 41 |
| 146 | 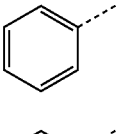 | 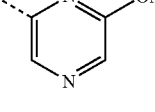 | CH | $R^{5a}$ = —CH₃ (R configuration) | 41 |
| 147 | 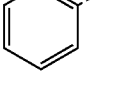 | 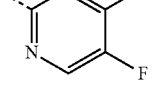 | CH | $R^{5a}$ = —CH₃ (R configuration) | 41 |
| 148 | 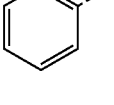 | 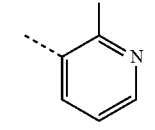 | CH | $R^{5a}$ = —CH₃ (R configuration) | 43 |
| 149 | 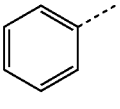 | 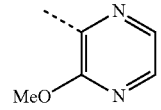 | CH | $R^{5a}$ = —CH₃ (R configuration) | 41 |
| 150 | 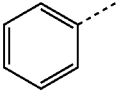 | 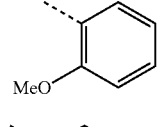 | CH | $R^{5a}$ = —CH₃ (R configuration) | 43 |
| 151 | 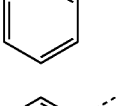 | 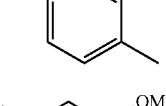 | CH | $R^{5a}$ = —CH₃ (R configuration) | 43 |
| 152 | 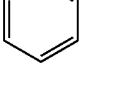 | 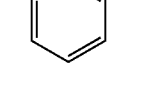 | CH | $R^{5a}$ = —CH₃ (R configuration) | 43 |

TABLE II-continued
| No. | Ar¹ | R² | Y | Other Substitutions* | Ref. Ex.** |
|---|---|---|---|---|---|
| 153 | 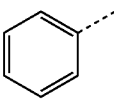 | 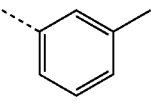 | CH | $R^{5a}$ = —CH₃ (R configuration) | 43 |
| 154 | 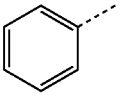 | 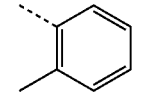 | CH | $R^{5a}$ = —CH₃ (R configuration) | 43 |
| 155 | 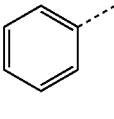 | 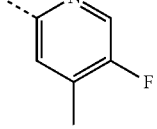 | CH | $R^{5a}$ = —CH₃ (R configuration) | 43 |
| 156 | 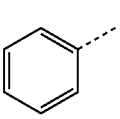 | 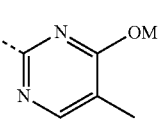 | CH | $R^{5a}$ = —CH₃ (R configuration) | 41 |
| 157 | 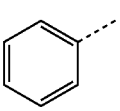 | 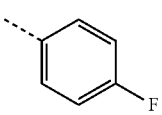 | CH | $R^{5a}$ = —CH₃ (S configuration) | 43 |
| 158 | 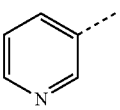 | 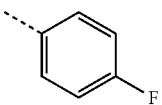 | CH | | 54 |
| 159 | 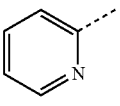 | 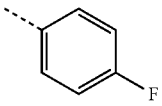 | CH | | 53 |
| 160 | 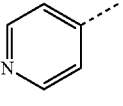 | 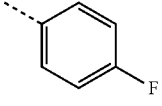 | CH | | 54 |
| 161 | 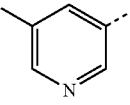 | 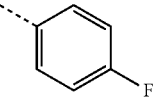 | CH | | 53 |
| 162 | 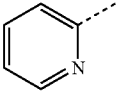 |  | CH | | 53 |
| 163 | 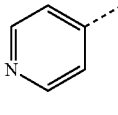 | 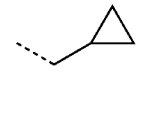 | CH | | 54 |
| 164 | 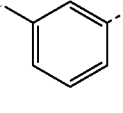 | 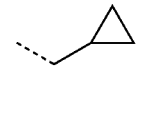 | CH | | 55 |
| 165 | 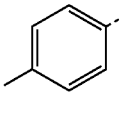 | 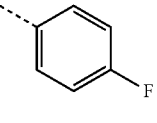 | CH | | 55 |

TABLE II-continued

| No. | Ar¹ | R² | Y | Other Substitutions* | Ref. Ex.** |
|---|---|---|---|---|---|
| 166 | 3-methylphenyl | 4-fluorophenyl | CH | | 55 |
| 167 | 4-fluorophenyl | cyclopropylmethyl | CH | | 55 |
| 168 | 3-methylphenyl | cyclopropylmethyl | CH | | 55 |
| 169 | 3-cyanophenyl | 4-fluorophenyl | CH | | 55 |
| 170 | pyridin-3-yl | cyclopropylmethyl | CH | | 54 |
| 171 | 5-fluoropyridin-3-yl | cyclopropylmethyl | CH | | 53 |
| 172 | pyridin-2-yl | 5-fluoropyridin-2-yl | CH | | 43 |
| 173 | 6-methylpyridin-2-yl | 4-fluorophenyl | CH | | 43 |
| 174 | 2-methylpyridin-4-yl | 4-fluorophenyl | CH | | 43 |
| 175 | 2,6-dimethylpyridin-4-yl | 4-fluorophenyl | CH | | 43 |
| 176 | pyridin-4-yl | 5-fluoropyridin-2-yl | CH | | 54 |
| 177 | 3-methylphenyl | 5-fluoropyridin-2-yl | CH | | 55 |

TABLE II-continued
| No. | Ar¹ | R² | Y | Other Substitutions* | Ref. Ex.** |
|---|---|---|---|---|---|
| 178 | 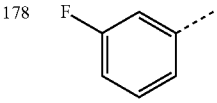 | 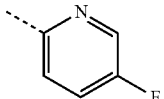 | CH | | 55 |
| 179 | 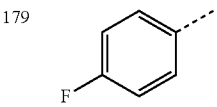 | 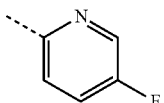 | CH | | 55 |
| 180 | 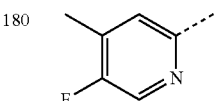 | 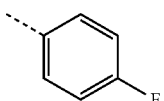 | CH | | 53 |
| 181 | 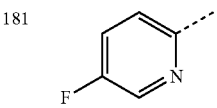 | 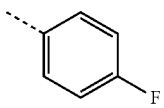 | CH | | 53 |
| 182 | 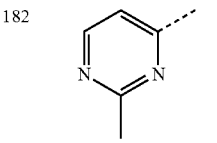 | 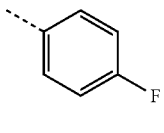 | CH | | 53 |
| 183 | 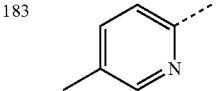 | 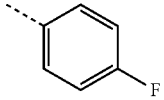 | CH | | 53 |
| 184 | 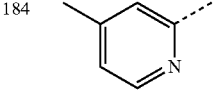 | 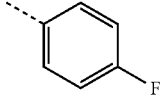 | CH | | 53 |
| 185 | 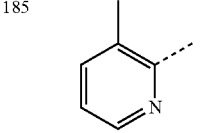 | 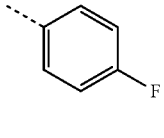 | CH | | 53 |
| 186 | 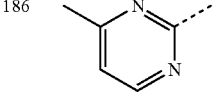 | 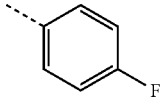 | CH | | 53 |
| 187 | 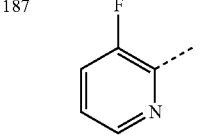 | 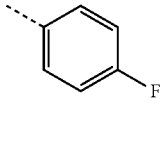 | CH | | 53 |
| 188 | 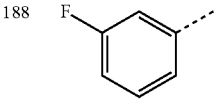 | 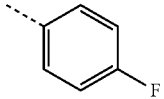 | CH | | 55 |
| 189 | 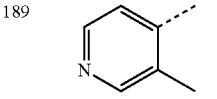 | 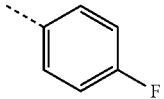 | CH | | 53 |

TABLE II-continued
| No. | Ar¹ | R² | Y | Other Substitutions* | Ref. Ex.** |
|---|---|---|---|---|---|
| 190 | 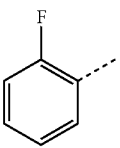 | 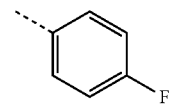 | CH | | 55 |
| 191 | 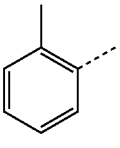 | 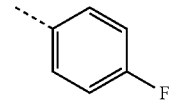 | CH | | 55 |
| 192 | 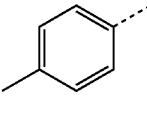 | 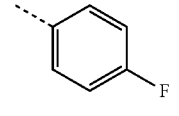 | CH | | 55 |
| 193 | 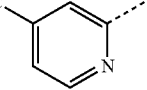 | 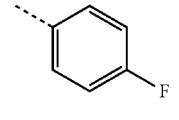 | CH | | 53 |
| 194 | 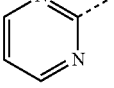 | 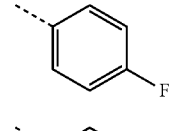 | CH | | 53 |
| 195 | 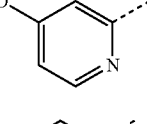 | 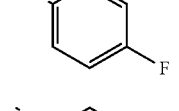 | CH | | 53 |
| 196 | 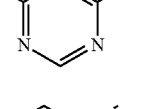 | 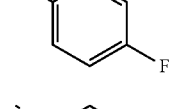 | CH | | 53 |
| 197 | 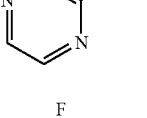 | 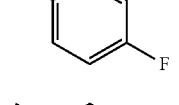 | CH | | 53 |
| 198 | 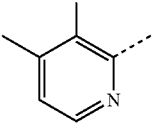 | 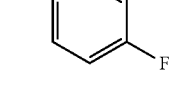 | CH | | 53 |
| 199 | 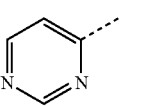 | 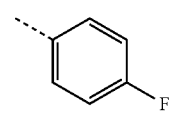 | CH | | 70 |
| 200 | 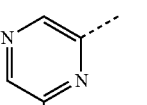 | 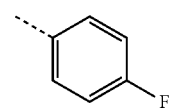 | CH | | 53 |
| 201 | 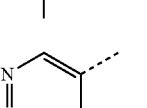 | 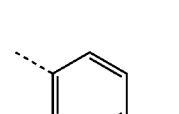 | CH | | 70 |

TABLE II-continued
| No. | Ar¹ | R² | Y | Other Substitutions* | Ref. Ex.** |
|---|---|---|---|---|---|
| 202 | 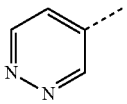 | 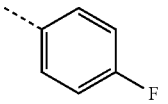 | CH | | 70 |
| 203 | 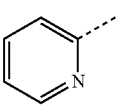 | 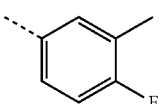 | CH | | 43 |
| 204 | 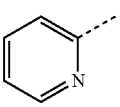 | 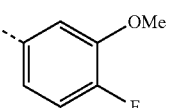 | CH | | 43 |
| 205 | 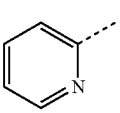 | 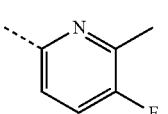 | CH | | 43 |
| 206 | 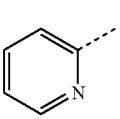 | 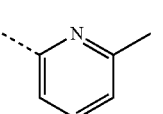 | CH | | 43 |
| 207 | 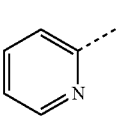 | 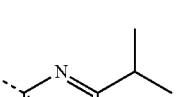 | CH | | 43 |
| 208 | 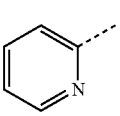 | 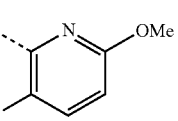 | CH | | 43 |
| 209 | 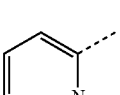 | 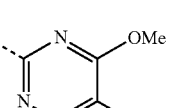 | CH | | 41 |
| 210 | 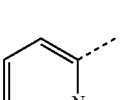 | 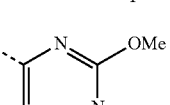 | CH | | 41 |
| 211 | 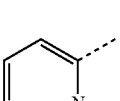 | 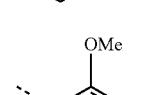 | CH | | 43 |
| 212 | 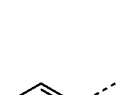 | 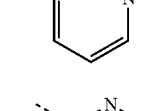 | CH | | 43 |
| 213 | 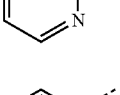 | 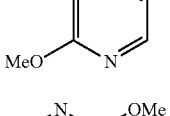 | CH | | 41 |

TABLE II-continued
| No. | Ar¹ | R² | Y | Other Substitutions* | Ref. Ex.** |
|---|---|---|---|---|---|
| 214 | 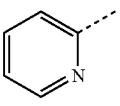 | 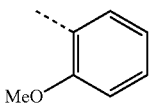 | CH | | 43 |
| 215 | 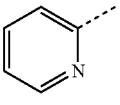 | 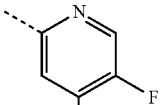 | CH | | 43 |
| 216 | 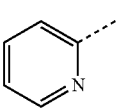 | 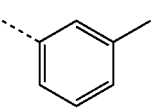 | CH | | 43 |
| 217 | 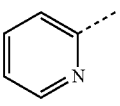 | 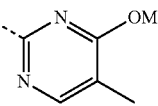 | CH | | 41 |
| 218 | 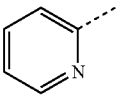 | 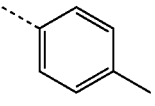 | CH | | 43 |
| 219 | 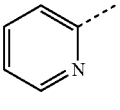 | 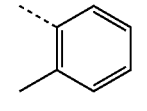 | CH | | 43 |
| 220 | 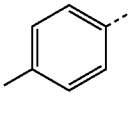 | 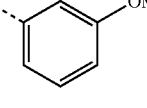 | CH | | 43 |
| 221 | 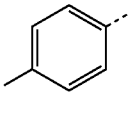 | 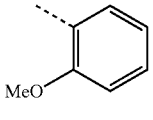 | CH | | 43 |
| 222 | 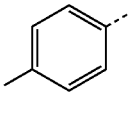 | 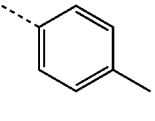 | CH | | 43 |
| 223 | 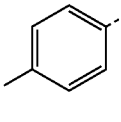 | 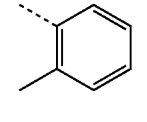 | CH | | 43 |
| 224 | 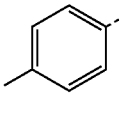 | 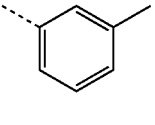 | CH | | 43 |
| 225 | 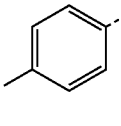 | 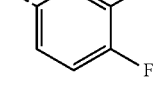 | CH | | 43 |
| 226 | 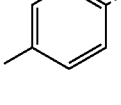 | 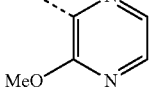 | CH | | 43 |

TABLE II-continued

| No. | Ar¹ | R² | Y | Other Substitutions* | Ref. Ex.** |
|---|---|---|---|---|---|
| 227 | 4-F-phenyl | 2-OMe-pyrimidin-4-yl | CH | | 41 |
| 228 | 4-F-phenyl | 3-OMe-4-F-phenyl | CH | | 43 |
| 229 | 4-F-phenyl | 2-OMe-pyridin-3-yl | CH | | 43 |
| 230 | 4-F-phenyl | 4-OMe-5-Me-pyrimidin-2-yl | CH | | 41 |
| 231 | 4-F-phenyl | 6-OMe-pyrazin-2-yl | CH | | 41 |
| 232 | 4-F-phenyl | 5-F-4-Me-pyridin-2-yl | CH | | 43 |
| 233 | 3-NC-phenyl | 5-F-pyridin-2-yl | CH | | 55 |
| 234 | 4-F-phenyl | 4-F-phenyl | CH | R⁴ᵃ = rac-CH₃ | 43 |
| 235 | 4-F-phenyl | 3-F-phenyl | CH | R⁴ᵃ = rac-CH₃ | 43 |
| 236 | 4-F-phenyl | 3-F-6-Me-pyridin-2-yl | CH | R⁴ᵃ = rac-CH₃ | 43 |
| 237 | 4-F-phenyl | 5-F-pyridin-2-yl | CH | R⁴ᵃ = rac-CH₃ | 43 |
| 238 | 4-F-phenyl | 4-F-phenyl | CH | R⁴ᵃ = —CH₃ (*S configuration) | 43 |

TABLE II-continued

| No. | Ar¹ | R² | Y | Other Substitutions* | Ref. Ex.** |
|---|---|---|---|---|---|
| 239 | 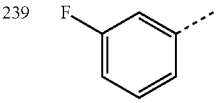 | 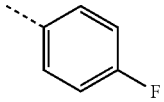 | CH | $R^{4a}$ = —CH₃ (*S configuration) | 43 |
| 240 | 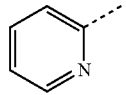 | 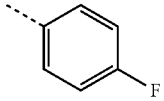 | CH | $R^{4a}$ = —CH₃ (*R configuration) | 43 |
| 241 | 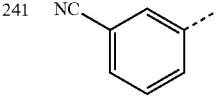 | 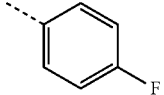 | CH | $R^{4a}$ = —CH₃ (*R configuration) | 55 |
| 242 | 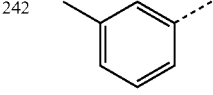 | 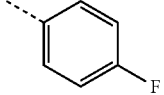 | CH | $R^{4a}$ = —CH₃ (*R configuration) | 55 |
| 243 | 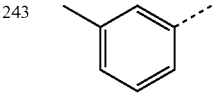 | 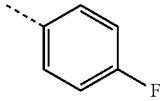 | CH | $R^{5a}$ = —CH₃ (R configuration) | 55 |
| 244 | 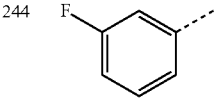 | 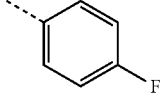 | CH | $R^{5a}$ = —CH₃ (R configuration) | 55 |
| 245 | 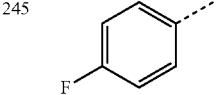 | 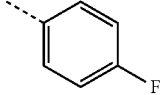 | CH | $R^{5a}$ = —CH₃ (R configuration) | 55 |
| 246 | 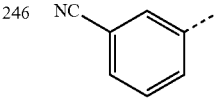 | 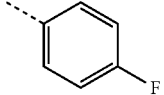 | CH | $R^{5a}$ = —CH₃ (R configuration) | 55 |
| 247 | 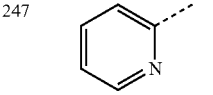 | 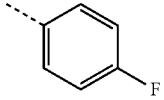 | CH | $R^{5a}$ = —CH₃ (R configuration) | 53 |
| 248 | 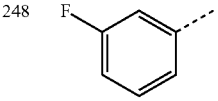 | H | CH | | 25 |
| 249 | 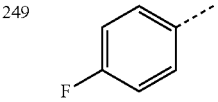 | H | CH | | 25 |
| 250 | 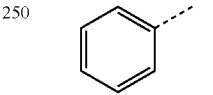 | H | CH | $R^{4a}$ = rac-CH₃ | 11 |
| 251 | 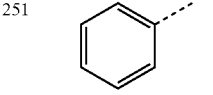 | H | CH | $R^{5a}$ = rac-CH₃ | 8 |

TABLE II-continued
| No. | Ar¹ | R² | Y | Other Substitutions* | Ref. Ex.** |
|---|---|---|---|---|---|
| 252 | 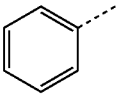 | H | CH | $R^{4a} = CH_3$ (*R configuration) | 12 |
| 253 | 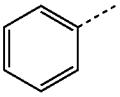 | H | CH | $R^{4a} = —CH_3$ (*S configuration) | 13 |
| 254 | 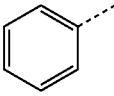 | H | CH | $R^{5a} = —CH_3$ (R configuration) | 9 |
| 255 | 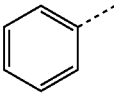 | H | CH | $R^{5a} = —CH_3$ (S configuration) | 10 |
| 256 | 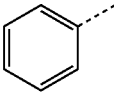 | H | CH | $R^{1a} = rac\text{-}CH_3$ | 24 |
| 257 | 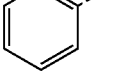 |  | CH | $R^{1a} = rac\text{-}CH_3$ | 42 |
| 258 | 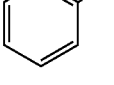 | 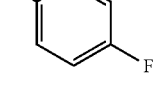 | CH | $R^{1a} = rac\text{-}CH_3$ | 43 |
| 259 | 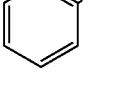 | 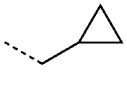 | CCl | | 42 |
| 260 | 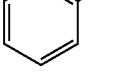 | 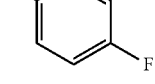 | CCl | | 43 |
| 261 | 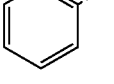 | 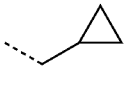 | CCH₃ | | 42 |
| 262 | 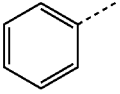 | 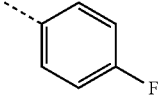 | CCH₃ | | 43 |
| 263 | 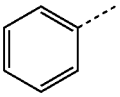 | 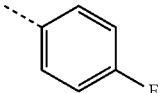 | CH | $R^{4a} = rac\text{-}CH_2OH$ | 34 |
| 264 | 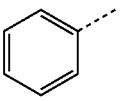 | 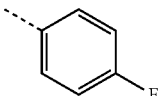 | CH | $R^{4a} = rac\text{-}CH_2F$ | 36 |

TABLE II-continued
| No. | Ar¹ | R² | Y | Other Substitutions* | Ref. Ex.** |
|---|---|---|---|---|---|
| 265 | 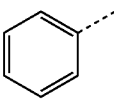 | 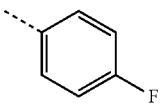 | CH | $R^{5a}$ = —CH$_2$OH (R configuration) | 34 |
| 266 | 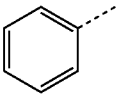 | 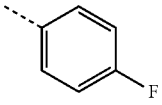 | CH | $R^{5a}$ = —CH$_2$F (R configuration) | 36 |
| 267 | 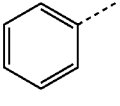 | 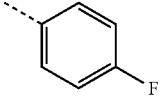 | CH | $R^{5a}$ = —CH$_2$OCH$_3$ (R configuration) | 35 |
| 268 | 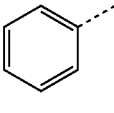 | 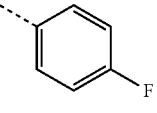 | CH | $R^{5a}$ = —CH$_2$OH (S configuration) | 34 |
| 269 | 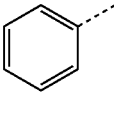 | 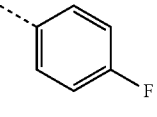 | CH | $R^{5a}$ = —CH$_2$F (S configuration) | 36 |
| 270 | 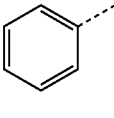 | 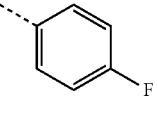 | CH | $R^{5a}$ = —CH$_2$OCH$_3$ (S configuration) | 35 |
| 271 | 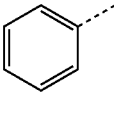 | 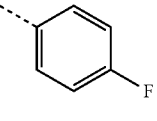 | CH | $R^{4a}$ = rac-F | 28 |
| 272 | 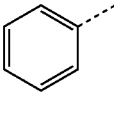 | 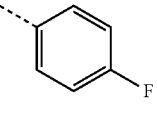 | CH | $R^{4a}$ = —F (*R configuration) | 28 |
| 273 | 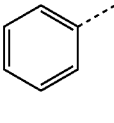 | 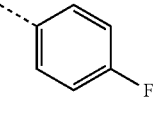 | CH | $R^{4a}$ = —F (*S configuration) | 28 |
| 274 | 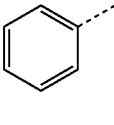 | 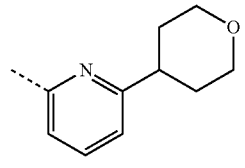 | CH | | 73 |
| 275 | 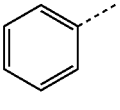 | 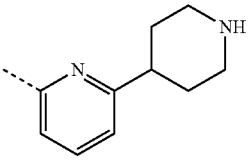 | CH | | 74 |
| 276 | 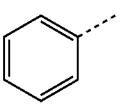 | 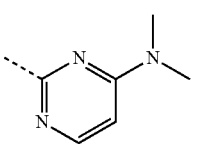 | CH | | 41 |

TABLE II-continued
| No. | Ar¹ | R² | Y | Other Substitutions* | Ref. Ex.** |
|---|---|---|---|---|---|
| 277 | 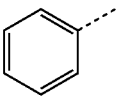 | 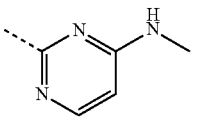 | CH | | 41 |
| 278 | 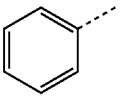 | 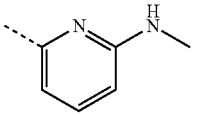 | CH | | 43 |
| 279 | 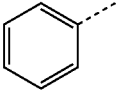 | 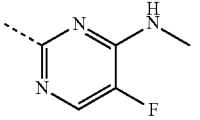 | CH | | 41 |
| 280 | 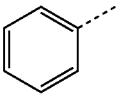 | 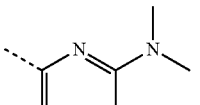 | CH | | 41 |
| 281 | 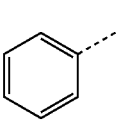 | 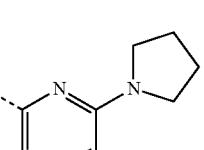 | CH | | 43 |
| 282 | 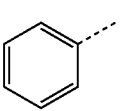 | 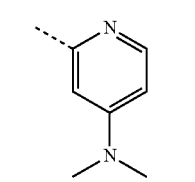 | CH | | 43 |
| 283 | 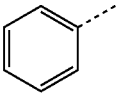 | 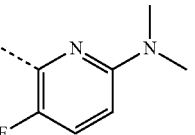 | CH | | 43 |
| 284 | 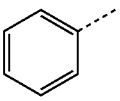 | 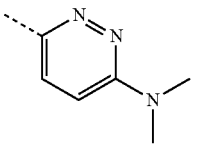 | CH | | 41 |
| 285 | 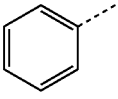 | 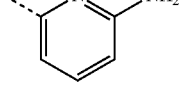 | CH | | 43 |
| 286 | 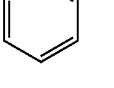 | 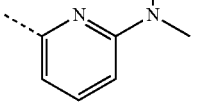 | CH | | 43 |

TABLE II-continued
| No. | Ar¹ | R² | Y | Other Substitutions* | Ref. Ex.** |
|---|---|---|---|---|---|
| 287 | 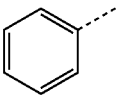 | 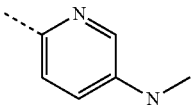 | CH | | 43 |
| 288 | 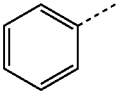 | 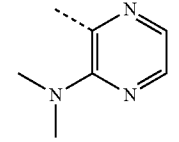 | CH | | 43 |
| 289 | 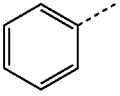 | 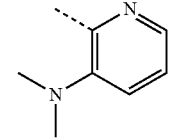 | CH | | 43 |
| 290 | 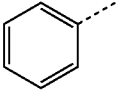 | 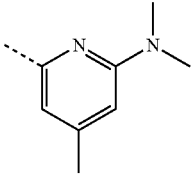 | CH | | 43 |
| 291 | 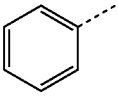 | 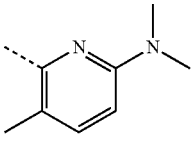 | CH | | 43 |
| 292 | 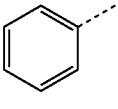 | 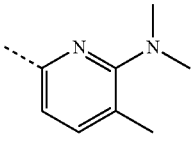 | CH | | 43 |
| 293 | 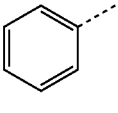 | 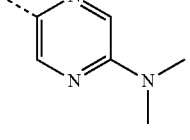 | CH | | 41 |
| 294 | 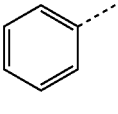 | 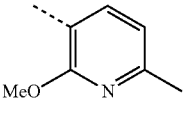 | CH | | 43 |
| 295 | 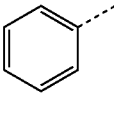 | 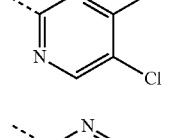 | CH | | 41 |
| 296 | 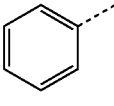 | 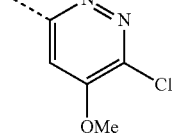 | CH | | 41 |

TABLE II-continued
| No. | Ar¹ | R² | Y | Other Substitutions* | Ref. Ex.** |
|---|---|---|---|---|---|
| 297 | 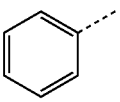 | 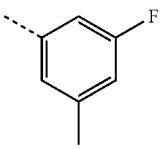 | CH | | 43 |
| 298 | 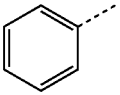 | 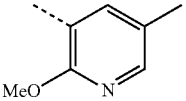 | CH | | 43 |
| 299 | 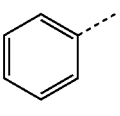 | 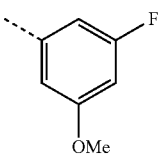 | CH | | 43 |
| 300 | 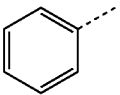 | 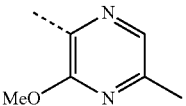 | CH | | 43 |
| 301 | 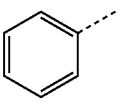 | 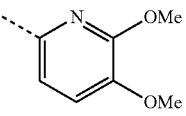 | CH | | 43 |
| 302 | 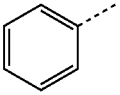 | 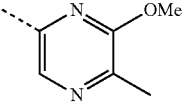 | CH | | 43 |
| 303 | 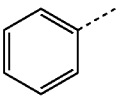 | 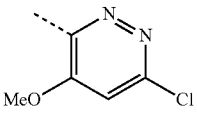 | CH | | 41 |
| 304 | 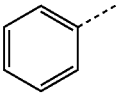 | 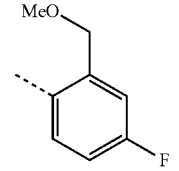 | CH | | 43 |
| 305 | 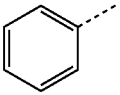 | 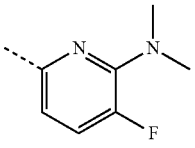 | CH | | 43 |
| 306 | 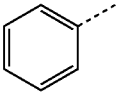 | 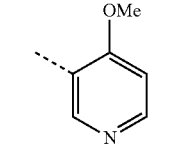 | CH | | 43 |

TABLE II-continued
| No. | Ar¹ | R² | Y | Other Substitutions* | Ref. Ex.** |
|---|---|---|---|---|---|
| 307 | 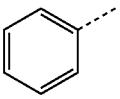 | 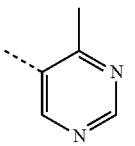 | CH | | 43 |
| 308 | 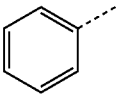 | 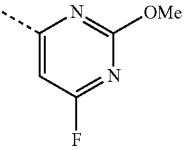 | CH | | 41 |
| 309 | 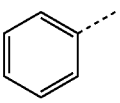 | 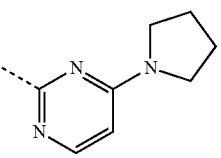 | CH | | 41 |
| 310 | 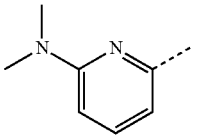 | 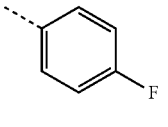 | CH | | 53 |
| 311 | 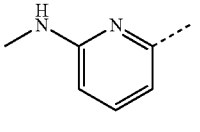 | 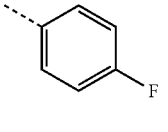 | CH | | 53 |
| 312 | 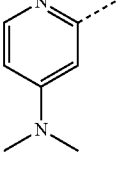 | 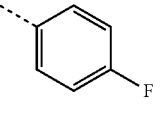 | CH | | 53 |
| 313 | 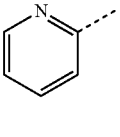 | 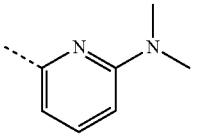 | CH | | 43 |
| 314 | 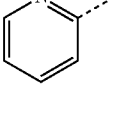 | 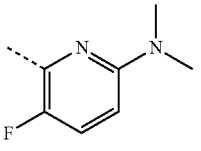 | CH | | 43 |
| 315 | 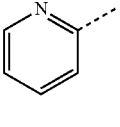 | 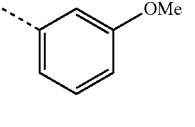 | CH | | 43 |
| 316 | 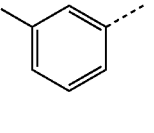 | 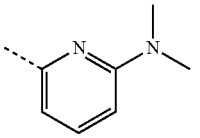 | CH | | 43 |

TABLE II-continued
| No. | Ar¹ | R² | Y | Other Substitutions* | Ref. Ex.** |
|---|---|---|---|---|---|
| 317 | 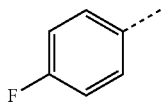 | 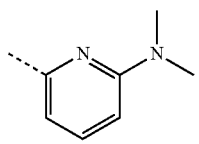 | CH | | 43 |
| 318 | 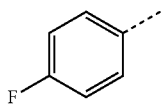 | 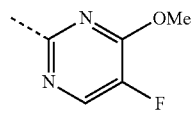 | CH | | 41 |
| 319 | 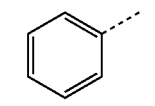 | 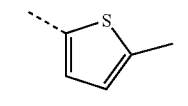 | CH | | 43 |
| 320 | 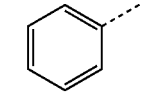 | 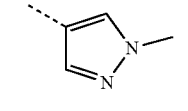 | CH | | 43 |
| 321 | 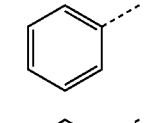 | 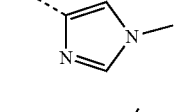 | CH | | 43 |
| 322 |  | 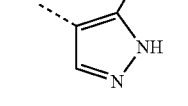 | CH | | 43 |
| 323 | 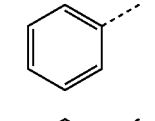 | 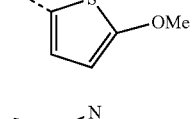 | CH | | 43 |
| 324 | 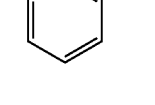 | 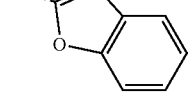 | CH | | 41 |
| 325 | 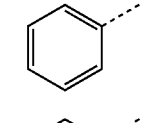 | H | CH | $R^{4a}$ = rac-OH | 27 |
| 326 | 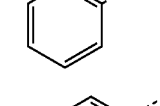 | H | CH | $R^{4a} = R^{4b}$ = —CH$_3$ | 14 |
| 327 | 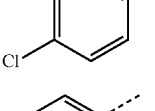 | 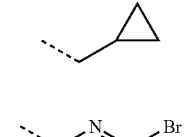 | CH | | 43 |
| 328 | 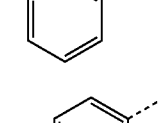 | 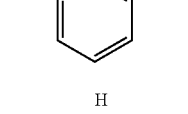 | CH | | 44 |
| 329 | 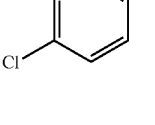 | H | CH | | 84 |

TABLE II-continued
| No. | Ar¹ | R² | Y | Other Substitutions* | Ref. Ex.** |
|---|---|---|---|---|---|
| 330 | 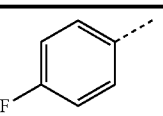 | H | CH | R$^{4a}$ = rac-CH$_3$ | 11 |
| 331 | 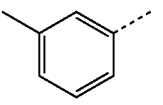 | H | CH | | 6 |
| 332 | 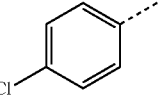 | 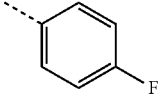 | CH | | 43 |
| 333 | 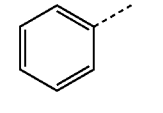 | H | CCl | | 78 |
| 334 | 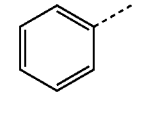 | 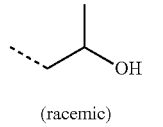 (racemic) | CH | | 38 |
| 335 | 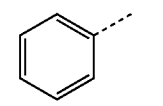 | H | CCH$_3$ | | 83 |
| 336 | 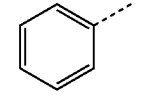 | H | CH | R$^{4a}$ = rac-F | 28 |
| 337 | 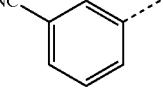 | H | CH | | 62 |
| 338 | 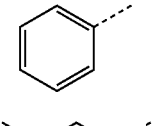 | H | CH | R$^{5a}$ = —CH$_2$OH (R configuration) | 31 |
| 339 | 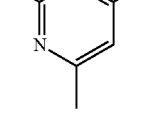 | H | CH | | 62 |
| 340 | 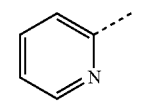 | H | CH | | 62 |
| 341 | 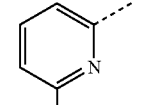 | H | CH | | 62 |
| 342 | 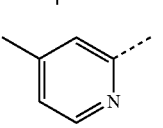 | H | CH | | 62 |

TABLE II-continued
| No. | Ar¹ | R² | Y | Other Substitutions* | Ref. Ex.** |
|-----|-----|-----|-----|-----|-----|
| 343 | 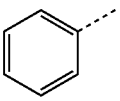 | H | CH | $R^{5a}$ = —CH$_2$OH (S configuration) | 31 |
| 344 | 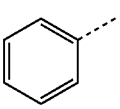 | H | CH | $R^{4a}$ = rac-OCH$_3$ | 27 |
| 345 | 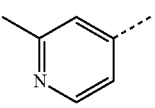 | H | CH | | 62 |
| 346 | 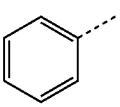 | 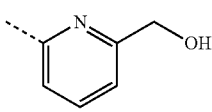 | CH | | 43 |
| 347 | 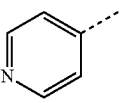 | H | CH | | 62 |
| 348 | 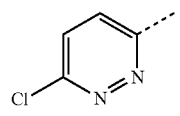 | 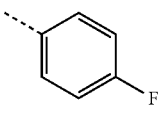 | CH | | 53 |
| 349 | 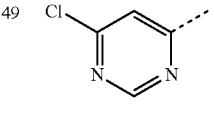 | 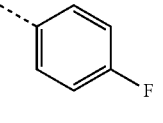 | CH | | 53 |
| 350 | 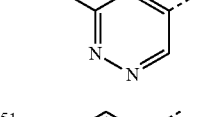 | 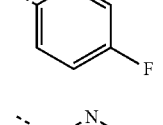 | CH | | 53 |
| 351 | 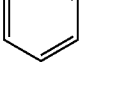 | 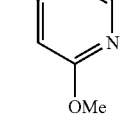 | CH | | 41 |
| 352 | 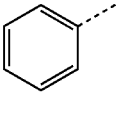 | 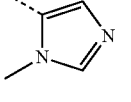 | CH | | 43 |
| 353 | 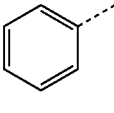 | 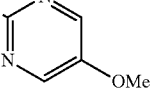 | CH | | 41 |
| 354 | 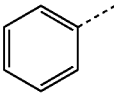 | 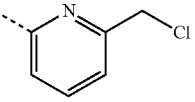 | CH | | 71 |
| 355 | 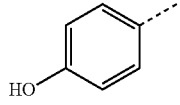 | 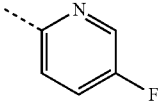 | CH | | 69 |

TABLE II-continued
| No. | Ar¹ | R² | Y | Other Substitutions* | Ref. Ex.** |
|---|---|---|---|---|---|
| 356 |  | 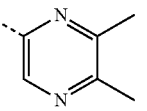 | CH | | 43 |
| 357 |  | 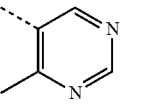 | CH | | 41 |
| 358 |  | 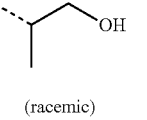<br>(racemic) | CH | | 38 |
| 359 |  | 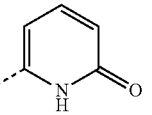 | CH | | 43 |
| 360 |  | 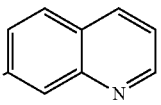 | CH | | 43 |
| 361 |  | 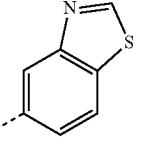 | CH | | 43 |
| 362 |  | 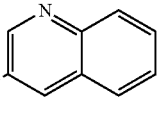 | CH | | 43 |
| 363 |  | 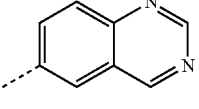 | CH | | 43 |
| 364 |  | 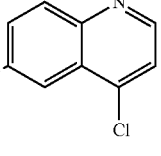 | CH | | 43 |
| 365 |  | 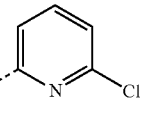 | CH | | 43 |
| 366 |  | 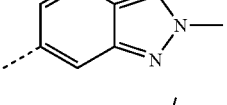 | CH | | 43 |
| 367 |  | 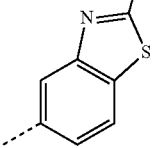 | CH | | 43 |

TABLE II-continued
| No. | Ar¹ | R² | Y | Other Substitutions* | Ref. Ex.** |
|---|---|---|---|---|---|
| 368 | 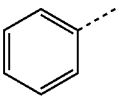 | 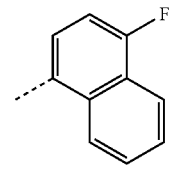 | CH | | 43 |
| 369 | 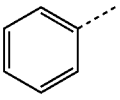 | 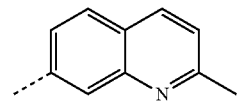 | CH | | 43 |
| 370 | 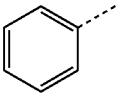 | 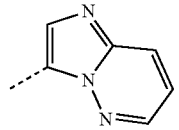 | CH | | 43 |
| 371 | 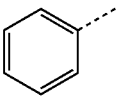 | 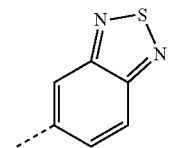 | CH | | 43 |
| 372 | 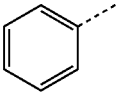 | 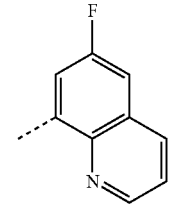 | CH | | 43 |
| 373 | 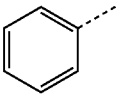 | 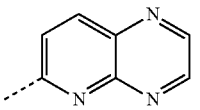 | CH | | 43 |
| 374 | 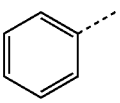 | 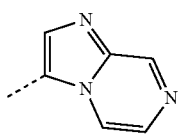 | CH | | 43 |
| 375 | 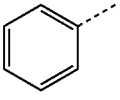 | 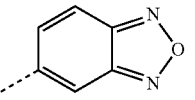 | CH | | 43 |
| 376 | 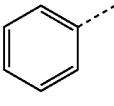 | 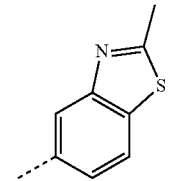 | CH | $R^{4a}$ = —CH₃ (*S configuration) | 43 |

TABLE II-continued

| No. | Ar¹ | R² | Y | Other Substitutions* | Ref. Ex.** |
|---|---|---|---|---|---|
| 377 |  | 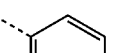 | CH | | 69 |

*The designations "*R" and "*S" indicates that an enantiomerically pure compound was isolated with "R" and "S" arbitrarily assigned to distinguish the enantiomers; absolute configuration was not determined in the examples designated with *S and *R.
**Reference Example 6 is 2-phenoxymethyl-6,7-dihydro-5H-pyrazolo[1,5-a]pyrazin-4-one; Reference Example 8 is (rac)-6-methyl-2-phenoxymethyl-6,7-dihydro-5H-pyrazolo[1,5-a]pyrazin-4-one; Reference Example 10 is (S)-6-methyl-2-phenoxymethyl-6,7-dihydro-5H-pyrazolo[1,5-a]pyrazin-4-one; Reference Example 11 is rac-7-methyl-2-phenoxymethyl-6,7-dihydro-5H-pyrazolo[1,5-a]pyrazin-4-one; Reference Example 12 is (R)-7-methyl-2-phenoxymethyl-6,7-dihydro-5H-pyrazolo[1,5-a]pyrazin-4-one; Reference Example 13 is (S)-7-methyl-2-phenoxymethyl-6,7-dihydro-5H-pyrazolo[1,5-a]pyrazin-4-one; Reference Example 14 is 7,7-dimethyl-2-phenoxymethyl-6,7-dihydro-5H-pyrazolo[1,5-a]pyrazin-4-one; Reference Example 21 is 7-(4-fluoro-phenyl)-2-phenoxymethyl-6,7-dihydro-5H-[1,2,4]triazolo[1,5-a]pyrazin-8-one; Reference Example 24 is (rac)-2-(1-Phenoxy-ethyl)-6,7-dihydro-5H-pyrazolo[1,5-a]pyrazin-4-one; Reference Example 25 2-(4-fluoro-phenoxymethyl)-6,7-dihydro-5H-pyrazolo[1,5-a]pyrazin-4-one; Reference Example 27 is (rac)-7-Hydroxy-2-phenoxymethyl-6,7-dihydro-5H-pyrazolo[1,5-a]pyrazin-4-one; Reference Example 28 is (rac)-7-Fluoro-2-phenoxymethyl-6,7-dihydro-5H-pyrazolo[1,5-a]pyrazin-4-one; Reference Example 31 is (S)-6-Hydroxymethyl-2-phenoxymethyl-6,7-dihydro-5H-pyrazolo[1,5-a]pyrazin-4-one; Reference Example 34 is (S)-5-(4-fluoro-phenyl)-6-hydroxymethyl-2-phenoxymethyl-6,7-dihydro-5H-pyrazolo[1,5-a]pyrazin-4-one; Reference Example 35 is (S)-5-(4-Fluoro-phenyl)-6-methoxymethyl-2-phenoxymethyl-6,7-dihydro-5H-pyrazolo[1,5-a]pyrazin-4-one; Reference Example 36 is (S)-6-Fluoromethyl-5-(4-fluoro-phenyl)-2-phenoxymethyl-6,7-dihydro-5H-pyrazolo[1,5-a]pyrazin-4-one; Reference Example 38 is (rac)-5-(2-Hydroxy-propyl)-2-phenoxymethyl-6,7-dihydro-5H-pyrazolo[1,5-a]pyrazin-4-one; Reference Example 39 is (rac)-5-(2-methoxy-propyl)-2-phenoxymethyl-6,7-dihydro-5H-pyrazolo[1,5-a]pyrazin-4-one; Reference Example 40 is (rac)-5-(2-Fluoro-propyl)-2-phenoxymethyl-6,7-dihydro-5H-pyrazolo[1,5-a]pyrazin-4-one; Reference Example 41 is 5-(5-Fluoro-4-methoxy-pyrimidin-2-yl)-2-phenoxymethyl-6,7-dihydro-5H-pyrazolo[1,5-a]pyrazin-4-one; Reference Example 42 is 5-methyl-2-phenoxymethyl-6,7-dihydro-5H-pyrazolo[1,5-a]pyrazin-4-one; Reference Example 43 is 5-(2,4-difluoro-phenyl)-2-phenoxymethyl-6,7-dihydro-5H-pyrazolo[1,5-a]pyrazin-4-one; Reference Example 45 is 5-(6-Cyclopropyl-pyridin-2-yl)-2-phenoxymethyl-6,7-dihydro-5H-pyrazolo[1,5-a]pyrazin-4-one; Reference Example 46 is 5-Cyclopropyl-2-phenoxymethyl-6,7-dihydro-5H-pyrazolo[1,5-a]pyrazin-4-one; Reference Example 53 is 5-(4-Fluoro-phenyl)-2-(pyridin-2-yloxymethyl)-6,7-dihydro-5H-pyrazolo[1,5-a]pyrazin-4-one; Reference Example 54 is 5-(4-Fluoro-phenyl)-2-(pyridin-3-yloxymethyl)-6,7-dihydro-5H-pyrazolo[1,5-a]pyrazin-4-one; Reference Example 55 is 5-(4-Fluoro-phenyl)-2-(p-tolyloxymethyl)-6,7-dihydro-5H-pyrazolo[1,5-a]pyrazin-4-one; Reference Example 62 is 2-(Pyridin-2-yloxymethyl)-6,7-dihydro-5H-pyrazolo[1,5-a]pyrazin-4-one; Reference Example 64 is (R)-5-(1-cyclopropyl-ethyl)-2-phenoxymethyl-6,7-dihydro-5H-pyrazolo[1,5-a]pyrazin-4-one; Reference Example 67 is (R)-2-Phenoxymethyl-5-(1,2,2-trimethyl-propyl)-6,7-dihydro-5H-pyrazolo[1,5-a]pyrazin-4-one; Reference Example 69 is 5-(5-Fluoro-pyridin-2-yl)-2-(4-hydroxy-phenoxymethyl)-6,7-dihydro-5H-pyrazolo[1,5-a]pyrazin-4-one; Reference Example 70 is 5-(4-Fluoro-phenyl)-2-(pyridazin-3-yloxymethyl)-6,7-dihydro-5H-pyrazolo[1,5-a]pyrazin-4-one; Reference Example 71 is 5-(6-Chloromethyl-pyridin-2-yl)-2-phenoxymethyl-6,7-dihydro-5H-pyrazolo[1,5-a]pyrazin-4-one; Reference Example 73 is 6-(4-Oxo-2-phenoxymethyl-6,7-dihydro-4H-pyrazolo[1,5-a]pyrazin-5-yl)-3',4',5',6'-tetrahydro-2'H-[2,4']bipyridinyl-1'-carboxylic acid tert-butyl ester; Reference Example 74 is 5-(1',2',3',4',5',6'-Hexahydro-[2,4']bipyridinyl-6-yl)-2-phenoxymethyl-6,7-dihydro-5H-pyrazolo[1,5-a]pyrazin-4-one; Reference Example 78 is 3-Chloro-2-phenoxymethyl-6,7-dihydro-5H-pyrazolo[1,5-a]pyrazin-4-one; Reference Example 83 is 3-Methyl-2-phenoxymethyl-6,7-dihydro-5H-pyrazolo[1,5-a]pyrazin-4-one; and Reference Example 84 is 2-(4-Chloro-phenoxymethyl)-6,7-dihydro-5H-pyrazolo[1,5-a]pyrazin-4-one.

TABLE III

| No. | Ar¹ | R² | Y | Reference Example* |
|---|---|---|---|---|
| 4 |  | 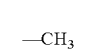 | N | 20 |
| 37 |  | —CH₃ | CH | 42 |
| 378 |  | —H | CH | 15 |

*Reference Example 15 is 2-phenoxymethyl-5H-pyrazolo[1,5-a]pyrazin-4-one; Reference Example 20 is 7-(4-fluoro-phenyl)-2-phenoxymethyl-7H-[1,2,4]triazolo[1,5-a]pyrazin-8-one; and Reference Example 42 is 5-methyl-2-phenoxymethyl-6,7-dihydro-5H-pyrazolo[1,5-a]pyrazin-4-one.

TABLE IV

| No. | M.p. (° C.) | [M + H]⁺ | $R_t$ | LCMS Method |
|---|---|---|---|---|
| 1 | 169.7 | 244 | 1.98 | 6 |
| 2 | n.d. | 258 | 2.25 | 1 |
| 3 | 181 | 356 | 2.76 | 3 |
| 4 | n.d. | 337 | 1.71 | 4 |
| 5 | n.d. | 337 | 1.71 | 4 |
| 6 | 209.7 | 338 | 2.33 | 2 |
| 7 | >300 | 356 | 2.55 | 5 |
| 8 | 155 | 338 | 2.44 | 5 |
| 9 | 154.7 | 338 | 2.35 | 5 |
| 10 | 129.7 | 335 | 3.38 | 1 |
| 11 | 135.3 | 339 | 3.32 | 1 |
| 12 | 140.4 | 321 | 2.08 | 5 |
| 13 | 153.6 | 321 | 1.67 | 5 |
| 14 | 271.3 | 321 | 1.77 | 5 |
| 15 | >300 | 339 | 1.97 | 5 |
| 16 | 183.4 | 335 | 2.38 | 5 |
| 17 | 131.3 | 335 | 2.37 | 5 |
| 18 | 129.8 | 352 | 2.52 | 5 |
| 19 | 99.5 | 352 | 2.72 | 5 |
| 20 | 133.3 | 366 | 2.99 | 5 |
| 21 | 62.5 | 298 | 2.11 | 5 |
| 22 | 155.3 | 335 | 1.93 | 5 |
| 23 | >300 | 335 | 1.85 | 5 |
| 24 | 132.1 | 326 | 2.44 | 5 |
| 25 | >300 | 286 | 2.12 | 5 |
| 26 | >300 | 300 | 2.50 | 5 |
| 27 | >300 | 312 | 2.68 | 5 |
| 28 | 180.2 | 334 | 2.43 | 5 |
| 29 | n.d. | 339 | 1.90 | 5 |
| 30 | n.d. | 335 | 1.99 | 5 |
| 31 | 240 | 322 | 1.54 | 5 |
| 32 | >300 | 335 | 1.78 | 5 |
| 33 | 283.4 | 336 | 1.63 | 5 |
| 34 | 155.9 | 353 | 2.93 | 5 |
| 35 | n.d. | 244 | 1.98 | 6 |
| 36 | n.d. | n.d. | n.d. | n.d. |
| 37 | n.d. | 256 | 1.56 | 5 |
| 38 | n.d. | 312 | 2.54 | 7 |
| 39 | n.d. | 328 | 3.67 | 10 |

TABLE IV-continued

| No. | M.p. (° C.) | [M + H]+ | R_t | LCMS Method |
|---|---|---|---|---|
| 40 | n.d. | 316 | 2.01 | 7 |
| 41 | n.d. | 312 | 2.53 | 7 |
| 42 | 138.0 | 328 | 2.96 | 7 |
| 43 | 71.6 | 316 | 2.00 | 7 |
| 44 | 83.0 | 304 | 2.07 | 7 |
| 45 | 68.9 | 304 | 2.00 | 7 |
| 46 | n.d. | 300 | 2.54 | 7 |
| 47 | 145.8 | 350 | 2.48 | 7 |
| 48 | >300 | 334 | 2.58 | 7 |
| 49 | >300 | 334 | 2.58 | 7 |
| 50 | >300 | 350 | 2.50 | 7 |
| 51 | 179.5 | 368 | 2.61 | 7 |
| 52 | 166.6 | 352 | 2.84 | 7 |
| 53 | 136.4 | 350 | 3.18 | 10 |
| 54 | 133.2 | 368 | 2.63 | 7 |
| 55 | 118.8 | 334 | 2.63 | 7 |
| 56 | 152.4 | 348 | 2.88 | 7 |
| 57 | 163.6 | 364 | 2.82 | 7 |
| 58 | 201.5 | 368 | 2.62 | 7 |
| 59 | 115.8 | 364 | 2.89 | 7 |
| 60 | 148.8 | 352 | 2.70 | 7 |
| 61 | 140.5 | 352 | 2.75 | 7 |
| 62 | 199.8 | 352 | 2.94 | 7 |
| 63 | 124.7 | 364 | 2.49 | 7 |
| 64 | 200.2 | 335 | 1.83 | 7 |
| 65 | 76.7 | 391 | 4.1 | 7 |
| 66 | >300 | 361 | 3.37 | 7 |
| 67 | 126.3 | 377 | 3.76 | 7 |
| 68 | 127.5 | 355 | 2.28 | 7 |
| 69 | 88.2 | 379 | 2.7 | 7 |
| 70 | 171.0 | 351 | 2.97 | 7 |
| 71 | 125.3 | 351 | 2.42 | 7 |
| 72 | 134.7 | 353 | 2.82 | 7 |
| 73 | 160.7 | 369 | 3.05 | 7 |
| 74 | n.d. | 383 | 3.0 | 7 |
| 75 | n.d. | 367 | 2.8 | 7 |
| 76 | 111.3 | 353 | 3.47 | 10 |
| 77 | >300 | 322 | 1.62 | 7 |
| 78 | 144.5 | 352 | 2.1 | 7 |
| 79 | 122.8 | 351 | 1.91 | 7 |
| 80 | 148.9 | 322 | 2.70 | 12 |
| 81 | 118.6 | 339 | 2.15 | 7 |
| 82 | 237.2 | 336 | 1.84 | 7 |
| 83 | 143.7 | 336 | 2.29 | 7 |
| 84 | 166.7 | 336 | 2.03 | 7 |
| 85 | n.d. | 395 | 2.91 | 7 |
| 86 | 130.6 | 353 | 2.4 | 7 |
| 87 | 239.3 | 322 | 2.11 | 7 |
| 88 | 149.4 | 353 | 2.46 | 7 |
| 89 | 157.3 | 352 | 2.31 | 7 |
| 90 | 177.1 | 354 | 2.17 | 7 |
| 91 | 134.6 | 370 | 2.46 | 7 |
| 92 | 145.5 | 336 | 2.38 | 7 |
| 93 | 149.5 | 336 | 2.03 | 7 |
| 94 | 147.6 | 336 | 2.36 | 7 |
| 95 | 180.8 | 346 | 3.43 | 13 |
| 96 | 124.2 | 351 | 2.2 | 7 |
| 97 | 177.0 | 366 | 2.44 | 7 |
| 98 | 152.6 | 366 | 2.7 | 7 |
| 99 | 183.7 | 366 | 2.33 | 7 |
| 100 | 235.5 | 336 | 2.25 | 7 |
| 101 | 145.4 | 352 | 2.51 | 7 |
| 102 | 158.1 | 366 | 2.81 | 7 |
| 103 | 194.3 | 352 | 2.81 | 10 |
| 104 | 140.9 | 365 | 3.67 | 10 |
| 105 | 131.9 | 366 | 2.96 | 7 |
| 106 | n.d. | 366 | 3.02 | 10 |
| 107 | 169.6 | 382 | 2.79 | 10 |
| 108 | 145.3 | 365 | 3.89 | 10 |
| 109 | 140.6 | 365 | 3.39 | 10 |
| 110 | 159.8 | 352 | 2.55 | 7 |
| 111 | 101.8 | 363 | 3.51 | 7 |
| 112 | 166.4 | 352 | 2.62 | 7 |
| 113 | n.d. | 352 | 1.88 | 7 |
| 114 | 136.3 | 365 | 2.43 | 7 |
| 115 | 133.0 | 351 | 2.43 | 7 |
| 116 | >300 | 349 | 2.0 | 7 |
| 117 | 158.9 | 336 | 1.98 | 7 |
| 118 | 98.6 | 352 | 1.53 | 9 |
| 119 | n.d. | 366 | 1.63 | 9 |
| 120 | 141.7 | 350 | 2.113 | 7 |
| 121 | 109.3 | 365 | 2.55 | 7 |
| 122 | 154.5 | 382 | 3.02 | 7 |
| 123 | 270.3 | 356 | 2.24 | 7 |
| 124 | n.d. | 386 | 2.59 | 7 |
| 125 | n.d. | 352 | 2.05 | 7 |
| 126 | 161.3 | 340 | 1.91 | 7 |
| 127 | 187.4 | 382 | 2.65 | 7 |
| 128 | 125.0 | 312 | 2.6 | 7 |
| 129 | 66.9 | 312 | 2.6 | 7 |
| 130 | 93.2 | 352 | 2.9 | 7 |
| 131 | 96.8 | 352 | 2.9 | 7 |
| 132 | 104.7 | 353 | 2.92 | 7 |
| 133 | 233.8 | 353 | 2.92 | 7 |
| 134 | 87.4 | 367 | 3.89 | 10 |
| 135 | 87.4 | 367 | 3.89 | 10 |
| 136 | n.d. | 312 | 2.5 | 7 |
| 137 | 64.6 | 312 | 2.5 | 7 |
| 138 | 93.3 | 367 | 3.12 | 7 |
| 139 | n.d. | 353 | 2.87 | 7 |
| 140 | 156.0 | 367 | 3.12 | 7 |
| 141 | 71.9 | 353 | 2.81 | 7 |
| 142 | 131.6 | 352 | 2.71 | 7 |
| 143 | 135.8 | 382 | 2.77 | 7 |
| 144 | 94.6 | 366 | 3.01 | 7 |
| 145 | 179.9 | 366 | 2.25 | 9 |
| 146 | 84.0 | 366 | 2.24 | 9 |
| 147 | 113.0 | 384 | 2.13 | 9 |
| 148 | 145.5 | 365 | 1.98 | 9 |
| 149 | 104.9 | 366 | 2.39 | 7 |
| 150 | 78.8 | 364 | 2.73 | 7 |
| 151 | 99.2 | 348 | 2.97 | 7 |
| 152 | 100.0 | 364 | 2.76 | 7 |
| 153 | 77.5 | 348 | 2.96 | 7 |
| 154 | 171.5 | 348 | 2.83 | 7 |
| 155 | 99.3 | 367 | 3.05 | 7 |
| 156 | >300 | 380 | 2.16 | 9 |
| 157 | 129.9 | 352 | 2.76 | 7 |
| 158 | n.d. | 339 | 1.64 | 7 |
| 159 | 173.2 | 339 | 2.06 | 7 |
| 160 | 149.5 | 339 | 1.58 | 7 |
| 161 | n.d. | 357 | 1.96 | 7 |
| 162 | n.d. | 299 | 1.78 | 7 |
| 163 | n.d. | 299 | 1.31 | 7 |
| 164 | 152.5 | 323 | 2.18 | 7 |
| 165 | 201.2 | 356 | 2.66 | 7 |
| 166 | 182.5 | 352 | 2.9 | 7 |
| 167 | 104.5 | 316 | 2.38 | 7 |
| 168 | 70.1 | 312 | 2.62 | 7 |
| 169 | n.d. | 363 | 2.46 | 7 |
| 170 | n.d. | 299 | 1.38 | 7 |
| 171 | 110.7 | 317 | 1.66 | 7 |
| 172 | 134.1 | 340 | 2.07 | 7 |
| 173 | 177.0 | 353 | 2.5 | 7 |
| 174 | >300 | 353 | 1.71 | 7 |
| 175 | n.d. | 367 | 1.78 | 7 |
| 176 | >300 | 340 | 1.49 | 7 |
| 177 | n.d. | 353 | 2.89 | 7 |
| 178 | >300 | 357 | 3.45 | 1 |
| 179 | >300 | 357 | 3.38 | 1 |
| 180 | >300 | 371 | 2.62 | 7 |
| 181 | 239.4 | 357 | 2.32 | 7 |
| 182 | 174.3 | 354 | 1.72 | 7 |
| 183 | 236.2 | 353 | 2.4 | 7 |
| 184 | 148.6 | 353 | 2.36 | 7 |
| 185 | 270.1 | 353 | 2.5 | 7 |
| 186 | 293.9 | 354 | 1.74 | 7 |
| 187 | 165.0 | 357 | 2.28 | 7 |
| 188 | 160.7 | 356 | 2.69 | 7 |
| 189 | 168.3 | 353 | 1.83 | 7 |
| 190 | 183.3 | 356 | 2.6 | 7 |
| 191 | 132.8 | 352 | 2.92 | 7 |
| 192 | n.d. | 352 | 2.86 | 7 |
| 193 | 202.6 | 364 | 2.27 | 7 |

TABLE IV-continued

| No. | M.p. (° C.) | [M + H]+ | R$_t$ | LCMS Method |
|---|---|---|---|---|
| 194 | 179.5 | 340 | 1.49 | 7 |
| 195 | >300 | 369 | 2.22 | 7 |
| 196 | 115.3 | 354 | 1.74 | 7 |
| 197 | 144.8 | 340 | 1.71 | 7 |
| 198 | 155.7 | 371 | 2.63 | 7 |
| 199 | 228.7 | 340 | 1.57 | 7 |
| 200 | 156.6 | 354 | 2.03 | 7 |
| 201 | n.d. | 340 | 1.2 | 7 |
| 202 | n.d. | 340 | 1.39 | 7 |
| 203 | 186.7 | 353 | 2.38 | 7 |
| 204 | 143.9 | 369 | 2.12 | 7 |
| 205 | 159.2 | 354 | 2.34 | 7 |
| 206 | 109.8 | 336 | 2.07 | 7 |
| 207 | 97.7 | 364 | 3.06 | 7 |
| 208 | n.d. | 370 | 2.21 | 7 |
| 209 | n.d. | 371 | 1.92 | 7 |
| 210 | n.d. | 353 | 2.03 | 7 |
| 211 | n.d. | 352 | 1.73 | 7 |
| 212 | n.d. | 353 | 1.65 | 7 |
| 213 | n.d. | 353 | 2.05 | 7 |
| 214 | 183.8 | 351 | 2.02 | 7 |
| 215 | 156.1 | 354 | 2.31 | 7 |
| 216 | n.d. | 335 | 2.3 | 7 |
| 217 | 120.6 | 367 | 1.99 | 7 |
| 218 | >300 | 335 | 2.31 | 7 |
| 219 | n.d. | 335 | 2.13 | 7 |
| 220 | 130.4 | 368 | 2.66 | 7 |
| 221 | 117.3 | 368 | 2.59 | 7 |
| 222 | 216.5 | 352 | 2.86 | 7 |
| 223 | 148.2 | 352 | 2.85 | 7 |
| 224 | 117.0 | 352 | 2.7 | 7 |
| 225 | n.d. | 370 | 2.93 | 7 |
| 226 | >300 | 370 | 2.22 | 7 |
| 227 | 168 | 370 | 2.08 | 9 |
| 228 | n.d. | 386 | 2.69 | 7 |
| 229 | 267.4 | 369 | 2.29 | 7 |
| 230 | >300 | 384 | 2.54 | 7 |
| 231 | n.d. | 370 | 2.1 | 9 |
| 232 | 209.4 | 371 | 2.87 | 7 |
| 233 | 181.3 | 364 | 2.41 | 7 |
| 234 | 164.2 | 370 | 2.98 | 7 |
| 235 | 128.1 | 370 | 3.08 | 7 |
| 236 | 123.5 | 385 | 3.94 | 10 |
| 237 | 157.5 | 371 | 3.01 | 7 |
| 238 | n.d. | 370 | 2.91 | 7 |
| 239 | n.d. | 370 | 2.99 | 7 |
| 240 | 87.2 | 353 | 2.4 | 7 |
| 241 | 110.2 | 377 | 2.74 | 7 |
| 242 | 70.2 | 366 | 3.17 | 7 |
| 243 | 227.0 | 366 | 3.05 | 7 |
| 244 | 144.9 | 370 | 2.89 | 7 |
| 245 | 146.4 | 370 | 2.86 | 7 |
| 246 | n.d. | 377 | 2.62 | 7 |
| 247 | 98.0 | 353 | 2.98 | 10 |
| 248 | n.d. | 262 | 0.78 | 9 |
| 249 | n.d. | 262 | 0.76 | 8 |
| 250 | n.d. | 258 | 1.48 | 5 |
| 251 | n.d. | 258 | 1.39 | 5 |
| 252 | n.d. | 258 | 1.61 | 7 |
| 253 | n.d. | 258 | 0.84 | 8 |
| 254 | n.d. | 258 | 1.55 | 7 |
| 255 | n.d. | 258 | 1.53 | 7 |
| 256 | n.d. | 258 | 2.18 | 6 |
| 257 | n.d. | 312 | 2.49 | 7 |
| 258 | 120.9 | 352 | 3.46 | 1 |
| 259 | 100.5 | 332 | 2.77 | 7 |
| 260 | 235.0 | 372 | 3.62 | 1 |
| 261 | n.d. | 312 | 2.69 | 7 |
| 262 | 186.9 | 352 | 3.37 | 10 |
| 263 | n.d. | 368 | 2.63 | 6 |
| 264 | n.d. | 370 | 2.77 | 7 |
| 265 | n.d. | 368 | 2.12 | 7 |
| 266 | n.d. | 370 | 2.71 | 7 |
| 267 | n.d. | 382 | 2.81 | 7 |
| 268 | n.d. | 368 | 2.10 | 7 |
| 269 | n.d. | 370 | 2.69 | 7 |
| 270 | n.d. | 382 | 2.80 | 7 |
| 271 | n.d. | 356 | 2.83 | 7 |
| 272 | n.d. | 356 | 0.78 | 15 |
| 273 | n.d. | 356 | 0.78 | 15 |
| 274 | 159.5 | 405 | 2.93 | 7 |
| 275 | n.d. | 404 | 3.49 | 14 |
| 276 | >300 | 365 | 2.05 | 7 |
| 277 | >300 | 351 | 1.68 | 7 |
| 278 | n.d. | 350 | 2.51 | 7 |
| 279 | 176.6 | 369 | 1.91 | 7 |
| 280 | 215.1 | 365 | 2.62 | 7 |
| 281 | n.d. | 390 | 3.61 | 7 |
| 282 | 190.2 | 364 | 2.38 | 7 |
| 283 | 134.8 | 382 | 2.94 | 7 |
| 284 | 209.2 | 365 | 2.11 | 7 |
| 285 | n.d. | 336 | 1.97 | 7 |
| 286 | 143.7 | 364 | 3.14 | 7 |
| 287 | 164.8 | 364 | 2.48 | 7 |
| 288 | 178.4 | 364 | 2.17 | 7 |
| 289 | n.d. | 364 | 2.15 | 7 |
| 290 | 220.6 | 378 | 3.84 | 10 |
| 291 | 117.9 | 378 | 3.62 | 10 |
| 292 | 125.0 | 378 | 3.96 | 10 |
| 293 | n.d. | 365 | 2.41 | 7 |
| 294 | >300 | 365 | 2.62 | 7 |
| 295 | 138.8 | 386 | 2.71 | 7 |
| 296 | n.d. | 386 | 2.59 | 7 |
| 297 | 116.3 | 352 | 2.94 | 7 |
| 298 | 103.4 | 365 | 2.48 | 7 |
| 299 | 127.8 | 368 | 2.82 | 7 |
| 300 | n.d. | 366 | 2.43 | 7 |
| 301 | 207.6 | 381 | 2.68 | 7 |
| 302 | n.d. | 366 | 2.76 | 7 |
| 303 | n.d. | 386 | 1.72 | 9 |
| 304 | 109.9 | 382 | 2.67 | 7 |
| 305 | 126.7 | 382 | 3.35 | 7 |
| 306 | 190.3 | 351 | 2.31 | 6 |
| 307 | 139.1 | 336 | 1.66 | 7 |
| 308 | >300 | 370 | 2.46 | 7 |
| 309 | 143.2 | 391 | 2.42 | 7 |
| 310 | 153.8 | 382 | 2.95 | 7 |
| 311 | n.d. | 368 | 2.34 | 7 |
| 312 | >300 | 382 | 2.20 | 7 |
| 313 | 97.5 | 365 | 2.65 | 7 |
| 314 | 107.1 | 383 | 2.46 | 7 |
| 315 | 86.4 | 351 | 2.11 | 7 |
| 316 | 121.2 | 382 | 2.98 | 6 |
| 317 | 166.6 | 382 | 3.19 | 7 |
| 318 | >300 | 388 | 2.48 | 7 |
| 319 | 194.5 | 340 | 2.97 | 7 |
| 320 | 215.8 | 324 | 1.78 | 7 |
| 321 | 203.7 | 324 | 1.80 | 7 |
| 322 | 175.8 | 324 | 1.58 | 7 |
| 323 | 169.5 | 356 | 2.78 | 7 |
| 324 | 187.0 | 361 | 2.80 | 7 |
| 325 | n.d. | 260 | 0.63 | 8 |
| 326 | n.d. | 272 | 1.75 | 5 |
| 327 | n.d. | 332 | 2.78 | 7 |
| 328 | n.d. | 399 | 3.14 | 7 |
| 329 | n.d. | 278 | 2.68 | 10 |
| 330 | n.d. | 276 | 0.86 | 8 |
| 331 | n.d. | 258 | 0.84 | 8 |
| 332 | n.d. | 372 | 3.00 | 7 |
| 333 | n.d. | 278 | 2.30 | 6 |
| 334 | n.d. | n.d. | n.d. | n.d. |
| 335 | n.d. | 258 | 0.86 | 8 |
| 336 | n.d. | 262 | 0.82 | 8 |
| 337 | n.d. | 269 | 0.68 | 8 |
| 338 | n.d. | 274 | 0.67 | 8 |
| 339 | n.d. | 273 | 0.44 | 8 |
| 340 | n.d. | 245 | 0.54 | 8 |
| 341 | n.d. | 259 | 0.68 | 8 |
| 342 | n.d. | 259 | 0.65 | 8 |
| 343 | n.d. | 274 | 0.67 | 8 |
| 344 | n.d. | 274 | 2.23 | 6 |
| 345 | n.d. | 259 | 0.60 | 7 |
| 346 | n.d. | 351 | 2.53 | 6 |
| 347 | n.d. | 245 | 0.38 | 8 |

TABLE IV-continued

| No. | M.p. (° C.) | [M + H]+ | R$_t$ | LCMS Method |
|---|---|---|---|---|
| 348 | n.d. | 374 | 2.28 | 11 |
| 349 | n.d. | 374 | 1.07 | 8 |
| 350 | n.d. | 374 | 0.89 | 8 |
| 351 | 146.6 | 352 | 2.66 | 7 |
| 352 | n.d. | 324 | 1.57 | 7 |
| 353 | 266.9 | 352 | 1.55 | 9 |
| 354 | n.d. | 369 | 2.95 | 7 |
| 355 | 212.7 | 355 | 1.69 | 7 |
| 356 | 160.3 | 350 | 2.48 | 7 |
| 358 | n.d. | n.d. | n.d. | n.d. |
| 359 | n.d. | 337 | n.d. | 15 |
| 360 | n.d. | 371 | n.d. | 15 |
| 361 | n.d. | 377 | n.d. | 15 |
| 362 | n.d. | 371 | n.d. | 16 |
| 363 | n.d. | 372 | n.d. | 15 |
| 364 | n.d. | 405 | n.d. | 16 |
| 365 | n.d. | 355 | n.d. | 15 |
| 366 | n.d. | 374 | n.d. | 16 |
| 367 | n.d. | 391 | n.d. | 16 |
| 368 | n.d. | 388 | n.d. | 15 |
| 369 | n.d. | 385 | n.d. | 15 |
| 370 | n.d. | 361 | n.d. | 15 |
| 371 | n.d. | 378 | n.d. | 15 |
| 372 | n.d. | 389 | n.d. | 15 |
| 373 | n.d. | 373 | n.d. | 15 |
| 374 | n.d. | 361 | n.d. | 15 |
| 375 | n.d. | 362 | n.d. | 16 |
| 376 | n.d. | 405 | n.d. | 16 |
| 377 | n.d. | 355 | n.d. | 15 |
| 378 | n.d. | 240 | 1.35 | 15 |

TABLE V

| No. | $\alpha_D$ (°) | Wavelength (nm) | Concentration w/v % | Solvent | Temp. (° C.) |
|---|---|---|---|---|---|
| 38 | −20.0 | 589 | 0.59 | DMF | 20 |
| 39 | −42.6 | 589 | 0.46 | DMF | 20 |
| 41 | +18.6 | 589 | 0.74 | DMF | 20 |
| 42 | −1.8 | 589 | 0.59 | DMF | 20 |
| 128 | +21.4 | 589 | 0.56 | DMF | 20 |
| 129 | −21.6 | 589 | 0.62 | DMF | 20 |
| 130 | +22.6 | 589 | 0.52 | DMF | 20 |
| 131 | −21.7 | 589 | 0.50 | DMF | 20 |
| 132 | +38.1 | 589 | 0.52 | DMF | 20 |
| 133 | −35.2 | 589 | 0.59 | DMF | 20 |
| 134 | +34.7 | 589 | 0.47 | DMF | 20 |
| 135 | +2.0 | 589 | 0.59 | DMF | 20 |
| 136 | −35.9 | 589 | 0.69 | DMF | 20 |
| 137 | +40.4 | 589 | 0.54 | DMF | 20 |
| 138 | −25.9 | 589 | 0.47 | DMF | 20 |
| 139 | −34.1 | 589 | 0.51 | DMF | 20 |
| 140 | +23.6 | 589 | 0.50 | DMF | 20 |
| 141 | +31.7 | 589 | 0.53 | DMF | 20 |
| 142 | +15.7 | 589 | 0.56 | DMF | 20 |
| 143 | +23.7 | 589 | 0.67 | DMF | 20 |
| 144 | +13.9 | 589 | 0.98 | DMF | 20 |
| 145 | +9.3 | 589 | 0.54 | DMF | 20 |
| 146 | +31.9 | 589 | 0.69 | DMF | 20 |
| 147 | +41.4 | 589 | 0.59 | DMF | 20 |
| 148 | −10.3 | 589 | 0.64 | DMF | 20 |
| 149 | +33.9 | 589 | 1.03 | DMF | 20 |
| 150 | +1.1 | 589 | 0.92 | DMF | 20 |
| 151 | +29.6 | 589 | 0.84 | DMF | 20 |
| 152 | +23.9 | 589 | 0.72 | DMF | 20 |
| 153 | +19.5 | 589 | 0.75 | DMF | 20 |
| 154 | −5.0 | 589 | 0.71 | DMF | 20 |
| 155 | +29.7 | 589 | 0.97 | DMF | 20 |
| 156 | +22.6 | 589 | 0.63 | DMF | 20 |
| 157 | −18.0 | 589 | 0.5 | DMF | 20 |
| 238 | +20.8 | 589 | 0.5 | DMF | 20 |
| 239 | +21.9 | 589 | 0.6 | DMF | 20 |
| 240 | −17.7 | 589 | 0.53 | DMF | 20 |
| 241 | −23.9 | 589 | 0.45 | DMF | 20 |
| 242 | −23.1 | 589 | 0.4 | DMF | 20 |
| 243 | +18.2 | 589 | 0.64 | DMF | 20 |
| 244 | +14.7 | 589 | 0.57 | DMF | 20 |
| 245 | +14.2 | 589 | 0.62 | DMF | 20 |
| 246 | +18.6 | 589 | 0.73 | DMF | 20 |
| 247 | +15.3 | 589 | 0.62 | DMF | 20 |
| 252 | −33.5 | 589 | 0.68 | DMF | 20 |
| 253 | +33.0 | 589 | 0.65 | DMF | 20 |
| 254 | −40.6 | 589 | 0.60 | DMF | 20 |
| 255 | +38.0 | 589 | 0.7 | DMF | 20 |
| 265 | +5.4 | 589 | 0.52 | DMF | 20 |
| 266 | +17.2 | 589 | 0.57 | DMF | 20 |
| 267 | +15.6 | 589 | 0.54 | DMF | 20 |
| 268 | −5.1 | 589 | 0.54 | DMF | 20 |
| 269 | −18.7 | 589 | 0.53 | DMF | 20 |
| 270 | −16.4 | 589 | 0.57 | DMF | 20 |
| 338 | −4.3 | 589 | 0.41 | DMF | 20 |
| 343 | +3.8 | 589 | 0.52 | DMF | 20 |

98. Generation of Human mGluR5 Stable Cell Line

Human mGluR5a cDNA in pCMV6-XL6 mammalian expression plasmid was purchased from OriGene Technologies, Inc. (catalogue number SC326357) and subcloned into pcDNA3.1(−). Human embryonic kidney (HEK) 293A cells were then transfected with human mGluR5a pcDNA3.1(−) using LipofectAmine-2000 (Invitrogen) and monoclones were selected and tested for functional response using a $Ca^{2+}$ mobilization assay. Monoclones were named for the species ("H" for human) plus the location on the plate (e.g. "10H").

99. Cell-Based Functional Assay

HEK cells transfected with the human mGluR5a receptor (H10H or H12H cell line) were plated at 15,000 cells/well in clear-bottomed poly-D-lysine-coated assay plates (BD Falcon) in glutamate-glutamine-free growth medium and incubated overnight at 37° C. and 5% $CO_2$. Cell-lines used were either the H10H or H12H cell-lines expressing the human mGluR5 receptor. The following day, the growth medium was removed and the cells were washed with assay buffer containing 1× Hank's balanced salt solution (Invitrogen, Carlsbad, Calif.), 20 mM HEPES, 2.5 mM probenecid, pH 7.4 and left with 20 µL of this reagent. Following this step, the cells were loaded with calcium indicator dye, fluo-4 AM, to a final concentration of 2 µM and incubated for 40-45 min at 37° C. The dye solution was removed and replaced with assay buffer. Cell plates were held for 10-15 min at room temperature and were then loaded into the Functional Drug Screening System 6000 (FDSS 6000, Hamamatsu, Japan).

After establishment of a fluorescence baseline for about 3 seconds, the compounds of the present invention were added to the cells, and the response in cells was measured. 2.3 minutes later an $EC_{20}$ concentration of the mGluR5 receptor agonist glutamate was added to the cells, and the response of the cells was measured for about 1.7 minutes. All test compounds were dissolved and diluted to a concentration of 10 mM in 100% DMSO and then serially diluted into assay buffer for a 2× stock solution in 0.6% DMSO; stock compounds were then added to the assay for a final DMSO concentration of 0.3% after the first addition to the assay well. Calcium fluorescence measures were recorded as fold over basal fluorescence; raw data was then normalized to the maximal response to glutamate. Potentiation of the agonist response of the mGluR5 receptor in the present invention was observed as an increase in response to submaximal concentrations of glutamate in the presence of compound compared to the response to glutamate in the absence of compound.

100. Data Analysis

The concentration-response curves of compounds of the present invention, obtained in the presence of $EC_{20}$ of mGluR5 receptor agonist glutamate to determine positive allosteric modulation, were generated using Microsoft Excel with IDBS XLfit add-ins. The raw data file containing all time points was used as the data source in the analysis template. This was saved by the FDSS as a tab-delimitted text file. Data were normalized using a static ratio function ($F/F_0$) for each measurement of the total 350 values per well divided by each well's initial value. Data was then reduced as to peak amplitudes (Max–Initial Min) using a time range that starts approximately 1 second after the glutamate $EC_{20}$ addition and continues for approximately 40 seconds. This is sufficient time to capture the peak amplitude of the cellular Calcium response. Individual amplitudes were expressed as % $E_{Max}$ by multiplying each amplitude by 100 and then dividing the product by the mean of the amplitudes derived from the glutamate $EC_{Max}$-treated wells. $pEC_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly. Individual values falling outside the 95% prediction limits of the curve fit were automatically excluded from the fit. A compound was designated as a positive allosteric modulator if the compound showed a concentration-dependent increase in the glutamate $EC_{20}$ addition. % $E_{max}$ for compounds may be estimated using the resulting corresponding parameter value determined using the curve fit or by taking an average of the overall maximum response at a single concentration. These two methods are in good agreement for curves with a clear plateau at the high concentration range. For data that show an increase in the $EC_{20}$ response, but, do not hit a plateau, the average of the maximum response at a single concentration is preferred. For consistency purposes across the range of potencies observed, all Emax values reported in this application are calculated using the maximum average response at a single concentration. The % $E_{Max}$ value for each compound reported in this application is defined as the maximum % effect obtained in a concentration-response curve of that compound expressed as a percent of the response of a maximally effect concentration of glutamate. Table I above shows the pharmacological data obtained for a selected set of compounds.

For compounds showing a lower potency (e.g. as indicated by a lack of a plateau in the concentration response curve), but with a greater than a 20% increase in glutamate response, a potency of >10 μM ($pEC_{50}$<5) was estimated.

101. Prospective In Vivo Effects

Generally clinically relevant antipsychotic agents (both typical and atypical) display efficacy in preclinical behavior challenge models. The compounds described in the preceding examples are expected to show in vivo effects in various animal behavioural challenge models known to the skilled person, such as amphetamine-induced or phencyclidine (PCP)-induced hyperlocomotion, and other models, such as NMDA receptor antagonist MK-801-induced locomotor activity conducted in rodent, such as rat or mouse, but may be conducted in other animal species as is convenient to the study goals. Compounds, products, and compositions disclosed herein are expected to show in vivo effects in various animal behavioural challenge models known to the skilled person, such as amphetamine-induced or phencyclidine (PCP)-induced hyperlocomotion in rodent, and other models, such as NMDA receptor antagonist MK-801-induced locomotor activity. These models are typically conducted in rodent, such as rat or mouse, but may be conducted in other animal species as is convenient to the study goals.

Compounds of the present invention are expected as a class to show in vivo efficacy in a preclinical rat behavioral model, where known, clinically useful antipsychotics display similar positive responses. For example, 5-(5-fluoropyridin-2-yl)-2-(phenoxymethyl)-6,7-dihydropyrazolo[1,5-a]pyrazin-4(5H)-one, which is viewed as representative of the compounds of the present invention was tested in reverse amphetamine-induced hyperlocomotion in male Sprague-Dawley rates at doses ranging from 1 to 100 mg/kg by oral gavage (see discussion below).

For example, disclosed compounds as described hereinbefore, or a pharmaceutically acceptable thereof, are expected to show such in vivo effects. Moreover, compounds prepared using the disclosed synthetic methods are also expected to show such in vivo effects.

102. 5-(5-fluoropyridin-2-yl)-2-(phenoxymethyl)-6,7-dihydropyrazolo[1,5-a]pyrazin-4(5H)-one

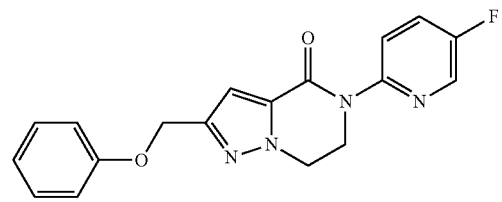 [SMILES: O=C1c2cc(COc3ccccc3)nn2CCN1c1ccc(F)cn1]

Locomotor activity was assessed as mean distance traveled (cm) in standard 16×16 photocell testing chambers measuring 43.2 cm (Length)×43.2 cm (Width)×30.5 cm (Height) (Med Associates, St. Albans, Vt.). Animals were habituated to individual activity chambers for at least 30 min prior to drug administration. Following administration of drug or vehicle, activity was recorded for a 90 minute time period. Data was expressed as the mean (±SEM) distance traveled recorded in 5 min intervals over the test period. The data was analyzed using repeated measures analysis of variance (ANOVA) followed by post-hoc testing using Dunnett's test, when appropriate. A difference was considered significant when $p \leq 0.05$.

Figure 4:
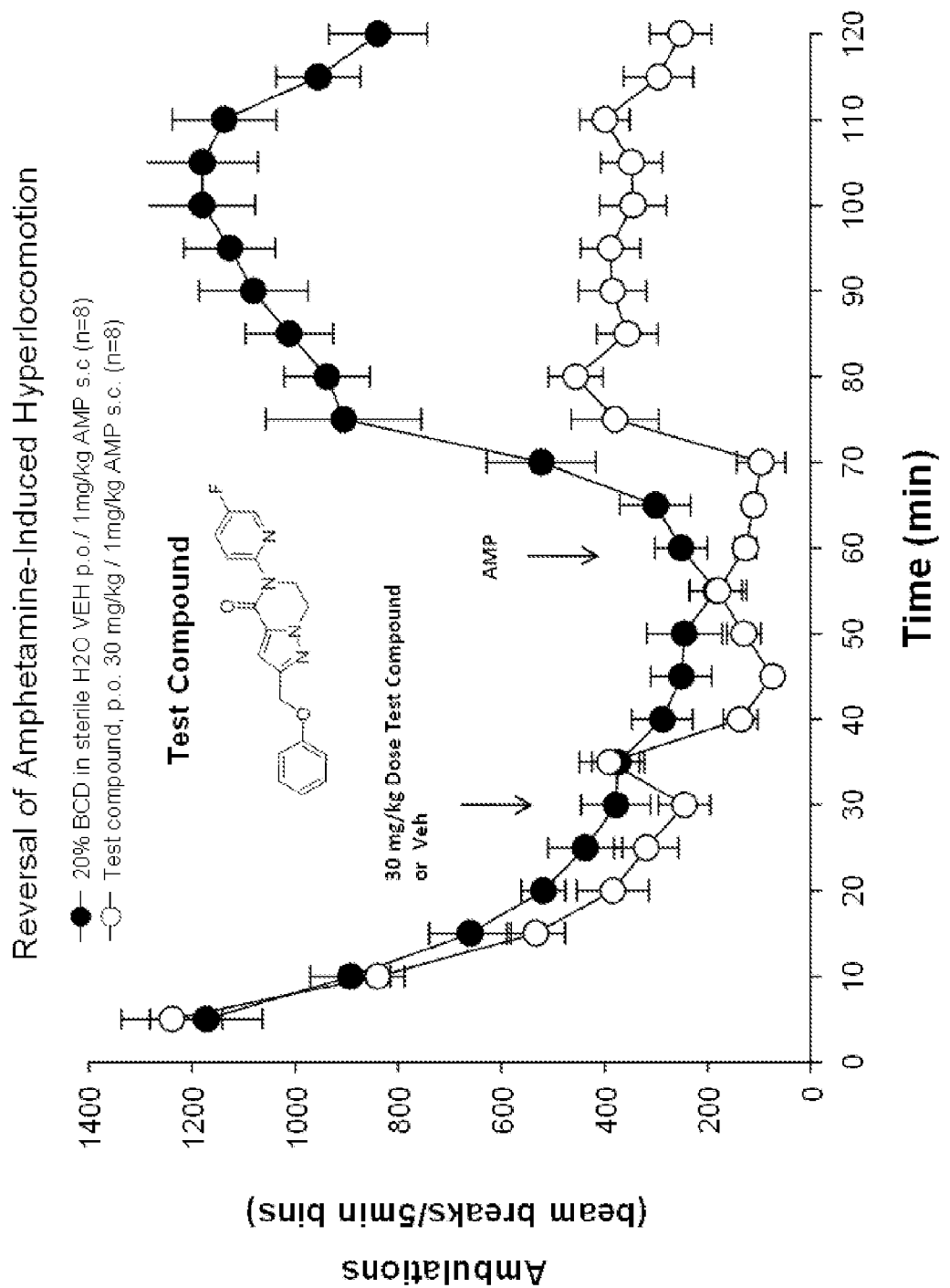
FIG. 4 shows reversal of amphetamine-induced hyperlocomotion by 5-(5-fluoropyridin-2-yl)-2-(phenoxymethyl)-6,7-dihydropryazolo[1,5-a]pyrazin-4(5H)-one.

Amphetamine sulfate was obtained from Sigma (Cat #A5880-1G; St. Louis, Mo.) and 10 mg was dissolved in 10 ml of water. Test compound, 5-(5-fluoropyridin-2-yl)-2-(phenoxymethyl)-6,7-dihydropyrazolo[1,5-a]pyrazin-4(5H)-one, was formulated in a volume of 10 ml with an amount of drug appropriate to the dosage indicated. The appropriate amount of compound was mixed into a 20% 2-hydroxypropyl-β-cyclodextrin (2-HP-β-CD; indicated as "BCD" in FIG. 4) solution. The solution was formulated so that animals were injected with a volume equal to about 10× body weight. The mixture was then ultrahomogenized on ice for 2-3 minutes using the Dismembrator (Fisher Scientific Model 150T). Then the pH was checked using 0-14 EMD strips and adjusted to a pH of 6-7 if necessary. The mixture was then vortexed and stored in a warm sonication bath until time to be injected. Animals were administered samples of the following: (a) Amphetamine sulfate, 1 mg/kg, administered subcutaneously; and, (b) 5-(5-fluoropyridin-2-yl)-2-(phenoxymethyl)-6,7-dihydropyrazolo[1,5-a]pyrazin-4(5H)-one, dose as indicated in FIG. 4, was administered by oral gavage.

The study was carried out using male Sprague-Dawley rats weighing 225 g-275 g, between 2-3 months old (Harlan, Inc., Indianapolis, Ind.), were used. The number of animals used is as indicated in FIG. 4. They were kept in the animal care facility certified by the American Association for the Accreditation of Laboratory Animal Care (AALAC) under a 12-hour light/dark cycle (lights on: 6 a.m.; lights off: 6 p.m.) and had free access to food and water. The experimental protocols performed during the light cycle were approved by the Institutional Animals Care and Use Committee of Vanderbilt University and conformed to the guidelines established by the National Research Council Guide for the Care and Use of Laboratory Animals.

The animals were habituated in Smart Open Field locomotor activity test chambers (Hamilton-Kinder, San Diego, Calif.) with 16×16 photobeams to automatically record locomotor activity for 30 min and then dosed with vehicle or test compound. The rats were then placed into cages. At 60 min, all rats were injected subcutaneously with 1 mg/kg amphetamine or vehicle and then monitored for an additional 60 min. Animals are monitored for a total of 120 minutes. Data are expressed as changes in ambulation defined as total number of beam breaks per 5 min periods.

The data for the dose-response studies were analyzed by a between-group analysis of variance. If there was a main effect of dose, then each dose group was compared with the vehicle amphetamine group. The calculations were performed using JMP IN 8 (SAS Institute, Cary, N.C.) statistical software and graphed using SigmaPlot9 (Saugua, Mass.). Results for reversal of amphetamine-induced hyperlocomotion by 5-(5-fluoropyridin-2-yl)-2-(phenoxymethyl)-6,7-dihydropyrazolo[1,5-a]pyrazin-4(5H)-one are shown in FIG. 4. The following abbreviations are used: (a) "Test compound" refers to 5-(5-fluoropyridin-2-yl)-2-(phenoxymethyl)-6,7-dihydropyrazolo[1,5-a]pyrazin-4(5H)-one; (b) subcutaneous administration of compound is indicated by "sc"; (c) oral gavage administration is indicated by "po"; and (d) amphetamine sulfate is indicated as "amph". The time of administration of amphetamine sulfate is indicated in FIG. 4 by "AMP" and the corresponding arrow. The vehicle for test compound is 20% wt/v HP-β-CD, and the vehicle for amphetamine is sterile water.

103. Prophetic Pharmaceutical Composition Examples

"Active ingredient" as used throughout these examples relates to one or more disclosed compounds or products of disclosed methods of making as described hereinbefore, or a pharmaceutically acceptable salt, hydrate, solvate, or polymorph thereof. The following examples of the formulation of the compounds of the present invention in tablets, suspension, injectables and ointments are prophetic. Typical examples of recipes for the formulation of the invention are as given below.

a. Tablets
A tablet can be prepared as follows:

| Component | Amount |
|---|---|
| Active ingredient | 5 to 50 mg |
| Di-calcium phosphate | 20 mg |
| Lactose | 30 mg |
| Talcum | 10 mg |
| Magnesium stearate | 5 |
| Potato starch | add to make total weight 200 mg |

In this Example, active ingredient can be replaced with the same amount of any of the compounds according to the present invention, in particular by the same amount of any of the exemplified compounds.

b. Suspension
An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

c. Injectable
A parenteral composition is prepared by stirring 1.5% by weight of active ingredient of the invention in 10% by volume propylene glycol in water.

d. Ointment
An ointment can be prepared as follows:

| Component | Amount |
|---|---|
| Active ingredient | 5 to 1000 mg |
| Stearyl alcohol | 3 g |
| Lanoline | 5 g |
| White petroleum | 15 g |
| Water | add to make total weight 100 g |

In this Example, active ingredient can be replaced with the same amount of any of the compounds according to the present invention, in particular by the same amount of any of the exemplified compounds.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A compound having a structure represented by a formula:

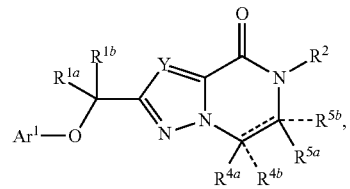

wherein each - - - - - is independently an optional covalent bond, wherein valence is satisfied;

wherein $Ar^1$ is phenyl with 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl; or $Ar^1$ is pyridinyl, pyridazinyl, pyrimidinyl, or pyrazinyl and has 0-3 substituents selected from halogen, cyano, hydroxyl, —$NH_2$, C1-C4 alkyl, hydroxy C1-C4 alkyl, C1-C4 alkyloxy, amino C1-C4 alkyl, C1-C4 alkylamino, C1-C4 dialkylamino, monohalo C1-C4 alkyl, and polyhalo C1-C4 alkyl;

wherein each of $R^{1a}$ and $R^{1b}$ is independently selected from hydrogen and C1-C4 alkyl;

wherein $R^2$ is selected from hydrogen; C1-C6 alkyl; hydroxy C1-C6 alkyl, (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; (halo C3-C8 cycloalkyl) C1-C6 alkyl, (polyhalo C3-C8 cycloalkyl) C1-C6 alkyl, C2-C5 heterocyclyl, (C2-C5 heterocyclyl) C1-C6 alkyl; aryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl; and heteroaryl with 0-3 substituents selected from halogen, cyano, hydroxyl, —$NH_2$, C1-C4 alkyl, hydroxy C1-C6 alkyl, C1-C4 alkyloxy, monohalo C1-C4 alkyl, polyhalo C1-C4 alkyl, amino C1-C4 alkyl, C1-C4 alkylamino, C1-C4 dialkylamino, halo C1-C4 alkyloxy, polyhalo C1-C4 alkyloxy, (C1-C4 alkyloxy) C1-C4 alkyl, (C1-C4 alkyloxy) C1-C4 alkyloxy, C2-C5 heterocycloalkyl, and C3-C6 cycloalkyl;

wherein Y is N or C—$R^3$, wherein $R^3$, when present, is selected from hydrogen, halogen, cyano, C1-C4 alkyl, monohalo C1-C4 alkyl, polyhalo C1-C4 alkyl, C2-C5 heterocyclyl, C3-C6 cycloalkyl, aryl and heteroaryl;

wherein $R^{4a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl;

wherein $R^{4b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{4a}$ and $R^{4b}$ are covalently bonded and, together with the intermediate carbon, comprise an optionally substituted 3- to 7-membered spirocycloalkyl;

wherein $R^{5a}$ is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; and wherein $R^{5b}$, when present, is selected from hydrogen, halogen, hydroxyl, C1-C4 alkyl, C1-C4 haloalkyl, C1-C4 polyhaloalkyl, C1-C4 alkyloxy, hydroxy C1-C4 alkyl, and (C1-C4 alkyloxy) C1-C4 alkyl; or $R^{5a}$ and $R^{5b}$ are covalently bonded and, together with the intermediate carbon, comprise an optionally substituted 3- to 7-membered spirocycloalkyl;

or a pharmaceutically acceptable salt thereof.

2. The compound of claim 1, wherein $Ar^1$ is phenyl with 0-3 substituents selected from halogen, cyano, C1-C4 alkyl, C1-C4 alkyloxy, monohalo C1-C4 alkyl, and polyhalo $C_1$-$C_4$ alkyl, or $Ar^1$ is pyridinyl, pyridazinyl, pyrimidinyl, or pyrazinyl and has 0-3 substituents selected from halogen, cyano, C1-C4 alkyl, C1-C4 alkyloxy, monohalo C1-C4 alkyl, and polyhalo C1-C4 alkyl;

wherein each of $R^{1a}$ and $R^{1b}$ is independently selected from hydrogen and C1-C4 alkyl;

wherein $R^2$ is selected from hydrogen; C1-C6 alkyl; (C1-C6 alkyloxy) C1-C6 alkyl; monohalo C1-C6 alkyl; polyhalo C1-C6 alkyl; C3-C8 cycloalkyl; (C3-C8 cycloalkyl) C1-C6 alkyl; C2-C5 heterocyclyl; phenyl with 0-3 substituents selected from halogen, cyano, C1-C4 alkyl, C1-C4 alkyloxy, monohalo C1-C4 alkyl, and polyhalo C1-C4 alkyl; and heteroaryl selected from pyridinyl, pyridazinyl, pyrimidinyl, and pyrazinyl, the heteroaryl having 0-3 substituents selected from halogen, cyano, C1-C4 alkyl, C1-C4 alkyloxy, monohalo C1-C4 alkyl, and polyhalo C1-C4 alkyl;

wherein $R^{4a}$ is selected from hydrogen and C1-C4 alkyl;

wherein $R^{4b}$, when present, is selected from hydrogen and C1-C4 alkyl, or $R^{4a}$ and $R^{4b}$ are covalently bonded and, together with the intermediate carbon, comprise an optionally substituted 3- to 7-membered spirocycloalkyl;

wherein $R^{5a}$ is selected from hydrogen and C1-C4 alkyl; and wherein $R^{5b}$, when present, is selected from hydrogen and C1-C4 alkyl, or $R^{5a}$ and $R^{5b}$ are covalently bonded and, together with the intermediate carbon, comprise an optionally substituted 3- to 7-membered spirocycloalkyl.

3. The compound of claim 1, wherein halogen is fluoro, chloro, or bromo.

4. The compound of claim 1, wherein $Ar^1$ is phenyl with 1-2 substituents selected from —F, —Cl, —OH, —CN, —$CH_3$, —$OCH_3$, —$NHCH_3$, and —$N(CH_3)_2$.

5. The compound of claim 1, wherein $Ar^1$ is pyridinyl, pyridazinyl, pyrimidinyl, or pyrazinyl and has 1-2 substituents selected from —F, —Cl, —OH, —CN, —$CH_3$, —$OCH_3$, —$NHCH_3$, and —$N(CH_3)_2$.

6. The compound of claim 1, wherein Y is N.

7. The compound of claim 1, wherein Y is C—$R^3$ and wherein $R^{1a}$, $R^{1b}$, and $R^3$ are each hydrogen.

8. The compound of claim 1, having a structure represented by a formula:

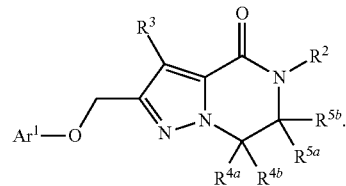

9. The compound of claim 1, having a structure represented by a formula:

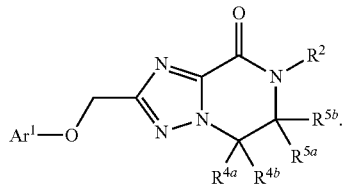

10. The compound of claim 1, having a structure represented by a formula:

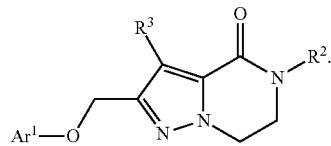

11. The compound of claim 1, having a structure represented by a formula:

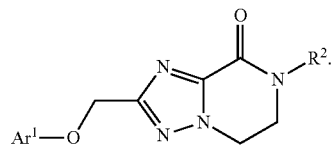

12. The compound of claim 1, wherein the compound exhibits potentiation of mGluR5 response to glutamate in human embryonic kidney cells transfected with rat mGluR5 with an $EC_{50}$ of less than about 10,000 nM.

* * * * *